United States Patent
Aebi et al.

(10) Patent No.: US 9,881,124 B2
(45) Date of Patent: Jan. 30, 2018

(54) RATIONAL DESIGN OF COMPONENTS OF THE OLIGO-SACCHARYLTRANSFERASE-CATALYSED ASPARAGINE-LINKED GLYCOSYLATION

(75) Inventors: Markus Aebi, Wettingen (CH); Kaspar Locher, Zurich (CH); Christian Lizak, Zurich (CH)

(73) Assignee: ETH ZURICH, Zurich (CH)

( * ) Notice: Subject to any disclaimer, the term of this patent is extended or adjusted under 35 U.S.C. 154(b) by 3 days.

(21) Appl. No.: 14/115,130

(22) PCT Filed: May 3, 2012

(86) PCT No.: PCT/EP2012/001902
§ 371 (c)(1),
(2), (4) Date: Dec. 19, 2013

(87) PCT Pub. No.: WO2012/150034
PCT Pub. Date: Nov. 8, 2012

(65) Prior Publication Data
US 2014/0100836 A1    Apr. 10, 2014

(30) Foreign Application Priority Data
May 4, 2011    (EP) .................................... 11003648

(51) Int. Cl.
*G06F 19/16*    (2011.01)
*C12Q 1/48*    (2006.01)

(52) U.S. Cl.
CPC ............... *G06F 19/16* (2013.01); *C12Q 1/48* (2013.01); *C07K 2299/00* (2013.01); *G01N 2333/924* (2013.01)

(58) Field of Classification Search
None
See application file for complete search history.

(56) References Cited

FOREIGN PATENT DOCUMENTS

WO    WO 2006/110814    10/2006

OTHER PUBLICATIONS

Igura et al., 2008, "Structure-guided identification of a new catalytic motif of oligosaccharyltransferase", EMBO J, 27(1):234-243.
Kelleher et al., 2006, "An evolving view of the eukaryotic oligosaccharyl transferase", Glycobiology, 16(4):47R-62R.
Kuntz et al., 2008, "Structural analysis of golgi α-mannosidase II inhibitors identified from a focused glycosidase inhibitor screen", Biochemistry, 47:10058-10068.
Li et al., 2008, "Structure of the oligosaccharyl transferase complex at 12 A resolution", Structure, 16(3):432-440.
Lizak et al., 2011, "X-ray structure of a bacterial oligosaccharyltransferase", Nature, 474(7351):350-355.
Maita et al., 2010, "Comparative structural biology of eubacterial and archaeal oligosaccharyltransferases", J Biol Chem, 285(7):4941-4950.
Nihon Denshi News, 2005, 37:2-5.

*Primary Examiner* — Suzanne M Noakes
(74) *Attorney, Agent, or Firm* — Jones Day

(57) ABSTRACT

The present invention is directed to methods for identifying or designing (a) a potential oligosaccharide donor, (b) a potential oligosaccharyltransferase (OST), (c) a potential consensus sequence motif polypeptide, and/or (d) a potential glycosylation inhibitor for use in the oligosaccharyltransferase (OST)—catalysed asparagine-linked ("N-linked") glycosylation, comprising the steps of generating a three-dimensional model of the catalytic domain and/or the polypeptide binding site of the oligosaccharyltransferase (OST) of *Campylobacter lari*, and designing or selecting a potential component selected from (a) to (d) which optimizes the stereo chemical complementarity of said three-dimensional model(s) and the potential component.

6 Claims, 102 Drawing Sheets

Fig. 2

1. LLO biosynthesis cluster (*C. jejuni*) with inactivated *pglB* gene gne › pglK › pglH › pglI › pglJ › ~~pglB~~ › pglA › pglC › pglD › pglE › pglF ›

2. Active PglB (*C. lari*)

pglB ›

3. Glycosylation acceptor protein scFv 3D5

[V_L]–DQNAT–[V_H]

Lanes: ev, wt, D154A, D56A, E319A, D56A/E319A, D154N, D56N, E319Q, D56N/E319Q anti-scFv: 50, 37 kDa — g1, g0
anti-glycan: 50, 37 kDa — g1
anti-PglB: 75, 50 kDa — g2, g1, g0

Table 1 (SEQ ID NO. 9, consisting of amino acids 2-711 of SEQ ID NO.1, complexed with SEQ ID NO. 2)

```
         1         2         3         4         5         6         7         8
12345678901234567890123456789012345678901234567890123456789012345678901234567890
                 Amino acid no.
                       1
ATOM      1  N   GLU A   2      24.265 -40.497  57.258  1.00282.44           N
ATOM      2  CA  GLU A   2      23.865 -40.443  55.854  1.00252.94           C
ATOM      3  C   GLU A   2      22.388 -40.631  55.652  1.00225.90           C
ATOM      4  O   GLU A   2      21.735 -39.779  55.059  1.00197.60           O
ATOM      5  CB  GLU A   2      24.654 -41.483  55.033  1.00204.11           C
ATOM      6  CG  GLU A   2      26.060 -41.060  54.630  1.00217.65           C
ATOM      7  CD  GLU A   2      26.729 -42.062  53.702  1.00225.06           C
ATOM      8  OE1 GLU A   2      26.015 -42.876  53.082  1.00208.68           O
ATOM      9  OE2 GLU A   2      27.972 -42.041  53.595  1.00248.69           O1-
ATOM     10  N   LEU A   3      21.842 -41.740  56.144  1.00199.23           N
ATOM     11  CA  LEU A   3      20.456 -42.092  55.827  1.00176.20           C
ATOM     12  C   LEU A   3      19.496 -42.136  57.009  1.00178.83           C
ATOM     13  O   LEU A   3      18.289 -42.266  56.815  1.00156.42           O
ATOM     14  CB  LEU A   3      20.393 -43.424  55.075  1.00161.40           C
ATOM     15  CG  LEU A   3      20.154 -43.345  53.566  1.00145.33           C
ATOM     16  CD1 LEU A   3      20.330 -44.715  52.935  1.00158.48           C
ATOM     17  CD2 LEU A   3      19.780 -42.786  53.257  1.00112.04           C
ATOM     18  N   GLN A   4      20.021 -42.032  58.224  1.00187.52           N
ATOM     19  CA  GLN A   4      19.179 -42.110  59.415  1.00195.67           C
ATOM     20  C   GLN A   4      18.736 -40.731  59.908  1.00184.83           C
ATOM     21  O   GLN A   4      18.030 -40.629  60.910  1.00190.65           O
ATOM     22  CB  GLN A   4      19.902 -42.860  60.533  1.00126.23           C
ATOM     23  CG  GLN A   4      19.113 -42.964  61.819  1.00139.97           C
ATOM     24  CD  GLN A   4      19.957 -43.451  62.992  1.00182.49           C
ATOM     25  NE2 GLN A   4      19.627 -42.935  64.195  1.00193.19           N
ATOM     26  OE1 GLN A   4      20.894 -44.232  62.817  1.00201.70           O
ATOM     27  N   GLN A   5      19.140 -39.679  59.195  1.00199.42           N
ATOM     28  CA  GLN A   5      18.842 -38.294  59.584  1.00187.32           C
ATOM     29  C   GLN A   5      17.435 -37.854  59.171  1.00158.58           C
ATOM     30  O   GLN A   5      16.894 -38.350  58.197  1.00138.14           O
ATOM     31  CB  GLN A   5      19.864 -37.338  58.962  1.00153.73           C
ATOM     32  CG  GLN A   5      21.313 -37.769  59.119  1.00179.41           C
ATOM     33  CD  GLN A   5      22.232 -37.083  58.126  1.00169.98           C
ATOM     34  NE2 GLN A   5      23.484 -37.522  58.073  1.00192.89           N
ATOM     35  OE1 GLN A   5      21.818 -36.180  57.407  1.00143.90           O
ATOM     36  N   ASN A   6      16.865 -36.903  59.902  1.00175.39           N
ATOM     37  CA  ASN A   6      15.547 -36.359  59.564  1.00150.45           C
ATOM     38  C   ASN A   6      15.608 -35.243  58.502  1.00125.55           C
ATOM     39  O   ASN A   6      16.101 -34.140  58.747  1.00126.03           O
ATOM     40  CB  ASN A   6      14.833 -35.863  60.828  1.00175.97           C
ATOM     41  CG  ASN A   6      13.358 -35.644  60.621  1.00155.29           C
ATOM     42  ND2 ASN A   6      12.960 -34.393  60.433  1.00151.32           N
ATOM     43  OD1 ASN A   6      12.379 -36.590  60.641  1.00140.62           O
ATOM     44  N   PHE A   7      15.112 -35.531  57.310  1.00167.15           N
ATOM     45  CA  PHE A   7      15.223 -34.553  56.249  1.00145.50           C
ATOM     46  C   PHE A   7      13.923 -33.802  56.073  1.00123.39           C
ATOM     47  O   PHE A   7      13.906 -32.671  55.587  1.00111.15           O
ATOM     48  CB  PHE A   7      15.601 -35.228  54.940  1.00105.72           C
ATOM     49  CG  PHE A   7      16.946 -35.904  54.958  1.00125.83           C
ATOM     50  CD1 PHE A   7      17.106 -37.139  55.563  1.00144.71           C
ATOM     51  CD2 PHE A   7      18.042 -35.318  54.333  1.00126.84           C
ATOM     52  CE1 PHE A   7      18.339 -37.761  55.566  1.00164.95           C
```

Fig. 7A

```
ATOM    57   C    THR A   8      11.523 -32.447  56.898  1.00131.14           C
ATOM    58   O    THR A   8      11.353 -31.407  56.364  1.00115.27           O
ATOM    59   CB   THR A   8      10.381 -34.700  56.752  1.00130.17           C
ATOM    60   CG2  THR A   8       9.022 -34.035  56.495  1.00111.76           C
ATOM    61   OG1  THR A   8      10.443 -35.961  56.070  1.00127.62           O
ATOM    62   N    ASP A   9      11.745 -32.472  58.313  1.00159.74           N
ATOM    63   CA   ASP A   9      11.566 -31.298  59.166  1.00167.59           C
ATOM    64   C    ASP A   9      12.665 -30.235  59.044  1.00167.58           C
ATOM    65   O    ASP A   9      12.632 -29.206  59.723  1.00170.06           O
ATOM    66   CB   ASP A   9      11.392 -31.690  60.639  1.00190.88           C
ATOM    67   CG   ASP A   9       9.965 -32.097  60.977  1.00191.85           C
ATOM    68   OD1  ASP A   9       9.025 -31.322  60.691  1.00173.93           O
ATOM    69   OD2  ASP A   9       9.790 -33.199  61.537  1.00209.17           O1-
ATOM    70   N    ASN A  10      13.639 -30.487  58.163  1.00150.00           N
ATOM    71   CA   ASN A  10      14.682 -29.503  57.940  1.00150.59           C
ATOM    72   C    ASN A  10      14.220 -28.493  56.898  1.00128.29           C
ATOM    73   O    ASN A  10      13.820 -28.874  55.798  1.00116.96           O
ATOM    74   CB   ASN A  10      15.968 -30.193  57.479  1.00131.11           C
ATOM    75   CG   ASN A  10      17.166 -29.255  57.451  1.00121.47           C
ATOM    76   ND2  ASN A  10      18.348 -29.800  57.735  1.00140.33           N
ATOM    77   OD1  ASN A  10      17.036 -28.060  57.176  1.00112.08           O
ATOM    78   N    ASN A  11      14.261 -27.211  57.251  1.00134.98           N
ATOM    79   CA   ASN A  11      13.895 -26.134  56.331  1.00116.35           C
ATOM    80   C    ASN A  11      14.927 -25.009  56.359  1.00121.41           C
ATOM    81   O    ASN A  11      14.581 -23.833  56.230  1.00118.69           O
ATOM    82   CB   ASN A  11      12.515 -25.561  56.678  1.00154.86           C
ATOM    83   CG   ASN A  11      11.390 -26.574  56.515  1.00148.83           C
ATOM    84   ND2  ASN A  11      11.147 -27.356  57.594  1.00157.70           N
ATOM    85   OD1  ASN A  11      10.740 -26.637  55.473  1.00133.86           O
ATOM    86   N    SER A  12      16.194 -25.381  56.519  1.00171.25           N
ATOM    87   CA   SER A  12      17.269 -24.413  56.722  1.00176.49           C
ATOM    88   C    SER A  12      17.771 -23.777  55.437  1.00164.72           C
ATOM    89   O    SER A  12      17.866 -24.353  54.355  1.00156.41           O
ATOM    90   CB   SER A  12      16.446 -25.070  57.443  1.00129.94           C
ATOM    91   OG   SER A  12      18.909 -26.204  56.732  1.00139.09           O
ATOM    92   N    ILE A  13      18.329 -22.581  55.579  1.00156.10           N
ATOM    93   CA   ILE A  13      18.995 -21.896  54.484  1.00148.80           C
ATOM    94   C    ILE A  13      19.909 -22.856  53.724  1.00153.85           C
ATOM    95   O    ILE A  13      19.701 -23.121  52.542  1.00143.98           O
ATOM    96   CB   ILE A  13      19.859 -20.743  55.024  1.00193.15           C
ATOM    97   CG1  ILE A  13      19.367 -20.321  56.422  1.00196.13           C
ATOM    98   CG2  ILE A  13      19.902 -19.589  54.015  1.00183.27           C
ATOM    99   CD1  ILE A  13      20.456 -19.781  57.352  1.00205.51           C
ATOM   100   N    LYS A  14      20.918 -23.376  54.429  1.00191.01           N
ATOM   101   CA   LYS A  14      21.957 -24.244  53.829  1.00199.59           C
ATOM   102   C    LYS A  14      21.293 -25.422  53.120  1.00197.24           C
ATOM   103   O    LYS A  14      21.626 -25.744  51.977  1.00190.06           O
ATOM   104   CB   LYS A  14      22.884 -24.745  54.927  1.00138.19           C
ATOM   105   CG   LYS A  14      24.172 -25.453  54.472  1.00152.16           C
ATOM   106   CD   LYS A  14      25.086 -25.775  55.683  1.00172.72           C
ATOM   107   CE   LYS A  14      25.536 -24.494  56.406  1.00175.90           C
ATOM   108   NZ   LYS A  14      26.201 -24.731  57.721  1.00194.19           N1+
ATOM   109   N    TYR A  15      20.359 -26.059  53.810  1.00146.16           N
ATOM   110   CA   TYR A  15      19.690 -27.225  53.274  1.00140.74           C
ATOM   111   C    TYR A  15      19.926 -26.874  52.013  1.00117.99           C
ATOM   112   O    TYR A  15      19.130 -27.470  50.953  1.00113.52           O
ATOM   113   CB   TYR A  15      18.723 -27.769  54.302  1.00130.34           C
ATOM   114   CG   TYR A  15      18.083 -29.072  53.919  1.00128.93           C
ATOM   115   CD1  TYR A  15      19.831 -30.230  53.807  1.00145.06           C
ATOM   116   CD2  TYR A  15      16.719 -29.152  53.699  1.00113.53           C
ATOM   117   CE1  TYR A  15      19.237 -31.425  53.477  1.00145.23           C
```

Fig. 7B

```
ATOM  118  CE2  TYR A  15      16.117 -30.344  53.370  1.00 110.67           C
ATOM  119  CZ   TYR A  15      16.877 -31.471  53.262  1.00 125.64           C
ATOM  120  OH   TYR A  15      16.261 -32.649  52.937  1.00 121.14           O
ATOM  121  N    THR A  16      18.033 -25.909  52.135  1.00 152.52           N
ATOM  122  CA   THR A  16      17.282 -25.438  50.968  1.00 132.69           C
ATOM  123  C    THR A  16      18.193 -25.141  49.790  1.00 129.79           C
ATOM  124  O    THR A  16      17.862 -25.503  48.668  1.00 119.87           O
ATOM  125  CB   THR A  16      16.415 -24.219  51.358  1.00 157.64           C
ATOM  126  CG2  THR A  16      16.241 -23.277  50.170  1.00  92.56           C
ATOM  127  OG1  THR A  16      15.128 -24.667  51.800  1.00 103.07           O
ATOM  128  N    CYS A  17      19.344 -24.513  50.021  1.00 113.88           N
ATOM  129  CA   CYS A  17      20.255 -24.169  48.917  1.00 113.11           C
ATOM  130  C    CYS A  17      21.049 -25.346  48.336  1.00 123.63           C
ATOM  131  O    CYS A  17      21.421 -25.335  47.157  1.00 120.40           O
ATOM  132  CB   CYS A  17      21.186 -23.021  49.303  1.00 139.19           C
ATOM  133  SG   CYS A  17      20.345 -21.433  49.296  1.00 124.92           S
ATOM  134  N    ILE A  18      21.310 -26.357  49.156  1.00 122.90           N
ATOM  135  CA   ILE A  18      21.928 -27.576  48.653  1.00 133.28           C
ATOM  136  C    ILE A  18      20.913 -28.348  47.821  1.00 119.15           C
ATOM  137  O    ILE A  18      21.260 -28.944  46.809  1.00 119.75           O
ATOM  138  CB   ILE A  18      22.487 -28.460  49.792  1.00 109.53           C
ATOM  139  CG1  ILE A  18      23.615 -27.866  50.306  1.00 126.45           C
ATOM  140  CG2  ILE A  18      22.673 -29.895  49.317  1.00 118.66           C
ATOM  141  CD1  ILE A  18      24.629 -28.853  51.139  1.00 150.53           C
ATOM  142  N    LEU A  19      19.652 -29.318  48.230  1.00 148.03           N
ATOM  143  CA   LEU A  19      18.606 -29.986  47.467  1.00 129.11           C
ATOM  144  C    LEU A  19      19.267 -29.238  46.160  1.00 126.45           C
ATOM  145  O    LEU A  19      17.947 -28.865  45.152  1.00 101.31           O
ATOM  146  CB   LEU A  19      17.348 -29.182  46.322  1.00 105.24           C
ATOM  147  CG   LEU A  19      17.487 -29.940  49.651  1.00 123.39           C
ATOM  148  CD1  LEU A  19      16.134 -30.461  50.159  1.00 114.28           C
ATOM  149  CD2  LEU A  19      18.478 -31.084  49.698  1.00 138.17           C
ATOM  150  N    ILE A  20      18.401 -26.907  46.189  1.00 107.76           N
ATOM  151  CA   ILE A  20      18.295 -26.072  44.960  1.00  94.55           C
ATOM  152  C    ILE A  20      19.453 -26.358  44.041  1.00 103.29           C
ATOM  153  O    ILE A  20      19.256 -26.459  42.823  1.00  93.68           O
ATOM  154  CB   ILE A  20      18.327 -24.569  45.326  1.00 103.49           C
ATOM  155  CG1  ILE A  20      16.920 -23.980  45.298  1.00  85.24           C
ATOM  156  CG2  ILE A  20      19.141 -23.815  44.297  1.00 105.23           C
ATOM  157  CD1  ILE A  20      16.507 -23.193  46.537  1.00  87.29           C
ATOM  158  N    LEU A  21      20.653 -26.491  44.606  1.00 107.43           N
ATOM  159  CA   LEU A  21      21.838 -26.940  43.836  1.00 119.61           C
ATOM  160  C    LEU A  21      21.705 -26.199  43.150  1.00 119.82           C
ATOM  161  O    LEU A  21      21.884 -26.304  41.946  1.00 116.20           O
ATOM  162  CB   LEU A  21      23.083 -26.820  44.716  1.00 125.51           C
ATOM  163  CG   LEU A  21      24.009 -25.641  44.422  1.00 125.69           C
ATOM  164  CD1  LEU A  21      25.027 -26.028  43.352  1.00 142.02           C
ATOM  165  CD2  LEU A  21      23.173 -24.414  44.018  1.00 107.91           C
ATOM  166  N    ILE A  22      21.400 -29.236  43.926  1.00 118.98           N
ATOM  167  CA   ILE A  22      21.213 -30.570  43.367  1.00 119.00           C
ATOM  168  C    ILE A  22      20.119 -30.568  42.323  1.00  97.42           C
ATOM  169  O    ILE A  22      20.292 -31.080  41.218  1.00  96.14           O
ATOM  170  CB   ILE A  22      20.816 -31.601  44.435  1.00  86.03           C
ATOM  171  CG1  ILE A  22      21.681 -31.448  45.691  1.00 108.85           C
ATOM  172  CG2  ILE A  22      20.899 -33.019  43.845  1.00  89.59           C
ATOM  173  CD1  ILE A  22      21.136 -32.151  46.930  1.00 116.13           C
ATOM  174  N    ALA A  23      18.958 -30.007  42.682  1.00 135.66           N
ATOM  175  CA   ALA A  23      17.823 -29.993  41.768  1.00 117.23           C
ATOM  176  C    ALA A  23      16.204 -29.357  40.451  1.00 112.47           C
ATOM  177  O    ALA A  23      17.999 -29.934  39.385  1.00 107.46           O
ATOM  178  CB   ALA A  23      16.698 -29.253  42.367  1.00  78.16           C
```

Fig. 7C

```
ATOM    179  N   PHE A  24      18.757 -28.157  40.528  1.00 89.85           N
ATOM    180  CA  PHE A  24      19.168 -27.431  39.340  1.00 87.29           C
ATOM    181  C   PHE A  24      20.217 -28.185  38.484  1.00 99.53           C
ATOM    182  O   PHE A  24      20.096 -28.296  37.247  1.00 94.79           O
ATOM    183  CB  PHE A  24      19.710 -26.076  39.755  1.00 95.16           C
ATOM    184  CG  PHE A  24      20.341 -25.334  38.643  1.00 96.71           C
ATOM    185  CD1 PHE A  24      19.610 -24.408  37.923  1.00 83.28           C
ATOM    186  CD2 PHE A  24      21.662 -25.578  38.291  1.00113.38           C
ATOM    187  CE1 PHE A  24      20.188 -23.721  36.876  1.00 86.19           C
ATOM    188  CE2 PHE A  24      22.256 -24.905  37.247  1.00116.41           C
ATOM    189  CZ  PHE A  24      21.525 -23.973  36.533  1.00102.74           C
ATOM    190  N   ALA A  25      21.254 -28.699  39.144  1.00116.39           N
ATOM    191  CA  ALA A  25      22.337 -29.410  38.462  1.00130.99           C
ATOM    192  C   ALA A  25      21.795 -30.621  37.732  1.00126.64           C
ATOM    193  O   ALA A  25      22.191 -30.902  36.615  1.00128.03           O
ATOM    194  CB  ALA A  25      23.408 -29.829  39.450  1.00 97.30           C
ATOM    195  N   PHE A  26      20.890 -31.329  38.391  1.00110.37           N
ATOM    196  CA  PHE A  26      20.174 -32.461  37.817  1.00105.44           C
ATOM    197  C   PHE A  26      19.327 -32.082  36.568  1.00 90.43           C
ATOM    198  O   PHE A  26      19.501 -32.637  35.481  1.00 94.07           O
ATOM    199  CB  PHE A  26      19.307 -33.055  38.916  1.00124.80           C
ATOM    200  CG  PHE A  26      18.209 -33.935  38.429  1.00112.90           C
ATOM    201  CD1 PHE A  26      16.818 -33.300  38.263  1.00121.16           C
ATOM    202  CD2 PHE A  26      16.963 -33.410  38.177  1.00 95.15           C
ATOM    203  CE1 PHE A  26      17.395 -36.141  37.826  1.00111.52           C
ATOM    204  CE2 PHE A  26      15.921 -34.236  37.752  1.00 86.26           C
ATOM    205  CZ  PHE A  26      16.146 -35.619  37.569  1.00 94.35           C
ATOM    206  N   SER A  27      18.410 -31.138  36.777  1.00118.28           N
ATOM    207  CA  SER A  27      17.685 -30.578  35.653  1.00106.58           C
ATOM    208  C   SER A  27      18.568 -30.127  34.497  1.00112.86           C
ATOM    209  O   SER A  27      18.130 -30.074  33.358  1.00108.83           O
ATOM    210  CB  SER A  27      16.793 -29.401  36.105  1.00 94.00           C
ATOM    211  OG  SER A  27      16.250 -28.694  34.997  1.00 85.91           O
ATOM    212  N   VAL A  28      19.820 -29.784  34.768  1.00 75.57           N
ATOM    213  CA  VAL A  28      20.696 -29.444  33.651  1.00 84.21           C
ATOM    214  C   VAL A  28      21.330 -30.674  33.002  1.00 97.30           C
ATOM    215  O   VAL A  28      21.375 -30.784  31.778  1.00100.53           O
ATOM    216  CB  VAL A  28      21.791 -28.445  34.036  1.00 98.26           C
ATOM    217  CG1 VAL A  28      22.749 -28.266  32.873  1.00110.56           C
ATOM    218  CG2 VAL A  28      21.172 -27.110  34.422  1.00 85.84           C
ATOM    219  N   LEU A  29      21.824 -31.593  33.825  1.00 98.58           N
ATOM    220  CA  LEU A  29      22.357 -32.856  33.335  1.00112.86           C
ATOM    221  C   LEU A  29      21.367 -33.516  32.418  1.00105.31           C
ATOM    222  O   LEU A  29      21.750 -34.644  31.396  1.00116.12           O
ATOM    223  CB  LEU A  29      22.681 -33.812  34.477  1.00108.68           C
ATOM    224  CG  LEU A  29      23.936 -33.480  35.285  1.00123.11           C
ATOM    225  CD1 LEU A  29      24.850 -34.699  35.341  1.00142.96           C
ATOM    226  CD2 LEU A  29      24.671 -32.243  34.736  1.00150.95           C
ATOM    227  N   CYS A  30      20.088 -33.490  32.766  1.00103.74           N
ATOM    228  CA  CYS A  30      19.106 -34.129  31.889  1.00 97.60           C
ATOM    229  C   CYS A  30      18.889 -33.478  30.539  1.00 94.56           C
ATOM    230  O   CYS A  30      18.729 -34.195  29.510  1.00 99.95           O
ATOM    231  CB  CYS A  30      17.787 -34.282  32.613  1.00100.72           C
ATOM    232  SG  CYS A  30      18.047 -35.112  34.141  1.00104.62           S
ATOM    233  N   ARG A  31      18.873 -32.141  30.447  1.00 99.66           N
ATOM    234  CA  ARG A  31      18.535 -31.449  29.181  1.00 97.69           C
ATOM    235  C   ARG A  31      19.745 -31.842  28.256  1.00114.40           C
ATOM    236  O   ARG A  31      19.645 -31.699  27.045  1.00117.51           O
ATOM    237  CB  ARG A  31      18.685 -29.909  29.329  1.00141.52           C
ATOM    238  CG  ARG A  31      17.954 -29.308  30.509  1.00128.69           C
ATOM    239  CD  ARG A  31      16.559 -28.944  30.160  1.00115.64           C
```

Fig. 7D

```
ATOM   240  NB   ARG A  31      15.679 -29.029  31.314  1.00 104.68           N
ATOM   241  CZ   ARG A  31      14.369 -28.801  31.316  1.00  93.41           C
ATOM   242  NH1  ARG A  31      13.772 -28.366  30.220  1.00  91.76           N1+
ATOM   243  NH2  ARG A  31      13.653 -28.999  32.413  1.00  85.06           N
ATOM   244  N    LEU A  32      20.791 -32.382  28.869  1.00  79.10           N
ATOM   245  CA   LEU A  32      22.130 -32.470  28.292  1.00  98.19           C
ATOM   246  C    LEU A  32      22.532 -33.857  27.746  1.00 113.21           C
ATOM   247  O    LEU A  32      23.684 -34.052  27.297  1.00 130.74           O
ATOM   248  CB   LEU A  32      23.120 -32.007  29.355  1.00  71.50           C
ATOM   249  CG   LEU A  32      24.532 -31.685  28.938  1.00  87.78           C
ATOM   250  CD1  LEU A  32      24.869 -30.255  29.310  1.00  78.80           C
ATOM   251  CD2  LEU A  32      25.457 -32.692  29.610  1.00 105.30           C
ATOM   252  N    TYR A  33      21.611 -34.813  27.783  1.00  94.67           N
ATOM   253  CA   TYR A  33      21.819 -36.102  27.142  1.00 107.78           C
ATOM   254  C    TYR A  33      21.684 -35.953  25.636  1.00 113.50           C
ATOM   255  O    TYR A  33      22.488 -36.486  24.866  1.00 131.43           O
ATOM   256  CB   TYR A  33      20.807 -37.114  27.675  1.00  96.46           C
ATOM   257  CG   TYR A  33      20.556 -38.307  26.783  1.00 106.39           C
ATOM   258  CD1  TYR A  33      20.573 -39.596  27.293  1.00 114.87           C
ATOM   259  CD2  TYR A  33      20.237 -38.146  25.450  1.00 108.56           C
ATOM   260  CE1  TYR A  33      30.326 -40.688  26.484  1.00 124.88           C
ATOM   261  CE2  TYR A  33      19.989 -39.226  24.640  1.00 119.18           C
ATOM   262  CZ   TYR A  33      20.030 -40.492  25.157  1.00 126.98           C
ATOM   263  OH   TYR A  33      19.774 -41.557  24.333  1.00 138.45           O
ATOM   264  N    TRP A  34      20.653 -35.233  25.214  1.00  96.57           N
ATOM   265  CA   TRP A  34      20.413 -35.034  23.801  1.00 102.60           C
ATOM   266  C    TRP A  34      21.646 -34.488  23.113  1.00 114.93           C
ATOM   267  O    TRP A  34      21.834 -34.708  21.919  1.00 116.67           O
ATOM   268  CB   TRP A  34      19.228 -34.111  23.571  1.00 104.99           C
ATOM   269  CG   TRP A  34      16.932 -33.897  22.127  1.00 110.43           C
ATOM   270  CD1  TRP A  34      18.141 -34.663  21.336  1.00 115.39           C
ATOM   271  CD2  TRP A  34      19.431 -32.846  21.297  1.00 104.59           C
ATOM   272  CE2  TRP A  34      18.694 -33.038  20.014  1.00 106.42           C
ATOM   273  CE3  TRP A  34      20.279 -31.756  21.514  1.00  96.96           C
ATOM   274  NE1  TRP A  34      18.114 -34.160  20.061  1.00 115.53           N
ATOM   275  CZ2  TRP A  34      19.175 -32.185  18.955  1.00 101.26           C
ATOM   276  CZ3  TRP A  34      20.553 -30.996  20.460  1.00  91.69           C
ATOM   277  CH2  TRP A  34      20.005 -31.126  19.199  1.00  93.98           C
ATOM   278  N    VAL A  35      22.494 -33.786  23.860  1.00 109.17           N
ATOM   279  CA   VAL A  35      23.788 -33.334  23.524  1.00 101.72           C
ATOM   280  C    VAL A  35      24.774 -34.494  23.278  1.00 121.05           C
ATOM   281  O    VAL A  35      25.525 -34.654  22.320  1.00 126.48           O
ATOM   282  CB   VAL A  35      24.401 -32.163  24.127  1.00 113.15           C
ATOM   283  CG1  VAL A  35      25.759 -31.790  23.564  1.00 117.09           C
ATOM   284  CG2  VAL A  35      23.478 -30.962  24.092  1.00  96.30           C
ATOM   285  N    ALA A  36      24.757 -35.311  24.320  1.00  95.22           N
ATOM   286  CA   ALA A  36      25.538 -36.524  24.320  1.00 116.33           C
ATOM   287  C    ALA A  36      25.166 -37.385  23.119  1.00 122.93           C
ATOM   288  O    ALA A  36      25.899 -38.310  22.767  1.00 138.75           O
ATOM   289  CB   ALA A  36      25.326 -37.294  25.617  1.00 135.97           C
ATOM   290  N    TRP A  37      24.030 -37.101  22.485  1.00 101.54           N
ATOM   291  CA   TRP A  37      23.548 -37.980  21.410  1.00 106.65           C
ATOM   292  C    TRP A  37      23.619 -37.401  20.013  1.00 103.42           C
ATOM   293  O    TRP A  37      23.867 -38.121  19.052  1.00 116.86           O
ATOM   294  CB   TRP A  37      22.121 -38.429  21.688  1.00 116.74           C
ATOM   295  CG   TRP A  37      21.449 -39.079  20.535  1.00 116.40           C
ATOM   296  CD1  TRP A  37      21.471 -40.390  20.223  1.00 130.92           C
ATOM   297  CD2  TRP A  37      20.626 -38.444  19.556  1.00 108.04           C
ATOM   298  CE2  TRP A  37      20.191 -39.435  18.677  1.00 119.98           C
ATOM   299  CE3  TRP A  37      20.214 -37.128  19.342  1.00  92.06           C
ATOM   300  NE1  TRP A  37      20.722 -40.619  19.107  1.00 133.08           N
```

Fig. 7E

| | | | | | | | | | |
|---|---|---|---|---|---|---|---|---|---|
| ATOM | 301 | CZ2 | TRP | A | 37 | 19.373 | -39.160 | 17.598 | 1.00 116.95 | C |
| ATOM | 302 | CZ3 | TRP | A | 37 | 19.397 | -36.858 | 18.272 | 1.00 88.96 | C |
| ATOM | 303 | CH2 | TRP | A | 37 | 18.991 | -37.869 | 17.411 | 1.00 101.57 | C |
| ATOM | 304 | N | ALA | A | 38 | 23.392 | -36.100 | 19.904 | 1.00 138.62 | N |
| ATOM | 305 | CA | ALA | A | 38 | 23.299 | -35.458 | 18.601 | 1.00 131.90 | C |
| ATOM | 306 | C | ALA | A | 38 | 24.631 | -34.954 | 18.063 | 1.00 138.38 | C |
| ATOM | 307 | O | ALA | A | 38 | 24.677 | -34.317 | 17.011 | 1.00 138.68 | O |
| ATOM | 308 | CB | ALA | A | 38 | 22.337 | -34.325 | 18.666 | 1.00 81.33 | C |
| ATOM | 309 | N | SER | A | 39 | 25.711 | -35.236 | 18.779 | 1.00 112.74 | N |
| ATOM | 310 | CA | SER | A | 39 | 27.031 | -34.784 | 18.395 | 1.00 117.03 | C |
| ATOM | 311 | C | SER | A | 39 | 27.724 | -35.780 | 17.523 | 1.00 136.24 | C |
| ATOM | 312 | O | SER | A | 39 | 28.566 | -35.435 | 16.696 | 1.00 140.86 | O |
| ATOM | 313 | CB | SER | A | 39 | 27.873 | -34.485 | 19.635 | 1.00 105.46 | C |
| ATOM | 314 | OG | SER | A | 39 | 27.075 | -33.990 | 20.693 | 1.00 103.07 | O |
| ATOM | 315 | N | GLU | A | 40 | 27.363 | -37.046 | 17.717 | 1.00 121.82 | N |
| ATOM | 316 | CA | GLU | A | 40 | 27.928 | -38.135 | 16.853 | 1.00 142.31 | C |
| ATOM | 317 | C | GLU | A | 40 | 27.226 | -39.217 | 15.589 | 1.00 143.84 | C |
| ATOM | 318 | O | GLU | A | 40 | 27.333 | -39.212 | 14.878 | 1.00 160.58 | O |
| ATOM | 319 | CB | GLU | A | 40 | 27.823 | -38.465 | 17.685 | 1.00 121.80 | C |
| ATOM | 320 | CG | GLU | A | 40 | 28.522 | -39.458 | 19.036 | 1.00 175.09 | C |
| ATOM | 321 | CD | GLU | A | 40 | 29.031 | -40.824 | 19.445 | 1.00 203.70 | C |
| ATOM | 322 | OE1 | GLU | A | 40 | 28.943 | -41.765 | 18.629 | 1.00 220.26 | O |
| ATOM | 323 | OE2 | GLU | A | 40 | 29.525 | -40.956 | 20.884 | 1.00 208.37 | O1- |
| ATOM | 324 | N | PHE | A | 41 | 26.587 | -37.155 | 15.050 | 1.00 116.27 | N |
| ATOM | 325 | CA | PHE | A | 41 | 25.789 | -37.069 | 13.988 | 1.00 117.86 | C |
| ATOM | 326 | C | PHE | A | 41 | 26.171 | -35.803 | 13.268 | 1.00 110.08 | C |
| ATOM | 327 | O | PHE | A | 41 | 25.996 | -34.704 | 13.775 | 1.00 110.49 | O |
| ATOM | 328 | CB | PHE | A | 41 | 24.293 | -37.097 | 14.230 | 1.00 126.36 | C |
| ATOM | 329 | CG | PHE | A | 41 | 23.784 | -38.440 | 14.576 | 1.00 138.85 | C |
| ATOM | 330 | CD1 | PHE | A | 41 | 22.842 | -38.597 | 15.556 | 1.00 135.31 | C |
| ATOM | 331 | CD2 | PHE | A | 41 | 24.261 | -39.553 | 13.919 | 1.00 156.07 | C |
| ATOM | 332 | CE1 | PHE | A | 41 | 22.383 | -39.835 | 15.877 | 1.00 148.62 | C |
| ATOM | 333 | CE2 | PHE | A | 41 | 23.804 | -40.797 | 14.232 | 1.00 169.71 | C |
| ATOM | 334 | CZ | PHE | A | 41 | 22.862 | -40.942 | 15.211 | 1.00 166.06 | C |
| ATOM | 335 | N | TYR | A | 42 | 26.698 | -35.952 | 12.069 | 1.00 139.14 | N |
| ATOM | 336 | CA | TYR | A | 42 | 27.324 | -34.812 | 11.447 | 1.00 132.97 | C |
| ATOM | 337 | C | TYR | A | 42 | 26.322 | -33.818 | 10.901 | 1.00 119.69 | C |
| ATOM | 338 | O | TYR | A | 42 | 26.616 | -32.630 | 10.810 | 1.00 116.85 | O |
| ATOM | 339 | CB | TYR | A | 42 | 28.301 | -35.233 | 10.355 | 1.00 302.42 | C |
| ATOM | 340 | CG | TYR | A | 42 | 29.143 | -34.065 | 9.988 | 1.00 300.25 | C |
| ATOM | 341 | CD1 | TYR | A | 42 | 30.313 | -33.781 | 10.651 | 1.00 294.21 | C |
| ATOM | 342 | CD2 | TYR | A | 42 | 28.731 | -33.198 | 8.974 | 1.00 305.94 | C |
| ATOM | 343 | CE1 | TYR | A | 42 | 31.072 | -32.697 | 10.329 | 1.00 293.91 | C |
| ATOM | 344 | CE2 | TYR | A | 42 | 29.479 | -32.098 | 8.645 | 1.00 306.12 | C |
| ATOM | 345 | CZ | TYR | A | 42 | 30.651 | -31.847 | 9.325 | 1.00 300.12 | C |
| ATOM | 346 | OH | TYR | A | 42 | 31.410 | -30.751 | 9.003 | 1.00 301.77 | O |
| ATOM | 347 | N | GLU | A | 43 | 25.144 | -34.317 | 10.541 | 1.00 153.18 | N |
| ATOM | 348 | CA | GLU | A | 43 | 24.121 | -33.526 | 9.871 | 1.00 140.73 | C |
| ATOM | 349 | C | GLU | A | 43 | 23.587 | -32.450 | 10.782 | 1.00 128.54 | C |
| ATOM | 350 | O | GLU | A | 43 | 22.748 | -31.809 | 10.328 | 1.00 116.29 | O |
| ATOM | 351 | CB | GLU | A | 43 | 23.026 | -34.459 | 9.372 | 1.00 152.32 | C |
| ATOM | 352 | CG | GLU | A | 43 | 23.554 | -35.839 | 8.973 | 1.00 165.24 | C |
| ATOM | 353 | CD | GLU | A | 43 | 22.471 | -36.759 | 8.445 | 1.00 170.43 | C |
| ATOM | 354 | OE1 | GLU | A | 43 | 21.299 | -36.641 | 8.878 | 1.00 167.81 | O |
| ATOM | 355 | OE2 | GLU | A | 43 | 22.798 | -37.599 | 7.589 | 1.00 177.54 | O1- |
| ATOM | 356 | N | PHE | A | 44 | 23.921 | -32.464 | 12.060 | 1.00 121.10 | N |
| ATOM | 357 | CA | PHE | A | 44 | 23.377 | -31.631 | 13.127 | 1.00 112.73 | C |
| ATOM | 358 | C | PHE | A | 44 | 24.288 | -30.481 | 13.512 | 1.00 108.09 | C |
| ATOM | 359 | O | PHE | A | 44 | 24.032 | -29.621 | 14.511 | 1.00 105.64 | O |
| ATOM | 360 | CB | PHE | A | 44 | 23.179 | -32.448 | 14.403 | 1.00 88.81 | C |
| ATOM | 361 | CG | PHE | A | 44 | 23.017 | -33.372 | 14.360 | 1.00 93.22 | C |

Fig. 7F

```
ATOM   362  CD1 PHE A  44      21.968 -34.475  15.186  1.00106.67           C
ATOM   363  CD2 PHE A  44      20.968 -33.134  13.510  1.00 85.49           C
ATOM   364  CE1 PHE A  44      20.893 -35.323  15.161  1.00112.56           C
ATOM   365  CE2 PHE A  44      19.901 -33.980  13.479  1.00 90.70           C
ATOM   366  CZ  PHE A  44      19.861 -35.073  14.311  1.00104.34           C
ATOM   367  N   PHE A  45      25.359 -30.266  12.761  1.00112.62           N
ATOM   368  CA  PHE A  45      26.336 -29.243  13.118  1.00109.00           C
ATOM   369  C   PHE A  45      25.467 -28.139  12.085  1.00105.62           C
ATOM   370  O   PHE A  45      25.350 -28.376  10.884  1.00105.29           O
ATOM   371  CB  PHE A  45      27.717 -29.857  13.319  1.00 95.12           C
ATOM   372  CG  PHE A  45      27.645 -30.681  14.554  1.00100.57           C
ATOM   373  CD1 PHE A  45      27.682 -32.056  14.506  1.00115.50           C
ATOM   374  CD2 PHE A  45      28.144 -30.090  15.768  1.00 92.81           C
ATOM   375  CE1 PHE A  45      27.804 -32.831  15.642  1.00122.83           C
ATOM   376  CE2 PHE A  45      28.253 -30.861  16.911  1.00 99.79           C
ATOM   377  CZ  PHE A  45      28.086 -32.235  16.847  1.00114.95           C
ATOM   378  N   PHE A  46      26.738 -26.935  12.573  1.00155.08           N
ATOM   379  CA  PHE A  46      27.120 -25.820  11.729  1.00155.68           C
ATOM   380  C   PHE A  46      28.044 -24.967  12.560  1.00156.35           C
ATOM   381  O   PHE A  46      27.943 -24.994  13.781  1.00149.86           O
ATOM   382  CB  PHE A  46      25.910 -25.009  11.354  1.00114.24           C
ATOM   383  CG  PHE A  46      26.159 -24.038  10.255  1.00113.67           C
ATOM   384  CD1 PHE A  46      26.004 -24.419   8.934  1.00112.74           C
ATOM   385  CD2 PHE A  46      26.535 -22.736  10.534  1.00116.06           C
ATOM   386  CE1 PHE A  46      26.222 -23.521   7.904  1.00114.30           C
ATOM   387  CE2 PHE A  46      26.750 -21.836   9.512  1.00117.68           C
ATOM   388  CZ  PHE A  46      26.593 -22.231   8.191  1.00116.88           C
ATOM   389  N   ASN A  47      28.917 -24.202  11.908  1.00101.63           N
ATOM   390  CA  ASN A  47      30.007 -23.494  12.593  1.00106.68           C
ATOM   391  C   ASN A  47      30.564 -24.201  13.831  1.00103.22           C
ATOM   392  O   ASN A  47      30.532 -23.621  14.922  1.00105.43           O
ATOM   393  CB  ASN A  47      29.630 -22.036  12.935  1.00126.66           C
ATOM   394  CG  ASN A  47      29.732 -21.109  11.744  1.00128.63           C
ATOM   395  ND2 ASN A  47      29.088 -19.954  11.837  1.00131.15           N
ATOM   396  OD1 ASN A  47      30.389 -21.424  10.752  1.00139.26           O
ATOM   397  N   ASP A  48      30.943 -25.466  13.643  1.00175.68           N
ATOM   398  CA  ASP A  48      31.617 -26.275  14.665  1.00174.71           C
ATOM   399  C   ASP A  48      30.862 -26.409  15.985  1.00165.11           C
ATOM   400  O   ASP A  48      31.489 -26.431  17.066  1.00166.52           O
ATOM   401  CB  ASP A  48      33.036 -25.750  14.891  1.00202.09           C
ATOM   402  CG  ASP A  48      33.733 -25.389  13.587  1.00208.42           C
ATOM   403  OD1 ASP A  48      33.428 -26.018  12.552  1.00216.81           O
ATOM   404  OD2 ASP A  48      34.579 -24.471  13.593  1.00206.30           O1-
ATOM   405  N   GLN A  49      29.533 -26.516  15.903  1.00141.63           N
ATOM   406  CA  GLN A  49      28.646 -26.648  17.064  1.00132.16           C
ATOM   407  C   GLN A  49      27.927 -27.943  16.659  1.00128.75           C
ATOM   408  O   GLN A  49      26.745 -26.642  15.602  1.00129.29           O
ATOM   409  CB  GLN A  49      28.605 -25.351  17.881  1.00129.66           C
ATOM   410  CG  GLN A  49      27.611 -25.365  19.036  1.00122.04           C
ATOM   411  CD  GLN A  49      27.747 -26.590  19.936  1.00129.64           C
ATOM   412  NE2 GLN A  49      26.771 -26.794  20.602  1.00129.14           N
ATOM   413  OE1 GLN A  49      28.713 -27.339  19.850  1.00137.12           O
ATOM   414  N   LEU A  50      26.566 -27.828  17.505  1.00126.82           N
ATOM   415  CA  LEU A  50      25.169 -28.230  17.253  1.00122.81           C
ATOM   416  C   LEU A  50      24.334 -27.017  16.927  1.00111.81           C
ATOM   417  O   LEU A  50      24.649 -25.912  17.358  1.00106.89           O
ATOM   418  CB  LEU A  50      24.627 -28.933  18.474  1.00 83.26           C
ATOM   419  CG  LEU A  50      24.998 -30.402  18.599  1.00 96.89           C
ATOM   420  CD1 LEU A  50      24.455 -30.971  19.889  1.00 97.06           C
ATOM   421  CD2 LEU A  50      24.443 -31.188  17.419  1.00104.07           C
ATOM   422  N   MET A  51      23.264 -27.200  16.165  1.00102.42           N
```

Fig. 7G

```
ATOM  423  CA   MET A  51      22.363 -26.033  15.838  1.00114.07           C
ATOM  424  C    MET A  51      21.060 -26.135  16.615  1.00105.80           C
ATOM  425  O    MET A  51      20.753 -27.155  17.230  1.00107.72           O
ATOM  426  CB   MET A  51      22.153 -25.901  14.314  1.00 73.95           C
ATOM  427  CG   MET A  51      22.565 -27.082  13.416  1.00 87.79           C
ATOM  428  SD   MET A  51      22.036 -27.105  11.656  1.00 96.79           S
ATOM  429  CE   MET A  51      22.650 -25.557  11.028  1.00 91.19           C
ATOM  430  N    ILE A  52      20.324 -25.015  16.585  1.00 93.52           N
ATOM  431  CA   ILE A  52      18.999 -24.781  17.201  1.00 85.92           C
ATOM  432  C    ILE A  52      17.899 -25.842  16.923  1.00 88.58           C
ATOM  433  O    ILE A  52      17.932 -26.551  15.926  1.00 96.24           O
ATOM  434  CB   ILE A  52      18.494 -23.403  16.727  1.00110.23           C
ATOM  435  CG1  ILE A  52      18.855 -22.315  17.710  1.00109.11           C
ATOM  436  CG2  ILE A  52      17.012 -23.355  16.578  1.00103.91           C
ATOM  437  CD1  ILE A  52      18.214 -21.010  17.307  1.00106.71           C
ATOM  438  N    THR A  53      16.900 -25.940  17.787  1.00 98.48           N
ATOM  439  CA   THR A  53      15.912 -26.987  17.624  1.00101.54           C
ATOM  440  C    THR A  53      14.674 -26.504  17.413  1.00 96.51           C
ATOM  441  O    THR A  53      13.545 -27.266  17.471  1.00 98.25           O
ATOM  442  CB   THR A  53      15.974 -27.925  18.813  1.00 80.27           C
ATOM  443  CG2  THR A  53      14.911 -28.980  18.735  1.00 84.64           C
ATOM  444  OG1  THR A  53      17.235 -28.592  18.794  1.00 87.48           O
ATOM  445  N    THR A  54      14.257 -25.223  17.170  1.00 93.89           N
ATOM  446  CA   THR A  54      12.905 -24.787  16.834  1.00 96.71           C
ATOM  447  C    THR A  54      12.968 -23.629  15.892  1.00 97.73           C
ATOM  448  O    THR A  54      13.678 -22.681  16.146  1.00 96.60           O
ATOM  449  CB   THR A  54      12.091 -24.318  18.045  1.00121.81           C
ATOM  450  CG2  THR A  54      10.775 -23.734  17.570  1.00119.64           C
ATOM  451  OG1  THR A  54      11.803 -25.430  18.889  1.00122.60           O
ATOM  452  N    ASN A  55      12.182 -23.697  14.822  1.00 98.54           N
ATOM  453  CA   ASN A  55      12.148 -22.643  13.828  1.00102.33           C
ATOM  454  C    ASN A  55      12.119 -21.258  14.494  1.00 97.61           C
ATOM  455  O    ASN A  55      12.984 -20.400  14.265  1.00101.28           O
ATOM  456  CB   ASN A  55      10.941 -22.888  12.894  1.00 81.50           C
ATOM  457  CG   ASN A  55      10.827 -24.377  12.438  1.00 86.23           C
ATOM  458  ND2  ASN A  55      10.616 -24.597  11.137  1.00 95.75           N
ATOM  459  OD1  ASN A  55      10.947 -25.299  13.246  1.00 86.29           O
ATOM  460  N    ASP A  56      11.126 -21.076  15.362  1.00121.13           N
ATOM  461  CA   ASP A  56      10.965 -19.867  16.207  1.00117.88           C
ATOM  462  C    ASP A  56      12.297 -19.259  16.601  1.00117.07           C
ATOM  463  O    ASP A  56      12.484 -18.066  16.418  1.00118.42           O
ATOM  464  CB   ASP A  56      10.151 -20.220  17.474  1.00136.91           C
ATOM  465  CG   ASP A  56       8.699 -19.723  17.396  1.00138.43           C
ATOM  466  OD1  ASP A  56       8.221 -19.437  16.265  1.00144.15           O
ATOM  467  OD2  ASP A  56       8.029 -19.621  18.457  1.00135.05           O1-
ATOM  468  N    GLY A  57      13.297 -20.064  17.149  1.00 70.21           N
ATOM  469  CA   GLY A  57      14.638 -19.626  17.554  1.00 70.81           C
ATOM  470  C    GLY A  57      15.399 -18.725  16.606  1.00 75.99           C
ATOM  471  O    GLY A  57      15.845 -17.727  17.039  1.00 75.97           O
ATOM  472  N    TYR A  58      15.328 -19.052  15.319  1.00 85.13           N
ATOM  473  CA   TYR A  58      16.133 -18.231  14.403  1.00 92.16           C
ATOM  474  C    TYR A  58      15.608 -16.814  14.322  1.00 92.98           C
ATOM  475  O    TYR A  58      16.300 -15.908  13.889  1.00 98.40           O
ATOM  476  CB   TYR A  58      16.208 -18.882  13.012  1.00101.12           C
ATOM  477  CG   TYR A  58      16.982 -20.141  12.969  1.00102.31           C
ATOM  478  CD1  TYR A  58      16.444 -21.300  13.476  1.00 98.50           C
ATOM  479  CD2  TYR A  58      18.236 -20.208  12.398  1.00108.80           C
ATOM  480  CE1  TYR A  58      17.123 -22.473  13.435  1.00101.81           C
ATOM  481  CE2  TYR A  58      18.926 -21.401  12.359  1.00111.61           C
ATOM  482  CZ   TYR A  58      18.357 -22.528  12.876  1.00108.49           C
ATOM  483  OH   TYR A  58      19.015 -23.734  12.838  1.00113.67           O
```

Fig. 7H

```
ATOM    484  N   ALA A  59      14.376 -16.633  14.755  1.00 97.50           N
ATOM    485  CA  ALA A  59      13.774 -15.321  14.851  1.00 99.70           C
ATOM    486  C   ALA A  59      14.632 -14.442  15.737  1.00 99.26           C
ATOM    487  O   ALA A  59      15.018 -13.336  15.349  1.00105.85           O
ATOM    488  CB  ALA A  59      12.376 -15.461  15.461  1.00 74.47           C
ATOM    489  N   PHE A  60      14.940 -14.975  16.923  1.00102.55           N
ATOM    490  CA  PHE A  60      15.732 -14.286  17.938  1.00102.12           C
ATOM    491  C   PHE A  60      17.197 -14.298  17.567  1.00105.60           C
ATOM    492  O   PHE A  60      17.818 -13.238  17.479  1.00109.68           O
ATOM    493  CB  PHE A  60      15.558 -14.968  19.276  1.00 92.68           C
ATOM    494  CG  PHE A  60      14.131 -15.073  19.710  1.00 89.24           C
ATOM    495  CD1 PHE A  60      13.565 -16.301  19.976  1.00 85.26           C
ATOM    496  CD2 PHE A  60      13.352 -13.939  19.853  1.00 91.51           C
ATOM    497  CE1 PHE A  60      12.259 -16.391  20.376  1.00 82.47           C
ATOM    498  CE2 PHE A  60      12.040 -14.029  20.249  1.00 89.42           C
ATOM    499  CZ  PHE A  60      11.495 -15.252  20.511  1.00 84.23           C
ATOM    500  N   ALA A  61      17.742 -15.493  17.365  1.00 93.88           N
ATOM    501  CA  ALA A  61      19.074 -15.661  16.806  1.00 98.37           C
ATOM    502  C   ALA A  61      19.339 -14.528  15.831  1.00106.23           C
ATOM    503  O   ALA A  61      20.345 -13.577  16.169  1.00110.50           O
ATOM    504  CB  ALA A  61      19.175 -16.997  16.124  1.00 45.68           C
ATOM    505  N   GLU A  62      18.729 -14.593  14.653  1.00 93.49           N
ATOM    506  CA  GLU A  62      18.775 -13.489  13.711  1.00102.17           C
ATOM    507  C   GLU A  62      18.842 -12.170  14.410  1.00104.12           C
ATOM    508  O   GLU A  62      19.898 -11.556  14.472  1.00109.96           O
ATOM    509  CB  GLU A  62      17.596 -13.465  12.810  1.00111.48           C
ATOM    510  CG  GLU A  62      17.554 -12.196  11.975  1.00121.81           C
ATOM    511  CD  GLU A  62      16.278 -12.008  11.183  1.00126.92           C
ATOM    512  OE1 GLU A  62      15.384 -12.131  11.793  1.00121.24           O
ATOM    513  OE2 GLU A  62      16.277 -11.697   9.969  1.00137.69           O1-
ATOM    514  N   GLY A  63      17.719 -11.756  14.988  1.00121.03           N
ATOM    515  CA  GLY A  63      17.657 -10.512  15.736  1.00124.88           C
ATOM    516  C   GLY A  63      18.918 -10.234  16.516  1.00124.71           C
ATOM    517  O   GLY A  63      19.580  -9.239  16.230  1.00132.75           O
ATOM    518  N   ALA A  64      19.267 -11.104  17.464  1.00 80.31           N
ATOM    519  CA  ALA A  64      20.474 -10.958  18.302  1.00 80.31           C
ATOM    520  C   ALA A  64      21.719 -10.744  17.473  1.00 87.47           C
ATOM    521  O   ALA A  64      22.465  -9.809  17.745  1.00 93.06           O
ATOM    522  CB  ALA A  64      20.644 -12.147  19.228  1.00 66.17           C
ATOM    523  N   ARG A  65      21.969 -11.825  16.504  1.00 90.84           N
ATOM    524  CA  ARG A  65      23.067 -11.411  15.583  1.00 99.02           C
ATOM    525  C   ARG A  65      23.053  -9.973  15.103  1.00109.17           C
ATOM    526  O   ARG A  65      24.034  -9.268  15.287  1.00117.11           O
ATOM    527  CB  ARG A  65      22.961 -12.384  14.420  1.00110.09           C
ATOM    528  CG  ARG A  65      24.013 -12.179  13.372  1.00118.61           C
ATOM    529  CD  ARG A  65      23.540 -12.699  12.033  1.00121.07           C
ATOM    530  NE  ARG A  65      22.326 -12.003  11.631  1.00123.41           N
ATOM    531  CZ  ARG A  65      21.478 -12.462  10.726  1.00127.90           C
ATOM    532  NH1 ARG A  65      21.715 -13.624  10.140  1.00130.53           N1+
ATOM    533  NH2 ARG A  65      20.396 -11.764  10.409  1.00131.35           N
ATOM    534  N   ASP A  66      21.927  -9.512  14.555  1.00128.63           N
ATOM    535  CA  ASP A  66      21.818  -8.117  14.126  1.00139.72           C
ATOM    536  C   ASP A  66      22.124  -7.124  15.247  1.00142.34           C
ATOM    537  O   ASP A  66      22.884  -6.189  15.036  1.00152.81           O
ATOM    538  CB  ASP A  66      20.434  -7.861  13.529  1.00157.12           C
ATOM    539  CG  ASP A  66      20.267  -8.499  12.150  1.00160.88           C
ATOM    540  OD1 ASP A  66      21.236  -8.763  11.496  1.00164.50           O
ATOM    541  OD2 ASP A  66      19.120  -8.728  11.795  1.00161.04           O1-
ATOM    542  N   MET A  67      21.601  -7.362  16.452  1.00110.94           N
ATOM    543  CA  MET A  67      21.851  -6.542  17.627  1.00113.19           C
ATOM    544  C   MET A  67      23.452  -6.493  17.887  1.00116.80           C
```

Fig. 7I

```
ATOM  545  O    MET A  67      24.002   -5.458   18.271  1.00 125.68           O
ATOM  546  CB   MET A  67      21.247   -7.377   18.886  1.00 121.90           C
ATOM  547  CG   MET A  67      19.743   -6.987   18.937  1.00 120.69           C
ATOM  548  SD   MET A  67      19.226   -6.815   20.652  1.00 113.92           S
ATOM  549  CE   MET A  67      20.722   -6.152   21.358  1.00 116.59           C
ATOM  550  N    ILE A  68      24.108   -7.631   17.679  1.00 104.27           N
ATOM  551  CA   ILE A  68      25.552   -7.714   17.816  1.00 108.81           C
ATOM  552  C    ILE A  68      26.241   -6.876   16.751  1.00 121.14           C
ATOM  553  O    ILE A  68      27.264   -6.262   17.031  1.00 129.10           O
ATOM  554  CB   ILE A  68      25.968   -9.186   17.714  1.00 102.93           C
ATOM  555  CG1  ILE A  68      25.552   -9.955   18.972  1.00  92.83           C
ATOM  556  CG2  ILE A  68      27.471   -9.272   17.525  1.00 109.40           C
ATOM  557  CD1  ILE A  68      25.391  -11.459   18.770  1.00  85.56           C
ATOM  558  N    ALA A  69      25.653   -6.848   15.539  1.00 112.95           N
ATOM  559  CA   ALA A  69      26.218   -6.023   14.452  1.00 125.66           C
ATOM  560  C    ALA A  69      26.124   -4.558   14.855  1.00 133.87           C
ATOM  561  O    ALA A  69      27.125   -3.848   14.885  1.00 144.88           O
ATOM  562  CB   ALA A  69      25.469   -6.241   13.147  1.00 167.62           C
ATOM  563  N    GLY A  70      24.916   -4.101   15.164  1.00 148.45           N
ATOM  564  CA   GLY A  70      24.693   -2.684   15.343  1.00 158.42           C
ATOM  565  C    GLY A  70      23.367   -2.395   14.740  1.00 166.40           C
ATOM  566  O    GLY A  70      22.631   -1.527   15.348  1.00 175.08           O
ATOM  567  N    PHE A  71      23.034   -2.807   13.562  1.00 153.66           N
ATOM  568  CA   PHE A  71      21.701   -2.593   13.083  1.00 160.75           C
ATOM  569  C    PHE A  71      21.079   -3.604   12.201  1.00 151.37           C
ATOM  570  O    PHE A  71      21.802   -4.435   11.665  1.00 139.97           O
ATOM  571  CB   PHE A  71      21.690   -1.111   12.433  1.00 192.32           C
ATOM  572  CG   PHE A  71      20.347   -0.402   12.490  1.00 205.64           C
ATOM  573  CD1  PHE A  71      19.970    0.374   13.588  1.00 207.90           C
ATOM  574  CD2  PHE A  71      19.466   -0.436   11.431  1.00 217.69           C
ATOM  575  CE1  PHE A  71      18.723    1.015   13.807  1.00 221.54           C
ATOM  576  CE2  PHE A  71      18.229    0.147   11.456  1.00 231.61           C
ATOM  577  CZ   PHE A  71      17.861    0.895   12.534  1.00 233.25           C
ATOM  578  N    HIS A  72      19.731   -3.609   12.144  1.00 175.76           N
ATOM  579  CA   HIS A  72      18.847   -4.481   11.335  1.00 169.63           C
ATOM  580  C    HIS A  72      18.383   -3.637   10.153  1.00 183.22           C
ATOM  581  O    HIS A  72      18.355   -2.436   10.276  1.00 195.25           O
ATOM  582  CB   HIS A  72      17.623   -4.924   12.171  1.00 160.59           C
ATOM  583  CG   HIS A  72      16.533   -3.890   12.285  1.00 173.36           C
ATOM  584  CD2  HIS A  72      16.222   -3.001   13.262  1.00 176.52           C
ATOM  585  ND1  HIS A  72      15.580   -3.711   11.302  1.00 185.40           N
ATOM  586  CE1  HIS A  72      14.748   -2.751   11.656  1.00 197.39           C
ATOM  587  NE2  HIS A  72      15.113   -2.302   12.844  1.00 191.88           N
ATOM  588  N    GLN A  73      17.986   -4.203    9.020  1.00 225.33           N
ATOM  589  CA   GLN A  73      17.613   -3.399    7.919  1.00 236.98           C
ATOM  590  C    GLN A  73      16.251   -2.653    7.956  1.00 246.65           C
ATOM  591  O    GLN A  73      15.393   -2.985    8.757  1.00 237.91           O
ATOM  592  CB   GLN A  73      17.765   -3.939    6.559  1.00 169.68           C
ATOM  593  CG   GLN A  73      19.196   -4.050    6.139  1.00 163.83           C
ATOM  594  CD   GLN A  73      19.689   -5.470    6.303  1.00 149.22           C
ATOM  595  NE2  GLN A  73      20.688   -5.842    5.491  1.00 144.40           N
ATOM  596  OE1  GLN A  73      19.167   -6.342    7.141  1.00 143.42           O
ATOM  597  N    PRO A  74      16.055   -1.696    7.064  1.00 125.92           N
ATOM  598  CA   PRO A  74      14.696   -1.187    6.948  1.00 137.19           C
ATOM  599  C    PRO A  74      13.626   -2.231    6.668  1.00 136.54           C
ATOM  600  O    PRO A  74      13.773   -2.973    5.722  1.00 142.97           O
ATOM  601  CB   PRO A  74      14.794   -0.203    5.756  1.00 217.78           C
ATOM  602  CG   PRO A  74      16.198   -0.416    5.164  1.00 217.33           C
ATOM  603  CD   PRO A  74      17.007   -0.866    6.311  1.00 157.80           C
ATOM  604  N    ASN A  75      12.566   -2.293    7.463  1.00 142.90           N
ATOM  605  CA   ASN A  75      11.371   -2.965    6.999  1.00 143.81           C
```

Fig. 7J

```
ATOM   606  C   ASN A  75     11.525  -4.466   6.703  1.00 129.01           C
ATOM   607  O   ASN A  75     10.604  -5.082   6.149  1.00 130.48           O
ATOM   608  CB  ASN A  75     10.864  -2.275   5.736  1.00 154.03           C
ATOM   609  CG  ASN A  75      9.526  -1.593   5.932  1.00 161.88           C
ATOM   610  ND2 ASN A  75      9.334  -0.487   5.235  1.00 186.03           N
ATOM   611  OD1 ASN A  75      8.667  -2.059   6.683  1.00 147.57           O
ATOM   612  N   ASP A  76     12.879  -5.049   7.019  1.00 205.80           N
ATOM   613  CA  ASP A  76     12.796  -6.501   7.089  1.00 190.39           C
ATOM   614  C   ASP A  76     12.426  -6.814   8.536  1.00 175.09           C
ATOM   615  O   ASP A  76     12.662  -6.015   9.423  1.00 173.10           O
ATOM   616  CB  ASP A  76     14.211  -6.957   6.746  1.00 185.95           C
ATOM   617  CG  ASP A  76     15.101  -7.064   7.959  1.00 174.52           C
ATOM   618  OD1 ASP A  76     14.981  -6.228   8.878  1.00 174.47           O
ATOM   619  OD2 ASP A  76     15.928  -7.992   7.992  1.00 167.19           O1-
ATOM   620  N   LEU A  77     11.794  -7.947   8.761  1.00 140.31           N
ATOM   621  CA  LEU A  77     11.060  -8.090  10.008  1.00 130.07           C
ATOM   622  C   LEU A  77     11.864  -8.604  11.199  1.00 115.26           C
ATOM   623  O   LEU A  77     11.413  -9.484  11.940  1.00 103.23           O
ATOM   624  CB  LEU A  77      9.851  -9.001   9.795  1.00 115.34           C
ATOM   625  CG  LEU A  77      8.714  -8.622   8.853  1.00 128.62           C
ATOM   626  CD1 LEU A  77      7.563  -9.571   9.130  1.00 121.46           C
ATOM   627  CD2 LEU A  77      9.269  -7.183   9.025  1.00 145.13           C
ATOM   628  N   SER A  78     13.063  -8.057  11.417  1.00 119.20           N
ATOM   629  CA  SER A  78     13.988  -8.650  12.416  1.00 106.55           C
ATOM   630  C   SER A  78     13.599  -8.371  13.867  1.00 108.21           C
ATOM   631  O   SER A  78     13.032  -7.339  14.178  1.00 108.34           O
ATOM   632  CB  SER A  78     15.462  -8.304  12.141  1.00  99.73           C
ATOM   633  OG  SER A  78     15.860  -7.123  12.791  1.00 109.96           O
ATOM   634  N   TYR A  79     13.816  -9.316  14.744  1.00 131.76           N
ATOM   635  CA  TYR A  79     13.585  -9.189  16.162  1.00 125.81           C
ATOM   636  C   TYR A  79     14.690  -8.482  16.946  1.00 128.01           C
ATOM   637  O   TYR A  79     14.921  -8.790  18.124  1.00 120.83           O
ATOM   638  CB  TYR A  79     13.296 -10.558  16.799  1.00 108.55           C
ATOM   639  CG  TYR A  79     11.868 -11.087  16.586  1.00 106.79           C
ATOM   640  CD1 TYR A  79     11.250 -10.984  15.339  1.00 114.16           C
ATOM   641  CD2 TYR A  79     11.205 -11.723  17.617  1.00  98.98           C
ATOM   642  CE1 TYR A  79      9.981 -11.477  15.137  1.00 113.68           C
ATOM   643  CE2 TYR A  79      9.930 -12.218  17.424  1.00  98.15           C
ATOM   644  CZ  TYR A  79      9.324 -12.093  16.183  1.00 105.49           C
ATOM   645  OH  TYR A  79      8.055 -12.590  15.976  1.00 104.86           O
ATOM   646  N   PHE A  80     15.381  -7.557  16.292  1.00 101.04           N
ATOM   647  CA  PHE A  80     16.322  -6.676  16.963  1.00 105.88           C
ATOM   648  C   PHE A  80     15.660  -6.023  18.164  1.00 106.64           C
ATOM   649  O   PHE A  80     14.653  -5.325  18.066  1.00 114.91           O
ATOM   650  CB  PHE A  80     16.769  -5.615  15.957  1.00 120.56           C
ATOM   651  CG  PHE A  80     17.784  -4.647  16.481  1.00 126.67           C
ATOM   652  CD1 PHE A  80     19.093  -5.033  16.658  1.00 121.83           C
ATOM   653  CD2 PHE A  80     17.433  -3.340  16.756  1.00 139.06           C
ATOM   654  CE1 PHE A  80     20.023  -4.148  17.124  1.00 127.48           C
ATOM   655  CE2 PHE A  80     18.364  -2.450  17.222  1.00 144.87           C
ATOM   656  CZ  PHE A  80     19.660  -2.853  17.410  1.00 138.68           C
ATOM   657  N   GLY A  81     16.218  -6.269  19.363  1.00 125.67           N
ATOM   658  CA  GLY A  81     15.681  -5.659  20.571  1.00 125.80           C
ATOM   659  C   GLY A  81     14.761  -6.586  21.355  1.00 111.58           C
ATOM   660  O   GLY A  81     14.480  -5.343  22.524  1.00 100.16           O
ATOM   661  N   SER A  82     14.286  -7.652  20.724  1.00 105.20           N
ATOM   662  CA  SER A  82     13.547  -8.683  21.453  1.00  94.15           C
ATOM   663  C   SER A  82     14.152  -8.987  22.829  1.00  91.44           C
ATOM   664  O   SER A  82     15.356  -9.069  23.047  1.00  85.46           O
ATOM   665  CB  SER A  82     13.483  -9.981  20.649  1.00 119.30           C
ATOM   666  OG  SER A  82     12.546 -10.870  21.227  1.00 121.79           O
```

Fig. 7K

| ATOM | 667 | N | SER | A | 83 | 13.286 | -9.375 | 23.750 | 1.00 | 102.67 | N |
| ATOM | 668 | CA | SER | A | 83 | 13.686 | -9.901 | 25.044 | 1.00 | 91.73 | C |
| ATOM | 669 | C | SER | A | 83 | 14.857 | -10.872 | 24.940 | 1.00 | 96.69 | C |
| ATOM | 670 | O | SER | A | 83 | 15.972 | -10.621 | 25.444 | 1.00 | 101.60 | O |
| ATOM | 671 | CB | SER | A | 83 | 12.472 | -10.638 | 25.630 | 1.00 | 75.09 | C |
| ATOM | 672 | OG | SER | A | 83 | 11.396 | -10.694 | 24.696 | 1.00 | 78.39 | O |
| ATOM | 673 | N | LEU | A | 84 | 14.691 | -11.992 | 24.277 | 1.00 | 95.54 | N |
| ATOM | 674 | CA | LEU | A | 84 | 15.564 | -13.067 | 24.150 | 1.00 | 98.90 | C |
| ATOM | 675 | C | LEU | A | 84 | 16.766 | -12.577 | 23.404 | 1.00 | 105.85 | C |
| ATOM | 676 | O | LEU | A | 84 | 17.905 | -12.860 | 23.809 | 1.00 | 106.64 | O |
| ATOM | 677 | CB | LEU | A | 84 | 14.956 | -14.294 | 23.487 | 1.00 | 99.36 | C |
| ATOM | 678 | CG | LEU | A | 84 | 15.853 | -15.532 | 23.332 | 1.00 | 97.82 | C |
| ATOM | 679 | CD1 | LEU | A | 84 | 16.480 | -15.909 | 24.664 | 1.00 | 98.53 | C |
| ATOM | 680 | CD2 | LEU | A | 84 | 15.071 | -16.692 | 22.767 | 1.00 | 93.88 | C |
| ATOM | 681 | N | SER | A | 85 | 16.569 | -11.835 | 22.323 | 1.00 | 89.10 | N |
| ATOM | 682 | CA | SER | A | 85 | 17.681 | -11.325 | 21.539 | 1.00 | 94.99 | C |
| ATOM | 683 | C | SER | A | 85 | 18.600 | -10.506 | 22.433 | 1.00 | 99.42 | C |
| ATOM | 684 | O | SER | A | 85 | 19.820 | -10.750 | 22.528 | 1.00 | 102.33 | O |
| ATOM | 685 | CB | SER | A | 85 | 17.166 | -10.473 | 20.386 | 1.00 | 105.12 | C |
| ATOM | 686 | OG | SER | A | 85 | 16.525 | -11.268 | 19.411 | 1.00 | 104.87 | O |
| ATOM | 687 | N | THR | A | 86 | 17.992 | -9.535 | 23.101 | 1.00 | 92.57 | N |
| ATOM | 688 | CA | THR | A | 86 | 18.698 | -8.696 | 24.048 | 1.00 | 96.07 | C |
| ATOM | 689 | C | THR | A | 86 | 19.505 | -9.538 | 25.019 | 1.00 | 90.83 | C |
| ATOM | 690 | O | THR | A | 86 | 20.711 | -9.384 | 25.092 | 1.00 | 94.07 | O |
| ATOM | 691 | CB | THR | A | 86 | 17.735 | -7.793 | 24.798 | 1.00 | 91.78 | C |
| ATOM | 692 | CG2 | THR | A | 86 | 18.497 | -6.826 | 25.640 | 1.00 | 92.47 | C |
| ATOM | 693 | OG1 | THR | A | 86 | 16.946 | -7.060 | 23.856 | 1.00 | 98.44 | O |
| ATOM | 694 | N | LEU | A | 87 | 18.859 | -10.455 | 25.733 | 1.00 | 81.42 | N |
| ATOM | 695 | CA | LEU | A | 87 | 19.608 | -11.283 | 26.697 | 1.00 | 77.90 | C |
| ATOM | 696 | C | LEU | A | 87 | 20.767 | -12.107 | 26.108 | 1.00 | 79.23 | C |
| ATOM | 697 | O | LEU | A | 87 | 21.821 | -12.311 | 26.748 | 1.00 | 81.28 | O |
| ATOM | 698 | CB | LEU | A | 87 | 18.667 | -12.142 | 27.518 | 1.00 | 76.63 | C |
| ATOM | 699 | CG | LEU | A | 87 | 19.391 | -12.896 | 28.647 | 1.00 | 75.08 | C |
| ATOM | 700 | CD1 | LEU | A | 87 | 19.871 | -11.911 | 29.709 | 1.00 | 76.60 | C |
| ATOM | 701 | CD2 | LEU | A | 87 | 18.519 | -13.978 | 29.270 | 1.00 | 64.24 | C |
| ATOM | 702 | N | THR | A | 88 | 20.581 | -12.606 | 24.893 | 1.00 | 117.49 | N |
| ATOM | 703 | CA | THR | A | 88 | 21.623 | -13.396 | 24.242 | 1.00 | 119.95 | C |
| ATOM | 704 | C | THR | A | 88 | 22.793 | -12.490 | 23.964 | 1.00 | 127.16 | C |
| ATOM | 705 | O | THR | A | 88 | 23.943 | -12.863 | 24.104 | 1.00 | 130.82 | O |
| ATOM | 706 | CB | THR | A | 88 | 21.153 | -14.015 | 22.899 | 1.00 | 109.23 | C |
| ATOM | 707 | CG2 | THR | A | 88 | 20.976 | -15.508 | 23.011 | 1.00 | 93.68 | C |
| ATOM | 708 | OG1 | THR | A | 88 | 19.898 | -13.443 | 22.524 | 1.00 | 101.36 | O |
| ATOM | 709 | N | TYR | A | 89 | 22.482 | -11.253 | 23.573 | 1.00 | 96.67 | N |
| ATOM | 710 | CA | TYR | A | 89 | 23.520 | -10.322 | 23.146 | 1.00 | 94.42 | C |
| ATOM | 711 | C | TYR | A | 89 | 24.237 | -9.654 | 24.315 | 1.00 | 96.81 | C |
| ATOM | 712 | O | TYR | A | 89 | 25.331 | -9.137 | 24.159 | 1.00 | 104.04 | O |
| ATOM | 713 | CB | TYR | A | 89 | 22.914 | -9.300 | 22.202 | 1.00 | 112.31 | C |
| ATOM | 714 | CG | TYR | A | 89 | 23.537 | -7.946 | 22.246 | 1.00 | 121.75 | C |
| ATOM | 715 | CD1 | TYR | A | 89 | 24.466 | -7.564 | 21.297 | 1.00 | 129.36 | C |
| ATOM | 716 | CD2 | TYR | A | 89 | 23.173 | -7.032 | 23.219 | 1.00 | 124.47 | C |
| ATOM | 717 | CE1 | TYR | A | 89 | 25.027 | -6.303 | 21.324 | 1.00 | 139.45 | C |
| ATOM | 718 | CE2 | TYR | A | 89 | 23.733 | -5.774 | 23.256 | 1.00 | 134.93 | C |
| ATOM | 719 | CZ | TYR | A | 89 | 24.650 | -5.410 | 22.310 | 1.00 | 142.41 | C |
| ATOM | 720 | OH | TYR | A | 89 | 25.193 | -4.146 | 22.352 | 1.00 | 153.31 | O |
| ATOM | 721 | N | TRP | A | 90 | 23.575 | -9.653 | 25.477 | 1.00 | 94.69 | N |
| ATOM | 722 | CA | TRP | A | 90 | 24.265 | -9.395 | 26.733 | 1.00 | 96.59 | C |
| ATOM | 723 | C | TRP | A | 90 | 25.175 | -10.571 | 27.003 | 1.00 | 96.79 | C |
| ATOM | 724 | O | TRP | A | 90 | 26.384 | -10.451 | 26.871 | 1.00 | 103.80 | O |
| ATOM | 725 | CB | TRP | A | 90 | 23.296 | -9.164 | 27.910 | 1.00 | 104.70 | C |
| ATOM | 726 | CG | TRP | A | 90 | 22.476 | -7.889 | 27.830 | 1.00 | 109.19 | C |
| ATOM | 727 | CD1 | TRP | A | 90 | 22.784 | -6.750 | 27.136 | 1.00 | 111.60 | C |

Fig. 7L

| ATOM | 728 | CD2 | TRP | A | 90 | 21.211 | -7.643 | 28.450 | 1.00 109.76 | C |
|------|-----|-----|-----|---|----|--------|--------|--------|-------------|---|
| ATOM | 729 | CE2 | TRP | A | 90 | 20.812 | -6.336 | 28.085 | 1.00 112.25 | C |
| ATOM | 730 | CE3 | TRP | A | 90 | 20.379 | -8.396 | 29.276 | 1.00 104.82 | C |
| ATOM | 731 | NE1 | TRP | A | 90 | 21.791 | -5.811 | 27.287 | 1.00 117.01 | N |
| ATOM | 732 | CZ2 | TRP | A | 90 | 19.625 | -5.773 | 28.515 | 1.00 105.35 | C |
| ATOM | 733 | CZ3 | TRP | A | 90 | 19.198 | -7.833 | 29.701 | 1.00 98.02 | C |
| ATOM | 734 | CH2 | TRP | A | 90 | 18.831 | -6.532 | 29.319 | 1.00 95.41 | C |
| ATOM | 735 | N | LEU | A | 91 | 24.607 | -11.727 | 27.337 | 1.00 99.58 | N |
| ATOM | 736 | CA | LEU | A | 91 | 25.449 | -12.879 | 27.693 | 1.00 101.62 | C |
| ATOM | 737 | C | LEU | A | 91 | 26.572 | -13.205 | 26.692 | 1.00 103.61 | C |
| ATOM | 738 | O | LEU | A | 91 | 27.490 | -13.946 | 27.006 | 1.00 114.35 | O |
| ATOM | 739 | CB | LEU | A | 91 | 24.590 | -14.125 | 27.875 | 1.00 110.19 | C |
| ATOM | 740 | CG | LEU | A | 91 | 23.694 | -14.235 | 29.098 | 1.00 104.68 | C |
| ATOM | 741 | CD1 | LEU | A | 91 | 22.333 | -14.742 | 28.645 | 1.00 97.98 | C |
| ATOM | 742 | CD2 | LEU | A | 91 | 24.314 | -15.147 | 30.164 | 1.00 108.81 | C |
| ATOM | 743 | N | TYR | A | 92 | 26.480 | -12.664 | 25.487 | 1.00 84.56 | N |
| ATOM | 744 | CA | TYR | A | 92 | 27.438 | -12.939 | 24.432 | 1.00 90.43 | C |
| ATOM | 745 | C | TYR | A | 92 | 28.669 | -12.075 | 24.509 | 1.00 99.67 | C |
| ATOM | 746 | O | TYR | A | 92 | 29.811 | -12.502 | 24.404 | 1.00 106.23 | O |
| ATOM | 747 | CB | TYR | A | 92 | 26.903 | -12.601 | 23.094 | 1.00 105.43 | C |
| ATOM | 748 | CG | TYR | A | 92 | 27.734 | -12.725 | 21.901 | 1.00 111.30 | C |
| ATOM | 749 | CD1 | TYR | A | 92 | 28.463 | -13.875 | 21.698 | 1.00 113.23 | C |
| ATOM | 750 | CD2 | TYR | A | 92 | 27.833 | -11.706 | 20.964 | 1.00 116.04 | C |
| ATOM | 751 | CE1 | TYR | A | 92 | 29.316 | -14.094 | 20.603 | 1.00 119.10 | C |
| ATOM | 752 | CE2 | TYR | A | 92 | 28.662 | -11.823 | 19.870 | 1.00 122.27 | C |
| ATOM | 753 | CZ | TYR | A | 92 | 29.406 | -12.973 | 19.693 | 1.00 124.09 | C |
| ATOM | 754 | OH | TYR | A | 92 | 30.243 | -13.100 | 18.603 | 1.00 131.62 | O |
| ATOM | 755 | N | SER | A | 93 | 28.414 | -10.833 | 24.978 | 1.00 112.84 | N |
| ATOM | 756 | CA | SER | A | 93 | 29.465 | -9.868 | 25.143 | 1.00 122.46 | C |
| ATOM | 757 | C | SER | A | 93 | 29.964 | -9.945 | 26.573 | 1.00 124.38 | C |
| ATOM | 758 | O | SER | A | 93 | 30.751 | -9.128 | 27.008 | 1.00 133.38 | O |
| ATOM | 759 | CB | SER | A | 93 | 28.921 | -8.484 | 24.819 | 1.00 110.96 | C |
| ATOM | 760 | OG | SER | A | 93 | 28.247 | -8.501 | 23.572 | 1.00 107.20 | O |
| ATOM | 761 | N | ILE | A | 94 | 29.498 | -10.941 | 27.306 | 1.00 110.39 | N |
| ATOM | 762 | CA | ILE | A | 94 | 29.944 | -11.152 | 28.671 | 1.00 112.32 | C |
| ATOM | 763 | C | ILE | A | 94 | 30.641 | -12.508 | 28.731 | 1.00 117.21 | C |
| ATOM | 764 | O | ILE | A | 94 | 31.214 | -12.872 | 29.745 | 1.00 122.77 | O |
| ATOM | 765 | CB | ILE | A | 94 | 28.749 | -11.129 | 29.675 | 1.00 113.83 | C |
| ATOM | 766 | CG1 | ILE | A | 94 | 28.175 | -9.715 | 29.819 | 1.00 114.40 | C |
| ATOM | 767 | CG2 | ILE | A | 94 | 29.181 | -11.842 | 31.041 | 1.00 114.75 | C |
| ATOM | 768 | CD1 | ILE | A | 94 | 26.979 | -9.625 | 30.788 | 1.00 106.62 | C |
| ATOM | 769 | N | LEU | A | 95 | 30.601 | -13.258 | 27.638 | 1.00 133.89 | N |
| ATOM | 770 | CA | LEU | A | 95 | 31.073 | -14.540 | 27.680 | 1.00 135.46 | C |
| ATOM | 771 | C | LEU | A | 95 | 31.952 | -15.023 | 26.499 | 1.00 138.82 | C |
| ATOM | 772 | O | LEU | A | 95 | 31.805 | -14.460 | 25.402 | 1.00 137.54 | O |
| ATOM | 773 | CB | LEU | A | 95 | 29.892 | -15.506 | 27.784 | 1.00 117.75 | C |
| ATOM | 774 | CG | LEU | A | 95 | 29.015 | -15.445 | 29.021 | 1.00 111.88 | C |
| ATOM | 775 | CD1 | LEU | A | 95 | 27.646 | -16.015 | 28.736 | 1.00 103.13 | C |
| ATOM | 776 | CD2 | LEU | A | 95 | 29.652 | -16.102 | 30.226 | 1.00 116.93 | C |
| ATOM | 777 | N | PRO | A | 96 | 32.855 | -15.990 | 26.724 | 1.00 122.19 | N |
| ATOM | 778 | CA | PRO | A | 96 | 33.905 | -16.398 | 25.794 | 1.00 127.07 | C |
| ATOM | 779 | C | PRO | A | 96 | 33.427 | -17.509 | 24.891 | 1.00 121.11 | C |
| ATOM | 780 | O | PRO | A | 96 | 34.249 | -18.153 | 24.245 | 1.00 123.00 | O |
| ATOM | 781 | CB | PRO | A | 96 | 34.964 | -16.957 | 26.735 | 1.00 92.33 | C |
| ATOM | 782 | CG | PRO | A | 96 | 34.162 | -17.633 | 27.783 | 1.00 89.29 | C |
| ATOM | 783 | CD | PRO | A | 96 | 32.911 | -16.787 | 27.962 | 1.00 82.50 | C |
| ATOM | 784 | N | PHE | A | 97 | 32.119 | -17.734 | 24.858 | 1.00 116.09 | N |
| ATOM | 785 | CA | PHE | A | 97 | 31.559 | -18.830 | 24.093 | 1.00 111.01 | C |
| ATOM | 786 | C | PHE | A | 97 | 30.943 | -18.290 | 22.812 | 1.00 107.62 | C |
| ATOM | 787 | O | PHE | A | 97 | 30.506 | -17.139 | 22.775 | 1.00 105.16 | O |
| ATOM | 788 | CB | PHE | A | 97 | 30.486 | -19.534 | 24.932 | 1.00 119.72 | C |

Fig. 7M

```
ATOM    789  CG  PHE A  97      30.937 -19.860  26.285  1.00 124.76           C
ATOM    790  CD1 PHE A  97      30.373 -19.399  27.419  1.00 123.81           C
ATOM    791  CD2 PHE A  97      31.904 -20.939  26.444  1.00 132.11           C
ATOM    792  CE1 PHE A  97      30.771 -19.802  28.680  1.00 130.11           C
ATOM    793  CE2 PHE A  97      32.306 -21.343  27.702  1.00 138.60           C
ATOM    794  CZ  PHE A  97      31.738 -20.775  28.818  1.00 137.59           C
ATOM    795  N   SER A  98      30.300 -19.119  21.768  1.00 123.23           N
ATOM    796  CA  SER A  98      30.405 -18.677  20.460  1.00 122.85           C
ATOM    797  C   SER A  98      28.893 -18.547  20.426  1.00 114.90           C
ATOM    798  O   SER A  98      28.163 -19.310  21.074  1.00 108.90           O
ATOM    799  CB  SER A  98      30.852 -19.622  19.338  1.00 146.51           C
ATOM    800  OG  SER A  98      29.899 -20.647  19.103  1.00 146.90           O
ATOM    801  N   PHE A  99      28.431 -17.572  19.655  1.00 129.76           N
ATOM    802  CA  PHE A  99      27.002 -17.354  19.470  1.00 124.17           C
ATOM    803  C   PHE A  99      26.270 -18.685  19.447  1.00 118.01           C
ATOM    804  O   PHE A  99      25.412 -18.932  20.272  1.00 116.38           O
ATOM    805  CB  PHE A  99      26.772 -16.597  18.167  1.00  99.14           C
ATOM    806  CG  PHE A  99      25.360 -16.147  17.954  1.00  96.33           C
ATOM    807  CD1 PHE A  99      24.926 -14.927  18.456  1.00  98.17           C
ATOM    808  CD2 PHE A  99      24.476 -16.926  17.213  1.00  93.60           C
ATOM    809  CE1 PHE A  99      23.622 -14.503  18.239  1.00  96.16           C
ATOM    810  CE2 PHE A  99      23.185 -16.510  16.982  1.00  92.25           C
ATOM    811  CZ  PHE A  99      22.747 -15.304  17.495  1.00  93.30           C
ATOM    812  N   GLU A 100      26.653 -19.553  18.522  1.00 103.62           N
ATOM    813  CA  GLU A 100      25.983 -20.828  18.318  1.00  99.70           C
ATOM    814  C   GLU A 100      25.852 -21.684  19.595  1.00  99.80           C
ATOM    815  O   GLU A 100      24.817 -22.356  19.808  1.00  97.97           O
ATOM    816  CB  GLU A 100      26.669 -21.625  17.189  1.00 133.11           C
ATOM    817  CG  GLU A 100      26.548 -21.024  15.770  1.00 135.63           C
ATOM    818  CD  GLU A 100      27.716 -20.115  15.405  1.00 136.42           C
ATOM    819  OE1 GLU A 100      28.709 -20.094  16.158  1.00 136.59           O
ATOM    820  OE2 GLU A 100      27.648 -19.426  14.365  1.00 138.15           O1-
ATOM    821  N   SER A 101      26.879 -21.653  20.445  1.00 116.94           N
ATOM    822  CA  SER A 101      26.875 -22.452  21.670  1.00 118.27           C
ATOM    823  C   SER A 101      26.048 -21.799  22.775  1.00 111.39           C
ATOM    824  O   SER A 101      25.401 -22.493  23.574  1.00 110.42           O
ATOM    825  CB  SER A 101      28.291 -22.693  22.162  1.00 116.18           C
ATOM    826  OG  SER A 101      29.219 -22.393  21.144  1.00 115.97           O
ATOM    827  N   ILE A 102      26.071 -20.468  22.817  1.00 104.16           N
ATOM    828  CA  ILE A 102      25.175 -19.706  23.691  1.00  98.78           C
ATOM    829  C   ILE A 102      23.708 -19.962  23.331  1.00  91.45           C
ATOM    830  O   ILE A 102      22.875 -20.648  24.073  1.00  86.43           O
ATOM    831  CB  ILE A 102      25.484 -18.217  23.602  1.00  81.63           C
ATOM    832  CG1 ILE A 102      26.933 -17.399  24.050  1.00  79.44           C
ATOM    833  CG2 ILE A 102      24.486 -17.418  24.413  1.00  82.85           C
ATOM    834  CD1 ILE A 102      27.340 -16.554  24.371  1.00  83.24           C
ATOM    835  N   ILE A 103      23.293 -19.393  22.198  1.00  84.17           N
ATOM    836  CA  ILE A 103      22.066 -19.776  21.515  1.00  79.15           C
ATOM    837  C   ILE A 103      21.695 -21.328  21.780  1.00  78.49           C
ATOM    838  O   ILE A 103      20.521 -21.540  22.009  1.00  74.06           O
ATOM    839  CB  ILE A 103      22.222 -19.652  20.001  1.00  84.35           C
ATOM    840  CG1 ILE A 103      21.516 -18.413  19.478  1.00  85.32           C
ATOM    841  CG2 ILE A 103      21.669 -20.890  19.285  1.00  82.82           C
ATOM    842  CD1 ILE A 103      21.217 -18.538  18.010  1.00  87.30           C
ATOM    843  N   LEU A 104      22.679 -22.127  21.762  1.00  86.52           N
ATOM    844  CA  LEU A 104      22.365 -23.523  22.018  1.00  80.72           C
ATOM    845  C   LEU A 104      21.957 -23.834  23.455  1.00  89.23           C
ATOM    846  O   LEU A 104      20.641 -24.317  23.669  1.00  85.55           O
ATOM    847  CB  LEU A 104      23.493 -24.447  21.616  1.00  67.14           C
ATOM    848  CG  LEU A 104      22.895 -25.848  21.562  1.00  73.62           C
ATOM    849  CD1 LEU A 104      22.511 -26.232  20.362  1.00  74.37           C
```

Fig. 7N

```
ATOM    850  CD2 LEU A 104      23.815 -26.885  22.245  1.00 73.79           C
ATOM    851  N   TYR A 105      22.845 -23.572  24.427  1.00 92.82           N
ATOM    852  CA  TYR A 105      22.619 -24.002  25.636  1.00 95.27           C
ATOM    853  C   TYR A 105      21.789 -23.067  26.752  1.00 89.57           C
ATOM    854  O   TYR A 105      21.408 -23.463  27.867  1.00 92.01           O
ATOM    855  CB  TYR A 105      23.944 -24.338  26.542  1.00 89.74           C
ATOM    856  CG  TYR A 105      24.712 -25.509  25.969  1.00 98.56           C
ATOM    857  CD1 TYR A 105      25.430 -25.372  24.801  1.00 99.80           C
ATOM    858  CD2 TYR A 105      24.737 -26.742  26.619  1.00107.66           C
ATOM    859  CE1 TYR A 105      26.142 -26.426  24.279  1.00109.39           C
ATOM    860  CE2 TYR A 105      25.447 -27.812  26.107  1.00117.92           C
ATOM    861  CZ  TYR A 105      26.153 -27.651  24.926  1.00118.61           C
ATOM    862  OH  TYR A 105      26.894 -28.691  24.367  1.00130.12           O
ATOM    863  N   MET A 106      21.526 -21.842  26.287  1.00 89.63           N
ATOM    864  CA  MET A 106      20.716 -20.883  27.043  1.00 86.74           C
ATOM    865  C   MET A 106      19.430 -21.481  27.619  1.00 81.22           C
ATOM    866  O   MET A 106      19.125 -21.315  28.789  1.00 75.46           O
ATOM    867  CB  MET A 106      20.356 -19.698  26.166  1.00101.98           C
ATOM    868  CG  MET A 106      21.436 -18.668  26.023  1.00105.49           C
ATOM    869  SD  MET A 106      20.669 -17.158  25.414  1.00103.71           S
ATOM    870  CE  MET A 106      19.766 -16.620  26.851  1.00 99.68           C
ATOM    871  N   SER A 107      18.667 -22.146  26.764  1.00 94.71           N
ATOM    872  CA  SER A 107      17.486 -22.917  27.140  1.00 86.60           C
ATOM    873  C   SER A 107      17.748 -23.819  28.346  1.00 84.71           C
ATOM    874  O   SER A 107      17.094 -23.719  29.392  1.00 74.40           O
ATOM    875  CB  SER A 107      17.116 -23.768  25.936  1.00 74.41           C
ATOM    876  OG  SER A 107      17.905 -23.357  24.805  1.00 77.07           O
ATOM    877  N   THR A 108      18.729 -24.694  28.180  1.00 98.24           N
ATOM    878  CA  THR A 108      19.221 -25.573  29.237  1.00 90.54           C
ATOM    879  C   THR A 108      19.494 -24.843  30.552  1.00 85.57           C
ATOM    880  O   THR A 108      19.144 -25.321  31.631  1.00 80.89           O
ATOM    881  CB  THR A 108      20.551 -26.225  28.813  1.00105.14           C
ATOM    882  CG2 THR A 108      20.642 -27.454  29.682  1.00109.05           C
ATOM    883  OG1 THR A 108      20.509 -26.570  27.422  1.00110.84           O
ATOM    884  N   PHE A 109      20.163 -23.696  30.479  1.00119.00           N
ATOM    885  CA  PHE A 109      20.465 -23.011  31.720  1.00117.90           C
ATOM    886  C   PHE A 109      19.208 -22.421  32.296  1.00102.15           C
ATOM    887  O   PHE A 109      18.672 -22.905  33.298  1.00 96.11           O
ATOM    888  CB  PHE A 109      21.489 -21.901  31.540  1.00123.81           C
ATOM    889  CG  PHE A 109      21.777 -21.145  32.814  1.00122.52           C
ATOM    890  CD1 PHE A 109      22.529 -21.727  33.827  1.00131.80           C
ATOM    891  CD2 PHE A 109      21.287 -19.865  33.006  1.00113.88           C
ATOM    892  CE1 PHE A 109      22.790 -21.045  34.994  1.00132.38           C
ATOM    893  CE2 PHE A 109      21.549 -19.183  34.174  1.00114.16           C
ATOM    894  CZ  PHE A 109      22.300 -19.777  35.167  1.00123.39           C
ATOM    895  N   PHE A 110      18.737 -21.365  31.660  1.00128.28           N
ATOM    896  CA  PHE A 110      17.516 -20.613  32.197  1.00115.67           C
ATOM    897  C   PHE A 110      16.431 -21.457  32.573  1.00105.44           C
ATOM    898  O   PHE A 110      15.874 -21.248  33.648  1.00 99.25           O
ATOM    899  CB  PHE A 110      17.210 -19.493  31.247  1.00 68.98           C
ATOM    900  CG  PHE A 110      18.194 -18.360  31.229  1.00 77.15           C
ATOM    901  CD1 PHE A 110      19.123 -18.231  30.196  1.00 89.07           C
ATOM    902  CD2 PHE A 110      18.218 -17.438  32.253  1.00 74.59           C
ATOM    903  CE1 PHE A 110      20.035 -17.190  30.172  1.00 96.53           C
ATOM    904  CE2 PHE A 110      19.127 -16.410  32.227  1.00 83.32           C
ATOM    905  CZ  PHE A 110      20.033 -16.297  31.178  1.00 93.90           C
ATOM    906  N   ALA A 111      15.989 -22.410  31.744  1.00101.63           N
ATOM    907  CA  ALA A 111      14.780 -23.129  32.133  1.00 92.81           C
ATOM    908  C   ALA A 111      14.979 -24.095  33.274  1.00 93.61           C
ATOM    909  O   ALA A 111      14.016 -24.620  33.788  1.00 86.62           O
ATOM    910  CB  ALA A 111      14.162 -23.822  31.002  1.00 70.23           C
```

Fig. 7O

| | | | | | | | | | |
|---|---|---|---|---|---|---|---|---|---|
| ATOM | 911 | N | SER | A | 112 | 16.221 | -24.292 | 33.678 | 1.00 100.56 | N |
| ATOM | 912 | CA | SER | A | 112 | 16.483 | -25.120 | 34.839 | 1.00 103.99 | C |
| ATOM | 913 | C | SER | A | 112 | 16.286 | -24.326 | 36.133 | 1.00 100.93 | C |
| ATOM | 914 | O | SER | A | 112 | 16.415 | -24.867 | 37.229 | 1.00 104.60 | O |
| ATOM | 915 | CB | SER | A | 112 | 17.886 | -25.730 | 34.766 | 1.00 81.36 | C |
| ATOM | 916 | OG | SER | A | 112 | 17.839 | -27.061 | 34.276 | 1.00 84.28 | O |
| ATOM | 917 | N | LEU | A | 113 | 15.946 | -23.050 | 36.005 | 1.00 111.66 | N |
| ATOM | 918 | CA | LEU | A | 113 | 15.820 | -22.190 | 37.175 | 1.00 110.10 | C |
| ATOM | 919 | C | LEU | A | 113 | 14.532 | -22.418 | 37.946 | 1.00 99.99 | C |
| ATOM | 920 | O | LEU | A | 113 | 14.393 | -21.976 | 39.089 | 1.00 99.34 | O |
| ATOM | 921 | CB | LEU | A | 113 | 15.929 | -20.718 | 36.774 | 1.00 69.21 | C |
| ATOM | 922 | CG | LEU | A | 113 | 17.169 | -20.038 | 37.339 | 1.00 79.92 | C |
| ATOM | 923 | CD1 | LEU | A | 113 | 18.282 | -21.068 | 37.815 | 1.00 93.06 | C |
| ATOM | 924 | CD2 | LEU | A | 113 | 17.596 | -19.859 | 36.460 | 1.00 82.38 | C |
| ATOM | 925 | N | ILE | A | 114 | 13.593 | -23.197 | 37.318 | 1.00 113.00 | N |
| ATOM | 926 | CA | ILE | A | 114 | 12.263 | -23.248 | 37.878 | 1.00 105.14 | C |
| ATOM | 927 | C | ILE | A | 114 | 12.314 | -24.086 | 39.176 | 1.00 108.79 | C |
| ATOM | 928 | O | ILE | A | 114 | 11.570 | -23.865 | 40.197 | 1.00 106.17 | O |
| ATOM | 929 | CB | ILE | A | 114 | 11.353 | -23.854 | 36.814 | 1.00 96.37 | C |
| ATOM | 930 | CG1 | ILE | A | 114 | 9.946 | -23.234 | 36.912 | 1.00 88.33 | C |
| ATOM | 931 | CG2 | ILE | A | 114 | 11.400 | -25.372 | 36.867 | 1.00 98.26 | C |
| ATOM | 932 | CD1 | ILE | A | 114 | 8.836 | -24.221 | 36.528 | 1.00 85.43 | C |
| ATOM | 933 | N | VAL | A | 115 | 13.238 | -25.036 | 39.125 | 1.00 102.12 | N |
| ATOM | 934 | CA | VAL | A | 115 | 13.640 | -25.831 | 40.273 | 1.00 109.88 | C |
| ATOM | 935 | C | VAL | A | 115 | 13.827 | -24.955 | 41.540 | 1.00 113.09 | C |
| ATOM | 936 | O | VAL | A | 115 | 13.778 | -25.464 | 42.665 | 1.00 117.64 | O |
| ATOM | 937 | CB | VAL | A | 115 | 14.924 | -26.656 | 39.909 | 1.00 94.15 | C |
| ATOM | 938 | CG1 | VAL | A | 115 | 16.162 | -26.173 | 40.697 | 1.00 107.14 | C |
| ATOM | 939 | CG2 | VAL | A | 115 | 14.683 | -28.187 | 40.013 | 1.00 96.35 | C |
| ATOM | 940 | N | VAL | A | 116 | 14.004 | -23.644 | 41.354 | 1.00 106.22 | N |
| ATOM | 941 | CA | VAL | A | 116 | 14.164 | -22.700 | 42.477 | 1.00 110.87 | C |
| ATOM | 942 | C | VAL | A | 116 | 12.840 | -22.293 | 43.160 | 1.00 103.16 | C |
| ATOM | 943 | O | VAL | A | 116 | 12.612 | -22.596 | 44.343 | 1.00 108.50 | O |
| ATOM | 944 | CB | VAL | A | 116 | 15.016 | -21.455 | 42.073 | 1.00 63.93 | C |
| ATOM | 945 | CG1 | VAL | A | 116 | 14.644 | -20.253 | 42.905 | 1.00 62.71 | C |
| ATOM | 946 | CG2 | VAL | A | 116 | 16.480 | -21.759 | 42.241 | 1.00 79.26 | C |
| ATOM | 947 | N | PRO | A | 117 | 11.957 | -21.590 | 42.430 | 1.00 99.33 | N |
| ATOM | 948 | CA | PRO | A | 117 | 10.700 | -21.337 | 43.117 | 1.00 95.02 | C |
| ATOM | 949 | C | PRO | A | 117 | 10.024 | -22.630 | 43.489 | 1.00 94.52 | C |
| ATOM | 950 | O | PRO | A | 117 | 9.390 | -22.607 | 44.535 | 1.00 96.56 | O |
| ATOM | 951 | CB | PRO | A | 117 | 9.863 | -20.559 | 42.094 | 1.00 77.32 | C |
| ATOM | 952 | CG | PRO | A | 117 | 10.487 | -20.804 | 40.826 | 1.00 75.46 | C |
| ATOM | 953 | CD | PRO | A | 117 | 11.955 | -20.986 | 41.088 | 1.00 84.05 | C |
| ATOM | 954 | N | ILE | A | 118 | 10.135 | -23.723 | 42.730 | 1.00 118.63 | N |
| ATOM | 955 | CA | ILE | A | 118 | 9.409 | -24.909 | 43.253 | 1.00 119.92 | C |
| ATOM | 956 | C | ILE | A | 118 | 9.709 | -25.166 | 44.753 | 1.00 128.60 | C |
| ATOM | 957 | O | ILE | A | 118 | 8.814 | -25.090 | 45.632 | 1.00 130.73 | O |
| ATOM | 958 | CB | ILE | A | 118 | 9.678 | -26.222 | 42.490 | 1.00 92.08 | C |
| ATOM | 959 | CG1 | ILE | A | 118 | 9.323 | -26.100 | 41.013 | 1.00 85.39 | C |
| ATOM | 960 | CG2 | ILE | A | 118 | 8.849 | -27.334 | 43.090 | 1.00 94.76 | C |
| ATOM | 961 | CD1 | ILE | A | 118 | 7.859 | -26.348 | 40.736 | 1.00 82.08 | C |
| ATOM | 962 | N | ILE | A | 119 | 10.973 | -25.463 | 45.042 | 1.00 89.40 | N |
| ATOM | 963 | CA | ILE | A | 119 | 11.375 | -25.805 | 46.402 | 1.00 102.17 | C |
| ATOM | 964 | C | ILE | A | 119 | 11.263 | -24.625 | 47.352 | 1.00 105.23 | C |
| ATOM | 965 | O | ILE | A | 119 | 11.019 | -24.824 | 48.530 | 1.00 113.21 | O |
| ATOM | 966 | CB | ILE | A | 119 | 12.770 | -26.519 | 46.487 | 1.00 96.18 | C |
| ATOM | 967 | CG1 | ILE | A | 119 | 13.935 | -25.591 | 46.191 | 1.00 102.05 | C |
| ATOM | 968 | CG2 | ILE | A | 119 | 12.853 | -27.792 | 45.520 | 1.00 93.50 | C |
| ATOM | 969 | CD1 | ILE | A | 119 | 15.161 | -26.405 | 45.795 | 1.00 113.42 | C |
| ATOM | 970 | N | LEU | A | 120 | 11.395 | -23.403 | 46.847 | 1.00 96.27 | N |
| ATOM | 971 | CA | LEU | A | 120 | 11.129 | -22.242 | 47.716 | 1.00 98.88 | C |

Fig. 7P

```
ATOM    972  C    LEU A 120       9.673 -22.135  48.235  1.00 93.25           C
ATOM    973  O    LEU A 120       9.428 -21.937  49.442  1.00101.09           O
ATOM    974  CB   LEU A 120      11.572 -20.923  47.960  1.00 81.77           C
ATOM    975  CG   LEU A 120      13.065 -20.618  46.989  1.00 93.20           C
ATOM    976  CD1  LEU A 120      13.206 -19.174  46.620  1.00 90.49           C
ATOM    977  CD2  LEU A 120      13.745 -20.917  48.316  1.00109.95           C
ATOM    978  N    ILE A 121       8.708 -22.254  47.332  1.00 91.76           N
ATOM    979  CA   ILE A 121       7.316 -22.251  47.755  1.00 91.15           C
ATOM    980  C    ILE A 121       7.045 -23.464  48.691  1.00 97.85           C
ATOM    981  O    ILE A 121       6.430 -23.321  49.669  1.00104.73           O
ATOM    982  CB   ILE A 121       6.373 -22.350  46.587  1.00 92.32           C
ATOM    983  CG1  ILE A 121       6.623 -21.181  45.649  1.00 86.73           C
ATOM    984  CG2  ILE A 121       4.932 -22.375  47.087  1.00 94.34           C
ATOM    985  CD1  ILE A 121       5.813 -21.232  44.379  1.00 79.97           C
ATOM    986  N    ALA A 122       7.484 -24.612  48.172  1.00 95.71           N
ATOM    987  CA   ALA A 122       7.382 -25.781  49.023  1.00104.23           C
ATOM    988  C    ALA A 122       7.795 -25.375  50.434  1.00116.68           C
ATOM    989  O    ALA A 122       7.083 -25.657  51.415  1.00123.96           O
ATOM    990  CB   ALA A 122       8.267 -26.988  48.504  1.00114.62           C
ATOM    991  N    ARG A 123       8.937 -24.691  50.548  1.00115.76           N
ATOM    992  CA   ARG A 123       9.527 -24.341  51.850  1.00132.23           C
ATOM    993  C    ARG A 123       8.712 -23.342  52.638  1.00134.47           C
ATOM    994  O    ARG A 123       8.711 -23.375  53.863  1.00143.21           O
ATOM    995  CB   ARG A 123      10.940 -23.799  51.676  1.00 92.90           C
ATOM    996  CG   ARG A 123      11.433 -22.975  52.812  1.00110.21           C
ATOM    997  CD   ARG A 123      12.698 -22.289  52.397  1.00114.09           C
ATOM    998  NE   ARG A 123      13.602 -22.188  53.527  1.00132.88           N
ATOM    999  CZ   ARG A 123      13.742 -21.101  54.274  1.00135.10           C
ATOM   1000  NH1  ARG A 123      13.042 -20.009  53.993  1.00130.26           N1+
ATOM   1001  NH2  ARG A 123      14.594 -21.103  55.295  1.00155.23           N
ATOM   1002  N    GLU A 124       8.037 -22.434  51.943  1.00103.95           N
ATOM   1003  CA   GLU A 124       7.087 -21.564  52.635  1.00107.67           C
ATOM   1004  C    GLU A 124       6.083 -22.396  53.416  1.00112.95           C
ATOM   1005  O    GLU A 124       5.677 -22.025  54.513  1.00124.30           O
ATOM   1006  CB   GLU A 124       6.343 -20.664  51.660  1.00150.58           C
ATOM   1007  CG   GLU A 124       7.226 -19.692  50.919  1.00146.75           C
ATOM   1008  CD   GLU A 124       8.012 -18.809  51.856  1.00159.01           C
ATOM   1009  OE1  GLU A 124       8.149 -19.159  53.050  1.00171.31           O
ATOM   1010  OE2  GLU A 124       8.495 -17.762  51.390  1.00167.57           O1-
ATOM   1011  N    TYR A 125       5.689 -23.524  52.829  1.00134.80           N
ATOM   1012  CA   TYR A 125       4.688 -24.418  53.404  1.00120.59           C
ATOM   1013  C    TYR A 125       5.300 -25.407  54.387  1.00133.14           C
ATOM   1014  O    TYR A 125       4.648 -26.359  54.832  1.00138.46           O
ATOM   1015  CB   TYR A 125       3.940 -25.135  52.289  1.00142.29           C
ATOM   1016  CG   TYR A 125       3.121 -24.170  51.466  1.00133.76           C
ATOM   1017  CD1  TYR A 125       2.950 -24.334  50.123  1.00122.66           C
ATOM   1018  CD2  TYR A 125       2.528 -23.078  52.097  1.00139.14           C
ATOM   1019  CE1  TYR A 125       2.201 -23.435  49.389  1.00117.18           C
ATOM   1020  CE2  TYR A 125       1.778 -22.180  51.375  1.00133.44           C
ATOM   1021  CZ   TYR A 125       1.616 -22.357  50.017  1.00122.47           C
ATOM   1022  OH   TYR A 125       0.867 -21.452  49.293  1.00116.10           O
ATOM   1023  N    LYS A 126       6.555 -25.149  54.733  1.00105.12           N
ATOM   1024  CA   LYS A 126       7.273 -25.946  55.713  1.00123.23           C
ATOM   1025  C    LYS A 126       7.494 -27.364  55.183  1.00121.25           C
ATOM   1026  O    LYS A 126       7.551 -28.321  55.952  1.00135.67           O
ATOM   1027  CB   LYS A 126       6.564 -25.898  57.075  1.00133.10           C
ATOM   1028  CG   LYS A 126       6.555 -24.481  57.691  1.00136.15           C
ATOM   1029  CD   LYS A 126       5.987 -24.405  59.109  1.00157.16           C
ATOM   1030  CE   LYS A 126       6.142 -23.006  59.732  1.00165.00           C
ATOM   1031  NZ   LYS A 126       5.574 -22.906  61.111  1.00184.27           N1+
ATOM   1032  N    LEU A 127       7.508 -27.473  53.853  1.00121.96           N
```

Fig. 7Q

```
ATOM   1033  CA  LEU A 127       7.711 -29.743  53.169  1.00119.15           C
ATOM   1034  C   LEU A 127       8.807 -29.535  52.121  1.00114.16           C
ATOM   1035  O   LEU A 127       8.532 -28.752  50.923  1.00100.38           O
ATOM   1036  CB  LEU A 127       6.448 -29.147  52.423  1.00102.22           C
ATOM   1037  CG  LEU A 127       5.080 -29.059  53.072  1.00104.75           C
ATOM   1038  CD1 LEU A 127       4.042 -29.705  52.166  1.00 95.99           C
ATOM   1039  CD2 LEU A 127       5.109 -29.738  54.422  1.00120.89           C
ATOM   1040  N   THR A 128      10.046 -28.423  52.541  1.00142.10           N
ATOM   1041  CA  THR A 128      11.107 -28.248  51.562  1.00139.13           C
ATOM   1042  C   THR A 128      11.432 -29.539  50.839  1.00139.38           C
ATOM   1043  O   THR A 128      11.225 -29.643  49.637  1.00126.10           O
ATOM   1044  CB  THR A 128      12.373 -27.705  52.184  1.00 97.20           C
ATOM   1045  CG2 THR A 128      13.548 -27.962  51.255  1.00 99.69           C
ATOM   1046  OG1 THR A 128      12.227 -26.291  52.383  1.00 92.64           O
ATOM   1047  N   THR A 129      11.946 -30.515  51.572  1.00127.83           N
ATOM   1048  CA  THR A 129      12.275 -31.809  50.991  1.00129.89           C
ATOM   1049  C   THR A 129      11.214 -32.338  50.014  1.00112.55           C
ATOM   1050  O   THR A 129      11.559 -32.957  49.021  1.00108.74           O
ATOM   1051  CB  THR A 129      12.551 -32.840  52.090  1.00105.00           C
ATOM   1052  CG2 THR A 129      13.060 -34.153  51.500  1.00109.58           C
ATOM   1053  OG1 THR A 129      13.515 -32.298  53.094  1.00123.25           O
ATOM   1054  N   TYR A 130       9.332 -32.099  50.268  1.00126.35           N
ATOM   1055  CA  TYR A 130       8.924 -32.480  49.279  1.00111.46           C
ATOM   1056  C   TYR A 130       8.980 -31.571  48.062  1.00 96.94           C
ATOM   1057  O   TYR A 130       8.751 -32.007  46.927  1.00 89.64           O
ATOM   1058  CB  TYR A 130       7.523 -32.501  49.869  1.00 87.97           C
ATOM   1059  CG  TYR A 130       7.375 -33.561  50.932  1.00102.19           C
ATOM   1060  CD1 TYR A 130       7.370 -33.216  53.275  1.00113.83           C
ATOM   1061  CD2 TYR A 130       7.366 -34.916  50.598  1.00105.59           C
ATOM   1062  CE1 TYR A 130       7.345 -34.185  53.256  1.00128.72           C
ATOM   1063  CE2 TYR A 130       7.343 -35.897  51.576  1.00119.91           C
ATOM   1064  CZ  TYR A 130       7.134 -35.523  52.902  1.00131.58           C
ATOM   1065  OH  TYR A 130       7.011 -36.482  53.880  1.00147.59           O
ATOM   1066  N   GLY A 131       9.297 -30.304  48.300  1.00110.57           N
ATOM   1067  CA  GLY A 131       9.586 -29.373  47.218  1.00100.18           C
ATOM   1068  C   GLY A 131      10.698 -29.860  46.297  1.00103.14           C
ATOM   1069  O   GLY A 131      10.586 -29.763  45.073  1.00 93.92           O
ATOM   1070  N   PHE A 132      11.778 -30.375  46.884  1.00115.95           N
ATOM   1071  CA  PHE A 132      12.922 -30.886  46.120  1.00122.05           C
ATOM   1072  C   PHE A 132      12.433 -31.875  45.072  1.00116.42           C
ATOM   1073  O   PHE A 132      12.770 -31.769  43.886  1.00111.68           O
ATOM   1074  CB  PHE A 132      13.928 -31.550  47.069  1.00 96.93           C
ATOM   1075  CG  PHE A 132      15.080 -32.227  46.371  1.00 95.96           C
ATOM   1076  CD1 PHE A 132      16.090 -31.480  45.774  1.00 98.61           C
ATOM   1077  CD2 PHE A 132      15.168 -33.615  46.337  1.00103.50           C
ATOM   1078  CE1 PHE A 132      17.159 -32.104  45.140  1.00108.77           C
ATOM   1079  CE2 PHE A 132      16.224 -34.237  45.708  1.00113.19           C
ATOM   1080  CZ  PHE A 132      17.215 -33.483  45.107  1.00116.11           C
ATOM   1081  N   ILE A 133      11.625 -32.829  45.528  1.00105.92           N
ATOM   1082  CA  ILE A 133      10.949 -33.772  44.644  1.00100.04           C
ATOM   1083  C   ILE A 133      10.021 -33.091  43.594  1.00 94.55           C
ATOM   1084  O   ILE A 133      10.153 -33.329  42.372  1.00 81.44           O
ATOM   1085  CB  ILE A 133      10.204 -34.852  45.472  1.00 99.20           C
ATOM   1086  CG1 ILE A 133      11.208 -35.751  46.178  1.00116.21           C
ATOM   1087  CG2 ILE A 133       9.320 -35.732  44.598  1.00 94.41           C
ATOM   1088  CD1 ILE A 133      10.625 -37.092  46.537  1.00122.74           C
ATOM   1089  N   ALA A 134       9.108 -32.234  44.056  1.00121.81           N
ATOM   1090  CA  ALA A 134       8.213 -31.538  43.124  1.00111.88           C
ATOM   1091  C   ALA A 134       8.996 -30.877  41.999  1.00107.79           C
ATOM   1092  O   ALA A 134       8.491 -30.734  40.892  1.00102.42           O
ATOM   1093  CB  ALA A 134       7.356 -30.507  43.840  1.00 66.86           C
```

Fig. 7R

```
ATOM   1094  N    ALA A 135      10.232 -30.482  42.286  1.00 82.79           N
ATOM   1095  CA   ALA A 135      11.063 -29.800  41.307  1.00 81.98           C
ATOM   1096  C    ALA A 135      11.932 -30.740  40.435  1.00 88.46           C
ATOM   1097  O    ALA A 135      12.139 -30.485  39.238  1.00 86.21           O
ATOM   1098  CB   ALA A 135      11.905 -28.744  42.004  1.00 75.56           C
ATOM   1099  N    LEU A 136      12.455 -31.817  41.006  1.00 99.40           N
ATOM   1100  CA   LEU A 136      13.067 -32.836  40.154  1.00106.08           C
ATOM   1101  C    LEU A 136      12.027 -33.261  39.111  1.00 97.70           C
ATOM   1102  O    LEU A 136      12.320 -33.202  37.922  1.00 98.58           O
ATOM   1103  CB   LEU A 136      13.520 -34.078  40.918  1.00 85.44           C
ATOM   1104  CG   LEU A 136      14.784 -34.020  41.767  1.00100.07           C
ATOM   1105  CD1  LEU A 136      15.405 -35.407  41.936  1.00115.38           C
ATOM   1106  CD2  LEU A 136      15.771 -33.061  41.141  1.00102.45           C
ATOM   1107  N    LEU A 137      10.799 -33.481  39.542  1.00 97.50           N
ATOM   1108  CA   LEU A 137       9.756 -33.872  38.599  1.00 92.33           C
ATOM   1109  C    LEU A 137       9.404 -32.742  37.645  1.00 84.48           C
ATOM   1110  O    LEU A 137       9.292 -32.941  36.433  1.00 84.27           O
ATOM   1111  CB   LEU A 137       8.481 -34.302  39.318  1.00 88.95           C
ATOM   1112  CG   LEU A 137       7.346 -34.460  38.302  1.00 84.88           C
ATOM   1113  CD1  LEU A 137       7.580 -35.684  37.470  1.00 91.08           C
ATOM   1114  CD2  LEU A 137       5.962 -34.496  38.946  1.00 82.53           C
ATOM   1115  N    GLY A 138       9.197 -31.554  38.200  1.00 98.50           N
ATOM   1116  CA   GLY A 138       8.721 -30.434  37.414  1.00 91.67           C
ATOM   1117  C    GLY A 138       9.732 -29.966  36.391  1.00 93.14           C
ATOM   1118  O    GLY A 138       9.376 -29.295  35.438  1.00 89.56           O
ATOM   1119  N    SER A 139      11.002 -30.311  36.575  1.00102.42           N
ATOM   1120  CA   SER A 139      12.027 -29.795  35.664  1.00106.49           C
ATOM   1121  C    SER A 139      12.297 -30.762  34.514  1.00113.40           C
ATOM   1122  O    SER A 139      13.256 -30.617  33.753  1.00120.65           O
ATOM   1123  CB   SER A 139      13.292 -29.568  36.469  1.00 75.35           C
ATOM   1124  OG   SER A 139      13.591 -30.710  37.243  1.00 81.89           O
ATOM   1125  N    ILE A 140      11.443 -31.770  34.397  1.00100.63           N
ATOM   1126  CA   ILE A 140      11.690 -32.836  33.448  1.00108.63           C
ATOM   1127  C    ILE A 140      10.430 -33.233  32.697  1.00105.77           C
ATOM   1128  O    ILE A 140      10.495 -33.601  31.522  1.00112.99           O
ATOM   1129  CB   ILE A 140      12.265 -34.035  34.161  1.00103.78           C
ATOM   1130  CG1  ILE A 140      13.745 -33.827  34.386  1.00111.77           C
ATOM   1131  CG2  ILE A 140      12.140 -35.240  33.318  1.00111.50           C
ATOM   1132  CD1  ILE A 140      14.464 -35.140  34.623  1.00124.54           C
ATOM   1133  N    ALA A 141       9.288 -33.140  33.373  1.00112.10           N
ATOM   1134  CA   ALA A 141       7.999 -33.462  32.771  1.00110.86           C
ATOM   1135  C    ALA A 141       7.930 -33.127  31.280  1.00114.74           C
ATOM   1136  O    ALA A 141       8.422 -32.088  30.837  1.00119.68           O
ATOM   1137  CB   ALA A 141       6.894 -32.778  33.513  1.00 75.54           C
ATOM   1138  N    ASN A 142       7.296 -34.019  30.524  1.00 87.58           N
ATOM   1139  CA   ASN A 142       7.330 -33.995  29.065  1.00 93.77           C
ATOM   1140  C    ASN A 142       7.231 -32.600  28.460  1.00 92.46           C
ATOM   1141  O    ASN A 142       8.246 -32.045  28.080  1.00 95.84           O
ATOM   1142  CB   ASN A 142       6.276 -34.944  28.490  1.00117.90           C
ATOM   1143  CG   ASN A 142       6.463 -36.385  28.941  1.00113.16           C
ATOM   1144  ND2  ASN A 142       7.709 -36.794  29.119  1.00112.54           N
ATOM   1145  OD1  ASN A 142       5.496 -37.116  29.140  1.00111.99           O
ATOM   1146  N    SER A 143       6.026 -32.040  28.381  1.00 87.02           N
ATOM   1147  CA   SER A 143       5.830 -30.672  27.893  1.00 86.42           C
ATOM   1148  C    SER A 143       6.987 -29.747  28.228  1.00 87.38           C
ATOM   1149  O    SER A 143       7.501 -29.047  27.353  1.00 91.30           O
ATOM   1150  CB   SER A 143       4.558 -30.061  28.473  1.00 82.49           C
ATOM   1151  OG   SER A 143       3.482 -30.953  28.314  1.00 87.34           O
ATOM   1152  N    TYR A 144       7.397 -29.733  29.498  1.00 75.12           N
ATOM   1153  CA   TYR A 144       8.435 -28.805  29.900  1.00 77.80           C
ATOM   1154  C    TYR A 144       9.751 -29.130  29.203  1.00 83.03           C
```

Fig. 7S

```
ATOM   1155  O    TYR A 144      10.310 -28.275  28.516  1.00 85.76           O
ATOM   1156  CB   TYR A 144       8.592 -28.688  31.427  1.00 75.82           C
ATOM   1157  CG   TYR A 144       9.315 -27.399  31.832  1.00 79.79           C
ATOM   1158  CD1  TYR A 144       8.638 -26.171  31.860  1.00 78.75           C
ATOM   1159  CD2  TYR A 144      10.673 -27.402  32.169  1.00 86.05           C
ATOM   1160  CE1  TYR A 144       9.289 -24.998  32.210  1.00 83.61           C
ATOM   1161  CE2  TYR A 144      11.321 -26.223  32.514  1.00 91.35           C
ATOM   1162  CZ   TYR A 144      10.622 -25.032  32.531  1.00 89.88           C
ATOM   1163  OH   TYR A 144      11.258 -23.868  32.868  1.00 96.47           O
ATOM   1164  N    TYR A 145      10.238 -30.359  29.352  1.00 84.28           N
ATOM   1165  CA   TYR A 145      11.493 -30.735  28.706  1.00 90.47           C
ATOM   1166  C    TYR A 145      11.441 -30.325  27.244  1.00 93.31           C
ATOM   1167  O    TYR A 145      12.324 -29.629  26.739  1.00 99.68           O
ATOM   1168  CB   TYR A 145      11.747 -32.241  28.807  1.00 73.30           C
ATOM   1169  CG   TYR A 145      12.923 -32.699  27.978  1.00 85.83           C
ATOM   1170  CD1  TYR A 145      14.205 -32.379  28.346  1.00 92.07           C
ATOM   1171  CD2  TYR A 145      12.749 -33.442  26.827  1.00 93.56           C
ATOM   1172  CE1  TYR A 145      15.284 -32.786  27.605  1.00105.56           C
ATOM   1173  CE2  TYR A 145      13.827 -33.861  26.076  1.00106.75           C
ATOM   1174  CZ   TYR A 145      15.096 -33.519  26.478  1.00112.70           C
ATOM   1175  OH   TYR A 145      16.201 -33.917  25.753  1.00127.76           O
ATOM   1176  N    ASN A 146      10.366 -30.746  26.598  1.00 71.27           N
ATOM   1177  CA   ASN A 146      10.209 -30.626  25.162  1.00 76.58           C
ATOM   1178  C    ASN A 146      10.383 -29.237  24.662  1.00 78.03           C
ATOM   1179  O    ASN A 146      10.906 -29.040  23.577  1.00 87.33           O
ATOM   1180  CB   ASN A 146       8.862 -31.144  24.757  1.00 87.51           C
ATOM   1181  CG   ASN A 146       8.794 -32.616  24.841  1.00 89.93           C
ATOM   1182  ND2  ASN A 146       9.631 -33.202  25.691  1.00 89.85           N
ATOM   1183  OD1  ASN A 146       8.009 -33.242  24.137  1.00 93.66           O
ATOM   1184  N    ARG A 147       9.847 -28.275  25.433  1.00 74.79           N
ATOM   1185  CA   ARG A 147       9.867 -26.857  25.029  1.00 75.70           C
ATOM   1186  C    ARG A 147      11.077 -26.095  25.561  1.00 77.98           C
ATOM   1187  O    ARG A 147      11.142 -24.857  25.519  1.00 79.22           O
ATOM   1188  CB   ARG A 147       8.569 -26.162  25.412  1.00 80.74           C
ATOM   1189  CG   ARG A 147       7.352 -26.901  24.949  1.00 85.64           C
ATOM   1190  CD   ARG A 147       6.212 -25.936  24.811  1.00 83.20           C
ATOM   1191  NE   ARG A 147       5.770 -25.676  23.435  1.00 90.32           N
ATOM   1192  CZ   ARG A 147       5.833 -24.768  22.716  1.00 96.95           C
ATOM   1193  NH1  ARG A 147       6.291 -23.663  23.254  1.00 96.29           N1+
ATOM   1194  NH2  ARG A 147       5.412 -24.763  21.463  1.00 98.05           N
ATOM   1195  N    THR A 148      12.053 -26.878  26.013  1.00111.49           N
ATOM   1196  CA   THR A 148      13.138 -26.394  26.825  1.00134.36           C
ATOM   1197  C    THR A 148      14.368 -27.286  26.700  1.00124.41           C
ATOM   1198  O    THR A 148      15.242 -27.252  27.560  1.00124.23           O
ATOM   1199  CB   THR A 148      12.714 -26.450  28.277  1.00 99.80           C
ATOM   1200  CG2  THR A 148      13.677 -25.726  29.096  1.00104.11           C
ATOM   1201  OG1  THR A 148      11.432 -25.844  28.432  1.00 91.59           O
ATOM   1202  N    MET A 149      14.437 -28.105  25.654  1.00121.53           N
ATOM   1203  CA   MET A 149      15.602 -28.978  25.471  1.00134.04           C
ATOM   1204  C    MET A 149      16.852 -28.139  25.395  1.00140.43           C
ATOM   1205  O    MET A 149      16.781 -26.914  25.357  1.00135.98           O
ATOM   1206  CB   MET A 149      15.548 -29.742  24.161  1.00104.15           C
ATOM   1207  CG   MET A 149      14.336 -30.539  23.893  1.00100.83           C
ATOM   1208  SD   MET A 149      14.302 -30.710  22.110  1.00114.98           S
ATOM   1209  CE   MET A 149      16.056 -30.646  21.740  1.00124.27           C
ATOM   1210  N    SER A 150      18.002 -28.798  25.316  1.00112.76           N
ATOM   1211  CA   SER A 150      19.251 -28.074  25.176  1.00118.09           C
ATOM   1212  C    SER A 150      19.238 -27.332  23.860  1.00111.73           C
ATOM   1213  O    SER A 150      20.313 -26.525  23.591  1.00110.98           O
ATOM   1214  CB   SER A 150      20.456 -29.014  25.237  1.00128.48           C
ATOM   1215  OG   SER A 150      20.716 -29.447  26.561  1.00135.26           O
```

Fig. 7T

```
ATOM   1216  N    GLY A 151      18.242 -27.601  23.035  1.00101.19           N
ATOM   1217  CA   GLY A 151      18.236 -27.008  21.723  1.00 97.94           C
ATOM   1218  C    GLY A 151      17.315 -25.819  21.527  1.00 88.94           C
ATOM   1219  O    GLY A 151      17.545 -25.022  20.611  1.00 87.64           O
ATOM   1220  N    TYR A 152      16.303 -25.688  22.396  1.00103.16           N
ATOM   1221  CA   TYR A 152      15.089 -24.675  22.161  1.00 96.87           C
ATOM   1222  C    TYR A 152      15.256 -23.378  22.365  1.00 92.25           C
ATOM   1223  O    TYR A 152      14.749 -22.827  23.326  1.00 90.42           O
ATOM   1224  CB   TYR A 152      13.961 -25.361  23.086  1.00108.50           C
ATOM   1225  CG   TYR A 152      12.574 -25.329  22.473  1.00106.21           C
ATOM   1226  CD1  TYR A 152      11.861 -26.494  22.263  1.00110.47           C
ATOM   1227  CD2  TYR A 152      11.982 -24.140  22.104  1.00101.40           C
ATOM   1228  CE1  TYR A 152      10.605 -26.470  21.702  1.00109.40           C
ATOM   1229  CE2  TYR A 152      10.729 -24.114  21.548  1.00100.64           C
ATOM   1230  CZ   TYR A 152      10.048 -25.276  21.348  1.00104.30           C
ATOM   1231  OH   TYR A 152       8.803 -25.233  20.784  1.00104.38           O
ATOM   1232  N    TYR A 153      15.940 -22.707  21.457  1.00 98.34           N
ATOM   1233  CA   TYR A 153      16.222 -21.286  21.629  1.00 96.34           C
ATOM   1234  C    TYR A 153      14.988 -20.425  21.263  1.00 92.50           C
ATOM   1235  O    TYR A 153      14.982 -19.697  20.263  1.00 91.36           O
ATOM   1236  CB   TYR A 153      17.511 -20.934  20.857  1.00 81.28           C
ATOM   1237  CG   TYR A 153      17.898 -19.472  20.818  1.00 82.04           C
ATOM   1238  CD1  TYR A 153      18.569 -18.875  21.875  1.00 83.69           C
ATOM   1239  CD2  TYR A 153      17.622 -18.697  19.704  1.00 83.12           C
ATOM   1240  CE1  TYR A 153      18.923 -17.548  21.827  1.00 86.25           C
ATOM   1241  CE2  TYR A 153      17.974 -17.380  19.653  1.00 86.01           C
ATOM   1242  CZ   TYR A 153      18.620 -16.815  20.711  1.00 87.53           C
ATOM   1243  OH   TYR A 153      18.960 -15.499  20.636  1.00 91.31           O
ATOM   1244  N    ASP A 154      13.939 -20.539  22.064  1.00 89.25           N
ATOM   1245  CA   ASP A 154      12.694 -19.784  21.866  1.00 86.73           C
ATOM   1246  C    ASP A 154      12.304 -19.210  23.254  1.00 84.97           C
ATOM   1247  O    ASP A 154      12.922 -19.616  24.305  1.00 81.85           O
ATOM   1248  CB   ASP A 154      11.606 -20.658  21.163  1.00 69.99           C
ATOM   1249  CG   ASP A 154      10.110 -20.179  21.368  1.00 70.45           C
ATOM   1250  OD1  ASP A 154       9.613 -19.220  20.701  1.00 70.72           O
ATOM   1251  OD2  ASP A 154       9.378 -20.850  22.123  1.00 71.86           O1-
ATOM   1252  N    THR A 155      11.493 -18.216  23.196  1.00120.82           N
ATOM   1253  CA   THR A 155      10.967 -17.446  24.334  1.00110.32           C
ATOM   1254  C    THR A 155      10.553 -18.281  25.520  1.00 99.43           C
ATOM   1255  O    THR A 155      10.187 -17.743  26.546  1.00 91.89           O
ATOM   1256  CB   THR A 155       9.741 -16.637  23.893  1.00 96.68           C
ATOM   1257  CG2  THR A 155       8.460 -17.029  24.671  1.00 86.98           C
ATOM   1258  OG1  THR A 155      10.008 -15.248  24.070  1.00102.49           O
ATOM   1259  N    ASP A 156      10.589 -19.597  25.377  1.00 92.15           N
ATOM   1260  CA   ASP A 156       9.958 -20.477  26.365  1.00 82.90           C
ATOM   1261  C    ASP A 156      10.798 -20.760  27.586  1.00 77.72           C
ATOM   1262  O    ASP A 156      10.330 -21.371  28.517  1.00 71.30           O
ATOM   1263  CB   ASP A 156       9.538 -21.796  25.705  1.00104.90           C
ATOM   1264  CG   ASP A 156       8.141 -21.739  25.148  1.00108.70           C
ATOM   1265  OD1  ASP A 156       7.772 -20.698  24.564  1.00112.01           O
ATOM   1266  OD2  ASP A 156       7.403 -22.732  25.306  1.00109.36           O1-
ATOM   1267  N    MET A 157      12.038 -20.306  27.605  1.00110.29           N
ATOM   1268  CA   MET A 157      12.931 -20.730  28.670  1.00109.04           C
ATOM   1269  C    MET A 157      12.644 -20.155  30.059  1.00100.88           C
ATOM   1270  O    MET A 157      13.089 -20.714  31.054  1.00 99.96           O
ATOM   1271  CB   MET A 157      14.396 -20.524  28.261  1.00 79.06           C
ATOM   1272  CG   MET A 157      14.734 -19.305  27.452  1.00 84.63           C
ATOM   1273  SD   MET A 157      16.504 -19.388  27.177  1.00 98.65           S
ATOM   1274  CE   MET A 157      16.466 -19.434  25.400  1.00106.09           C
ATOM   1275  N    LEU A 158      11.919 -19.041  30.122  1.00104.16           N
ATOM   1276  CA   LEU A 158      11.942 -19.412  31.399  1.00 97.92           C
```

Fig. 7U

| | | | | | | | | | |
|---|---|---|---|---|---|---|---|---|---|
| ATOM | 1277 | C | LEU | A | 158 | 10.033 | -19.212 | 31.509 | 1.00 92.38 | C |
| ATOM | 1278 | O | LEU | A | 158 | 9.564 | -17.516 | 32.407 | 1.00 88.66 | O |
| ATOM | 1279 | CB | LEU | A | 158 | 12.194 | -17.037 | 31.565 | 1.00 58.44 | C |
| ATOM | 1280 | CG | LEU | A | 158 | 13.699 | -16.825 | 31.530 | 1.00 66.52 | C |
| ATOM | 1281 | CD1 | LEU | A | 158 | 14.008 | -15.343 | 31.484 | 1.00 69.53 | C |
| ATOM | 1282 | CD2 | LEU | A | 158 | 14.339 | -17.474 | 32.727 | 1.00 67.34 | C |
| ATOM | 1283 | N | VAL | A | 159 | 9.265 | -18.807 | 30.584 | 1.00 94.88 | N |
| ATOM | 1284 | CA | VAL | A | 159 | 7.848 | -18.594 | 30.483 | 1.00 92.59 | C |
| ATOM | 1285 | C | VAL | A | 159 | 7.137 | -19.151 | 31.688 | 1.00 86.51 | C |
| ATOM | 1286 | O | VAL | A | 159 | 6.063 | -18.670 | 32.063 | 1.00 84.42 | O |
| ATOM | 1287 | CB | VAL | A | 159 | 7.292 | -19.262 | 29.233 | 1.00 78.03 | C |
| ATOM | 1288 | CG1 | VAL | A | 159 | 5.778 | -19.304 | 29.265 | 1.00 77.24 | C |
| ATOM | 1289 | CG2 | VAL | A | 159 | 7.780 | -18.553 | 28.018 | 1.00 85.80 | C |
| ATOM | 1290 | N | LEU | A | 160 | 7.753 | -20.160 | 32.297 | 1.00100.29 | N |
| ATOM | 1291 | CA | LEU | A | 160 | 7.225 | -20.737 | 33.525 | 1.00 95.97 | C |
| ATOM | 1292 | C | LEU | A | 160 | 8.021 | -20.429 | 34.808 | 1.00 94.89 | C |
| ATOM | 1293 | O | LEU | A | 160 | 7.523 | -20.622 | 35.920 | 1.00 92.51 | O |
| ATOM | 1294 | CB | LEU | A | 160 | 7.051 | -22.227 | 33.358 | 1.00 86.73 | C |
| ATOM | 1295 | CG | LEU | A | 160 | 5.716 | -22.515 | 32.706 | 1.00 87.59 | C |
| ATOM | 1296 | CD1 | LEU | A | 160 | 5.235 | -23.869 | 33.154 | 1.00 86.86 | C |
| ATOM | 1297 | CD2 | LEU | A | 160 | 4.761 | -21.489 | 33.155 | 1.00 86.09 | C |
| ATOM | 1298 | N | VAL | A | 161 | 9.250 | -19.948 | 34.645 | 1.00 99.54 | N |
| ATOM | 1299 | CA | VAL | A | 161 | 10.089 | -19.534 | 35.763 | 1.00101.18 | C |
| ATOM | 1300 | C | VAL | A | 161 | 9.550 | -18.240 | 36.363 | 1.00 99.25 | C |
| ATOM | 1301 | O | VAL | A | 161 | 9.415 | -18.106 | 37.576 | 1.00 98.86 | O |
| ATOM | 1302 | CB | VAL | A | 161 | 11.554 | -19.330 | 35.294 | 1.00102.08 | C |
| ATOM | 1303 | CG1 | VAL | A | 161 | 12.039 | -17.927 | 35.616 | 1.00104.65 | C |
| ATOM | 1304 | CG2 | VAL | A | 161 | 12.478 | -20.394 | 35.887 | 1.00106.41 | C |
| ATOM | 1305 | N | LEU | A | 162 | 9.216 | -17.294 | 35.500 | 1.00119.43 | N |
| ATOM | 1306 | CA | LEU | A | 162 | 8.605 | -15.964 | 35.940 | 1.00119.21 | C |
| ATOM | 1307 | C | LEU | A | 162 | 7.471 | -15.881 | 36.737 | 1.00115.76 | C |
| ATOM | 1308 | O | LEU | A | 162 | 7.442 | -15.326 | 37.846 | 1.00117.51 | O |
| ATOM | 1309 | CB | LEU | A | 162 | 8.841 | -14.988 | 34.756 | 1.00 68.81 | C |
| ATOM | 1310 | CG | LEU | A | 162 | 10.216 | -14.416 | 34.374 | 1.00 74.02 | C |
| ATOM | 1311 | CD1 | LEU | A | 162 | 10.247 | -14.204 | 32.901 | 1.00 78.02 | C |
| ATOM | 1312 | CD2 | LEU | A | 162 | 10.530 | -13.100 | 35.065 | 1.00 76.08 | C |
| ATOM | 1313 | N | PRO | A | 163 | 6.373 | -16.444 | 36.202 | 1.00123.12 | N |
| ATOM | 1314 | CA | PRO | A | 163 | 5.127 | -16.344 | 36.970 | 1.00123.55 | C |
| ATOM | 1315 | C | PRO | A | 163 | 5.204 | -17.226 | 38.214 | 1.00124.20 | C |
| ATOM | 1316 | O | PRO | A | 163 | 4.643 | -16.900 | 39.254 | 1.00126.46 | O |
| ATOM | 1317 | CB | PRO | A | 163 | 4.068 | -16.887 | 36.006 | 1.00118.18 | C |
| ATOM | 1318 | CG | PRO | A | 163 | 4.819 | -17.468 | 34.837 | 1.00118.54 | C |
| ATOM | 1319 | CD | PRO | A | 163 | 6.275 | -17.456 | 35.143 | 1.00118.57 | C |
| ATOM | 1320 | N | MET | A | 164 | 5.903 | -18.343 | 38.095 | 1.00107.44 | N |
| ATOM | 1321 | CA | MET | A | 164 | 6.181 | -19.183 | 39.245 | 1.00109.37 | C |
| ATOM | 1322 | C | MET | A | 164 | 7.033 | -18.484 | 40.306 | 1.00112.94 | C |
| ATOM | 1323 | O | MET | A | 164 | 7.011 | -18.877 | 41.470 | 1.00116.44 | O |
| ATOM | 1324 | CB | MET | A | 164 | 6.855 | -20.471 | 38.795 | 1.00100.07 | C |
| ATOM | 1325 | CG | MET | A | 164 | 5.889 | -21.480 | 38.238 | 1.00 99.08 | C |
| ATOM | 1326 | SD | MET | A | 164 | 4.913 | -22.183 | 39.566 | 1.00100.66 | S |
| ATOM | 1327 | CE | MET | A | 164 | 6.227 | -22.729 | 40.650 | 1.00102.12 | C |
| ATOM | 1328 | N | LEU | A | 165 | 7.805 | -17.472 | 39.907 | 1.00106.04 | N |
| ATOM | 1329 | CA | LEU | A | 165 | 8.505 | -16.649 | 40.890 | 1.00110.81 | C |
| ATOM | 1330 | C | LEU | A | 165 | 7.511 | -15.695 | 41.508 | 1.00112.22 | C |
| ATOM | 1331 | O | LEU | A | 165 | 7.444 | -15.544 | 42.734 | 1.00117.17 | O |
| ATOM | 1332 | CB | LEU | A | 165 | 9.664 | -15.875 | 40.263 | 1.00 70.84 | C |
| ATOM | 1333 | CG | LEU | A | 165 | 11.024 | -16.579 | 40.281 | 1.00 75.26 | C |
| ATOM | 1334 | CD1 | LEU | A | 165 | 12.166 | -15.713 | 39.753 | 1.00 80.36 | C |
| ATOM | 1335 | CD2 | LEU | A | 165 | 11.303 | -17.036 | 41.699 | 1.00 80.44 | C |
| ATOM | 1336 | N | ILE | A | 166 | 6.723 | -15.066 | 40.645 | 1.00103.59 | N |
| ATOM | 1337 | CA | ILE | A | 166 | 5.676 | -14.145 | 41.078 | 1.00105.69 | C |

Fig. 7V

```
ATOM  1338  C    ILE A 166     4.750 -14.742  42.151  1.00108.30           C
ATOM  1339  O    ILE A 166     4.348 -14.050  43.094  1.00113.74           O
ATOM  1340  CB   ILE A 166     4.839 -13.672  39.974  1.00 65.02           C
ATOM  1341  CG1  ILE A 166     5.648 -12.687  39.020  1.00 65.88           C
ATOM  1342  CG2  ILE A 166     3.348 -13.072  40.341  1.00 67.98           C
ATOM  1343  CD1  ILE A 166     4.903 -12.144  37.818  1.00 65.55           C
ATOM  1344  N    LEU A 167     4.433 -16.025  42.008  1.00 83.94           N
ATOM  1345  CA   LEU A 167     3.327 -16.713  42.913  1.00 87.41           C
ATOM  1346  C    LEU A 167     4.159 -17.905  44.283  1.00 92.66           C
ATOM  1347  O    LEU A 167     3.892 -16.919  45.324  1.00 98.54           O
ATOM  1348  CB   LEU A 167     3.921 -18.011  43.266  1.00 85.95           C
ATOM  1349  CG   LEU A 167     2.264 -19.049  43.128  1.00 90.00           C
ATOM  1350  CD1  LEU A 167     0.744 -19.039  42.923  1.00 92.38           C
ATOM  1351  CD2  LEU A 167     2.805 -20.439  42.854  1.00 87.86           C
ATOM  1352  N    LEU A 168     5.435 -17.372  44.295  1.00122.57           N
ATOM  1353  CA   LEU A 168     6.317 -17.342  45.566  1.00129.33           C
ATOM  1354  C    LEU A 168     6.132 -16.197  46.217  1.00135.03           C
ATOM  1355  O    LEU A 168     6.143 -16.080  47.427  1.00142.95           O
ATOM  1356  CB   LEU A 168     7.532 -18.047  45.384  1.00 76.65           C
ATOM  1357  CG   LEU A 168     8.422 -17.535  46.506  1.00 85.49           C
ATOM  1358  CD1  LEU A 168     9.272 -18.643  47.123  1.00 91.12           C
ATOM  1359  CD2  LEU A 168     9.256 -16.377  45.983  1.00 85.13           C
ATOM  1360  N    THR A 169     6.358 -15.171  45.401  1.00 89.90           N
ATOM  1361  CA   THR A 169     6.292 -13.815  45.911  1.00 95.41           C
ATOM  1362  C    THR A 169     4.945 -13.577  46.653  1.00 99.90           C
ATOM  1363  O    THR A 169     4.927 -13.198  47.849  1.00108.93           O
ATOM  1364  CB   THR A 169     6.481 -12.901  44.760  1.00 80.59           C
ATOM  1365  CG2  THR A 169     5.533 -11.535  44.908  1.00 83.03           C
ATOM  1366  OG1  THR A 169     7.846 -12.342  44.742  1.00 84.48           O
ATOM  1367  N    PHE A 170     3.839 -13.818  45.941  1.00 92.31           N
ATOM  1368  CA   PHE A 170     2.494 -13.694  46.512  1.00 97.44           C
ATOM  1369  C    PHE A 170     2.424 -14.396  47.847  1.00104.97           C
ATOM  1370  O    PHE A 170     2.094 -13.709  48.867  1.00114.00           O
ATOM  1371  CB   PHE A 170     1.425 -14.307  45.602  1.00107.60           C
ATOM  1372  CG   PHE A 170     1.019 -13.430  44.440  1.00104.80           C
ATOM  1373  CD1  PHE A 170     1.734 -12.272  44.122  1.00103.64           C
ATOM  1374  CD2  PHE A 170    -0.086 -13.766  43.660  1.00108.62           C
ATOM  1375  CE1  PHE A 170     1.350 -11.466  43.049  1.00102.26           C
ATOM  1376  CE2  PHE A 170    -0.480 -12.967  42.584  1.00103.68           C
ATOM  1377  CZ   PHE A 170     0.236 -11.814  42.280  1.00102.45           C
ATOM  1378  N    ILE A 171     2.735 -15.687  47.839  1.00 89.44           N
ATOM  1379  CA   ILE A 171     2.624 -16.498  49.062  1.00 97.20           C
ATOM  1380  C    ILE A 171     3.491 -15.971  50.208  1.00106.33           C
ATOM  1381  O    ILE A 171     3.014 -15.841  51.336  1.00115.60           O
ATOM  1382  CB   ILE A 171     2.865 -17.999  48.739  1.00 83.31           C
ATOM  1383  CG1  ILE A 171     2.049 -18.371  47.496  1.00 86.06           C
ATOM  1384  CG2  ILE A 171     2.534 -18.890  49.941  1.00102.19           C
ATOM  1385  CD1  ILE A 171     1.897 -19.843  47.261  1.00 83.11           C
ATOM  1386  N    ARG A 172     4.745 -15.634  49.924  1.00 99.76           N
ATOM  1387  CA   ARG A 172     5.633 -15.151  50.965  1.00109.97           C
ATOM  1388  C    ARG A 172     5.014 -13.895  51.558  1.00118.08           C
ATOM  1389  O    ARG A 172     5.086 -13.669  52.766  1.00130.02           O
ATOM  1390  CB   ARG A 172     7.067 -14.813  50.459  1.00139.00           C
ATOM  1391  CG   ARG A 172     8.114 -14.967  51.578  1.00147.60           C
ATOM  1392  CD   ARG A 172     9.518 -15.149  51.061  1.00147.73           C
ATOM  1393  NE   ARG A 172    10.360 -14.030  51.431  1.00149.94           N
ATOM  1394  CZ   ARG A 172    10.045 -12.769  51.178  1.00143.27           C
ATOM  1395  NH1  ARG A 172     8.908 -12.476  50.553  1.00136.07           N1+
ATOM  1396  NH2  ARG A 172    10.957 -11.765  51.541  1.00147.42           N
ATOM  1397  N    LEU A 173     4.370 -13.090  50.699  1.00 95.45           N
ATOM  1398  CA   LEU A 173     3.603 -11.957  51.242  1.00103.92           C
```

Fig. 7W

| | | | | | | | | | |
|---|---|---|---|---|---|---|---|---|---|
| ATOM | 1399 | C | LEU | A | 173 | 2.495 | -12.424 | 52.161 | 1.00 111.74 | C |
| ATOM | 1400 | O | LEU | A | 173 | 2.396 | -11.935 | 53.269 | 1.00 124.00 | O |
| ATOM | 1401 | CB | LEU | A | 173 | 3.000 | -11.057 | 50.163 | 1.00 107.68 | C |
| ATOM | 1402 | CG | LEU | A | 173 | 2.315 | -9.834 | 50.779 | 1.00 117.91 | C |
| ATOM | 1403 | CD1 | LEU | A | 173 | 3.378 | -8.971 | 51.400 | 1.00 125.35 | C |
| ATOM | 1404 | CD2 | LEU | A | 173 | 1.514 | -9.057 | 49.753 | 1.00 113.16 | C |
| ATOM | 1405 | N | THR | A | 174 | 1.663 | -13.357 | 51.704 | 1.00 110.31 | N |
| ATOM | 1406 | CA | THR | A | 174 | 0.579 | -13.861 | 52.550 | 1.00 118.56 | C |
| ATOM | 1407 | C | THR | A | 174 | 1.071 | -14.248 | 53.936 | 1.00 130.36 | C |
| ATOM | 1408 | O | THR | A | 174 | 0.462 | -13.900 | 54.956 | 1.00 143.29 | O |
| ATOM | 1409 | CB | THR | A | 174 | -0.088 | -15.139 | 52.002 | 1.00 109.84 | C |
| ATOM | 1410 | CG2 | THR | A | 174 | -1.546 | -15.218 | 52.461 | 1.00 118.10 | C |
| ATOM | 1411 | OG1 | THR | A | 174 | -0.018 | -15.167 | 50.576 | 1.00 97.91 | O |
| ATOM | 1412 | N | ILE | A | 175 | 2.166 | -14.994 | 53.976 | 1.00 124.89 | N |
| ATOM | 1413 | CA | ILE | A | 175 | 2.607 | -15.575 | 55.234 | 1.00 136.96 | C |
| ATOM | 1414 | C | ILE | A | 175 | 3.438 | -14.627 | 56.098 | 1.00 146.66 | C |
| ATOM | 1415 | O | ILE | A | 175 | 3.027 | -14.263 | 57.195 | 1.00 163.26 | O |
| ATOM | 1416 | CB | ILE | A | 175 | 3.341 | -16.895 | 55.000 | 1.00 142.52 | C |
| ATOM | 1417 | CG1 | ILE | A | 175 | 2.342 | -17.931 | 54.477 | 1.00 134.11 | C |
| ATOM | 1418 | CG2 | ILE | A | 175 | 4.036 | -17.348 | 56.277 | 1.00 157.78 | C |
| ATOM | 1419 | CD1 | ILE | A | 175 | 2.732 | -19.361 | 54.745 | 1.00 133.97 | C |
| ATOM | 1420 | N | ASN | A | 176 | 4.593 | -14.221 | 55.571 | 1.00 132.96 | N |
| ATOM | 1421 | CA | ASN | A | 176 | 5.508 | -13.385 | 56.341 | 1.00 145.26 | C |
| ATOM | 1422 | C | ASN | A | 176 | 5.163 | -11.903 | 56.314 | 1.00 148.10 | C |
| ATOM | 1423 | O | ASN | A | 176 | 5.646 | -11.144 | 57.148 | 1.00 161.70 | O |
| ATOM | 1424 | CB | ASN | A | 176 | 6.950 | -13.584 | 55.879 | 1.00 190.14 | C |
| ATOM | 1425 | CG | ASN | A | 176 | 7.414 | -15.014 | 56.032 | 1.00 185.99 | C |
| ATOM | 1426 | ND2 | ASN | A | 176 | 6.746 | -15.774 | 56.883 | 1.00 193.93 | N |
| ATOM | 1427 | OD1 | ASN | A | 176 | 8.357 | -15.437 | 55.358 | 1.00 176.73 | O |
| ATOM | 1428 | N | LYS | A | 177 | 4.338 | -11.509 | 55.354 | 1.00 126.70 | N |
| ATOM | 1429 | CA | LYS | A | 177 | 3.922 | -10.100 | 55.201 | 1.00 130.47 | C |
| ATOM | 1430 | C | LYS | A | 177 | 5.092 | -9.102 | 55.234 | 1.00 132.38 | C |
| ATOM | 1431 | O | LYS | A | 177 | 4.874 | -7.911 | 55.470 | 1.00 139.91 | O |
| ATOM | 1432 | CB | LYS | A | 177 | 2.877 | -9.720 | 56.255 | 1.00 111.72 | C |
| ATOM | 1433 | CG | LYS | A | 177 | 1.715 | -10.699 | 56.360 | 1.00 112.03 | C |
| ATOM | 1434 | CD | LYS | A | 177 | 0.587 | -10.130 | 57.184 | 1.00 125.20 | C |
| ATOM | 1435 | CE | LYS | A | 177 | -0.551 | -11.116 | 57.300 | 1.00 126.17 | C |
| ATOM | 1436 | NZ | LYS | A | 177 | -1.679 | -10.486 | 58.031 | 1.00 139.64 | N1+ |
| ATOM | 1437 | N | ASP | A | 178 | 6.298 | -9.591 | 54.994 | 1.00 211.62 | N |
| ATOM | 1438 | CA | ASP | A | 178 | 7.484 | -8.743 | 55.007 | 1.00 213.71 | C |
| ATOM | 1439 | C | ASP | A | 178 | 7.499 | -7.873 | 53.763 | 1.00 209.07 | C |
| ATOM | 1440 | O | ASP | A | 178 | 7.071 | -8.295 | 52.691 | 1.00 199.56 | O |
| ATOM | 1441 | CB | ASP | A | 178 | 8.780 | -9.585 | 55.092 | 1.00 169.89 | C |
| ATOM | 1442 | CG | ASP | A | 178 | 9.139 | -10.215 | 53.761 | 1.00 171.80 | C |
| ATOM | 1443 | OD1 | ASP | A | 178 | 8.235 | -10.500 | 52.946 | 1.00 176.06 | O |
| ATOM | 1444 | OD2 | ASP | A | 178 | 10.352 | -10.420 | 53.534 | 1.00 169.81 | O1- |
| ATOM | 1445 | N | ILE | A | 179 | 8.092 | -6.656 | 53.908 | 1.00 193.10 | N |
| ATOM | 1446 | CA | ILE | A | 179 | 7.887 | -5.673 | 52.846 | 1.00 191.17 | C |
| ATOM | 1447 | C | ILE | A | 179 | 8.681 | -5.966 | 51.580 | 1.00 181.89 | C |
| ATOM | 1448 | O | ILE | A | 179 | 8.319 | -5.511 | 50.516 | 1.00 177.51 | O |
| ATOM | 1449 | CB | ILE | A | 179 | 8.255 | -4.259 | 53.329 | 1.00 179.01 | C |
| ATOM | 1450 | CG1 | ILE | A | 179 | 7.569 | -3.946 | 54.659 | 1.00 189.61 | C |
| ATOM | 1451 | CG2 | ILE | A | 179 | 7.866 | -3.227 | 52.292 | 1.00 178.14 | C |
| ATOM | 1452 | CD1 | ILE | A | 179 | 7.945 | -2.590 | 55.234 | 1.00 202.73 | C |
| ATOM | 1453 | N | PHE | A | 180 | 9.755 | -6.762 | 51.657 | 1.00 160.29 | N |
| ATOM | 1454 | CA | PHE | A | 180 | 10.526 | -7.002 | 50.439 | 1.00 152.75 | C |
| ATOM | 1455 | C | PHE | A | 180 | 9.655 | -7.922 | 49.281 | 1.00 142.47 | C |
| ATOM | 1456 | O | PHE | A | 180 | 9.960 | -7.186 | 48.116 | 1.00 137.66 | O |
| ATOM | 1457 | CB | PHE | A | 180 | 11.744 | -7.899 | 50.712 | 1.00 161.22 | C |
| ATOM | 1458 | CG | PHE | A | 180 | 12.918 | -7.154 | 51.315 | 1.00 172.03 | C |
| ATOM | 1459 | CD1 | PHE | A | 180 | 12.756 | -6.386 | 52.465 | 1.00 182.22 | C |

Fig. 7X

| | | | | | | | | |
|---|---|---|---|---|---|---|---|---|
|ATOM|1460|CD2|PHE A 180|14.175|-7.201|50.719|1.00|172.10|C|
|ATOM|1461|CE1|PHE A 180|13.822|-5.690|53.007|1.00|193.72|C|
|ATOM|1462|CE2|PHE A 180|15.242|-6.507|51.262|1.00|183.36|C|
|ATOM|1463|CZ|PHE A 180|15.063|-5.751|52.409|1.00|194.57|C|
|ATOM|1464|N|THR A 181|8.623|-6.308|49.599|1.00|145.34|N|
|ATOM|1465|CA|THR A 181|7.635|-6.751|48.598|1.00|137.98|C|
|ATOM|1466|C|THR A 181|7.095|-7.618|47.723|1.00|138.84|C|
|ATOM|1467|O|THR A 181|7.050|-7.750|46.503|1.00|133.08|O|
|ATOM|1468|CB|THR A 181|6.447|-9.512|49.232|1.00|140.97|C|
|ATOM|1469|CG2|THR A 181|5.248|-9.484|48.312|1.00|137.76|C|
|ATOM|1470|OG1|THR A 181|6.809|-10.680|49.451|1.00|136.94|O|
|ATOM|1471|N|LEU A 182|6.678|-6.519|48.349|1.00|126.10|N|
|ATOM|1472|CA|LEU A 182|6.221|-5.320|47.622|1.00|128.88|C|
|ATOM|1473|C|LEU A 182|7.172|-4.869|46.507|1.00|126.73|C|
|ATOM|1474|O|LEU A 182|6.738|-4.252|45.534|1.00|127.04|O|
|ATOM|1475|CB|LEU A 182|6.009|-4.133|48.587|1.00|126.45|C|
|ATOM|1476|CG|LEU A 182|4.776|-3.869|49.459|1.00|131.31|C|
|ATOM|1477|CD1|LEU A 182|5.077|-2.702|50.334|1.00|141.95|C|
|ATOM|1478|CD2|LEU A 182|3.519|-3.656|48.822|1.00|126.13|C|
|ATOM|1479|N|LEU A 183|8.473|-5.116|46.670|1.00|114.07|N|
|ATOM|1480|CA|LEU A 183|9.406|-4.676|45.633|1.00|112.16|C|
|ATOM|1481|C|LEU A 183|9.467|-5.722|44.536|1.00|102.75|C|
|ATOM|1482|O|LEU A 183|9.535|-5.396|43.342|1.00|101.14|O|
|ATOM|1483|CB|LEU A 183|10.801|-4.443|46.257|1.00|109.69|C|
|ATOM|1484|CG|LEU A 183|11.146|-2.950|46.291|1.00|113.53|C|
|ATOM|1485|CD1|LEU A 183|12.636|-2.736|46.127|1.00|123.11|C|
|ATOM|1486|CD2|LEU A 183|10.379|-2.188|45.226|1.00|120.57|C|
|ATOM|1487|N|LEU A 184|9.382|-6.982|44.962|1.00|118.31|N|
|ATOM|1488|CA|LEU A 184|9.504|-8.122|44.084|1.00|110.69|C|
|ATOM|1489|C|LEU A 184|8.463|-8.412|43.112|1.00|108.80|C|
|ATOM|1490|O|LEU A 184|8.688|-8.444|41.903|1.00|104.70|O|
|ATOM|1491|CB|LEU A 184|10.007|-9.360|44.892|1.00|93.16|C|
|ATOM|1492|CG|LEU A 184|11.287|-9.091|45.695|1.00|98.68|C|
|ATOM|1493|CD1|LEU A 184|12.146|-10.328|45.890|1.00|96.34|C|
|ATOM|1494|CD2|LEU A 184|12.108|-8.027|44.998|1.00|99.82|C|
|ATOM|1495|N|SER A 185|7.243|-8.599|43.602|1.00|105.86|N|
|ATOM|1496|CA|SER A 185|6.169|-8.951|42.673|1.00|103.86|C|
|ATOM|1497|C|SER A 185|5.947|-7.933|41.542|1.00|105.71|C|
|ATOM|1498|O|SER A 185|5.795|-8.327|40.386|1.00|102.20|O|
|ATOM|1499|CB|SER A 185|4.858|-9.269|43.390|1.00|80.70|C|
|ATOM|1500|OG|SER A 185|4.609|-8.304|44.371|1.00|87.92|O|
|ATOM|1501|N|PRO A 186|5.971|-6.633|41.859|1.00|105.77|N|
|ATOM|1502|CA|PRO A 186|5.835|-5.680|40.743|1.00|108.52|C|
|ATOM|1503|C|PRO A 186|7.091|-5.620|39.865|1.00|106.97|C|
|ATOM|1504|O|PRO A 186|6.374|-5.261|38.719|1.00|108.38|O|
|ATOM|1505|CB|PRO A 186|5.568|-4.348|41.434|1.00|89.44|C|
|ATOM|1506|CG|PRO A 186|6.142|-4.503|42.773|1.00|90.66|C|
|ATOM|1507|CD|PRO A 186|5.927|-5.930|43.168|1.00|84.67|C|
|ATOM|1508|N|ILE A 187|8.252|-5.981|40.434|1.00|100.13|N|
|ATOM|1509|CA|ILE A 187|9.444|-6.205|39.607|1.00|98.69|C|
|ATOM|1510|C|ILE A 187|9.337|-7.471|38.731|1.00|92.03|C|
|ATOM|1511|O|ILE A 187|9.453|-7.400|37.502|1.00|92.26|O|
|ATOM|1512|CB|ILE A 187|10.713|-6.281|40.453|1.00|94.68|C|
|ATOM|1513|CG1|ILE A 187|11.342|-4.881|40.729|1.00|102.83|C|
|ATOM|1514|CG2|ILE A 187|11.796|-7.147|39.760|1.00|91.06|C|
|ATOM|1515|CD1|ILE A 187|12.622|-4.887|41.320|1.00|106.19|C|
|ATOM|1516|N|PHE A 188|9.113|-8.624|39.347|1.00|100.08|N|
|ATOM|1517|CA|PHE A 188|8.906|-9.822|38.557|1.00|94.77|C|
|ATOM|1518|C|PHE A 188|7.844|-9.500|37.478|1.00|95.82|C|
|ATOM|1519|O|PHE A 188|8.147|-9.710|36.283|1.00|95.34|O|
|ATOM|1520|CB|PHE A 188|8.370|-11.009|39.441|1.00|106.25|C|

Fig. 7Y

```
ATOM   1521  CG  PHE A 188       9.747 -11.533  40.190  1.00105.40           C
ATOM   1522  CD1 PHE A 188       9.589 -12.420  41.241  1.00105.58           C
ATOM   1523  CD2 PHE A 188      11.023 -11.132  39.841  1.00105.78           C
ATOM   1524  CE1 PHE A 188      10.682 -12.899  41.920  1.00104.53           C
ATOM   1525  CE2 PHE A 188      12.118 -11.610  40.515  1.00105.32           C
ATOM   1526  CZ  PHE A 188      11.951 -12.492  41.555  1.00103.70           C
ATOM   1527  N   ILE A 189       6.623  -9.264  37.896  1.00103.30           N
ATOM   1528  CA  ILE A 189       5.824  -8.903  36.982  1.00105.65           C
ATOM   1529  C   ILE A 189       5.939  -8.013  35.804  1.00109.99           C
ATOM   1530  O   ILE A 189       5.319  -8.052  34.734  1.00112.61           O
ATOM   1531  CB  ILE A 189       4.420  -8.162  37.730  1.00 99.69           C
ATOM   1532  CG1 ILE A 189       3.177  -9.019  37.848  1.00 98.10           C
ATOM   1533  CG2 ILE A 189       4.630  -6.931  36.971  1.00104.95           C
ATOM   1534  CD1 ILE A 189       2.137  -8.693  36.802  1.00 98.84           C
ATOM   1535  N   MET A 190       6.969  -7.190  36.015  1.00 97.32           N
ATOM   1536  CA  MET A 190       7.496  -6.316  34.965  1.00103.71           C
ATOM   1537  C   MET A 190       8.417  -7.081  34.016  1.00102.63           C
ATOM   1538  O   MET A 190       8.215  -7.097  32.794  1.00107.29           O
ATOM   1539  CB  MET A 190       8.266  -5.143  35.582  1.00 99.55           C
ATOM   1540  CG  MET A 190       7.417  -4.080  36.273  1.00104.43           C
ATOM   1541  SD  MET A 190       8.348  -2.547  36.512  1.00113.42           S
ATOM   1542  CE  MET A 190       8.302  -1.883  34.849  1.00120.68           C
ATOM   1543  N   ILE A 191       9.425  -7.719  34.601  1.00 93.17           N
ATOM   1544  CA  ILE A 191      10.346  -8.539  33.842  1.00 92.65           C
ATOM   1545  C   ILE A 191       9.589  -9.541  32.989  1.00 90.48           C
ATOM   1546  O   ILE A 191       9.806  -9.592  31.777  1.00 94.57           O
ATOM   1547  CB  ILE A 191      11.292  -9.295  34.762  1.00 74.14           C
ATOM   1548  CG1 ILE A 191      12.138  -8.292  35.564  1.00 78.84           C
ATOM   1549  CG2 ILE A 191      12.123 -10.319  33.959  1.00 72.90           C
ATOM   1550  CD1 ILE A 191      12.822  -8.886  36.815  1.00 76.40           C
ATOM   1551  N   TYR A 192       8.702 -10.329  33.610  1.00 84.77           N
ATOM   1552  CA  TYR A 192       7.836 -11.255  32.863  1.00 83.78           C
ATOM   1553  C   TYR A 192       7.194 -10.541  31.678  1.00 91.42           C
ATOM   1554  O   TYR A 192       7.245 -11.018  30.547  1.00 94.66           O
ATOM   1555  CB  TYR A 192       6.750 -11.858  33.757  1.00102.87           C
ATOM   1556  CG  TYR A 192       6.061 -13.081  33.166  1.00101.17           C
ATOM   1557  CD1 TYR A 192       6.624 -13.783  32.124  1.00101.97           C
ATOM   1558  CD2 TYR A 192       4.842 -13.530  33.652  1.00 99.87           C
ATOM   1559  CE1 TYR A 192       5.996 -14.901  31.578  1.00101.50           C
ATOM   1560  CE2 TYR A 192       4.207 -14.640  33.107  1.00 99.40           C
ATOM   1561  CZ  TYR A 192       4.793 -15.322  32.069  1.00100.20           C
ATOM   1562  OH  TYR A 192       4.134 -16.434  31.510  1.00100.69           O
ATOM   1563  N   LEU A 193       6.620  -9.371  31.946  1.00 75.32           N
ATOM   1564  CA  LEU A 193       5.918  -8.690  30.924  1.00 84.21           C
ATOM   1565  C   LEU A 193       6.885  -8.057  29.846  1.00 91.13           C
ATOM   1566  O   LEU A 193       6.521  -7.865  28.682  1.00 99.40           O
ATOM   1567  CB  LEU A 193       5.126  -7.450  31.601  1.00 84.71           C
ATOM   1568  CG  LEU A 193       3.644  -7.221  31.261  1.00 90.47           C
ATOM   1569  CD1 LEU A 193       2.912  -8.530  31.115  1.00 87.13           C
ATOM   1570  CD2 LEU A 193       2.979  -6.370  32.318  1.00 94.07           C
ATOM   1571  N   TRP A 194       8.123  -7.796  30.244  1.00117.66           N
ATOM   1572  CA  TRP A 194       9.135  -7.403  29.282  1.00124.58           C
ATOM   1573  C   TRP A 194       9.389  -8.550  28.357  1.00124.97           C
ATOM   1574  O   TRP A 194       9.257  -8.434  27.140  1.00132.36           O
ATOM   1575  CB  TRP A 194      10.461  -7.105  29.976  1.00 97.53           C
ATOM   1576  CG  TRP A 194      11.627  -7.023  29.001  1.00 94.32           C
ATOM   1577  CD1 TRP A 194      11.892  -6.278  27.853  1.00104.82           C
ATOM   1578  CD2 TRP A 194      12.883  -7.693  29.108  1.00 89.41           C
ATOM   1579  CE2 TRP A 194      13.654  -7.315  28.000  1.00 97.25           C
ATOM   1580  CE3 TRP A 194      13.425  -8.595  30.031  1.00 79.36           C
ATOM   1581  NE1 TRP A 194      12.908  -6.449  27.248  1.00106.63           N
```

Fig. 7Z

```
ATOM   1582  CZ2 TRP A 194      14.932  -7.800  27.794  1.00 93.28           C
ATOM   1583  CZ3 TRP A 194      14.693  -9.056  29.927  1.00 75.39           C
ATOM   1584  CH2 TRP A 194      15.432  -8.668  28.719  1.00 82.28           C
ATOM   1585  N   TRP A 195       9.752  -9.663  28.981  1.00 98.64           N
ATOM   1586  CA  TRP A 195      10.427 -10.769  28.329  1.00 93.08           C
ATOM   1587  C   TRP A 195       9.446 -11.788  27.770  1.00 90.87           C
ATOM   1588  O   TRP A 195       9.822 -12.911  27.425  1.00 83.15           O
ATOM   1589  CB  TRP A 195      11.417 -11.402  29.314  1.00137.33           C
ATOM   1590  CG  TRP A 195      12.101 -12.656  28.844  1.00128.60           C
ATOM   1591  CD1 TRP A 195      13.363 -12.784  28.311  1.00127.33           C
ATOM   1592  CD2 TRP A 195      11.561 -13.957  28.898  1.00121.40           C
ATOM   1593  NE1 TRP A 195      12.524 -14.835  28.377  1.00115.74           N
ATOM   1594  CE2 TRP A 195      10.342 -14.469  29.330  1.00126.70           C
ATOM   1595  NE1 TRP A 195      13.623 -14.097  28.025  1.00119.63           N
ATOM   1596  CZ2 TRP A 195      12.305 -16.181  28.299  1.00109.24           C
ATOM   1597  CZ3 TRP A 195      10.123 -15.792  29.230  1.00114.68           C
ATOM   1598  CH2 TRP A 195      11.094 -16.644  28.719  1.00106.66           C
ATOM   1599  N   TYR A 196       9.187 -11.363  27.669  1.00 86.38           N
ATOM   1600  CA  TYR A 196       7.118 -12.104  26.398  1.00 90.49           C
ATOM   1601  C   TYR A 196       5.875 -11.225  27.000  1.00 98.36           C
ATOM   1602  O   TYR A 196       5.894 -11.246  27.953  1.00 93.33           O
ATOM   1603  CB  TYR A 196       6.826 -13.424  27.714  1.00 98.79           C
ATOM   1604  CG  TYR A 196       5.991 -14.412  26.926  1.00101.38           C
ATOM   1605  CD1 TYR A 196       5.899 -15.722  27.322  1.00 95.73           C
ATOM   1606  CD2 TYR A 196       5.301 -14.034  25.787  1.00110.94           C
ATOM   1607  CE1 TYR A 196       5.145 -16.630  26.614  1.00 99.54           C
ATOM   1608  CE2 TYR A 196       4.545 -14.939  25.077  1.00114.94           C
ATOM   1609  CZ  TYR A 196       4.473 -16.236  25.501  1.00107.78           C
ATOM   1610  OH  TYR A 196       3.723 -17.160  24.819  1.00108.77           O
ATOM   1611  N   PRO A 197       5.673 -10.465  25.919  1.00 87.07           N
ATOM   1612  CA  PRO A 197       4.603  -9.470  25.859  1.00 94.60           C
ATOM   1613  C   PRO A 197       3.219 -10.069  26.126  1.00 94.80           C
ATOM   1614  O   PRO A 197       2.250  -9.356  26.407  1.00101.21           O
ATOM   1615  CB  PRO A 197       4.668  -8.994  24.406  1.00143.81           C
ATOM   1616  CG  PRO A 197       5.147 -10.180  23.682  1.00141.72           C
ATOM   1617  CD  PRO A 197       6.201 -10.763  24.577  1.00127.07           C
ATOM   1618  N   SER A 198       3.125 -11.383  26.023  1.00 98.34           N
ATOM   1619  CA  SER A 198       1.828 -12.002  25.920  1.00101.70           C
ATOM   1620  C   SER A 198       1.399 -13.512  27.265  1.00 90.37           C
ATOM   1621  O   SER A 198       0.245 -12.861  27.467  1.00 92.04           O
ATOM   1622  CB  SER A 198       1.866 -13.112  24.879  1.00 97.64           C
ATOM   1623  OG  SER A 198       2.427 -12.639  23.670  1.00104.57           O
ATOM   1624  N   SER A 199       2.327 -12.532  28.203  1.00 92.98           N
ATOM   1625  CA  SER A 199       1.982 -12.986  29.530  1.00 84.03           C
ATOM   1626  C   SER A 199       0.370 -12.004  30.037  1.00 87.58           C
ATOM   1627  O   SER A 199       0.492 -12.153  31.217  1.00 82.98           O
ATOM   1628  CB  SER A 199       3.226 -13.084  30.414  1.00 80.87           C
ATOM   1629  OG  SER A 199       3.922 -11.853  30.472  1.00 83.70           O
ATOM   1630  N   TYR A 200       0.619 -11.000  29.303  1.00 90.52           N
ATOM   1631  CA  TYR A 200      -0.292  -9.868  29.776  1.00103.90           C
ATOM   1632  C   TYR A 200      -1.504 -10.538  30.502  1.00102.60           C
ATOM   1633  O   TYR A 200      -1.587 -10.498  31.730  1.00 97.33           O
ATOM   1634  CB  TYR A 200      -0.750  -9.051  28.554  1.00108.69           C
ATOM   1635  CG  TYR A 200      -1.643  -7.907  29.206  1.00114.79           C
ATOM   1636  CD1 TYR A 200      -0.909  -6.818  29.786  1.00113.64           C
ATOM   1637  CD2 TYR A 200      -2.921  -7.937  29.203  1.00122.95           C
ATOM   1638  CE1 TYR A 200      -1.628  -5.783  30.316  1.00119.91           C
ATOM   1639  CE2 TYR A 200      -3.650  -6.904  29.727  1.00129.61           C
ATOM   1640  CZ  TYR A 200      -3.902  -5.830  30.283  1.00127.62           C
ATOM   1641  OH  TYR A 200      -3.741  -4.798  30.810  1.00135.07           O
ATOM   1642  N   SER A 201      -2.456 -11.069  29.745  1.00125.83           N
```

Fig. 7AA

```
ATOM   1643  CA  SER A 201      -3.616 -11.703  30.341  1.00125.56           C
ATOM   1644  C   SER A 201      -3.283 -12.539  31.580  1.00113.58           C
ATOM   1645  O   SER A 201      -3.872 -12.297  32.617  1.00112.15           O
ATOM   1646  CB  SER A 201      -4.346 -12.536  29.313  1.00119.38           C
ATOM   1647  OG  SER A 201      -3.400 -13.169  28.491  1.00118.44           O
ATOM   1648  N   LEU A 202      -2.360 -13.503  31.485  1.00 98.59           N
ATOM   1649  CA  LEU A 202      -1.937 -14.307  32.651  1.00 88.69           C
ATOM   1650  C   LEU A 202      -1.620 -13.473  33.929  1.00 84.91           C
ATOM   1651  O   LEU A 202      -2.025 -13.797  35.069  1.00 81.69           O
ATOM   1652  CB  LEU A 202      -0.738 -15.181  32.258  1.00 93.88           C
ATOM   1653  CG  LEU A 202      -0.030 -16.146  33.230  1.00 85.09           C
ATOM   1654  CD1 LEU A 202       0.753 -15.452  34.386  1.00 78.84           C
ATOM   1655  CD2 LEU A 202      -0.971 -17.214  33.770  1.00 84.81           C
ATOM   1656  N   ASN A 203      -0.906 -12.376  33.741  1.00105.24           N
ATOM   1657  CA  ASN A 203      -0.604 -11.460  34.833  1.00103.90           C
ATOM   1658  C   ASN A 203      -1.919 -10.738  35.362  1.00109.88           C
ATOM   1659  O   ASN A 203      -2.044 -10.684  36.588  1.00109.30           O
ATOM   1660  CB  ASN A 203       0.390 -10.429  34.352  1.00 89.58           C
ATOM   1661  CG  ASN A 203       1.727 -11.041  34.038  1.00 82.93           C
ATOM   1662  ND2 ASN A 203       2.224 -10.820  32.816  1.00 87.01           N
ATOM   1663  OD1 ASN A 203       2.306 -11.727  34.895  1.00 76.02           O
ATOM   1664  N   PHE A 204      -2.600 -10.229  34.425  1.00 91.63           N
ATOM   1665  CA  PHE A 204      -3.858  -9.614  34.775  1.00 98.67           C
ATOM   1666  C   PHE A 204      -4.581 -10.535  35.730  1.00 95.08           C
ATOM   1667  O   PHE A 204      -4.767 -10.205  36.879  1.00 94.24           O
ATOM   1668  CB  PHE A 204      -4.733  -9.376  33.551  1.00 84.77           C
ATOM   1669  CG  PHE A 204      -5.942  -8.545  33.841  1.00 94.38           C
ATOM   1670  CD1 PHE A 204      -5.850  -7.159  33.912  1.00101.17           C
ATOM   1671  CD2 PHE A 204      -7.168  -9.144  34.084  1.00 99.64           C
ATOM   1672  CE1 PHE A 204      -6.971  -6.389  34.190  1.00111.86           C
ATOM   1673  CE2 PHE A 204      -8.289  -8.379  34.330  1.00111.02           C
ATOM   1674  CZ  PHE A 204      -8.191  -7.001  34.389  1.00117.02           C
ATOM   1675  N   ALA A 205      -4.968 -11.698  35.230  1.00117.75           N
ATOM   1676  CA  ALA A 205      -5.594 -12.766  35.996  1.00115.79           C
ATOM   1677  C   ALA A 205      -4.978 -13.057  37.372  1.00110.19           C
ATOM   1678  O   ALA A 205      -5.689 -13.046  38.388  1.00113.40           O
ATOM   1679  CB  ALA A 205      -5.623 -14.013  35.165  1.00 64.00           C
ATOM   1680  N   MET A 206      -3.679 -13.353  37.419  1.00119.42           N
ATOM   1681  CA  MET A 206      -3.076 -13.590  38.739  1.00116.66           C
ATOM   1682  C   MET A 206      -3.264 -12.432  39.715  1.00121.40           C
ATOM   1683  O   MET A 206      -3.472 -12.643  40.923  1.00122.94           O
ATOM   1684  CB  MET A 206      -1.606 -13.912  38.593  1.00112.32           C
ATOM   1685  CG  MET A 206      -1.371 -15.321  38.195  1.00107.87           C
ATOM   1686  SD  MET A 206       0.373 -15.606  38.095  1.00100.57           S
ATOM   1687  CE  MET A 206       0.862 -15.252  39.775  1.00100.61           C
ATOM   1688  N   ILE A 207      -3.198 -11.204  39.195  1.00 86.03           N
ATOM   1689  CA  ILE A 207      -3.496 -10.029  40.025  1.00 92.49           C
ATOM   1690  C   ILE A 207      -4.969  -9.953  40.461  1.00 99.69           C
ATOM   1691  O   ILE A 207      -5.242  -9.739  41.632  1.00104.14           O
ATOM   1692  CB  ILE A 207      -3.061  -8.738  39.321  1.00 69.56           C
ATOM   1693  CG1 ILE A 207      -1.594  -8.863  38.908  1.00 63.20           C
ATOM   1694  CG2 ILE A 207      -3.294  -7.544  40.194  1.00 76.49           C
ATOM   1695  CD1 ILE A 207      -0.970  -7.563  38.508  1.00 65.35           C
ATOM   1696  N   GLY A 208      -5.909 -10.153  39.541  1.00 97.03           N
ATOM   1697  CA  GLY A 208      -7.312 -10.209  39.890  1.00103.54           C
ATOM   1698  C   GLY A 208      -7.487 -11.155  41.059  1.00103.31           C
ATOM   1699  O   GLY A 208      -7.991 -10.780  42.147  1.00109.23           O
ATOM   1700  N   LEU A 209      -7.070 -12.399  40.854  1.00112.16           N
ATOM   1701  CA  LEU A 209      -7.170 -13.374  41.914  1.00112.41           C
ATOM   1702  C   LEU A 209      -6.604 -12.761  43.174  1.00113.97           C
ATOM   1703  O   LEU A 209      -7.337 -12.619  44.127  1.00121.18           O
```

Fig. 7AB

```
ATOM   1704  CB  LEU A 209      -6.412 -14.644  41.578  1.00 75.63           C
ATOM   1705  CG  LEU A 209      -7.129 -15.838  42.177  1.00 76.81           C
ATOM   1706  CD1 LEU A 209      -8.493 -15.963  41.514  1.00 77.98           C
ATOM   1707  CD2 LEU A 209      -6.326 -17.151  42.048  1.00 79.01           C
ATOM   1708  N   PHE A 210      -5.317 -12.390  43.152  1.00102.86           N
ATOM   1709  CA  PHE A 210      -4.664 -11.849  44.346  1.00104.50           C
ATOM   1710  C   PHE A 210      -5.483 -10.783  45.093  1.00114.07           C
ATOM   1711  O   PHE A 210      -5.394 -10.629  46.325  1.00119.36           O
ATOM   1712  CB  PHE A 210      -3.310 -11.293  43.988  1.00105.58           C
ATOM   1713  CG  PHE A 210      -2.535 -10.846  45.175  1.00107.04           C
ATOM   1714  CD1 PHE A 210      -1.951 -11.786  46.005  1.00104.06           C
ATOM   1715  CD2 PHE A 210      -2.403  -9.496  45.483  1.00107.55           C
ATOM   1716  CE1 PHE A 210      -1.242 -11.391  47.112  1.00106.64           C
ATOM   1717  CE2 PHE A 210      -1.687  -9.094  46.590  1.00115.03           C
ATOM   1718  CZ  PHE A 210      -1.108 -10.040  47.410  1.00112.19           C
ATOM   1719  N   GLY A 211      -6.266 -10.033  44.329  1.00 88.63           N
ATOM   1720  CA  GLY A 211      -7.150  -9.026  44.860  1.00 98.92           C
ATOM   1721  C   GLY A 211      -8.395  -9.602  45.521  1.00105.16           C
ATOM   1722  O   GLY A 211      -8.678  -9.282  46.655  1.00110.60           O
ATOM   1723  N   LEU A 212      -9.152 -10.431  44.790  1.00121.09           N
ATOM   1724  CA  LEU A 212     -10.383 -10.998  45.375  1.00128.12           C
ATOM   1725  C   LEU A 212     -10.012 -11.762  46.635  1.00127.34           C
ATOM   1726  O   LEU A 212     -10.770 -11.816  47.611  1.00135.97           O
ATOM   1727  CB  LEU A 212     -11.119 -11.920  44.408  1.00104.84           C
ATOM   1728  CG  LEU A 212     -11.476 -11.487  42.980  1.00105.13           C
ATOM   1729  CD1 LEU A 212     -12.873 -12.297  42.509  1.00110.69           C
ATOM   1730  CD2 LEU A 212     -11.734  -9.956  42.741  1.00112.07           C
ATOM   1731  N   TYR A 213      -8.813 -12.323  46.601  1.00128.44           N
ATOM   1732  CA  TYR A 213      -8.245 -13.092  47.693  1.00127.08           C
ATOM   1733  C   TYR A 213      -7.877 -12.175  48.853  1.00132.66           C
ATOM   1734  O   TYR A 213      -8.212 -12.462  50.003  1.00138.99           O
ATOM   1735  CB  TYR A 213      -7.012 -13.856  47.208  1.00129.50           C
ATOM   1736  CG  TYR A 213      -6.287 -14.552  48.278  1.00127.63           C
ATOM   1737  CD1 TYR A 213      -6.337 -15.918  48.497  1.00126.12           C
ATOM   1738  CD2 TYR A 213      -5.286 -13.849  49.035  1.00129.14           C
ATOM   1739  CE1 TYR A 213      -5.591 -16.551  49.450  1.00125.28           C
ATOM   1740  CE2 TYR A 213      -4.536 -14.475  49.993  1.00127.45           C
ATOM   1741  CZ  TYR A 213      -4.691 -15.820  50.200  1.00126.00           C
ATOM   1742  OH  TYR A 213      -3.927 -16.414  51.174  1.00126.35           O
ATOM   1743  N   THR A 214      -7.201 -11.068  48.554  1.00107.62           N
ATOM   1744  CA  THR A 214      -6.988 -10.024  49.578  1.00115.12           C
ATOM   1745  C   THR A 214      -6.303  -9.619  50.281  1.00127.24           C
ATOM   1746  O   THR A 214      -6.353  -9.401  51.456  1.00135.93           O
ATOM   1747  CB  THR A 214      -6.314  -8.755  49.000  1.00126.47           C
ATOM   1748  CG2 THR A 214      -6.743  -7.513  49.765  1.00137.28           C
ATOM   1749  OG1 THR A 214      -4.893  -8.881  49.105  1.00119.35           O
ATOM   1750  N   LEU A 215      -9.363  -9.504  49.461  1.00117.47           N
ATOM   1751  CA  LEU A 215     -10.689  -9.141  49.936  1.00129.65           C
ATOM   1752  C   LEU A 215     -11.273 -10.198  50.838  1.00134.49           C
ATOM   1753  O   LEU A 215     -11.876  -9.890  51.852  1.00145.31           O
ATOM   1754  CB  LEU A 215     -11.646  -8.904  49.763  1.00110.56           C
ATOM   1755  CG  LEU A 215     -11.412  -7.592  47.995  1.00111.48           C
ATOM   1756  CD1 LEU A 215     -12.757  -7.018  47.585  1.00121.34           C
ATOM   1757  CD2 LEU A 215     -10.595  -6.597  48.824  1.00115.15           C
ATOM   1758  N   VAL A 216     -11.114 -11.455  50.472  1.00130.36           N
ATOM   1759  CA  VAL A 216     -11.579 -12.494  51.369  1.00125.75           C
ATOM   1760  C   VAL A 216     -10.676 -12.596  52.590  1.00126.53           C
ATOM   1761  O   VAL A 216     -10.975 -12.039  53.646  1.00135.31           O
ATOM   1762  CB  VAL A 216     -11.674 -13.874  50.724  1.00103.53           C
ATOM   1763  CG1 VAL A 216     -11.936 -14.912  51.804  1.00107.08           C
ATOM   1764  CG2 VAL A 216     -12.783 -13.893  49.696  1.00108.78           C
```

Fig. 7AC

```
ATOM   1765  N    PHE A 217      -9.859 -13.291  52.434  1.00112.25           N
ATOM   1766  CA   PHE A 217      -8.698 -13.630  53.550  1.00113.63           C
ATOM   1767  C    PHE A 217      -7.972 -12.471  54.216  1.00119.07           C
ATOM   1768  O    PHE A 217      -7.322 -12.642  55.250  1.00124.73           O
ATOM   1769  CB   PHE A 217      -7.735 -14.691  53.088  1.00127.30           C
ATOM   1770  CG   PHE A 217      -8.431 -15.876  52.561  1.00126.98           C
ATOM   1771  CD1  PHE A 217      -9.049 -15.827  51.325  1.00123.83           C
ATOM   1772  CD2  PHE A 217      -8.534 -17.020  53.318  1.00131.27           C
ATOM   1773  CE1  PHE A 217      -9.736 -16.920  50.827  1.00124.83           C
ATOM   1774  CE2  PHE A 217      -9.208 -18.110  52.833  1.00132.03           C
ATOM   1775  CZ   PHE A 217      -9.815 -18.063  51.578  1.00128.83           C
ATOM   1776  N    HIS A 218      -8.113 -11.283  53.650  1.00148.32           N
ATOM   1777  CA   HIS A 218      -7.320 -10.172  54.123  1.00154.61           C
ATOM   1778  C    HIS A 218      -7.965  -8.806  53.972  1.00160.08           C
ATOM   1779  O    HIS A 218      -7.245  -7.829  53.790  1.00161.78           O
ATOM   1780  CB   HIS A 218      -5.969 -10.161  53.397  1.00163.23           C
ATOM   1781  CG   HIS A 218      -5.097 -11.327  53.729  1.00169.02           C
ATOM   1782  CD2  HIS A 218      -4.879 -12.496  53.080  1.00153.18           C
ATOM   1783  ND1  HIS A 218      -4.315 -11.376  54.866  1.00165.20           N
ATOM   1784  CE1  HIS A 218      -3.659 -12.517  54.900  1.00161.53           C
ATOM   1785  NE2  HIS A 218      -3.979 -13.219  53.825  1.00154.24           N
ATOM   1786  N    ARG A 219      -9.288  -8.690  54.052  1.00142.81           N
ATOM   1787  CA   ARG A 219      -9.854  -7.375  53.742  1.00142.09           C
ATOM   1788  C    ARG A 219      -9.437  -6.354  54.698  1.00140.67           C
ATOM   1789  O    ARG A 219      -9.819  -5.198  54.503  1.00136.33           O
ATOM   1790  CB   ARG A 219     -11.364  -7.385  53.451  1.00177.28           C
ATOM   1791  CG   ARG A 219     -12.272  -8.023  54.466  1.00178.77           C
ATOM   1792  CD   ARG A 219     -13.686  -8.061  53.883  1.00184.75           C
ATOM   1793  NE   ARG A 219     -14.577  -9.000  54.567  1.00191.03           N
ATOM   1794  CZ   ARG A 219     -15.598  -9.630  53.988  1.00198.56           C
ATOM   1795  NH1  ARG A 219     -15.864  -9.438  52.702  1.00200.14           N1+
ATOM   1796  NH2  ARG A 219     -16.356 -10.461  54.694  1.00205.39           N
ATOM   1797  N    LYS A 220      -8.612  -6.580  55.691  1.00132.99           N
ATOM   1798  CA   LYS A 220      -8.186  -5.610  56.703  1.00133.43           C
ATOM   1799  C    LYS A 220      -6.719  -5.204  56.598  1.00129.51           C
ATOM   1800  O    LYS A 220      -6.377  -4.069  56.929  1.00127.49           O
ATOM   1801  CB   LYS A 220      -8.443  -6.145  58.113  1.00177.52           C
ATOM   1802  CG   LYS A 220      -9.772  -5.740  58.715  1.00183.21           C
ATOM   1803  CD   LYS A 220     -10.113  -6.648  59.896  1.00190.54           C
ATOM   1804  CE   LYS A 220     -11.474  -6.325  60.513  1.00196.49           C
ATOM   1805  NZ   LYS A 220     -11.843  -7.303  61.593  1.00204.12           N1+
ATOM   1806  N    GLU A 221      -5.856  -6.125  56.153  1.00141.62           N
ATOM   1807  CA   GLU A 221      -4.399  -5.927  56.200  1.00139.57           C
ATOM   1808  C    GLU A 221      -3.949  -4.806  55.274  1.00134.39           C
ATOM   1809  O    GLU A 221      -4.513  -4.622  54.201  1.00131.97           O
ATOM   1810  CB   GLU A 221      -3.630  -7.217  55.869  1.00191.98           C
ATOM   1811  CG   GLU A 221      -3.573  -8.305  56.939  1.00198.17           C
ATOM   1812  CD   GLU A 221      -4.852  -9.253  56.768  1.00199.41           C
ATOM   1813  OE1  GLU A 221      -5.732  -8.961  55.937  1.00195.29           O
ATOM   1814  OE2  GLU A 221      -4.904 -10.293  57.460  1.00204.98           O1-
ATOM   1815  N    LYS A 222      -2.934  -4.056  55.696  1.00145.55           N
ATOM   1816  CA   LYS A 222      -2.526  -2.684  54.914  1.00142.02           C
ATOM   1817  C    LYS A 222      -1.678  -3.251  53.716  1.00141.33           C
ATOM   1818  O    LYS A 222      -2.113  -3.084  52.573  1.00138.91           O
ATOM   1819  CB   LYS A 222      -1.806  -1.851  55.793  1.00136.65           C
ATOM   1820  CG   LYS A 222      -2.652  -0.606  56.090  1.00136.54           C
ATOM   1821  CD   LYS A 222      -2.338   0.000  57.433  1.00138.06           C
ATOM   1822  CE   LYS A 222      -3.456   0.929  57.844  1.00137.78           C
ATOM   1823  NZ   LYS A 222      -3.326   1.390  59.249  1.00139.46           N1+
ATOM   1824  N    ILE A 223      -0.476  -3.753  53.991  1.00157.77           N
ATOM   1825  CA   ILE A 223       0.476  -4.097  52.944  1.00157.99           C
```

Fig. 7AD

| | | | | | | | | | |
|---|---|---|---|---|---|---|---|---|---|
| ATOM | 1826 | C | ILE | A | 223 | -0.221 | -4.574 | 51.676 | 1.00 156.37 | C |
| ATOM | 1827 | O | ILE | A | 223 | 0.194 | -4.234 | 50.571 | 1.00 155.61 | O |
| ATOM | 1828 | CB | ILE | A | 223 | 1.476 | -5.178 | 53.398 | 1.00 112.23 | C |
| ATOM | 1829 | CG1 | ILE | A | 223 | 2.520 | -4.591 | 54.348 | 1.00 114.45 | C |
| ATOM | 1830 | CG2 | ILE | A | 223 | 2.193 | -5.726 | 52.207 | 1.00 112.51 | C |
| ATOM | 1831 | CD1 | ILE | A | 223 | 3.957 | -4.825 | 53.903 | 1.00 117.62 | C |
| ATOM | 1832 | N | PHE | A | 224 | -1.294 | -5.339 | 51.851 | 1.00 128.89 | N |
| ATOM | 1833 | CA | PHE | A | 224 | -1.989 | -5.959 | 50.731 | 1.00 128.17 | C |
| ATOM | 1834 | C | PHE | A | 224 | -2.586 | -5.056 | 49.658 | 1.00 125.05 | C |
| ATOM | 1835 | O | PHE | A | 224 | -2.427 | -5.311 | 48.469 | 1.00 125.01 | O |
| ATOM | 1836 | CB | PHE | A | 224 | -3.033 | -6.942 | 51.252 | 1.00 127.22 | C |
| ATOM | 1837 | CG | PHE | A | 224 | -2.436 | -8.168 | 51.850 | 1.00 130.98 | C |
| ATOM | 1838 | CD1 | PHE | A | 224 | -1.503 | -8.068 | 52.867 | 1.00 132.84 | C |
| ATOM | 1839 | CD2 | PHE | A | 224 | -2.782 | -9.420 | 51.387 | 1.00 133.13 | C |
| ATOM | 1840 | CE1 | PHE | A | 224 | -0.949 | -9.191 | 53.422 | 1.00 136.85 | C |
| ATOM | 1841 | CE2 | PHE | A | 224 | -2.223 | -10.544 | 51.939 | 1.00 137.02 | C |
| ATOM | 1842 | CZ | PHE | A | 224 | -1.305 | -10.430 | 52.959 | 1.00 138.89 | C |
| ATOM | 1843 | N | TYR | A | 225 | -3.271 | -3.998 | 50.052 | 1.00 148.60 | N |
| ATOM | 1844 | CA | TYR | A | 225 | -3.831 | -3.115 | 49.042 | 1.00 146.19 | C |
| ATOM | 1845 | C | TYR | A | 225 | -2.730 | -2.342 | 48.334 | 1.00 146.04 | C |
| ATOM | 1846 | O | TYR | A | 225 | -2.792 | -2.103 | 47.120 | 1.00 145.65 | O |
| ATOM | 1847 | CB | TYR | A | 225 | -4.657 | -2.196 | 49.871 | 1.00 126.73 | C |
| ATOM | 1848 | CG | TYR | A | 225 | -5.968 | -2.977 | 50.299 | 1.00 127.81 | C |
| ATOM | 1849 | CD1 | TYR | A | 225 | -5.941 | -3.279 | 51.649 | 1.00 129.91 | C |
| ATOM | 1850 | CD2 | TYR | A | 225 | -7.027 | -3.457 | 49.535 | 1.00 127.53 | C |
| ATOM | 1851 | CE1 | TYR | A | 225 | -6.963 | -4.013 | 52.236 | 1.00 131.88 | C |
| ATOM | 1852 | CE2 | TYR | A | 225 | -8.055 | -4.189 | 50.114 | 1.00 129.31 | C |
| ATOM | 1853 | CZ | TYR | A | 225 | -8.012 | -4.460 | 51.468 | 1.00 131.54 | C |
| ATOM | 1854 | OH | TYR | A | 225 | -9.008 | -5.178 | 52.076 | 1.00 134.17 | O |
| ATOM | 1855 | N | LEU | A | 226 | -1.709 | -1.975 | 49.099 | 1.00 109.20 | N |
| ATOM | 1856 | CA | LEU | A | 226 | -0.519 | -1.402 | 48.516 | 1.00 110.09 | C |
| ATOM | 1857 | C | LEU | A | 226 | -0.013 | -2.329 | 47.428 | 1.00 111.97 | C |
| ATOM | 1858 | O | LEU | A | 226 | 0.285 | -1.902 | 46.310 | 1.00 112.24 | O |
| ATOM | 1859 | CB | LEU | A | 226 | 0.569 | -1.217 | 49.560 | 1.00 116.06 | C |
| ATOM | 1860 | CG | LEU | A | 226 | 1.434 | 0.038 | 49.369 | 1.00 115.68 | C |
| ATOM | 1861 | CD1 | LEU | A | 226 | 2.878 | -0.281 | 49.664 | 1.00 117.62 | C |
| ATOM | 1862 | CD2 | LEU | A | 226 | 1.317 | 0.667 | 47.973 | 1.00 116.16 | C |
| ATOM | 1863 | N | ALA | A | 227 | 0.096 | -3.611 | 47.743 | 1.00 118.69 | N |
| ATOM | 1864 | CA | ALA | A | 227 | 0.575 | -4.558 | 46.762 | 1.00 120.06 | C |
| ATOM | 1865 | C | ALA | A | 227 | -0.337 | -4.620 | 45.541 | 1.00 119.67 | C |
| ATOM | 1866 | O | ALA | A | 227 | 0.140 | -4.421 | 44.439 | 1.00 120.88 | O |
| ATOM | 1867 | CB | ALA | A | 227 | 0.756 | -5.930 | 47.368 | 1.00 66.57 | C |
| ATOM | 1868 | N | ILE | A | 228 | -1.635 | -4.874 | 45.716 | 1.00 116.43 | N |
| ATOM | 1869 | CA | ILE | A | 228 | -2.530 | -4.867 | 44.558 | 1.00 116.30 | C |
| ATOM | 1870 | C | ILE | A | 228 | -2.238 | -3.651 | 43.695 | 1.00 115.79 | C |
| ATOM | 1871 | O | ILE | A | 228 | -2.138 | -3.753 | 42.478 | 1.00 117.39 | O |
| ATOM | 1872 | CB | ILE | A | 228 | -4.018 | -4.775 | 44.913 | 1.00 129.20 | C |
| ATOM | 1873 | CG1 | ILE | A | 228 | -4.498 | -6.000 | 45.665 | 1.00 130.19 | C |
| ATOM | 1874 | CG2 | ILE | A | 228 | -4.855 | -4.676 | 43.647 | 1.00 130.64 | C |
| ATOM | 1875 | CD1 | ILE | A | 228 | -5.995 | -5.960 | 45.898 | 1.00 129.40 | C |
| ATOM | 1876 | N | ALA | A | 229 | -2.106 | -2.490 | 44.326 | 1.00 119.09 | N |
| ATOM | 1877 | CA | ALA | A | 229 | -1.895 | -1.264 | 43.559 | 1.00 117.97 | C |
| ATOM | 1878 | C | ALA | A | 229 | -0.560 | -1.218 | 42.797 | 1.00 121.56 | C |
| ATOM | 1879 | O | ALA | A | 229 | -0.316 | -0.778 | 41.651 | 1.00 123.80 | O |
| ATOM | 1880 | CB | ALA | A | 229 | -2.054 | -0.050 | 44.451 | 1.00 95.64 | C |
| ATOM | 1881 | N | LEU | A | 230 | 0.518 | -1.671 | 43.427 | 1.00 115.53 | N |
| ATOM | 1882 | CA | LEU | A | 230 | 1.817 | -1.667 | 42.768 | 1.00 119.33 | C |
| ATOM | 1883 | C | LEU | A | 230 | 1.893 | -2.697 | 41.634 | 1.00 119.88 | C |
| ATOM | 1884 | O | LEU | A | 230 | 2.471 | -2.433 | 40.579 | 1.00 120.90 | O |
| ATOM | 1885 | CB | LEU | A | 230 | 2.929 | -1.941 | 43.770 | 1.00 113.10 | C |
| ATOM | 1886 | CG | LEU | A | 230 | 3.062 | -1.038 | 44.986 | 1.00 113.60 | C |

Fig. 7AE

```
ATOM   1887  CD1 LEU A 230      4.148  -1.596  45.887  1.00113.51           C
ATOM   1888  CD2 LEU A 230      3.371   0.386  44.584  1.00113.52           C
ATOM   1889  N   MET A 231      1.348  -3.883  41.862  1.00135.43           N
ATOM   1890  CA  MET A 231      1.234  -4.878  40.816  1.00136.60           C
ATOM   1891  C   MET A 231      0.453  -4.268  39.650  1.00138.39           C
ATOM   1892  O   MET A 231      0.890  -4.309  38.495  1.00139.19           O
ATOM   1893  CB  MET A 231      0.528  -6.121  41.362  1.00111.20           C
ATOM   1894  CG  MET A 231      1.375  -6.951  42.325  1.00109.76           C
ATOM   1895  SD  MET A 231      0.438  -8.200  43.244  1.00112.66           S
ATOM   1896  CE  MET A 231     -0.835  -6.585  42.056  1.00114.82           C
ATOM   1897  N   ILE A 232     -0.691  -3.674  39.967  1.00113.28           N
ATOM   1898  CA  ILE A 232     -1.550  -3.072  38.963  1.00113.79           C
ATOM   1899  C   ILE A 232     -0.827  -1.994  38.156  1.00116.54           C
ATOM   1900  O   ILE A 232     -1.022  -1.879  36.952  1.00119.93           O
ATOM   1901  CB  ILE A 232     -2.837  -2.484  39.556  1.00107.93           C
ATOM   1902  CG1 ILE A 232     -3.694  -3.562  39.748  1.00107.13           C
ATOM   1903  CG2 ILE A 232     -3.397  -1.437  39.638  1.00108.34           C
ATOM   1904  CD1 ILE A 232     -5.204  -3.101  40.357  1.00104.13           C
ATOM   1905  N   ILE A 233      0.006  -1.211  38.833  1.00107.23           N
ATOM   1906  CA  ILE A 233      0.857  -0.205  38.180  1.00107.33           C
ATOM   1907  C   ILE A 233      1.928  -0.844  37.290  1.00107.19           C
ATOM   1908  O   ILE A 233      2.313  -0.286  36.254  1.00108.89           O
ATOM   1909  CB  ILE A 233      1.546   0.729  39.226  1.00105.49           C
ATOM   1910  CG1 ILE A 233      0.654   1.922  39.558  1.00105.02           C
ATOM   1911  CG2 ILE A 233      2.911   1.215  38.736  1.00104.78           C
ATOM   1912  CD1 ILE A 233      1.327   2.920  40.442  1.00103.92           C
ATOM   1913  N   ALA A 234      2.402  -2.016  37.710  1.00106.36           N
ATOM   1914  CA  ALA A 234      3.428  -2.755  36.985  1.00106.57           C
ATOM   1915  C   ALA A 234      2.836  -3.336  35.707  1.00108.11           C
ATOM   1916  O   ALA A 234      3.534  -3.520  34.713  1.00110.73           O
ATOM   1917  CB  ALA A 234      4.007  -3.857  37.373  1.00 66.92           C
ATOM   1918  N   LEU A 235      1.530  -3.598  35.756  1.00113.10           N
ATOM   1919  CA  LEU A 235      0.782  -4.126  34.620  1.00116.47           C
ATOM   1920  C   LEU A 235      0.659  -3.109  33.486  1.00118.75           C
ATOM   1921  O   LEU A 235      0.927  -3.431  32.337  1.00119.95           O
ATOM   1922  CB  LEU A 235     -0.610  -4.568  35.077  1.00111.67           C
ATOM   1923  CG  LEU A 235     -1.299  -5.651  34.244  1.00114.81           C
ATOM   1924  CD1 LEU A 235     -0.473  -6.927  34.244  1.00114.04           C
ATOM   1925  CD2 LEU A 235     -2.716  -5.926  34.740  1.00117.20           C
ATOM   1926  N   SER A 236      0.261  -1.883  33.809  1.00115.36           N
ATOM   1927  CA  SER A 236      0.016  -0.856  32.769  1.00118.74           C
ATOM   1928  C   SER A 236      1.261  -0.470  31.981  1.00121.24           C
ATOM   1929  O   SER A 236      2.368  -0.943  32.255  1.00120.37           O
ATOM   1930  CB  SER A 236     -0.606   0.399  33.410  1.00150.90           C
ATOM   1931  OG  SER A 236      0.392   1.171  34.071  1.00146.97           O
ATOM   1932  N   MET A 237      1.050   0.409  30.994  1.00165.68           N
ATOM   1933  CA  MET A 237      2.071   0.815  30.013  1.00165.19           C
ATOM   1934  C   MET A 237      2.636   2.210  30.279  1.00167.15           C
ATOM   1935  O   MET A 237      2.161   3.200  29.729  1.00172.01           O
ATOM   1936  CB  MET A 237      1.480   0.779  28.601  1.00205.05           C
ATOM   1937  CG  MET A 237      0.371  -0.136  28.473  1.00205.64           C
ATOM   1938  SD  MET A 237      0.390  -1.325  27.128  1.00209.07           S
ATOM   1939  CE  MET A 237     -0.815  -2.548  27.651  1.00206.91           C
ATOM   1940  N   LEU A 238      3.674   2.269  31.109  1.00120.21           N
ATOM   1941  CA  LEU A 238      4.252   3.525  31.561  1.00122.46           C
ATOM   1942  C   LEU A 238      5.764   3.433  31.483  1.00117.70           C
ATOM   1943  O   LEU A 238      6.353   2.591  32.111  1.00110.94           O
ATOM   1944  CB  LEU A 238      3.815   3.761  33.068  1.00128.80           C
ATOM   1945  CG  LEU A 238      2.538   4.148  33.621  1.00134.36           C
ATOM   1946  CD1 LEU A 238      2.898   4.295  35.126  1.00133.97           C
ATOM   1947  CD2 LEU A 238      2.057   5.430  32.995  1.00141.91           C
```

Fig. 7AF

| | | | | | | | | | |
|---|---|---|---|---|---|---|---|---|---|
| ATOM | 1948 | N | ALA | A | 239 | 6.400 | 4.340 | 30.739 | 1.00140.79 N |
| ATOM | 1949 | CA | ALA | A | 239 | 7.862 | 4.345 | 30.640 | 1.00137.57 C |
| ATOM | 1950 | C | ALA | A | 239 | 8.509 | 3.732 | 31.892 | 1.00133.31 C |
| ATOM | 1951 | O | ALA | A | 239 | 8.219 | 4.145 | 33.012 | 1.00130.58 O |
| ATOM | 1952 | CB | ALA | A | 239 | 8.374 | 5.756 | 30.407 | 1.00357.41 C |
| ATOM | 1953 | N | TRP | A | 240 | 9.371 | 2.735 | 31.697 | 1.00159.97 N |
| ATOM | 1954 | CA | TRP | A | 240 | 9.986 | 1.982 | 32.800 | 1.00156.41 C |
| ATOM | 1955 | C | TRP | A | 240 | 10.321 | 2.847 | 34.039 | 1.00154.70 C |
| ATOM | 1956 | O | TRP | A | 240 | 10.203 | 2.398 | 35.188 | 1.00151.25 O |
| ATOM | 1957 | CB | TRP | A | 240 | 11.243 | 1.262 | 32.286 | 1.00163.56 C |
| ATOM | 1958 | CG | TRP | A | 240 | 12.447 | 2.155 | 32.241 | 1.00166.60 C |
| ATOM | 1959 | CD1 | TRP | A | 240 | 12.575 | 3.334 | 31.555 | 1.00171.45 C |
| ATOM | 1960 | CD2 | TRP | A | 240 | 13.687 | 1.952 | 32.923 | 1.00165.69 C |
| ATOM | 1961 | CE2 | TRP | A | 240 | 14.520 | 3.044 | 32.609 | 1.00170.22 C |
| ATOM | 1962 | CE3 | TRP | A | 240 | 14.175 | 0.952 | 33.769 | 1.00162.08 C |
| ATOM | 1963 | NE1 | TRP | A | 240 | 13.817 | 3.875 | 31.774 | 1.00173.71 N |
| ATOM | 1964 | CZ2 | TRP | A | 240 | 15.812 | 3.162 | 33.112 | 1.00171.20 C |
| ATOM | 1965 | CZ3 | TRP | A | 240 | 15.455 | 1.069 | 34.284 | 1.00162.99 C |
| ATOM | 1966 | CH2 | TRP | A | 240 | 16.260 | 2.165 | 33.936 | 1.00167.52 C |
| ATOM | 1967 | N | GLN | A | 241 | 10.726 | 4.091 | 33.780 | 1.00158.04 N |
| ATOM | 1968 | CA | GLN | A | 241 | 11.163 | 5.036 | 34.808 | 1.00157.49 C |
| ATOM | 1969 | C | GLN | A | 241 | 10.062 | 5.394 | 35.808 | 1.00154.48 C |
| ATOM | 1970 | O | GLN | A | 241 | 10.299 | 5.394 | 37.018 | 1.00152.04 O |
| ATOM | 1971 | CB | GLN | A | 241 | 11.746 | 6.295 | 34.147 | 1.00199.43 C |
| ATOM | 1972 | CG | GLN | A | 241 | 11.056 | 6.704 | 32.846 | 1.00203.31 C |
| ATOM | 1973 | CD | GLN | A | 241 | 11.877 | 7.688 | 32.026 | 1.00209.01 C |
| ATOM | 1974 | NE2 | GLN | A | 241 | 11.202 | 8.475 | 31.199 | 1.00212.32 N |
| ATOM | 1975 | OE1 | GLN | A | 241 | 13.102 | 7.733 | 32.134 | 1.00210.97 O |
| ATOM | 1976 | N | TYR | A | 242 | 8.869 | 5.698 | 35.295 | 1.00160.29 N |
| ATOM | 1977 | CA | TYR | A | 242 | 7.692 | 5.982 | 36.121 | 1.00158.22 C |
| ATOM | 1978 | C | TYR | A | 242 | 7.342 | 4.800 | 37.016 | 1.00154.10 C |
| ATOM | 1979 | O | TYR | A | 242 | 6.945 | 4.972 | 38.171 | 1.00152.25 O |
| ATOM | 1980 | CB | TYR | A | 242 | 6.484 | 6.331 | 35.245 | 1.00133.18 C |
| ATOM | 1981 | CG | TYR | A | 242 | 6.613 | 7.664 | 34.532 | 1.00137.93 C |
| ATOM | 1982 | CD1 | TYR | A | 242 | 5.566 | 8.174 | 33.764 | 1.00143.05 C |
| ATOM | 1983 | CD2 | TYR | A | 242 | 7.785 | 8.418 | 34.629 | 1.00138.05 C |
| ATOM | 1984 | CE1 | TYR | A | 242 | 5.679 | 9.392 | 33.119 | 1.00146.08 C |
| ATOM | 1985 | CE2 | TYR | A | 242 | 7.907 | 9.623 | 33.986 | 1.00143.07 C |
| ATOM | 1986 | CZ | TYR | A | 242 | 6.851 | 10.093 | 33.233 | 1.00148.07 C |
| ATOM | 1987 | OH | TYR | A | 242 | 6.973 | 11.290 | 32.593 | 1.00153.77 O |
| ATOM | 1988 | N | LYS | A | 243 | 7.488 | 3.600 | 36.465 | 1.00116.03 N |
| ATOM | 1989 | CA | LYS | A | 243 | 7.256 | 2.371 | 37.206 | 1.00112.70 C |
| ATOM | 1990 | C | LYS | A | 243 | 8.291 | 2.185 | 38.326 | 1.00110.86 C |
| ATOM | 1991 | O | LYS | A | 243 | 7.982 | 2.304 | 39.499 | 1.00109.43 O |
| ATOM | 1992 | CB | LYS | A | 243 | 7.242 | 1.182 | 36.244 | 1.00131.73 C |
| ATOM | 1993 | CG | LYS | A | 243 | 6.161 | 1.254 | 35.156 | 1.00134.11 C |
| ATOM | 1994 | CD | LYS | A | 243 | 5.054 | 0.227 | 35.394 | 1.00134.40 C |
| ATOM | 1995 | CE | LYS | A | 243 | 4.577 | -0.444 | 34.100 | 1.00136.19 C |
| ATOM | 1996 | NZ | LYS | A | 243 | 5.599 | -1.360 | 33.496 | 1.00136.31 N1+ |
| ATOM | 1997 | N | LEU | A | 244 | 9.540 | 1.907 | 37.970 | 1.00142.96 N |
| ATOM | 1998 | CA | LEU | A | 244 | 10.593 | 1.794 | 38.973 | 1.00142.04 C |
| ATOM | 1999 | C | LEU | A | 244 | 10.432 | 2.867 | 40.057 | 1.00141.80 C |
| ATOM | 2000 | O | LEU | A | 244 | 10.379 | 2.563 | 41.247 | 1.00140.22 O |
| ATOM | 2001 | CB | LEU | A | 244 | 11.964 | 1.939 | 38.312 | 1.00126.27 C |
| ATOM | 2002 | CG | LEU | A | 244 | 12.985 | 0.817 | 38.514 | 1.00126.33 C |
| ATOM | 2003 | CD1 | LEU | A | 244 | 14.358 | 1.270 | 38.038 | 1.00129.74 C |
| ATOM | 2004 | CD2 | LEU | A | 244 | 13.043 | 0.346 | 39.968 | 1.00124.89 C |
| ATOM | 2005 | N | ALA | A | 245 | 10.366 | 4.125 | 39.624 | 1.00142.81 N |
| ATOM | 2006 | CA | ALA | A | 245 | 10.211 | 5.273 | 40.618 | 1.00143.39 C |
| ATOM | 2007 | C | ALA | A | 245 | 9.092 | 5.165 | 41.463 | 1.00141.63 C |
| ATOM | 2008 | O | ALA | A | 245 | 9.148 | 4.852 | 42.627 | 1.00140.25 O |

Fig. 7AG

```
ATOM   2009  CB  ALA A 245      10.116   6.531  39.701  1.00 98.29           C
ATOM   2010  N   LEU A 246       7.826   5.463  40.891  1.00137.85           N
ATOM   2011  CA  LEU A 246       6.541   5.352  41.585  1.00136.97           C
ATOM   2012  C   LEU A 246       6.502   4.173  42.581  1.00134.71           C
ATOM   2013  O   LEU A 246       6.106   4.339  43.756  1.00134.57           O
ATOM   2014  CB  LEU A 246       5.414   5.281  40.536  1.00 98.43           C
ATOM   2015  CG  LEU A 246       3.896   5.357  40.797  1.00 98.82           C
ATOM   2016  CD1 LEU A 246       3.535   6.304  42.118  1.00 97.90           C
ATOM   2017  CD2 LEU A 246       3.149   6.043  39.636  1.00101.63           C
ATOM   2018  N   ILE A 247       6.965   3.000  42.128  1.00147.29           N
ATOM   2019  CA  ILE A 247       7.143   1.857  43.028  1.00145.70           C
ATOM   2020  C   ILE A 247       8.042   2.195  44.210  1.00145.53           C
ATOM   2021  O   ILE A 247       7.605   2.120  45.354  1.00145.11           O
ATOM   2022  CB  ILE A 247       7.770   0.643  42.324  1.00153.30           C
ATOM   2023  CG1 ILE A 247       6.754  -0.016  41.398  1.00153.79           C
ATOM   2024  CG2 ILE A 247       8.278  -0.361  43.354  1.00152.28           C
ATOM   2025  CD1 ILE A 247       5.592  -0.480  42.099  1.00153.89           C
ATOM   2026  N   VAL A 248       9.297   2.551  43.939  1.00146.05           N
ATOM   2027  CA  VAL A 248      10.246   2.849  45.016  1.00146.82           C
ATOM   2028  C   VAL A 248       9.762   3.931  46.011  1.00147.83           C
ATOM   2029  O   VAL A 248       9.907   3.748  47.230  1.00148.22           O
ATOM   2030  CB  VAL A 248      11.697   3.117  44.521  1.00113.59           C
ATOM   2031  CG1 VAL A 248      12.286   4.394  45.165  1.00116.05           C
ATOM   2032  CG2 VAL A 248      12.578   1.894  44.833  1.00113.62           C
ATOM   2033  N   LEU A 249       9.172   5.032  45.524  1.00150.31           N
ATOM   2034  CA  LEU A 249       8.603   6.035  46.451  1.00151.78           C
ATOM   2035  C   LEU A 249       7.477   5.411  47.279  1.00151.30           C
ATOM   2036  O   LEU A 249       7.551   5.349  48.523  1.00152.34           O
ATOM   2037  CB  LEU A 249       8.118   7.315  45.741  1.00144.65           C
ATOM   2038  CG  LEU A 249       8.992   7.970  44.654  1.00145.90           C
ATOM   2039  CD1 LEU A 249       8.360   9.281  44.177  1.00148.39           C
ATOM   2040  CD2 LEU A 249      10.469   8.160  45.060  1.00146.69           C
ATOM   2041  N   LEU A 250       6.452   4.923  46.581  1.00132.72           N
ATOM   2042  CA  LEU A 250       5.361   4.210  47.248  1.00132.24           C
ATOM   2043  C   LEU A 250       5.826   3.060  48.149  1.00132.34           C
ATOM   2044  O   LEU A 250       5.017   2.438  48.838  1.00130.99           O
ATOM   2045  CB  LEU A 250       4.344   3.705  46.219  1.00129.57           C
ATOM   2046  CG  LEU A 250       3.199   4.679  45.807  1.00126.87           C
ATOM   2047  CD1 LEU A 250       2.429   4.408  44.719  1.00126.29           C
ATOM   2048  CD2 LEU A 250       2.275   4.606  47.215  1.00123.21           C
ATOM   2049  N   PHE A 251       7.125   2.794  48.136  1.00158.70           N
ATOM   2050  CA  PHE A 251       7.701   1.737  48.971  1.00159.01           C
ATOM   2051  C   PHE A 251       8.312   2.352  50.211  1.00160.95           C
ATOM   2052  O   PHE A 251       7.841   2.133  51.331  1.00162.87           O
ATOM   2053  CB  PHE A 251       8.780   0.980  48.196  1.00152.51           C
ATOM   2054  CG  PHE A 251       9.535  -0.036  49.020  1.00153.54           C
ATOM   2055  CD1 PHE A 251       9.041  -1.318  49.184  1.00153.43           C
ATOM   2056  CD2 PHE A 251      10.752   0.302  49.610  1.00153.27           C
ATOM   2057  CE1 PHE A 251       9.740  -2.255  49.927  1.00155.07           C
ATOM   2058  CE2 PHE A 251      11.456  -0.631  50.361  1.00156.93           C
ATOM   2059  CZ  PHE A 251      10.947  -1.913  50.518  1.00156.85           C
ATOM   2060  N   ALA A 252       9.367   3.130  50.011  1.00183.80           N
ATOM   2061  CA  ALA A 252       9.979   3.830  51.124  1.00186.14           C
ATOM   2062  C   ALA A 252       8.894   4.489  51.990  1.00190.19           C
ATOM   2063  O   ALA A 252       8.879   4.298  53.213  1.00192.63           O
ATOM   2064  CB  ALA A 252      11.025   4.849  50.632  1.00128.44           C
ATOM   2065  N   ILE A 253       7.965   5.243  51.394  1.00172.52           N
ATOM   2066  CA  ILE A 253       6.971   5.892  52.263  1.00169.66           C
ATOM   2067  C   ILE A 253       6.322   4.848  53.182  1.00168.13           C
ATOM   2068  O   ILE A 253       6.108   5.130  54.349  1.00167.86           O
ATOM   2069  CB  ILE A 253       5.838   6.709  51.563  1.00133.74           C
```

Fig. 7AH

```
ATOM   2070  CG1 ILE A 253      4.830   5.760  56.903  1.00130.55           C
ATOM   2071  CG2 ILE A 253      6.396   7.843  50.662  1.00129.83           C
ATOM   2072  CD1 ILE A 253      3.634   6.430  50.292  1.00130.06           C
ATOM   2073  N   PHE A 254      6.018   3.650  52.676  1.00131.78           N
ATOM   2074  CA  PHE A 254      5.351   2.623  53.492  1.00131.17           C
ATOM   2075  C   PHE A 254      6.256   1.955  54.524  1.00135.41           C
ATOM   2076  O   PHE A 254      5.804   1.609  55.606  1.00135.83           O
ATOM   2077  CB  PHE A 254      4.677   1.554  52.633  1.00159.50           C
ATOM   2078  CG  PHE A 254      3.841   0.582  53.428  1.00159.06           C
ATOM   2079  CD1 PHE A 254      2.472   0.773  53.567  1.00156.09           C
ATOM   2080  CD2 PHE A 254      4.423  -0.614  54.064  1.00162.40           C
ATOM   2081  CE1 PHE A 254      1.690  -0.118  54.290  1.00156.61           C
ATOM   2082  CE2 PHE A 254      3.645  -1.409  54.803  1.00162.84           C
ATOM   2083  CZ  PHE A 254      2.277  -1.209  54.915  1.00160.05           C
ATOM   2084  N   ALA A 255      7.529   1.768  54.193  1.00166.44           N
ATOM   2085  CA  ALA A 255      8.453   1.168  55.157  1.00170.21           C
ATOM   2086  C   ALA A 255      8.801   2.119  56.300  1.00173.54           C
ATOM   2087  O   ALA A 255      8.906   1.702  57.456  1.00176.36           O
ATOM   2088  CB  ALA A 255      9.694   0.663  54.477  1.00193.12           C
ATOM   2089  N   PHE A 256      9.027   3.390  55.969  1.00216.51           N
ATOM   2090  CA  PHE A 256      9.470   4.238  56.996  1.00219.62           C
ATOM   2091  C   PHE A 256      8.381   5.248  57.561  1.00216.93           C
ATOM   2092  O   PHE A 256      8.632   5.997  58.501  1.00220.27           O
ATOM   2093  CB  PHE A 256     10.630   5.174  56.472  1.00186.51           C
ATOM   2094  CG  PHE A 256     11.791   4.356  55.992  1.00184.76           C
ATOM   2095  CD1 PHE A 256     11.959   4.079  54.639  1.00181.06           C
ATOM   2096  CD2 PHE A 256     12.724   3.874  56.890  1.00187.46           C
ATOM   2097  CE1 PHE A 256     13.037   3.333  54.195  1.00180.06           C
ATOM   2098  CE2 PHE A 256     13.804   3.127  56.451  1.00186.43           C
ATOM   2099  CZ  PHE A 256     13.961   2.856  55.105  1.00192.70           C
ATOM   2100  N   LYS A 257      7.183   5.205  56.981  1.00168.15           N
ATOM   2101  CA  LYS A 257      6.029   5.895  57.580  1.00165.86           C
ATOM   2102  C   LYS A 257      5.232   4.965  58.462  1.00165.71           C
ATOM   2103  O   LYS A 257      4.017   5.105  58.566  1.00163.67           O
ATOM   2104  CB  LYS A 257      5.104   6.525  56.545  1.00161.35           C
ATOM   2105  CG  LYS A 257      5.789   7.632  55.766  1.00161.63           C
ATOM   2106  CD  LYS A 257      6.319   8.740  56.636  1.00162.16           C
ATOM   2107  CE  LYS A 257      7.264   9.564  55.780  1.00162.68           C
ATOM   2108  NZ  LYS A 257      7.492  10.950  56.290  1.00163.50          N1+
ATOM   2109  N   GLU A 258      5.934   3.984  59.029  1.00286.64           N
ATOM   2110  CA  GLU A 258      5.438   3.249  60.186  1.00290.85           C
ATOM   2111  C   GLU A 258      4.085   2.567  59.900  1.00286.08           C
ATOM   2112  O   GLU A 258      4.031   1.354  59.671  1.00283.87           O
ATOM   2113  CB  GLU A 258      5.398   4.194  61.419  1.00205.21           C
ATOM   2114  CG  GLU A 258      6.767   4.887  61.730  1.00208.79           C
ATOM   2115  CD  GLU A 258      6.695   6.018  62.772  1.00216.24           C
ATOM   2116  OE1 GLU A 258      5.647   6.163  63.436  1.00219.90           O
ATOM   2117  OE2 GLU A 258      7.696   6.761  62.926  1.00216.98          O1-
ATOM   2118  N   GLU A 259      3.004   3.348  59.893  1.00365.15           N
ATOM   2119  CA  GLU A 259      1.653   2.800  59.730  1.00361.63           C
ATOM   2120  C   GLU A 259      0.632   3.783  59.156  1.00358.30           C
ATOM   2121  O   GLU A 259     -0.517   3.413  58.926  1.00358.08           O
ATOM   2122  CB  GLU A 259      1.113   2.277  61.079  1.00251.22           C
ATOM   2123  CG  GLU A 259      1.497   0.834  61.443  1.00254.41           C
ATOM   2124  CD  GLU A 259      0.509   0.166  62.396  1.00259.39           C
ATOM   2125  OE1 GLU A 259     -0.587   0.722  62.621  1.00260.73           O
ATOM   2126  OE2 GLU A 259      0.827  -0.924  62.918  1.00262.54          O1-
ATOM   2127  N   LYS A 260      1.041   5.020  58.906  1.00241.79           N
ATOM   2128  CA  LYS A 260      0.062   6.097  58.736  1.00239.90           C
ATOM   2129  C   LYS A 260     -0.430   6.373  57.303  1.00234.85           C
ATOM   2130  O   LYS A 260      0.097   7.227  56.577  1.00231.70           O
```

Fig. 7AI

```
ATOM   2131  CB  LYS A 260       0.537   7.344  59.483  1.00182.75           C
ATOM   2132  CG  LYS A 260       0.824   7.011  60.961  1.00184.57           C
ATOM   2133  CD  LYS A 260       1.138   8.238  61.843  1.00186.05           C
ATOM   2134  CE  LYS A 260       1.437   7.806  63.285  1.00188.21           C
ATOM   2135  NZ  LYS A 260       1.776   8.902  64.232  1.00190.30           N1+
ATOM   2136  N   ILE A 261      -1.470   5.615  56.945  1.00183.71           N
ATOM   2137  CA  ILE A 261      -2.108   5.600  55.635  1.00179.77           C
ATOM   2138  C   ILE A 261      -3.481   4.953  55.811  1.00178.83           C
ATOM   2139  O   ILE A 261      -3.553   3.792  56.261  1.00180.49           O
ATOM   2140  CB  ILE A 261      -1.270   4.776  54.814  1.00157.66           C
ATOM   2141  CG1 ILE A 261       0.121   5.395  54.392  1.00159.39           C
ATOM   2142  CG2 ILE A 261      -1.978   4.699  53.299  1.00154.38           C
ATOM   2143  CD1 ILE A 261       0.793   5.040  53.055  1.00160.26           C
ATOM   2144  N   ASN A 262      -4.565   5.634  55.479  1.00208.67           N
ATOM   2145  CA  ASN A 262      -5.906   5.072  55.689  1.00208.37           C
ATOM   2146  C   ASN A 262      -6.506   4.494  54.411  1.00207.11           C
ATOM   2147  O   ASN A 262      -6.082   4.840  53.314  1.00205.65           O
ATOM   2148  CB  ASN A 262      -6.853   6.070  56.414  1.00199.83           C
ATOM   2149  CG  ASN A 262      -7.616   6.995  55.465  1.00199.91           C
ATOM   2150  ND2 ASN A 262      -8.556   7.758  56.026  1.00205.45           N
ATOM   2151  OD1 ASN A 262      -7.371   7.025  54.256  1.00205.86           O
ATOM   2152  N   PHE A 263      -7.464   3.588  54.561  1.00191.55           N
ATOM   2153  CA  PHE A 263      -8.003   2.857  53.424  1.00190.98           C
ATOM   2154  C   PHE A 263      -8.423   3.775  52.290  1.00189.19           C
ATOM   2155  O   PHE A 263      -8.032   3.553  51.177  1.00188.44           O
ATOM   2156  CB  PHE A 263      -9.150   1.926  53.850  1.00247.43           C
ATOM   2157  CG  PHE A 263      -9.765   0.954  54.935  1.00250.75           C
ATOM   2158  CD1 PHE A 263      -8.995   1.270  56.276  1.00253.88           C
ATOM   2159  CD2 PHE A 263      -8.163  -0.263  54.623  1.00251.46           C
ATOM   2160  CE1 PHE A 263      -8.640   0.388  57.284  1.00257.70           C
ATOM   2161  CE2 PHE A 263      -7.806  -1.149  55.621  1.00255.06           C
ATOM   2162  CZ  PHE A 263      -8.043  -0.828  56.953  1.00258.22           C
ATOM   2163  N   TYR A 264      -9.185   4.818  52.556  1.00545.27           N
ATOM   2164  CA  TYR A 264      -9.661   5.608  51.436  1.00545.95           C
ATOM   2165  C   TYR A 264      -8.541   5.043  50.490  1.00546.08           C
ATOM   2166  O   TYR A 264      -8.748   6.021  49.280  1.00546.05           O
ATOM   2167  CB  TYR A 264     -10.510   6.789  51.896  1.00202.82           C
ATOM   2168  CG  TYR A 264     -11.662   6.402  52.807  1.00205.02           C
ATOM   2169  CD1 TYR A 264     -11.459   6.229  54.173  1.00206.95           C
ATOM   2170  CD2 TYR A 264     -12.954   6.223  52.308  1.00206.01           C
ATOM   2171  CE1 TYR A 264     -12.497   5.869  55.010  1.00209.97           C
ATOM   2172  CE2 TYR A 264     -14.000   5.862  53.146  1.00208.85           C
ATOM   2173  CZ  TYR A 264     -13.760   5.716  54.493  1.00210.96           C
ATOM   2174  OH  TYR A 264     -14.787   5.375  55.336  1.00214.65           O
ATOM   2175  N   MET A 265      -7.360   6.386  51.019  1.00187.35           N
ATOM   2176  CA  MET A 265      -6.271   6.910  50.166  1.00187.43           C
ATOM   2177  C   MET A 265      -5.578   5.791  49.380  1.00187.18           C
ATOM   2178  O   MET A 265      -5.025   5.987  48.293  1.00187.39           O
ATOM   2179  CB  MET A 265      -5.248   7.699  50.973  1.00200.06           C
ATOM   2180  CG  MET A 265      -4.514   6.858  51.976  1.00201.03           C
ATOM   2181  SD  MET A 265      -3.548   7.876  53.095  1.00206.42           S
ATOM   2182  CE  MET A 265      -4.845   8.495  54.161  1.00211.39           C
ATOM   2183  N   ILE A 266      -5.657   4.601  49.942  1.00190.87           N
ATOM   2184  CA  ILE A 266      -5.234   3.419  49.246  1.00191.04           C
ATOM   2185  C   ILE A 266      -6.212   3.047  48.132  1.00190.40           C
ATOM   2186  O   ILE A 266      -5.781   2.646  47.087  1.00190.88           O
ATOM   2187  CB  ILE A 266      -5.113   2.277  50.216  1.00104.23           C
ATOM   2188  CG1 ILE A 266      -3.980   2.542  51.197  1.00107.32           C
ATOM   2189  CG2 ILE A 266      -4.809   0.991  49.498  1.00102.85           C
ATOM   2190  CD1 ILE A 266      -4.001   1.528  52.378  1.00108.65           C
ATOM   2191  N   TRP A 267      -7.514   3.179  48.353  1.00193.99           N
```

Fig. 7AJ

```
ATOM   2192  CA  TRP A 267      -8.510   2.860  47.343  1.00193.89           C
ATOM   2193  C   TRP A 267      -8.474   3.922  46.256  1.00194.71           C
ATOM   2194  O   TRP A 267      -8.915   3.710  45.148  1.00196.10           O
ATOM   2195  CB  TRP A 267      -9.905   2.838  47.939  1.00245.86           C
ATOM   2196  CG  TRP A 267     -10.126   1.879  49.083  1.00246.53           C
ATOM   2197  CD1 TRP A 267     -10.137   2.178  50.410  1.00247.25           C
ATOM   2198  CD2 TRP A 267     -10.418   0.481  48.997  1.00247.43           C
ATOM   2199  CE2 TRP A 267     -10.581  -0.003  50.301  1.00249.80           C
ATOM   2200  CE3 TRP A 267     -10.549  -0.408  47.919  1.00247.77           C
ATOM   2201  NE1 TRP A 267     -10.406   1.054  51.152  1.00248.77           N
ATOM   2202  CZ2 TRP A 267     -10.867  -1.339  50.571  1.00250.49           C
ATOM   2203  CZ3 TRP A 267     -10.832  -1.733  48.189  1.00249.17           C
ATOM   2204  CH2 TRP A 267     -10.989  -2.165  49.503  1.00250.52           C
ATOM   2205  N   ALA A 268      -7.991   5.096  46.536  1.00150.54           N
ATOM   2206  CA  ALA A 268      -7.699   6.092  45.632  1.00151.96           C
ATOM   2207  C   ALA A 268      -6.416   5.711  44.867  1.00153.22           C
ATOM   2208  O   ALA A 268      -6.384   5.821  43.668  1.00155.04           O
ATOM   2209  CB  ALA A 268      -7.592   7.500  46.252  1.00139.87           C
ATOM   2210  N   LEU A 269      -5.363   5.190  45.525  1.00161.65           N
ATOM   2211  CA  LEU A 269      -4.244   4.659  44.768  1.00163.42           C
ATOM   2212  C   LEU A 269      -4.655   3.578  43.770  1.00164.48           C
ATOM   2213  O   LEU A 269      -4.129   3.496  42.653  1.00167.09           O
ATOM   2214  CB  LEU A 269      -3.155   4.112  45.687  1.00130.43           C
ATOM   2215  CG  LEU A 269      -2.236   5.207  46.226  1.00131.61           C
ATOM   2216  CD1 LEU A 269      -1.619   4.765  47.531  1.00132.49           C
ATOM   2217  CD2 LEU A 269      -1.184   5.553  45.203  1.00134.03           C
ATOM   2218  N   ILE A 270      -5.561   2.721  44.201  1.00144.90           N
ATOM   2219  CA  ILE A 270      -6.117   1.685  43.399  1.00145.80           C
ATOM   2220  C   ILE A 270      -6.902   2.268  42.232  1.00147.24           C
ATOM   2221  O   ILE A 270      -6.638   1.991  41.072  1.00150.35           O
ATOM   2222  CB  ILE A 270      -6.994   0.762  44.282  1.00126.75           C
ATOM   2223  CG1 ILE A 270      -6.110  -0.191  45.132  1.00126.20           C
ATOM   2224  CG2 ILE A 270      -7.966  -0.036  43.431  1.00129.21           C
ATOM   2225  CD1 ILE A 270      -6.874  -1.391  45.692  1.00127.29           C
ATOM   2226  N   PHE A 271      -7.842   3.170  42.508  1.00193.51           N
ATOM   2227  CA  PHE A 271      -8.676   3.740  41.443  1.00195.23           C
ATOM   2228  C   PHE A 271      -7.879   4.524  40.397  1.00197.50           C
ATOM   2229  O   PHE A 271      -8.010   4.293  39.193  1.00200.33           O
ATOM   2230  CB  PHE A 271      -9.793   4.611  42.044  1.00193.39           C
ATOM   2231  CG  PHE A 271     -10.809   5.090  41.047  1.00195.50           C
ATOM   2232  CD1 PHE A 271     -12.113   4.617  41.084  1.00196.31           C
ATOM   2233  CD2 PHE A 271     -10.462   6.013  40.074  1.00197.43           C
ATOM   2234  CE1 PHE A 271     -13.057   5.068  40.172  1.00198.85           C
ATOM   2235  CE2 PHE A 271     -11.401   6.466  39.157  1.00200.07           C
ATOM   2236  CZ  PHE A 271     -12.703   5.987  39.210  1.00200.73           C
ATOM   2237  N   ILE A 272      -7.087   5.464  40.894  1.00184.76           N
ATOM   2238  CA  ILE A 272      -6.047   6.172  40.157  1.00187.28           C
ATOM   2239  C   ILE A 272      -5.228   5.269  39.270  1.00190.34           C
ATOM   2240  O   ILE A 272      -5.156   5.432  38.038  1.00193.61           O
ATOM   2241  CB  ILE A 272      -5.062   6.850  41.149  1.00113.97           C
ATOM   2242  CG1 ILE A 272      -5.634   8.271  41.479  1.00113.02           C
ATOM   2243  CG2 ILE A 272      -3.639   6.861  40.584  1.00116.78           C
ATOM   2244  CD1 ILE A 272      -4.599   9.060  42.380  1.00112.68           C
ATOM   2245  N   SER A 273      -4.587   4.283  39.897  1.00164.58           N
ATOM   2246  CA  SER A 273      -3.730   3.386  39.155  1.00167.90           C
ATOM   2247  C   SER A 273      -4.515   2.688  38.029  1.00169.65           C
ATOM   2248  O   SER A 273      -4.084   2.645  36.877  1.00174.04           O
ATOM   2249  CB  SER A 273      -3.031   2.411  40.100  1.00119.10           C
ATOM   2250  OG  SER A 273      -3.160   1.113  39.603  1.00115.75           O
ATOM   2251  N   ILE A 274      -5.694   2.175  38.337  1.00169.90           N
ATOM   2252  CA  ILE A 274      -6.551   1.577  37.317  1.00172.07           C
```

Fig. 7AK

```
ATOM   2253  C   ILE A 274      -6.960   2.578  35.206  1.00175.03           C
ATOM   2254  O   ILE A 274      -7.308   2.205  35.065  1.00177.58           O
ATOM   2255  CB  ILE A 274      -7.787   0.946  37.957  1.00145.16           C
ATOM   2256  CG1 ILE A 274      -7.378   0.096  39.151  1.00143.34           C
ATOM   2257  CG2 ILE A 274      -8.617   0.183  36.917  1.00147.78           C
ATOM   2258  CD1 ILE A 274      -9.428  -0.885  39.564  1.00141.56           C
ATOM   2259  N   SER A 275      -6.838   3.837  36.552  1.00169.27           N
ATOM   2260  CA  SER A 275      -7.065   4.899  35.560  1.00173.61           C
ATOM   2261  C   SER A 275      -5.842   4.946  34.661  1.00178.20           C
ATOM   2262  O   SER A 275      -5.985   5.106  33.454  1.00183.96           O
ATOM   2263  CB  SER A 275      -7.311   6.244  36.220  1.00192.31           C
ATOM   2264  OG  SER A 275      -8.514   6.214  36.946  1.00190.15           O
ATOM   2265  N   ILE A 276      -4.649   4.810  35.262  1.00142.57           N
ATOM   2266  CA  ILE A 276      -3.416   4.606  34.656  1.00147.36           C
ATOM   2267  C   ILE A 276      -3.626   3.868  33.459  1.00151.17           C
ATOM   2268  O   ILE A 276      -3.540   3.625  32.219  1.00159.95           O
ATOM   2269  CB  ILE A 276      -2.170   4.369  35.361  1.00110.04           C
ATOM   2270  CG1 ILE A 276      -2.194   5.303  36.557  1.00105.49           C
ATOM   2271  CG2 ILE A 276      -0.875   4.504  34.594  1.00115.98           C
ATOM   2272  CD1 ILE A 276      -0.876   5.383  37.303  1.00104.00           C
ATOM   2273  N   LEU A 277      -3.917   2.267  34.004  1.00145.97           N
ATOM   2274  CA  LEU A 277      -4.420   1.190  33.143  1.00149.97           C
ATOM   2275  C   LEU A 277      -5.306   1.721  32.003  1.00154.66           C
ATOM   2276  O   LEU A 277      -4.946   1.529  30.848  1.00161.04           O
ATOM   2277  CB  LEU A 277      -5.177   0.133  33.950  1.00112.57           C
ATOM   2278  CG  LEU A 277      -4.604  -1.279  34.111  1.00113.30           C
ATOM   2279  CD1 LEU A 277      -5.703  -2.345  34.248  1.00114.49           C
ATOM   2280  CD2 LEU A 277      -3.705  -1.614  32.893  1.00118.87           C
ATOM   2281  N   HIS A 278      -6.416   2.409  32.307  1.00182.05           N
ATOM   2282  CA  HIS A 278      -7.357   2.854  31.248  1.00186.40           C
ATOM   2283  C   HIS A 278      -6.754   3.737  30.159  1.00191.84           C
ATOM   2284  O   HIS A 278      -6.982   3.512  28.974  1.00196.09           O
ATOM   2285  CB  HIS A 278      -8.588   3.547  31.839  1.00191.54           C
ATOM   2286  CG  HIS A 278      -9.799   3.449  30.974  1.00195.29           C
ATOM   2287  CD2 HIS A 278     -10.262   4.245  29.980  1.00199.82           C
ATOM   2288  ND1 HIS A 278     -10.684   2.396  31.062  1.00195.25           N
ATOM   2289  CE1 HIS A 278     -11.649   2.559  30.179  1.00199.54           C
ATOM   2290  NE2 HIS A 278     -11.417   3.675  29.508  1.00202.41           N
ATOM   2291  N   LEU A 279      -6.013   4.765  30.578  1.00168.84           N
ATOM   2292  CA  LEU A 279      -5.257   5.621  29.676  1.00174.55           C
ATOM   2293  C   LEU A 279      -4.314   4.796  28.797  1.00180.49           C
ATOM   2294  O   LEU A 279      -4.041   5.163  27.651  1.00184.36           O
ATOM   2295  CB  LEU A 279      -4.475   6.650  30.505  1.00182.03           C
ATOM   2296  CG  LEU A 279      -5.324   7.630  31.335  1.00176.44           C
ATOM   2297  CD1 LEU A 279      -4.457   8.715  31.994  1.00175.10           C
ATOM   2298  CD2 LEU A 279      -6.450   8.278  30.518  1.00178.52           C
ATOM   2299  N   SER A 280      -3.813   3.676  29.327  1.00302.19           N
ATOM   2300  CA  SER A 280      -2.890   2.850  28.522  1.00302.39           C
ATOM   2301  C   SER A 280      -3.561   1.794  27.622  1.00306.20           C
ATOM   2302  O   SER A 280      -3.263   1.687  26.437  1.00310.43           O
ATOM   2303  CB  SER A 280      -1.819   2.212  29.415  1.00164.44           C
ATOM   2304  OG  SER A 280      -0.956   3.204  29.940  1.00162.01           O
ATOM   2305  N   GLY A 281      -4.469   1.023  28.200  1.00163.22           N
ATOM   2306  CA  GLY A 281      -5.145  -0.056  27.504  1.00166.58           C
ATOM   2307  C   GLY A 281      -5.208  -1.218  28.464  1.00162.51           C
ATOM   2308  O   GLY A 281      -4.176  -1.849  28.977  1.00159.54           O
ATOM   2309  N   GLY A 282      -6.411  -1.715  28.730  1.00130.45           N
ATOM   2310  CA  GLY A 282      -6.591  -2.739  29.736  1.00126.52           C
ATOM   2311  C   GLY A 282      -7.966  -3.371  29.687  1.00125.51           C
ATOM   2312  O   GLY A 282      -8.868  -2.947  30.385  1.00121.64           O
TER    2313      GLY A 282
```

Fig. 7AL

```
ATOM  2314  N   ALA A 307   -14.527  -8.193  -0.017  1.00 175.74           N
ATOM  2315  CA  ALA A 307   -14.394  -8.729   1.337  1.00 174.84           C
ATOM  2316  C   ALA A 307   -13.117  -9.612   1.586  1.00 163.71           C
ATOM  2317  O   ALA A 307   -12.535  -9.567   2.674  1.00 150.53           O
ATOM  2318  CB  ALA A 307   -15.704  -9.440   1.748  1.00 113.26           C
ATOM  2319  N   PHE A 308   -12.688 -10.375   0.568  1.00 167.18           N
ATOM  2320  CA  PHE A 308   -11.426 -11.178   0.550  1.00 177.79           C
ATOM  2321  C   PHE A 308   -11.045 -12.089   1.765  1.00 177.92           C
ATOM  2322  O   PHE A 308   -10.471 -11.972   2.740  1.00 159.69           O
ATOM  2323  CB  PHE A 308   -10.219 -10.323   0.124  1.00 137.81           C
ATOM  2324  CG  PHE A 308   -10.059 -10.174  -1.380  1.00 143.52           C
ATOM  2325  CD1 PHE A 308   -11.096  -9.691  -2.162  1.00 155.71           C
ATOM  2326  CD2 PHE A 308    -8.861 -10.489  -1.998  1.00 137.69           C
ATOM  2327  CE1 PHE A 308   -10.948  -9.545  -3.533  1.00 161.57           C
ATOM  2328  CE2 PHE A 308    -8.709 -10.349  -3.383  1.00 143.98           C
ATOM  2329  CZ  PHE A 308    -9.757  -9.871  -4.128  1.00 155.64           C
ATOM  2330  N   MET A 309   -11.319 -13.365   1.642  1.00 119.67           N
ATOM  2331  CA  MET A 309   -11.128 -14.380   2.696  1.00 119.95           C
ATOM  2332  C   MET A 309   -10.104 -15.445   2.289  1.00 120.03           C
ATOM  2333  O   MET A 309   -10.145 -15.945   1.169  1.00 140.09           O
ATOM  2334  CB  MET A 309   -12.454 -15.105   2.991  1.00 131.39           C
ATOM  2335  CG  MET A 309   -13.750 -14.329   2.649  1.00 138.38           C
ATOM  2336  SD  MET A 309   -15.083 -15.298   1.887  1.00 168.84           S
ATOM  2337  CE  MET A 309   -15.306 -16.655   3.032  1.00 156.15           C
ATOM  2338  N   TYR A 310    -9.211 -15.815   3.205  1.00 129.14           N
ATOM  2339  CA  TYR A 310    -8.145 -16.786   2.920  1.00 127.27           C
ATOM  2340  C   TYR A 310    -8.216 -17.985   3.881  1.00 134.24           C
ATOM  2341  O   TYR A 310    -8.769 -17.861   4.967  1.00 126.24           O
ATOM  2342  CB  TYR A 310    -6.769 -16.113   3.024  1.00 164.44           C
ATOM  2343  CG  TYR A 310    -6.650 -14.785   2.291  1.00 154.29           C
ATOM  2344  CD1 TYR A 310    -7.116 -13.607   2.860  1.00 138.43           C
ATOM  2345  CD2 TYR A 310    -6.062 -14.706   1.035  1.00 159.78           C
ATOM  2346  CE1 TYR A 310    -7.015 -12.390   2.199  1.00 132.38           C
ATOM  2347  CE2 TYR A 310    -5.950 -13.494   0.367  1.00 154.18           C
ATOM  2348  CZ  TYR A 310    -6.427 -12.346   0.951  1.00 143.70           C
ATOM  2349  OH  TYR A 310    -6.318 -11.151   0.295  1.00 141.27           O
ATOM  2350  N   PHE A 311    -7.672 -19.134   3.431  1.00 143.26           N
ATOM  2351  CA  PHE A 311    -7.657 -20.360   4.301  1.00 141.84           C
ATOM  2352  C   PHE A 311    -7.080 -20.090   5.697  1.00 111.27           C
ATOM  2353  O   PHE A 311    -6.404 -19.097   5.893  1.00  94.87           O
ATOM  2354  CB  PHE A 311    -6.831 -21.418   3.564  1.00 121.05           C
ATOM  2355  CG  PHE A 311    -6.846 -22.788   4.195  1.00 113.65           C
ATOM  2356  CD1 PHE A 311    -7.825 -23.699   3.882  1.00 128.95           C
ATOM  2357  CD2 PHE A 311    -5.839 -23.186   5.055  1.00  94.13           C
ATOM  2358  CE1 PHE A 311    -7.816 -24.964   4.446  1.00 124.20           C
ATOM  2359  CE2 PHE A 311    -5.835 -24.452   5.617  1.00  90.22           C
ATOM  2360  CZ  PHE A 311    -6.820 -25.334   5.314  1.00 104.66           C
ATOM  2361  N   ASN A 312    -7.317 -20.948   6.681  1.00 135.60           N
ATOM  2362  CA  ASN A 312    -6.910 -20.597   8.052  1.00 109.71           C
ATOM  2363  C   ASN A 312    -5.607 -21.245   8.537  1.00 100.84           C
ATOM  2364  O   ASN A 312    -5.510 -22.455   8.580  1.00 105.05           O
ATOM  2365  CB  ASN A 312    -8.048 -20.913   9.034  1.00 144.47           C
ATOM  2366  CG  ASN A 312    -7.798 -20.360  10.419  1.00 121.46           C
ATOM  2367  ND2 ASN A 312    -8.819 -20.395  11.264  1.00 114.34           N
ATOM  2368  OD1 ASN A 312    -6.695 -19.898  10.730  1.00 112.03           O
ATOM  2369  N   VAL A 313    -4.610 -20.462   8.936  1.00 113.42           N
ATOM  2370  CA  VAL A 313    -3.340 -21.068   9.372  1.00 105.89           C
ATOM  2371  C   VAL A 313    -3.399 -21.771  10.714  1.00  90.40           C
ATOM  2372  O   VAL A 313    -2.353 -22.103  11.269  1.00  82.69           O
ATOM  2373  CB  VAL A 313    -2.187 -20.042   9.520  1.00 115.00           C
ATOM  2374  CG1 VAL A 313    -0.949 -20.502   8.756  1.00 111.77           C
```

Fig. 7AM

```
ATOM   2375  CG2 VAL A 313      -2.637 -18.664   9.095  1.00106.76           C
ATOM   2376  N   ASN A 314      -4.587 -21.977  11.262  1.00123.80           N
ATOM   2377  CA  ASN A 314      -4.652 -22.499  12.621  1.00110.32           C
ATOM   2378  C   ASN A 314      -4.821 -24.020  12.708  1.00116.77           C
ATOM   2379  O   ASN A 314      -4.246 -24.668  13.591  1.00109.60           O
ATOM   2380  CB  ASN A 314      -5.690 -21.742  13.456  1.00139.52           C
ATOM   2381  CG  ASN A 314      -5.211 -20.357  13.868  1.00129.81           C
ATOM   2382  ND2 ASN A 314      -6.091 -19.369  13.762  1.00130.61           N
ATOM   2383  OD1 ASN A 314      -4.063 -20.180  14.270  1.00122.68           O
ATOM   2384  N   GLU A 315      -5.586 -24.596  11.788  1.00115.40           N
ATOM   2385  CA  GLU A 315      -5.656 -26.050  11.697  1.00125.19           C
ATOM   2386  C   GLU A 315      -4.414 -26.565  10.975  1.00132.69           C
ATOM   2387  O   GLU A 315      -4.422 -27.637  10.362  1.00146.39           O
ATOM   2388  CB  GLU A 315      -6.942 -26.515  10.996  1.00160.80           C
ATOM   2389  CG  GLU A 315      -7.201 -25.902   9.629  1.00176.80           C
ATOM   2390  CD  GLU A 315      -8.235 -24.796   9.678  1.00173.95           C
ATOM   2391  OE1 GLU A 315      -9.301 -24.453   8.619  1.00190.26           O
ATOM   2392  OE2 GLU A 315      -8.468 -24.269  10.780  1.00158.16           O1-
ATOM   2393  N   THR A 316      -3.339 -25.787  11.064  1.00 73.77           N
ATOM   2394  CA  THR A 316      -2.124 -26.064  10.313  1.00 81.39           C
ATOM   2395  C   THR A 316      -0.876 -26.034  11.183  1.00 71.40           C
ATOM   2396  O   THR A 316       0.114 -26.584  10.703  1.00 74.47           O
ATOM   2397  CB  THR A 316      -1.989 -25.156   9.012  1.00 75.11           C
ATOM   2398  CG2 THR A 316      -0.533 -24.376   8.692  1.00 73.66           C
ATOM   2399  OG1 THR A 316      -2.643 -25.844   7.882  1.00 88.15           O
ATOM   2400  N   ILE A 317      -0.914 -25.453  12.375  1.00103.51           N
ATOM   2401  CA  ILE A 317      -0.330 -25.297  13.147  1.00 92.03           C
ATOM   2402  C   ILE A 317       0.639 -26.458  14.093  1.00 88.14           C
ATOM   2403  O   ILE A 317      -0.193 -26.790  14.905  1.00 83.45           O
ATOM   2404  CB  ILE A 317       0.284 -24.015  13.970  1.00100.78           C
ATOM   2405  CG1 ILE A 317      -0.980 -22.634  13.051  1.00103.29           C
ATOM   2406  CG2 ILE A 317       1.565 -23.832  14.750  1.00 87.94           C
ATOM   2407  CD1 ILE A 317      -0.837 -21.629  13.247  1.00 81.93           C
ATOM   2408  N   MET A 318       1.819 -27.068  14.020  1.00 90.07           N
ATOM   2409  CA  MET A 318       2.045 -28.308  14.784  1.00 90.23           C
ATOM   2410  C   MET A 318       1.844 -28.122  16.272  1.00 77.84           C
ATOM   2411  O   MET A 318       1.162 -28.893  16.954  1.00 79.97           O
ATOM   2412  CB  MET A 318       3.477 -28.799  14.630  1.00102.79           C
ATOM   2413  CG  MET A 318       3.923 -29.188  13.259  1.00117.25           C
ATOM   2414  SD  MET A 318       5.343 -30.244  13.528  1.00117.44           S
ATOM   2415  CE  MET A 318       4.564 -31.577  14.447  1.00123.04           C
ATOM   2416  N   GLU A 319       2.540 -27.095  16.740  1.00106.62           N
ATOM   2417  CA  GLU A 319       2.642 -26.628  18.108  1.00100.52           C
ATOM   2418  C   GLU A 319       1.276 -26.424  18.777  1.00100.19           C
ATOM   2419  O   GLU A 319       1.157 -26.312  19.995  1.00 98.86           O
ATOM   2420  CB  GLU A 319       3.407 -25.309  18.013  1.00144.15           C
ATOM   2421  CG  GLU A 319       3.623 -24.551  19.265  1.00138.48           C
ATOM   2422  CD  GLU A 319       4.165 -23.174  18.984  1.00122.40           C
ATOM   2423  OE1 GLU A 319       3.535 -22.442  18.186  1.00119.67           O
ATOM   2424  OE2 GLU A 319       5.218 -22.826  19.563  1.00113.84           O1-
ATOM   2425  N   VAL A 320       0.233 -26.399  17.971  1.00111.50           N
ATOM   2426  CA  VAL A 320      -1.072 -26.032  18.472  1.00111.28           C
ATOM   2427  C   VAL A 320      -2.153 -27.069  18.060  1.00118.34           C
ATOM   2428  O   VAL A 320      -3.362 -26.811  18.107  1.00120.25           O
ATOM   2429  CB  VAL A 320      -1.368 -24.694  19.034  1.00 97.62           C
ATOM   2430  CG1 VAL A 320      -2.301 -24.664  16.836  1.00100.48           C
ATOM   2431  CG2 VAL A 320      -1.880 -23.791  19.199  1.00 93.00           C
ATOM   2432  N   ASN A 321      -1.678 -28.255  17.676  1.00122.50           N
ATOM   2433  CA  ASN A 321      -2.514 -29.418  17.404  1.00134.71           C
ATOM   2434  C   ASN A 321      -3.162 -29.808  18.728  1.00134.51           C
ATOM   2435  O   ASN A 321      -2.835 -29.217  19.750  1.00126.33           O
```

Fig. 7AN

```
ATOM   2436  CB   ASN A 321      -1.631  -30.557  16.866  1.00 121.08           C
ATOM   2437  CG   ASN A 321      -2.430  -31.662  16.197  1.00 137.54           C
ATOM   2438  ND2  ASN A 321      -1.806  -32.826  16.025  1.00 147.61           N
ATOM   2439  OD1  ASN A 321      -3.590  -31.473  15.834  1.00 142.36           O
ATOM   2440  N    THR A 322      -4.054  -30.797  18.736  1.00  89.32           N
ATOM   2441  CA   THR A 322      -4.792  -31.169  19.947  1.00  92.64           C
ATOM   2442  C    THR A 322      -4.260  -32.363  20.733  1.00 100.46           C
ATOM   2443  O    THR A 322      -3.166  -32.854  20.476  1.00  99.98           O
ATOM   2444  CB   THR A 322      -6.232  -31.428  19.606  1.00 115.49           C
ATOM   2445  CG2  THR A 322      -7.137  -30.829  20.674  1.00 114.81           C
ATOM   2446  OG1  THR A 322      -6.501  -30.836  18.333  1.00 114.96           O
ATOM   2447  N    ILE A 323      -5.021  -32.636  21.712  1.00  93.21           N
ATOM   2448  CA   ILE A 323      -4.586  -34.051  22.381  1.00 103.51           C
ATOM   2449  C    ILE A 323      -5.684  -35.031  22.856  1.00 120.09           C
ATOM   2450  O    ILE A 323      -6.845  -34.647  23.074  1.00 122.73           O
ATOM   2451  CB   ILE A 323      -3.640  -33.744  23.545  1.00 129.86           C
ATOM   2452  CG1  ILE A 323      -2.689  -32.615  23.198  1.00 114.82           C
ATOM   2453  CG2  ILE A 323      -2.797  -34.944  23.840  1.00 138.85           C
ATOM   2454  CD1  ILE A 323      -1.255  -32.951  23.521  1.00 110.80           C
ATOM   2455  N    ASP A 324      -5.290  -36.306  22.972  1.00 150.31           N
ATOM   2456  CA   ASP A 324      -6.069  -37.328  23.671  1.00 169.03           C
ATOM   2457  C    ASP A 324      -5.674  -37.177  25.114  1.00 171.97           C
ATOM   2458  O    ASP A 324      -4.560  -37.265  25.443  1.00 168.54           O
ATOM   2459  CB   ASP A 324      -5.651  -38.735  23.238  1.00 300.27           C
ATOM   2460  CG   ASP A 324      -5.555  -38.883  21.740  1.00 301.52           C
ATOM   2461  OD1  ASP A 324      -6.283  -38.176  21.016  1.00 296.97           O
ATOM   2462  OD2  ASP A 324      -4.745  -39.718  21.290  1.00 309.35           O1-
ATOM   2463  N    PRO A 325      -6.660  -36.970  25.987  1.00 119.92           N
ATOM   2464  CA   PRO A 325      -6.387  -36.689  27.406  1.00 116.77           C
ATOM   2465  C    PRO A 325      -5.269  -37.582  27.992  1.00 120.96           C
ATOM   2466  O    PRO A 325      -4.703  -37.205  29.001  1.00 117.32           O
ATOM   2467  CB   PRO A 325      -7.743  -36.942  28.096  1.00  78.12           C
ATOM   2468  CG   PRO A 325      -8.599  -37.658  27.050  1.00  84.10           C
ATOM   2469  CD   PRO A 325      -8.093  -37.185  25.720  1.00  77.92           C
ATOM   2470  N    GLU A 326      -5.024  -38.733  27.371  1.00  97.96           N
ATOM   2471  CA   GLU A 326      -3.907  -39.587  27.761  1.00 102.23           C
ATOM   2472  C    GLU A 326      -2.635  -38.766  27.751  1.00  90.63           C
ATOM   2473  O    GLU A 326      -1.945  -38.630  28.760  1.00  89.03           O
ATOM   2474  CB   GLU A 326      -3.753  -40.753  26.778  1.00 156.62           C
ATOM   2475  CG   GLU A 326      -4.522  -42.018  27.145  1.00 172.43           C
ATOM   2476  CD   GLU A 326      -3.608  -43.191  27.483  1.00 182.71           C
ATOM   2477  OE1  GLU A 326      -2.373  -43.054  27.337  1.00 177.63           O
ATOM   2478  OE2  GLU A 326      -4.126  -44.251  27.896  1.00 194.01           O1-
ATOM   2479  N    VAL A 327      -2.332  -38.214  26.586  1.00 107.83           N
ATOM   2480  CA   VAL A 327      -1.181  -37.394  26.421  1.00  97.45           C
ATOM   2481  C    VAL A 327      -1.326  -36.073  27.139  1.00  87.06           C
ATOM   2482  O    VAL A 327      -0.365  -35.409  27.445  1.00  79.61           O
ATOM   2483  CB   VAL A 327      -0.845  -37.077  24.943  1.00  93.06           C
ATOM   2484  CG1  VAL A 327       0.647  -37.118  24.703  1.00  89.64           C
ATOM   2485  CG2  VAL A 327      -1.574  -38.023  24.001  1.00 104.31           C
ATOM   2486  N    PHE A 328      -2.550  -35.647  27.379  1.00 112.53           N
ATOM   2487  CA   PHE A 328      -2.694  -34.447  28.165  1.00 104.37           C
ATOM   2488  C    PHE A 328      -1.977  -34.760  29.481  1.00 106.93           C
ATOM   2489  O    PHE A 328      -0.902  -34.188  29.792  1.00 106.28           O
ATOM   2490  CB   PHE A 328      -4.167  -34.109  28.365  1.00 101.03           C
ATOM   2491  CG   PHE A 328      -4.387  -32.867  29.147  1.00  93.63           C
ATOM   2492  CD1  PHE A 328      -3.963  -31.650  28.657  1.00  82.73           C
ATOM   2493  CD2  PHE A 328      -4.999  -32.912  30.384  1.00  98.87           C
ATOM   2494  CE1  PHE A 328      -4.153  -30.497  29.393  1.00  76.72           C
ATOM   2495  CE2  PHE A 328      -5.194  -31.766  31.110  1.00  93.36           C
ATOM   2496  CZ   PHE A 328      -4.766  -30.559  30.607  1.00  82.09           C
```

Fig. 7AO

```
ATOM  2497  N    MET A 329    -2.540 -35.711  30.225  1.00117.86         N
ATOM  2498  CA   MET A 329    -1.944 -36.114  31.483  1.00117.36         C
ATOM  2499  C    MET A 329    -0.462 -36.240  31.259  1.00119.76         C
ATOM  2500  O    MET A 329     0.289 -35.525  31.867  1.00101.60         O
ATOM  2501  CB   MET A 329    -2.493 -37.437  32.000  1.00 98.43         C
ATOM  2502  CG   MET A 329    -3.799 -37.860  31.382  1.00110.31         C
ATOM  2503  SD   MET A 329    -5.166 -37.888  32.541  1.00116.50         S
ATOM  2504  CE   MET A 329    -4.420 -36.796  33.867  1.00113.23         C
ATOM  2505  N    GLN A 330    -0.041 -37.115  30.343  1.00105.00         N
ATOM  2506  CA   GLN A 330     1.399 -37.367  30.124  1.00100.71         C
ATOM  2507  C    GLN A 330     2.222 -36.102  30.035  1.00 91.11         C
ATOM  2508  O    GLN A 330     2.953 -35.786  30.949  1.00 93.36         O
ATOM  2509  CB   GLN A 330     1.639 -38.195  28.874  1.00102.82         C
ATOM  2510  CG   GLN A 330     1.398 -39.665  29.071  1.00107.85         C
ATOM  2511  CD   GLN A 330     1.223 -40.363  27.761  1.00122.03         C
ATOM  2512  NE2  GLN A 330     0.346 -41.363  27.730  1.00130.98         N
ATOM  2513  OE1  GLN A 330     1.852 -39.994  26.772  1.00121.89         O
ATOM  2514  N    ARG A 331     2.129 -35.408  28.912  1.00 96.97         N
ATOM  2515  CA   ARG A 331     2.824 -34.042  28.765  1.00 85.89         C
ATOM  2516  C    ARG A 331     2.702 -33.229  30.069  1.00 80.67         C
ATOM  2517  O    ARG A 331     3.740 -32.620  30.373  1.00 74.67         O
ATOM  2518  CB   ARG A 331     1.779 -33.284  27.740  1.00 79.84         C
ATOM  2519  CG   ARG A 331     2.069 -33.638  26.303  1.00 85.73         C
ATOM  2520  CD   ARG A 331     1.532 -32.566  25.398  1.00 74.64         C
ATOM  2521  NE   ARG A 331     2.523 -31.953  24.493  1.00 70.42         N
ATOM  2522  CZ   ARG A 331     3.005 -30.714  24.606  1.00 62.19         C
ATOM  2523  NH1  ARG A 331     2.615 -29.962  25.618  1.00 57.08         N1+
ATOM  2524  NH2  ARG A 331     3.869 -30.208  23.721  1.00 66.28         N
ATOM  2525  N    ILE A 332     1.628 -33.193  30.844  1.00 96.83         N
ATOM  2526  CA   ILE A 332     1.718 -32.419  32.088  1.00 92.37         C
ATOM  2527  C    ILE A 332     2.581 -33.059  33.192  1.00 89.45         C
ATOM  2528  O    ILE A 332     3.304 -32.352  33.891  1.00 81.35         O
ATOM  2529  CB   ILE A 332     0.355 -32.013  32.616  1.00 76.35         C
ATOM  2530  CG1  ILE A 332    -0.197 -30.896  31.746  1.00 73.85         C
ATOM  2531  CG2  ILE A 332     0.453 -31.545  34.045  1.00 75.38         C
ATOM  2532  CD1  ILE A 332    -1.696 -30.719  31.864  1.00 77.04         C
ATOM  2533  N    SER A 333     2.529 -34.386  33.331  1.00110.48         N
ATOM  2534  CA   SER A 333     3.283 -35.090  34.383  1.00105.53         C
ATOM  2535  C    SER A 333     4.077 -36.371  33.987  1.00106.71         C
ATOM  2536  O    SER A 333     4.834 -36.899  34.797  1.00102.25         O
ATOM  2537  CB   SER A 333     2.404 -35.327  35.631  1.00103.68         C
ATOM  2538  OG   SER A 333     1.032 -35.491  35.309  1.00111.23         O
ATOM  2539  N    SER A 334     3.923 -36.852  32.755  1.00134.83         N
ATOM  2540  CA   SER A 334     4.670 -38.016  32.267  1.00137.43         C
ATOM  2541  C    SER A 334     4.229 -39.293  32.939  1.00141.35         C
ATOM  2542  O    SER A 334     5.076 -40.066  33.376  1.00138.10         O
ATOM  2543  CB   SER A 334     6.172 -37.865  32.536  1.00113.58         C
ATOM  2544  OG   SER A 334     6.726 -36.756  31.864  1.00112.61         O
ATOM  2545  N    SER A 335     2.921 -39.513  33.031  1.00116.55         N
ATOM  2546  CA   SER A 335     2.394 -40.683  33.767  1.00121.58         C
ATOM  2547  C    SER A 335     0.984 -40.446  34.318  1.00126.73         C
ATOM  2548  O    SER A 335     0.819 -39.797  35.351  1.00121.93         O
ATOM  2549  CB   SER A 335     3.321 -41.008  34.930  1.00201.79         C
ATOM  2550  OG   SER A 335     2.873 -42.164  35.606  1.00206.69         O
ATOM  2551  N    VAL A 336    -0.026 -41.009  33.653  1.00 97.09         N
ATOM  2552  CA   VAL A 336    -1.418 -40.834  34.093  1.00104.32         C
ATOM  2553  C    VAL A 336    -1.676 -41.061  35.596  1.00103.23         C
ATOM  2554  O    VAL A 336    -2.364 -40.282  36.234  1.00104.41         O
ATOM  2555  CB   VAL A 336    -2.391 -41.694  33.261  1.00 72.65         C
ATOM  2556  CG1  VAL A 336    -3.763 -41.730  33.911  1.00 81.04         C
ATOM  2557  CG2  VAL A 336    -2.485 -41.145  31.863  1.00 76.99         C
```

Fig. 7AP

| | | | | | | | | |
|---|---|---|---|---|---|---|---|---|
| ATOM | 2558 | N | LEU A 337 | -1.124 | -42.131 | 36.149 | 1.00 95.54 | N |
| ATOM | 2559 | CA | LEU A 337 | -1.267 | -42.438 | 37.570 | 1.00 96.04 | C |
| ATOM | 2560 | C | LEU A 337 | -0.733 | -41.267 | 38.386 | 1.00 86.28 | C |
| ATOM | 2561 | O | LEU A 337 | -1.375 | -40.801 | 39.340 | 1.00 88.86 | O |
| ATOM | 2562 | CB | LEU A 337 | -0.540 | -43.773 | 37.881 | 1.00 105.18 | C |
| ATOM | 2563 | CG | LEU A 337 | -0.263 | -44.417 | 39.251 | 1.00 108.63 | C |
| ATOM | 2564 | CD1 | LEU A 337 | 1.251 | -44.363 | 39.562 | 1.00 102.17 | C |
| ATOM | 2565 | CD2 | LEU A 337 | -1.115 | -43.838 | 40.395 | 1.00 113.44 | C |
| ATOM | 2566 | N | VAL A 338 | 0.430 | -40.770 | 37.972 | 1.00 121.98 | N |
| ATOM | 2567 | CA | VAL A 338 | 1.072 | -39.633 | 38.618 | 1.00 112.87 | C |
| ATOM | 2568 | C | VAL A 338 | 0.249 | -38.356 | 38.449 | 1.00 113.11 | C |
| ATOM | 2569 | O | VAL A 338 | 0.278 | -37.485 | 39.297 | 1.00 110.05 | O |
| ATOM | 2570 | CB | VAL A 338 | 2.495 | -39.417 | 38.073 | 1.00 103.18 | C |
| ATOM | 2571 | CG1 | VAL A 338 | 3.196 | -38.335 | 38.838 | 1.00 94.57 | C |
| ATOM | 2572 | CG2 | VAL A 338 | 3.263 | -40.675 | 38.195 | 1.00 104.67 | C |
| ATOM | 2573 | N | PHE A 339 | -0.482 | -38.251 | 37.347 | 1.00 100.43 | N |
| ATOM | 2574 | CA | PHE A 339 | -1.354 | -37.109 | 37.110 | 1.00 102.54 | C |
| ATOM | 2575 | C | PHE A 339 | -2.513 | -37.158 | 38.089 | 1.00 110.01 | C |
| ATOM | 2576 | O | PHE A 339 | -2.877 | -36.151 | 38.677 | 1.00 108.63 | O |
| ATOM | 2577 | CB | PHE A 339 | -1.863 | -37.153 | 35.670 | 1.00 102.69 | C |
| ATOM | 2578 | CG | PHE A 339 | -2.704 | -35.985 | 35.281 | 1.00 105.67 | C |
| ATOM | 2579 | CD1 | PHE A 339 | -2.126 | -34.838 | 34.823 | 1.00 96.28 | C |
| ATOM | 2580 | CD2 | PHE A 339 | -4.075 | -36.049 | 35.352 | 1.00 115.83 | C |
| ATOM | 2581 | CE1 | PHE A 339 | -2.897 | -33.778 | 34.462 | 1.00 97.89 | C |
| ATOM | 2582 | CE2 | PHE A 339 | -4.850 | -34.990 | 34.986 | 1.00 115.55 | C |
| ATOM | 2583 | CZ | PHE A 339 | -4.265 | -33.857 | 34.544 | 1.00 106.35 | C |
| ATOM | 2584 | N | ILE A 340 | -3.086 | -38.343 | 38.268 | 1.00 105.04 | N |
| ATOM | 2585 | CA | ILE A 340 | -4.216 | -38.512 | 39.179 | 1.00 114.56 | C |
| ATOM | 2586 | C | ILE A 340 | -3.732 | -38.322 | 40.603 | 1.00 111.23 | C |
| ATOM | 2587 | O | ILE A 340 | -4.528 | -37.987 | 41.478 | 1.00 117.87 | O |
| ATOM | 2588 | CB | ILE A 340 | -4.886 | -39.921 | 39.107 | 1.00 79.33 | C |
| ATOM | 2589 | CG1 | ILE A 340 | -4.449 | -40.732 | 37.869 | 1.00 79.66 | C |
| ATOM | 2590 | CG2 | ILE A 340 | -6.397 | -39.791 | 39.228 | 1.00 92.68 | C |
| ATOM | 2591 | CD1 | ILE A 340 | -5.507 | -40.909 | 36.785 | 1.00 94.07 | C |
| ATOM | 2592 | N | LEU A 341 | -2.443 | -38.564 | 40.853 | 1.00 124.70 | N |
| ATOM | 2593 | CA | LEU A 341 | -1.916 | -38.372 | 42.213 | 1.00 122.51 | C |
| ATOM | 2594 | C | LEU A 341 | -1.875 | -36.892 | 42.592 | 1.00 114.97 | C |
| ATOM | 2595 | O | LEU A 341 | -1.931 | -36.572 | 43.596 | 1.00 117.46 | O |
| ATOM | 2596 | CB | LEU A 341 | -0.523 | -39.173 | 42.429 | 1.00 93.55 | C |
| ATOM | 2597 | CG | LEU A 341 | -0.792 | -40.684 | 42.642 | 1.00 102.36 | C |
| ATOM | 2598 | CD1 | LEU A 341 | 0.485 | -41.374 | 43.192 | 1.00 98.73 | C |
| ATOM | 2599 | CD2 | LEU A 341 | -1.362 | -40.969 | 43.575 | 1.00 114.50 | C |
| ATOM | 2600 | N | SER A 342 | -1.795 | -36.229 | 41.450 | 1.00 117.42 | N |
| ATOM | 2601 | CA | SER A 342 | -0.830 | -34.826 | 41.461 | 1.00 109.93 | C |
| ATOM | 2602 | C | SER A 342 | -2.061 | -33.944 | 41.589 | 1.00 118.36 | C |
| ATOM | 2603 | O | SER A 342 | -2.040 | -32.998 | 42.350 | 1.00 114.72 | O |
| ATOM | 2604 | CB | SER A 342 | -0.053 | -34.470 | 40.186 | 1.00 107.74 | C |
| ATOM | 2605 | OG | SER A 342 | 1.241 | -35.050 | 40.170 | 1.00 101.39 | O |
| ATOM | 2606 | N | PHE A 343 | -3.125 | -34.243 | 40.849 | 1.00 109.43 | N |
| ATOM | 2607 | CA | PHE A 343 | -4.345 | -33.444 | 40.938 | 1.00 116.36 | C |
| ATOM | 2608 | C | PHE A 343 | -4.868 | -33.407 | 42.377 | 1.00 123.42 | C |
| ATOM | 2609 | O | PHE A 343 | -5.301 | -32.340 | 42.932 | 1.00 124.68 | O |
| ATOM | 2610 | CB | PHE A 343 | -5.405 | -33.995 | 39.927 | 1.00 105.45 | C |
| ATOM | 2611 | CG | PHE A 343 | -6.533 | -33.050 | 39.746 | 1.00 112.23 | C |
| ATOM | 2612 | CD1 | PHE A 343 | -6.293 | -31.780 | 39.262 | 1.00 104.58 | C |
| ATOM | 2613 | CD2 | PHE A 343 | -7.842 | -33.430 | 39.976 | 1.00 125.43 | C |
| ATOM | 2614 | CE1 | PHE A 343 | -7.341 | -30.903 | 39.020 | 1.00 107.57 | C |
| ATOM | 2615 | CE2 | PHE A 343 | -8.893 | -32.556 | 39.732 | 1.00 128.52 | C |
| ATOM | 2616 | CZ | PHE A 343 | -8.641 | -31.287 | 39.255 | 1.00 119.52 | C |
| ATOM | 2617 | N | ILE A 344 | -4.918 | -34.592 | 42.976 | 1.00 106.23 | N |
| ATOM | 2618 | CA | ILE A 344 | -5.310 | -34.776 | 44.370 | 1.00 114.20 | C |

Fig. 7AQ

```
ATOM   2619  C    ILE A 344      -4.387 -34.005  45.301  1.00105.88           C
ATOM   2620  O    ILE A 344      -4.855 -33.245  46.143  1.00111.23           O
ATOM   2621  CB   ILE A 344      -5.283 -36.281  44.765  1.00 95.72           C
ATOM   2622  CG1  ILE A 344      -6.407 -37.049  44.063  1.00106.22           C
ATOM   2623  CG2  ILE A 344      -5.365 -36.440  46.282  1.00103.41           C
ATOM   2624  CD1  ILE A 344      -6.182 -38.519  43.999  1.00109.60           C
ATOM   2625  N    GLY A 345      -3.079 -34.209  45.146  1.00146.15           N
ATOM   2626  CA   GLY A 345      -2.097 -33.502  45.952  1.00139.27           C
ATOM   2627  C    GLY A 345      -2.283 -31.996  45.904  1.00135.67           C
ATOM   2628  O    GLY A 345      -2.054 -31.295  46.889  1.00137.19           O
ATOM   2629  N    PHE A 346      -2.709 -31.512  44.744  1.00135.18           N
ATOM   2630  CA   PHE A 346      -2.958 -30.099  44.520  1.00122.99           C
ATOM   2631  C    PHE A 346      -4.222 -29.651  45.237  1.00124.74           C
ATOM   2632  O    PHE A 346      -4.249 -28.568  45.839  1.00125.67           O
ATOM   2633  CB   PHE A 346      -3.077 -29.789  43.030  1.00 98.64           C
ATOM   2634  CG   PHE A 346      -3.538 -28.396  42.757  1.00 98.12           C
ATOM   2635  CD1  PHE A 346      -2.651 -27.338  42.798  1.00 89.87           C
ATOM   2636  CD2  PHE A 346      -4.869 -28.134  42.499  1.00107.14           C
ATOM   2637  CE1  PHE A 346      -3.083 -26.048  42.566  1.00 89.91           C
ATOM   2638  CE2  PHE A 346      -5.305 -26.834  42.262  1.00107.47           C
ATOM   2639  CZ   PHE A 346      -4.410 -25.795  42.299  1.00 98.76           C
ATOM   2640  N    ILE A 347      -5.272 -30.464  45.147  1.00 73.68           N
ATOM   2641  CA   ILE A 347      -6.518 -30.228  45.894  1.00 87.13           C
ATOM   2642  C    ILE A 347      -6.334 -30.149  47.406  1.00 92.94           C
ATOM   2643  O    ILE A 347      -6.794 -29.220  48.051  1.00100.18           O
ATOM   2644  CB   ILE A 347      -7.537 -31.338  45.634  1.00118.39           C
ATOM   2645  CG1  ILE A 347      -8.163 -31.168  44.251  1.00119.64           C
ATOM   2646  CG2  ILE A 347      -8.587 -31.313  46.718  1.00133.19           C
ATOM   2647  CD1  ILE A 347      -8.663 -29.754  44.000  1.00124.15           C
ATOM   2648  N    LEU A 348      -5.679 -31.148  47.972  1.00101.38           N
ATOM   2649  CA   LEU A 348      -5.405 -31.127  49.393  1.00106.57           C
ATOM   2650  C    LEU A 348      -4.515 -29.933  49.685  1.00100.75           C
ATOM   2651  O    LEU A 348      -4.876 -29.093  50.511  1.00108.29           O
ATOM   2652  CB   LEU A 348      -4.753 -32.433  49.851  1.00 89.63           C
ATOM   2653  CG   LEU A 348      -5.378 -33.744  49.328  1.00 96.29           C
ATOM   2654  CD1  LEU A 348      -4.519 -34.996  49.646  1.00 97.45           C
ATOM   2655  CD2  LEU A 348      -6.830 -33.902  49.791  1.00112.12           C
ATOM   2656  N    LEU A 349      -3.372 -29.831  49.025  1.00118.99           N
ATOM   2657  CA   LEU A 349      -2.490 -28.672  49.214  1.00111.31           C
ATOM   2658  C    LEU A 349      -3.242 -27.342  49.280  1.00114.76           C
ATOM   2659  O    LEU A 349      -2.961 -26.505  50.137  1.00118.34           O
ATOM   2660  CB   LEU A 349      -1.450 -29.596  48.099  1.00121.61           C
ATOM   2661  CG   LEU A 349      -0.469 -27.416  48.246  1.00113.95           C
ATOM   2662  CD1  LEU A 349       0.261 -27.533  49.556  1.00117.98           C
ATOM   2663  CD2  LEU A 349       0.483 -27.350  47.083  1.00101.54           C
ATOM   2664  N    CYS A 350      -4.180 -27.148  48.354  1.00 90.70           N
ATOM   2665  CA   CYS A 350      -5.038 -25.965  48.323  1.00 95.71           C
ATOM   2666  C    CYS A 350      -5.873 -25.938  49.561  1.00110.49           C
ATOM   2667  O    CYS A 350      -5.564 -25.191  50.471  1.00112.58           O
ATOM   2668  CB   CYS A 350      -5.942 -25.959  47.097  1.00132.41           C
ATOM   2669  SG   CYS A 350      -5.160 -25.200  45.686  1.00118.08           S
ATOM   2670  N    LYS A 351      -6.913 -26.771  49.609  1.00113.12           N
ATOM   2671  CA   LYS A 351      -7.763 -26.842  50.809  1.00129.61           C
ATOM   2672  C    LYS A 351      -6.979 -27.408  51.999  1.00133.83           C
ATOM   2673  O    LYS A 351      -7.437 -28.312  52.701  1.00146.83           O
ATOM   2674  CB   LYS A 351      -9.049 -27.640  50.556  1.00192.81           C
ATOM   2675  CG   LYS A 351      -9.415 -27.833  49.079  1.00186.98           C
ATOM   2676  CD   LYS A 351      -9.666 -26.532  48.318  1.00183.80           C
ATOM   2677  CE   LYS A 351      -9.740 -26.815  46.818  1.00174.54           C
ATOM   2678  NZ   LYS A 351      -9.995 -25.605  46.007  1.00175.39           N1+
ATOM   2679  N    ASP A 352      -5.767 -26.873  52.152  1.00118.85           N
```

Fig. 7AR

| ATOM | 2680 | CA  | ASP | A | 352 | -4.907 | -27.016 | 53.314 | 1.00 | 121.87 | C |
|------|------|-----|-----|---|-----|--------|---------|--------|------|--------|---|
| ATOM | 2681 | C   | ASP | A | 352 | -4.045 | -25.754 | 53.437 | 1.00 | 112.96 | C |
| ATOM | 2682 | O   | ASP | A | 352 | -3.298 | -25.611 | 54.394 | 1.00 | 114.88 | O |
| ATOM | 2683 | CB  | ASP | A | 352 | -3.977 | -28.218 | 53.162 | 1.00 | 149.20 | C |
| ATOM | 2684 | CG  | ASP | A | 352 | -4.420 | -29.412 | 53.975 | 1.00 | 161.40 | C |
| ATOM | 2685 | OD1 | ASP | A | 352 | -5.639 | -29.589 | 54.168 | 1.00 | 173.67 | O |
| ATOM | 2686 | OD2 | ASP | A | 352 | -3.543 | -30.182 | 54.413 | 1.00 | 159.77 | O1- |
| ATOM | 2687 | N   | HIS | A | 353 | -4.131 | -24.841 | 52.471 | 1.00 | 209.35 | N |
| ATOM | 2688 | CA  | HIS | A | 353 | -3.244 | -23.674 | 52.482 | 1.00 | 201.47 | C |
| ATOM | 2689 | C   | HIS | A | 353 | -3.786 | -22.366 | 51.894 | 1.00 | 198.70 | C |
| ATOM | 2690 | O   | HIS | A | 353 | -3.379 | -21.287 | 52.318 | 1.00 | 197.91 | O |
| ATOM | 2691 | CB  | HIS | A | 353 | -1.903 | -24.029 | 51.858 | 1.00 | 126.85 | C |
| ATOM | 2692 | CG  | HIS | A | 353 | -1.015 | -24.817 | 52.772 | 1.00 | 129.75 | C |
| ATOM | 2693 | CD2 | HIS | A | 353 | -1.056 | -26.116 | 53.152 | 1.00 | 133.06 | C |
| ATOM | 2694 | ND1 | HIS | A | 353 |  0.055 | -24.257 | 53.432 | 1.00 | 130.13 | N |
| ATOM | 2695 | CE1 | HIS | A | 353 |  0.645 | -25.183 | 54.172 | 1.00 | 133.49 | C |
| ATOM | 2696 | NE2 | HIS | A | 353 | -0.009 | -26.316 | 54.023 | 1.00 | 136.21 | N |
| ATOM | 2697 | N   | LYS | A | 354 | -4.679 | -22.462 | 50.915 | 1.00 | 114.65 | N |
| ATOM | 2698 | CA  | LYS | A | 354 | -5.429 | -21.298 | 50.423 | 1.00 | 114.96 | C |
| ATOM | 2699 | C   | LYS | A | 354 | -4.613 | -20.440 | 49.484 | 1.00 | 101.42 | C |
| ATOM | 2700 | O   | LYS | A | 354 | -5.130 | -19.967 | 48.494 | 1.00 |  98.25 | O |
| ATOM | 2701 | CB  | LYS | A | 354 | -5.947 | -20.426 | 51.576 | 1.00 | 135.67 | C |
| ATOM | 2702 | CG  | LYS | A | 354 | -6.766 | -21.152 | 52.633 | 1.00 | 151.08 | C |
| ATOM | 2703 | CD  | LYS | A | 354 | -6.832 | -20.334 | 53.930 | 1.00 | 162.08 | C |
| ATOM | 2704 | CE  | LYS | A | 354 | -7.446 | -21.144 | 55.074 | 1.00 | 177.32 | C |
| ATOM | 2705 | NZ  | LYS | A | 354 | -7.740 | -20.315 | 56.278 | 1.00 | 189.68 | N1+ |
| ATOM | 2706 | N   | SER | A | 355 | -3.347 | -20.227 | 49.818 | 1.00 | 144.90 | N |
| ATOM | 2707 | CA  | SER | A | 355 | -2.452 | -19.419 | 48.997 | 1.00 | 132.54 | C |
| ATOM | 2708 | C   | SER | A | 355 | -2.144 | -20.131 | 47.693 | 1.00 | 122.93 | C |
| ATOM | 2709 | O   | SER | A | 355 | -1.978 | -19.508 | 46.639 | 1.00 | 115.97 | O |
| ATOM | 2710 | CB  | SER | A | 355 | -1.149 | -19.188 | 49.745 | 1.00 |  93.65 | C |
| ATOM | 2711 | OG  | SER | A | 355 | -1.360 | -19.388 | 51.126 | 1.00 | 105.18 | O |
| ATOM | 2712 | N   | MET | A | 356 | -2.050 | -21.452 | 47.788 | 1.00 | 126.34 | N |
| ATOM | 2713 | CA  | MET | A | 356 | -1.803 | -22.304 | 46.642 | 1.00 | 119.25 | C |
| ATOM | 2714 | C   | MET | A | 356 | -2.959 | -22.137 | 45.675 | 1.00 | 122.49 | C |
| ATOM | 2715 | O   | MET | A | 356 | -2.835 | -22.400 | 44.491 | 1.00 | 117.00 | O |
| ATOM | 2716 | CB  | MET | A | 356 | -1.664 | -23.748 | 47.108 | 1.00 | 136.92 | C |
| ATOM | 2717 | CG  | MET | A | 356 | -0.956 | -24.659 | 46.138 | 1.00 | 128.74 | C |
| ATOM | 2718 | SD  | MET | A | 356 |  0.423 | -23.687 | 45.260 | 1.00 | 115.57 | S |
| ATOM | 2719 | CE  | MET | A | 356 |  1.331 | -23.144 | 46.603 | 1.00 | 115.87 | C |
| ATOM | 2720 | N   | LEU | A | 357 | -4.082 | -21.673 | 46.202 | 1.00 | 106.80 | N |
| ATOM | 2721 | CA  | LEU | A | 357 | -5.246 | -21.312 | 45.407 | 1.00 | 112.14 | C |
| ATOM | 2722 | C   | LEU | A | 357 | -4.826 | -20.252 | 44.390 | 1.00 | 104.42 | C |
| ATOM | 2723 | O   | LEU | A | 357 | -5.324 | -20.189 | 43.262 | 1.00 | 103.17 | O |
| ATOM | 2724 | CB  | LEU | A | 357 | -6.319 | -20.760 | 46.347 | 1.00 |  74.02 | C |
| ATOM | 2725 | CG  | LEU | A | 357 | -7.783 | -20.976 | 46.079 | 1.00 |  84.79 | C |
| ATOM | 2726 | CD1 | LEU | A | 357 | -8.041 | -22.437 | 45.784 | 1.00 |  89.96 | C |
| ATOM | 2727 | CD2 | LEU | A | 357 | -8.548 | -20.529 | 47.293 | 1.00 |  95.56 | C |
| ATOM | 2728 | N   | LEU | A | 358 | -3.874 | -19.431 | 44.797 | 1.00 | 143.06 | N |
| ATOM | 2729 | CA  | LEU | A | 358 | -3.384 | -18.379 | 43.947 | 1.00 | 136.83 | C |
| ATOM | 2730 | C   | LEU | A | 358 | -2.688 | -18.906 | 42.703 | 1.00 | 128.42 | C |
| ATOM | 2731 | O   | LEU | A | 358 | -2.293 | -18.128 | 41.846 | 1.00 | 120.98 | O |
| ATOM | 2732 | CB  | LEU | A | 358 | -2.467 | -17.454 | 44.735 | 1.00 |  79.84 | C |
| ATOM | 2733 | CG  | LEU | A | 358 | -3.109 | -16.297 | 45.502 | 1.00 |  87.58 | C |
| ATOM | 2734 | CD1 | LEU | A | 358 | -2.059 | -15.410 | 46.171 | 1.00 |  84.45 | C |
| ATOM | 2735 | CD2 | LEU | A | 358 | -3.976 | -15.480 | 44.565 | 1.00 |  90.02 | C |
| ATOM | 2736 | N   | ALA | A | 359 | -2.526 | -20.226 | 42.596 | 1.00 | 117.46 | N |
| ATOM | 2737 | CA  | ALA | A | 359 | -1.943 | -20.835 | 41.393 | 1.00 | 110.57 | C |
| ATOM | 2738 | C   | ALA | A | 359 | -2.991 | -21.071 | 40.329 | 1.00 | 112.04 | C |
| ATOM | 2739 | O   | ALA | A | 359 | -2.661 | -21.203 | 39.155 | 1.00 | 107.22 | O |
| ATOM | 2740 | CB  | ALA | A | 359 | -1.250 | -22.122 | 41.722 | 1.00 |  55.94 | C |

Fig. 7AS

```
ATOM  2741  N    LEU A 360      -4.255 -21.127  40.729  1.00100.35           N
ATOM  2742  CA   LEU A 360      -5.298 -21.545  39.791  1.00102.23           C
ATOM  2743  C    LEU A 360      -5.155 -21.092  38.323  1.00 91.77           C
ATOM  2744  O    LEU A 360      -5.223 -21.940  37.436  1.00 90.97           O
ATOM  2745  CB   LEU A 360      -6.714 -21.304  40.334  1.00 86.08           C
ATOM  2746  CG   LEU A 360      -7.248 -22.410  41.259  1.00 97.27           C
ATOM  2747  CD1  LEU A 360      -8.405 -21.892  42.096  1.00108.47           C
ATOM  2748  CD2  LEU A 360      -7.632 -23.673  40.478  1.00 98.93           C
ATOM  2749  N    PRO A 361      -4.936 -19.786  38.049  1.00109.37           N
ATOM  2750  CA   PRO A 361      -4.771 -19.371  36.641  1.00 99.96           C
ATOM  2751  C    PRO A 361      -3.810 -20.276  35.837  1.00 95.45           C
ATOM  2752  O    PRO A 361      -4.185 -20.841  34.785  1.00 92.54           O
ATOM  2753  CB   PRO A 361      -4.190 -17.965  36.766  1.00100.84           C
ATOM  2754  CG   PRO A 361      -4.724 -17.462  38.041  1.00109.35           C
ATOM  2755  CD   PRO A 361      -4.783 -18.647  38.968  1.00117.18           C
ATOM  2756  N    MET A 362      -2.591 -20.437  36.354  1.00 91.41           N
ATOM  2757  CA   MET A 362      -1.598 -21.284  35.712  1.00 88.29           C
ATOM  2758  C    MET A 362      -2.046 -22.726  35.566  1.00 94.27           C
ATOM  2759  O    MET A 362      -1.695 -23.378  34.596  1.00 92.67           O
ATOM  2760  CB   MET A 362      -0.313 -21.262  36.490  1.00121.15           C
ATOM  2761  CG   MET A 362       0.346 -19.943  36.517  1.00115.53           C
ATOM  2762  SD   MET A 362       1.964 -20.299  37.179  1.00115.47           S
ATOM  2763  CE   MET A 362       2.577 -21.432  35.949  1.00113.00           C
ATOM  2764  N    LEU A 363      -2.794 -23.246  36.528  1.00 77.51           N
ATOM  2765  CA   LEU A 363      -3.441 -24.521  36.298  1.00 84.28           C
ATOM  2766  C    LEU A 363      -4.353 -24.401  35.072  1.00 83.43           C
ATOM  2767  O    LEU A 363      -4.131 -25.090  34.062  1.00 82.17           O
ATOM  2768  CB   LEU A 363      -4.241 -24.956  37.519  1.00 87.98           C
ATOM  2769  CG   LEU A 363      -3.886 -26.280  38.209  1.00 91.72           C
ATOM  2770  CD1  LEU A 363      -5.155 -27.035  38.601  1.00102.30           C
ATOM  2771  CD2  LEU A 363      -3.003 -27.153  37.346  1.00 87.08           C
ATOM  2772  N    ALA A 364      -5.321 -23.491  35.142  1.00 97.49           N
ATOM  2773  CA   ALA A 364      -6.327 -23.364  34.097  1.00 94.39           C
ATOM  2774  C    ALA A 364      -5.724 -23.288  32.684  1.00 85.52           C
ATOM  2775  O    ALA A 364      -6.147 -24.034  31.782  1.00 87.12           O
ATOM  2776  CB   ALA A 364      -7.210 -22.168  34.369  1.00 56.11           C
ATOM  2777  N    LEU A 365      -4.737 -22.406  32.496  1.00 87.34           N
ATOM  2778  CA   LEU A 365      -3.982 -22.333  31.242  1.00 80.83           C
ATOM  2779  C    LEU A 365      -3.852 -23.711  30.676  1.00 84.14           C
ATOM  2780  O    LEU A 365      -3.847 -24.039  29.512  1.00 84.01           O
ATOM  2781  CB   LEU A 365      -2.771 -21.434  31.429  1.00 70.23           C
ATOM  2782  CG   LEU A 365      -2.835 -20.170  30.591  1.00 64.37           C
ATOM  2783  CD1  LEU A 365      -1.620 -19.285  30.808  1.00 59.42           C
ATOM  2784  CD2  LEU A 365      -2.952 -20.587  29.149  1.00 65.04           C
ATOM  2785  N    GLY A 366      -2.809 -24.524  31.505  1.00 67.04           N
ATOM  2786  CA   GLY A 366      -2.543 -25.885  31.117  1.00 71.75           C
ATOM  2787  C    GLY A 366      -3.745 -26.840  30.600  1.00 77.89           C
ATOM  2788  O    GLY A 366      -3.724 -27.218  29.515  1.00 78.78           O
ATOM  2789  N    PHE A 367      -4.823 -26.588  31.375  1.00 71.42           N
ATOM  2790  CA   PHE A 367      -6.066 -27.240  30.998  1.00 76.25           C
ATOM  2791  C    PHE A 367      -6.669 -26.615  29.751  1.00 74.00           C
ATOM  2792  O    PHE A 367      -7.299 -27.317  28.941  1.00 78.79           O
ATOM  2793  CB   PHE A 367      -7.051 -27.228  32.162  1.00101.89           C
ATOM  2794  CG   PHE A 367      -6.720 -28.224  33.212  1.00110.77           C
ATOM  2795  CD1  PHE A 367      -5.724 -27.961  34.139  1.00109.88           C
ATOM  2796  CD2  PHE A 367      -7.370 -29.448  33.253  1.00121.37           C
ATOM  2797  CE1  PHE A 367      -5.397 -28.890  35.105  1.00116.47           C
ATOM  2798  CE2  PHE A 367      -7.051 -30.378  34.215  1.00130.87           C
ATOM  2799  CZ   PHE A 367      -6.063 -30.099  35.147  1.00126.43           C
ATOM  2800  N    MET A 368      -6.461 -25.303  29.579  1.00 95.95           N
ATOM  2801  CA   MET A 368      -7.001 -24.636  28.406  1.00 97.12           C
```

Fig. 7AT

| | | | | | | | | | |
|---|---|---|---|---|---|---|---|---|---|
| ATOM | 2802 | C | MET | A | 368 | -6.453 | -25.402 | 27.205 | 1.00 98.34 | C |
| ATOM | 2803 | O | MET | A | 368 | -7.099 | -25.509 | 26.162 | 1.00101.82 | O |
| ATOM | 2804 | CB | MET | A | 368 | -6.600 | -23.162 | 28.374 | 1.00156.82 | C |
| ATOM | 2805 | CG | MET | A | 368 | -7.472 | -22.333 | 27.455 | 1.00156.31 | C |
| ATOM | 2806 | SD | MET | A | 368 | -6.741 | -20.775 | 26.914 | 1.00148.84 | S |
| ATOM | 2807 | CE | MET | A | 368 | -5.071 | -21.281 | 26.509 | 1.00144.89 | C |
| ATOM | 2808 | N | ALA | A | 369 | -5.264 | -25.975 | 27.388 | 1.00101.72 | N |
| ATOM | 2809 | CA | ALA | A | 369 | -4.633 | -26.781 | 26.357 | 1.00104.38 | C |
| ATOM | 2810 | C | ALA | A | 369 | -5.658 | -27.611 | 25.603 | 1.00112.75 | C |
| ATOM | 2811 | O | ALA | A | 369 | -5.743 | -27.571 | 24.373 | 1.00114.78 | O |
| ATOM | 2812 | CB | ALA | A | 369 | -3.609 | -27.688 | 26.986 | 1.00 57.03 | C |
| ATOM | 2813 | N | LEU | A | 370 | -6.451 | -28.348 | 26.364 | 1.00 96.79 | N |
| ATOM | 2814 | CA | LEU | A | 370 | -7.365 | -29.330 | 25.805 | 1.00106.23 | C |
| ATOM | 2815 | C | LEU | A | 370 | -8.276 | -28.828 | 24.676 | 1.00108.90 | C |
| ATOM | 2816 | O | LEU | A | 370 | -8.794 | -29.640 | 23.905 | 1.00117.43 | O |
| ATOM | 2817 | CB | LEU | A | 370 | -8.200 | -29.973 | 26.917 | 1.00 76.60 | C |
| ATOM | 2818 | CG | LEU | A | 370 | -7.478 | -30.874 | 27.927 | 1.00 80.80 | C |
| ATOM | 2819 | CD1 | LEU | A | 370 | -6.226 | -30.839 | 29.226 | 1.00 87.91 | C |
| ATOM | 2820 | CD2 | LEU | A | 370 | -7.318 | -32.320 | 27.450 | 1.00 98.46 | C |
| ATOM | 2821 | N | ARG | A | 371 | -8.478 | -27.509 | 24.576 | 1.00131.41 | N |
| ATOM | 2822 | CA | ARG | A | 371 | -9.323 | -26.943 | 23.509 | 1.00134.77 | C |
| ATOM | 2823 | C | ARG | A | 371 | -8.610 | -25.804 | 22.795 | 1.00128.27 | C |
| ATOM | 2824 | O | ARG | A | 371 | -9.067 | -25.264 | 21.795 | 1.00131.74 | O |
| ATOM | 2825 | CB | ARG | A | 371 | -10.682 | -26.473 | 24.059 | 1.00198.73 | C |
| ATOM | 2826 | CG | ARG | A | 371 | -11.588 | -25.813 | 23.024 | 1.00205.14 | C |
| ATOM | 2827 | CD | ARG | A | 371 | -13.045 | -25.755 | 23.471 | 1.00210.33 | C |
| ATOM | 2828 | NE | ARG | A | 371 | -13.832 | -26.885 | 22.967 | 1.00221.24 | N |
| ATOM | 2829 | CZ | ARG | A | 371 | -15.142 | -26.843 | 22.712 | 1.00229.21 | C |
| ATOM | 2830 | NH1 | ARG | A | 371 | -15.829 | -25.723 | 22.905 | 1.00227.57 | N1+ |
| ATOM | 2831 | NH2 | ARG | A | 371 | -15.771 | -27.922 | 22.258 | 1.00239.74 | N |
| ATOM | 2832 | N | ALA | A | 372 | -7.439 | -25.467 | 23.314 | 1.00114.42 | N |
| ATOM | 2833 | CA | ALA | A | 372 | -6.744 | -24.270 | 22.890 | 1.00108.03 | C |
| ATOM | 2834 | C | ALA | A | 372 | -5.497 | -24.639 | 22.125 | 1.00108.61 | C |
| ATOM | 2835 | O | ALA | A | 372 | -5.127 | -23.995 | 21.139 | 1.00110.18 | O |
| ATOM | 2836 | CB | ALA | A | 372 | -6.372 | -23.436 | 24.097 | 1.00 84.76 | C |
| ATOM | 2837 | N | GLY | A | 373 | -4.839 | -25.683 | 22.599 | 1.00111.34 | N |
| ATOM | 2838 | CA | GLY | A | 373 | -3.568 | -26.072 | 22.009 | 1.00112.99 | C |
| ATOM | 2839 | C | GLY | A | 373 | -2.767 | -27.013 | 22.849 | 1.00110.62 | C |
| ATOM | 2840 | O | GLY | A | 373 | -2.909 | -27.132 | 24.059 | 1.00106.91 | O |
| ATOM | 2841 | N | LEU | A | 374 | -1.836 | -27.688 | 22.147 | 1.00102.39 | N |
| ATOM | 2842 | CA | LEU | A | 374 | -0.950 | -28.613 | 22.711 | 1.00102.93 | C |
| ATOM | 2843 | C | LEU | A | 374 | 0.067 | -27.885 | 23.548 | 1.00 93.47 | C |
| ATOM | 2844 | O | LEU | A | 374 | 0.553 | -28.401 | 24.549 | 1.00 93.01 | O |
| ATOM | 2845 | CB | LEU | A | 374 | -0.282 | -29.289 | 21.535 | 1.00 86.98 | C |
| ATOM | 2846 | CG | LEU | A | 374 | 1.045 | -29.962 | 21.713 | 1.00 92.56 | C |
| ATOM | 2847 | CD1 | LEU | A | 374 | 0.742 | -31.384 | 21.388 | 1.00100.36 | C |
| ATOM | 2848 | CD2 | LEU | A | 374 | 2.020 | -29.375 | 20.730 | 1.00 69.13 | C |
| ATOM | 2849 | N | ARG | A | 375 | 0.433 | -26.672 | 23.129 | 1.00116.01 | N |
| ATOM | 2850 | CA | ARG | A | 375 | 1.575 | -25.959 | 23.689 | 1.00109.23 | C |
| ATOM | 2851 | C | ARG | A | 375 | 1.279 | -25.305 | 25.023 | 1.00103.80 | C |
| ATOM | 2852 | O | ARG | A | 375 | 2.139 | -24.614 | 25.577 | 1.00 98.87 | O |
| ATOM | 2853 | CB | ARG | A | 375 | 2.069 | -24.894 | 22.713 | 1.00128.87 | C |
| ATOM | 2854 | CG | ARG | A | 375 | 1.732 | -23.477 | 23.119 | 1.00121.80 | C |
| ATOM | 2855 | CD | ARG | A | 375 | 1.428 | -22.627 | 21.911 | 1.00123.54 | C |
| ATOM | 2856 | NE | ARG | A | 375 | 0.661 | -21.442 | 22.287 | 1.00119.69 | N |
| ATOM | 2857 | CZ | ARG | A | 375 | 1.244 | -20.914 | 22.694 | 1.00115.07 | C |
| ATOM | 2858 | NH1 | ARG | A | 375 | 2.570 | -20.239 | 22.758 | 1.00113.68 | N1+ |
| ATOM | 2859 | NH2 | ARG | A | 375 | 0.496 | -19.270 | 23.041 | 1.00112.61 | N |
| ATOM | 2860 | N | PHE | A | 376 | 0.069 | -25.528 | 25.333 | 1.00 82.23 | N |
| ATOM | 2861 | CA | PHE | A | 376 | -0.364 | -24.935 | 26.801 | 1.00 79.16 | C |
| ATOM | 2862 | C | PHE | A | 376 | -0.187 | -25.814 | 28.049 | 1.00 82.94 | C |

Fig. 7AU

```
ATOM   2863  O    PHE A 376      -0.044 -25.299  29.152  1.00 81.17           O
ATOM   2864  CB   PHE A 376      -1.797 -24.422  26.690  1.00 91.91           C
ATOM   2865  CG   PHE A 376      -1.939 -23.272  25.747  1.00 89.55           C
ATOM   2866  CD1  PHE A 376      -2.610 -23.412  24.560  1.00 93.33           C
ATOM   2867  CD2  PHE A 376      -1.372 -22.050  26.038  1.00 83.18           C
ATOM   2868  CE1  PHE A 376      -2.737 -22.347  23.698  1.00 92.50           C
ATOM   2869  CE2  PHE A 376      -1.485 -20.992  25.173  1.00 81.90           C
ATOM   2870  CZ   PHE A 376      -2.168 -21.141  24.009  1.00 86.78           C
ATOM   2871  N    THR A 377      -0.182 -27.128  27.966  1.00 96.80           N
ATOM   2872  CA   THR A 377       0.033 -28.062  26.959  1.00102.49           C
ATOM   2873  C    THR A 377       1.177 -27.632  29.851  1.00 99.35           C
ATOM   2874  O    THR A 377       1.133 -27.830  31.066  1.00103.71           O
ATOM   2875  CB   THR A 377       0.374 -29.429  28.416  1.00 95.16           C
ATOM   2876  CG2  THR A 377      -0.858 -30.301  28.354  1.00102.18           C
ATOM   2877  OG1  THR A 377       0.879 -29.276  27.095  1.00 93.94           O
ATOM   2878  N    ILE A 378       2.206 -27.060  29.234  1.00 89.89           N
ATOM   2879  CA   ILE A 378       3.357 -26.485  29.339  1.00 86.38           C
ATOM   2880  C    ILE A 378       2.981 -25.697  31.224  1.00 86.12           C
ATOM   2881  O    ILE A 378       3.503 -25.978  32.320  1.00 89.03           O
ATOM   2882  CB   ILE A 378       4.179 -25.560  28.957  1.00 82.11           C
ATOM   2883  CG1  ILE A 378       5.442 -26.378  28.524  1.00 86.13           C
ATOM   2884  CG2  ILE A 378       4.557 -24.222  29.588  1.00 77.01           C
ATOM   2885  CD1  ILE A 378       6.511 -26.229  29.574  1.00 86.82           C
ATOM   2886  N    TYR A 379       2.056 -24.751  31.077  1.00101.64           N
ATOM   2887  CA   TYR A 379       1.578 -23.924  32.178  1.00102.12           C
ATOM   2888  C    TYR A 379       1.164 -24.708  33.417  1.00110.49           C
ATOM   2889  O    TYR A 379       1.242 -24.209  34.534  1.00110.87           O
ATOM   2890  CB   TYR A 379       0.409 -23.094  31.696  1.00109.19           C
ATOM   2891  CG   TYR A 379       0.856 -21.980  30.805  1.00101.72           C
ATOM   2892  CD1  TYR A 379       0.213 -21.724  29.623  1.00 99.73           C
ATOM   2893  CD2  TYR A 379       1.934 -21.191  31.148  1.00 98.11           C
ATOM   2894  CE1  TYR A 379       0.627 -20.705  28.800  1.00 94.86           C
ATOM   2895  CE2  TYR A 379       2.354 -20.158  30.342  1.00 92.60           C
ATOM   2896  CZ   TYR A 379       1.697 -19.920  29.164  1.00 91.20           C
ATOM   2897  OH   TYR A 379       2.095 -18.897  28.327  1.00 87.55           O
ATOM   2898  N    ALA A 380       0.723 -25.941  33.230  1.00103.63           N
ATOM   2899  CA   ALA A 380       0.197 -26.668  34.362  1.00110.75           C
ATOM   2900  C    ALA A 380       1.200 -27.649  34.943  1.00111.60           C
ATOM   2901  O    ALA A 380       0.871 -28.361  35.876  1.00114.88           O
ATOM   2902  CB   ALA A 380      -1.102 -27.356  33.991  1.00 74.29           C
ATOM   2903  N    VAL A 381       2.422 -27.681  34.408  1.00 98.72           N
ATOM   2904  CA   VAL A 381       3.462 -28.554  34.981  1.00 97.25           C
ATOM   2905  C    VAL A 381       3.814 -28.183  36.424  1.00 91.79           C
ATOM   2906  O    VAL A 381       3.442 -28.912  37.356  1.00 93.18           O
ATOM   2907  CB   VAL A 381       4.780 -28.604  34.144  1.00 92.37           C
ATOM   2908  CG1  VAL A 381       5.941 -29.044  35.009  1.00 86.11           C
ATOM   2909  CG2  VAL A 381       4.645 -29.541  32.956  1.00 97.81           C
ATOM   2910  N    PRO A 382       4.500 -27.030  36.620  1.00106.48           N
ATOM   2911  CA   PRO A 382       5.034 -26.692  37.923  1.00101.42           C
ATOM   2912  C    PRO A 382       4.086 -26.775  39.061  1.00105.14           C
ATOM   2913  O    PRO A 382       4.361 -27.454  40.051  1.00104.48           O
ATOM   2914  CB   PRO A 382       5.615 -25.264  37.727  1.00100.16           C
ATOM   2915  CG   PRO A 382       4.898 -24.739  36.551  1.00104.33           C
ATOM   2916  CD   PRO A 382       4.595 -25.907  35.671  1.00108.77           C
ATOM   2917  N    VAL A 383       2.929 -26.140  38.911  1.00 97.60           N
ATOM   2918  CA   VAL A 383       1.870 -26.291  39.900  1.00103.06           C
ATOM   2919  C    VAL A 383       1.545 -27.763  40.158  1.00107.57           C
ATOM   2920  O    VAL A 383       1.662 -28.242  41.333  1.00109.05           O
ATOM   2921  CB   VAL A 383       0.611 -25.563  39.469  1.00103.31           C
ATOM   2922  CG1  VAL A 383      -0.575 -26.061  40.266  1.00111.54           C
ATOM   2923  CG2  VAL A 383       0.798 -24.087  39.672  1.00100.27           C
```

Fig. 7AV

```
ATOM   2924  N    MET A 384       1.188  -28.800  39.143  1.00100.40           N
ATOM   2925  CA   MET A 384       0.799  -29.881  39.337  1.00105.64           C
ATOM   2926  C    MET A 384       1.965  -30.695  39.864  1.00100.96           C
ATOM   2927  O    MET A 384       1.815  -31.864  40.163  1.00105.36           O
ATOM   2928  CB   MET A 384       0.312  -30.468  38.028  1.00 90.90           C
ATOM   2929  CG   MET A 384      -1.081  -30.090  37.659  1.00 98.89           C
ATOM   2930  SD   MET A 384      -2.145  -31.447  38.083  1.00108.88           S
ATOM   2931  CE   MET A 384      -3.062  -30.734  39.434  1.00114.86           C
ATOM   2932  N    ALA A 385       3.140  -30.088  39.967  1.00 99.36           N
ATOM   2933  CA   ALA A 385       4.255  -30.791  40.582  1.00 94.74           C
ATOM   2934  C    ALA A 385       4.229  -30.598  42.105  1.00 96.47           C
ATOM   2935  O    ALA A 385       4.325  -31.563  42.860  1.00100.02           O
ATOM   2936  CB   ALA A 385       5.583  -30.355  39.969  1.00 67.86           C
ATOM   2937  N    LEU A 386       4.047  -29.360  42.555  1.00 89.28           N
ATOM   2938  CA   LEU A 386       3.955  -29.116  43.992  1.00 93.32           C
ATOM   2939  C    LEU A 386       2.855  -30.018  44.520  1.00102.65           C
ATOM   2940  O    LEU A 386       3.035  -30.702  45.529  1.00107.36           O
ATOM   2941  CB   LEU A 386       3.625  -27.649  44.310  1.00103.55           C
ATOM   2942  CG   LEU A 386       4.666  -26.565  44.022  1.00 96.51           C
ATOM   2943  CD1  LEU A 386       4.075  -25.179  44.191  1.00 97.95           C
ATOM   2944  CD2  LEU A 386       5.882  -26.739  44.911  1.00 95.65           C
ATOM   2945  N    GLY A 387       1.730  -30.013  43.830  1.00113.25           N
ATOM   2946  CA   GLY A 387       0.622  -30.907  44.120  1.00123.20           C
ATOM   2947  C    GLY A 387       1.178  -32.278  44.414  1.00124.98           C
ATOM   2948  O    GLY A 387       1.073  -32.774  45.540  1.00132.11           O
ATOM   2949  N    PHE A 388       1.799  -32.881  43.404  1.00 97.65           N
ATOM   2950  CA   PHE A 388       2.362  -34.200  43.591  1.00 99.25           C
ATOM   2951  C    PHE A 388       3.169  -34.261  44.872  1.00 99.15           C
ATOM   2952  O    PHE A 388       2.903  -35.118  45.712  1.00106.62           O
ATOM   2953  CB   PHE A 388       3.295  -34.656  42.408  1.00 96.65           C
ATOM   2954  CG   PHE A 388       3.803  -36.033  42.597  1.00 98.65           C
ATOM   2955  CD1  PHE A 388       2.998  -37.162  42.584  1.00106.64           C
ATOM   2956  CD2  PHE A 388       5.165  -36.204  42.802  1.00 93.99           C
ATOM   2957  CE1  PHE A 388       3.535  -38.421  42.759  1.00109.13           C
ATOM   2958  CE2  PHE A 388       5.704  -37.468  42.974  1.00 96.80           C
ATOM   2959  CZ   PHE A 388       4.897  -38.573  42.949  1.00104.21           C
ATOM   2960  N    GLY A 389       4.121  -33.348  45.037  1.00101.70           N
ATOM   2961  CA   GLY A 389       4.992  -33.330  46.243  1.00103.09           C
ATOM   2962  C    GLY A 389       4.076  -33.399  47.492  1.00113.09           C
ATOM   2963  O    GLY A 389       4.266  -34.262  48.353  1.00118.89           O
ATOM   2964  N    TYR A 390       3.111  -32.503  47.586  1.00 97.55           N
ATOM   2965  CA   TYR A 390       2.279  -32.464  48.758  1.00108.69           C
ATOM   2966  C    TYR A 390       1.700  -33.842  49.031  1.00118.30           C
ATOM   2967  O    TYR A 390       1.732  -34.302  50.169  1.00126.03           O
ATOM   2968  CB   TYR A 390       1.190  -31.393  48.612  1.00 83.34           C
ATOM   2969  CG   TYR A 390       0.539  -31.065  49.936  1.00 96.11           C
ATOM   2970  CD1  TYR A 390       1.292  -30.547  50.988  1.00 98.75           C
ATOM   2971  CD2  TYR A 390      -0.817  -31.297  50.150  1.00106.55           C
ATOM   2972  CE1  TYR A 390       0.715  -30.266  52.210  1.00113.76           C
ATOM   2973  CE2  TYR A 390      -1.404  -31.004  51.371  1.00119.37           C
ATOM   2974  CZ   TYR A 390      -0.629  -30.489  52.397  1.00122.09           C
ATOM   2975  OH   TYR A 390      -1.194  -30.190  53.615  1.00135.51           O
ATOM   2976  N    PHE A 391       1.209  -34.511  47.987  1.00 96.44           N
ATOM   2977  CA   PHE A 391       0.551  -35.813  48.139  1.00105.32           C
ATOM   2978  C    PHE A 391       1.415  -36.836  48.859  1.00108.94           C
ATOM   2979  O    PHE A 391       0.910  -37.753  49.487  1.00120.58           O
ATOM   2980  CB   PHE A 391       0.105  -36.372  46.789  1.00 98.96           C
ATOM   2981  CG   PHE A 391      -0.448  -37.761  46.869  1.00108.46           C
ATOM   2982  CD1  PHE A 391      -1.780  -37.963  47.200  1.00119.56           C
ATOM   2983  CD2  PHE A 391       0.366  -38.866  46.723  1.00107.23           C
ATOM   2984  CE1  PHE A 391      -2.288  -39.231  47.321  1.00129.25           C
```

Fig. 7AW

```
ATOM   2985  CE2 PHE A 391      -0.142 -40.130  46.844  1.00116.62           C
ATOM   2986  CZ  PHE A 391      -1.468 -40.312  47.145  1.00137.63           C
ATOM   2987  N   LEU A 392       2.731 -36.698  48.707  1.00 96.01           N
ATOM   2988  CA  LEU A 392       3.631 -37.628  49.379  1.00 99.46           C
ATOM   2989  C   LEU A 392       3.561 -37.301  50.861  1.00109.40           C
ATOM   2990  O   LEU A 392       3.227 -38.172  51.663  1.00121.14           O
ATOM   2991  CB  LEU A 392       5.049 -37.495  48.837  1.00121.09           C
ATOM   2992  CG  LEU A 392       5.131 -37.868  47.314  1.00111.74           C
ATOM   2993  CD1 LEU A 392       6.577 -37.697  46.827  1.00103.61           C
ATOM   2994  CD2 LEU A 392       4.282 -38.898  46.744  1.00117.64           C
ATOM   2995  N   TYR A 393       3.815 -36.033  51.209  1.00119.06           N
ATOM   2996  CA  TYR A 393       3.628 -35.541  52.582  1.00130.15           C
ATOM   2997  C   TYR A 393       2.381 -36.035  53.065  1.00164.19           C
ATOM   2998  O   TYR A 393       2.201 -36.904  53.933  1.00167.12           O
ATOM   2999  CB  TYR A 393       3.692 -34.004  52.641  1.00112.37           C
ATOM   3000  CG  TYR A 393       3.201 -33.397  53.946  1.00125.80           C
ATOM   3001  CD1 TYR A 393       3.820 -33.694  55.160  1.00133.99           C
ATOM   3002  CD2 TYR A 393       2.125 -32.523  53.963  1.00130.39           C
ATOM   3003  CE1 TYR A 393       3.366 -32.737  56.366  1.00144.94           C
ATOM   3004  CE2 TYR A 393       1.666 -31.963  55.158  1.00141.11           C
ATOM   3005  CZ  TYR A 393       2.290 -32.274  56.354  1.00149.44           C
ATOM   3006  OH  TYR A 393       1.837 -31.720  57.531  1.00165.48           O
ATOM   3007  N   ALA A 394       1.328 -35.478  52.476  1.00102.65           N
ATOM   3008  CA  ALA A 394      -0.119 -36.008  52.611  1.00115.19           C
ATOM   3009  C   ALA A 394      -0.084 -37.475  53.024  1.00124.99           C
ATOM   3010  O   ALA A 394      -0.420 -37.816  54.165  1.00141.05           O
ATOM   3011  CB  ALA A 394      -0.881 -35.847  51.282  1.00107.62           C
ATOM   3012  N   PHE A 395       0.362 -38.326  52.099  1.00119.60           N
ATOM   3013  CA  PHE A 395       0.340 -39.778  52.282  1.00127.72           C
ATOM   3014  C   PHE A 395       1.146 -40.260  53.486  1.00136.71           C
ATOM   3015  O   PHE A 395       0.660 -41.056  54.301  1.00151.88           O
ATOM   3016  CB  PHE A 395       0.842 -40.482  51.019  1.00 98.65           C
ATOM   3017  CG  PHE A 395       0.877 -41.999  51.124  1.00103.52           C
ATOM   3018  CD1 PHE A 395      -0.248 -42.762  50.808  1.00110.73           C
ATOM   3019  CD2 PHE A 395       2.028 -42.655  51.567  1.00104.72           C
ATOM   3020  CE1 PHE A 395      -0.220 -44.114  50.909  1.00118.62           C
ATOM   3021  CE2 PHE A 395       2.054 -44.010  51.672  1.00112.59           C
ATOM   3022  CZ  PHE A 395       0.936 -44.742  51.341  1.00119.37           C
ATOM   3023  N   PHE A 396       2.381 -39.780  53.589  1.00114.08           N
ATOM   3024  CA  PHE A 396       3.247 -40.167  54.695  1.00123.19           C
ATOM   3025  C   PHE A 396       2.649 -39.721  56.025  1.00139.33           C
ATOM   3026  O   PHE A 396       3.132 -40.089  57.091  1.00151.90           O
ATOM   3027  CB  PHE A 396       4.648 -39.596  54.499  1.00153.01           C
ATOM   3028  CG  PHE A 396       5.539 -40.476  53.696  1.00143.64           C
ATOM   3029  CD1 PHE A 396       5.062 -41.104  52.568  1.00134.68           C
ATOM   3030  CD2 PHE A 396       6.849 -40.685  54.074  1.00145.23           C
ATOM   3031  CE1 PHE A 396       5.876 -41.932  51.829  1.00127.43           C
ATOM   3032  CE2 PHE A 396       7.670 -41.507  53.340  1.00137.64           C
ATOM   3033  CZ  PHE A 396       7.186 -42.133  52.216  1.00128.70           C
ATOM   3034  N   ASN A 397       1.595 -38.916  55.941  1.00143.76           N
ATOM   3035  CA  ASN A 397       0.785 -38.600  57.099  1.00161.55           C
ATOM   3036  C   ASN A 397      -0.102 -39.769  57.481  1.00176.58           C
ATOM   3037  O   ASN A 397      -0.008 -40.274  58.597  1.00193.28           O
ATOM   3038  CB  ASN A 397      -0.074 -37.377  56.839  1.00141.11           C
ATOM   3039  CG  ASN A 397       0.286 -36.242  57.737  1.00138.39           C
ATOM   3040  ND2 ASN A 397      -0.719 -35.638  58.357  1.00141.77           N
ATOM   3041  OD1 ASN A 397       1.465 -35.925  57.908  1.00134.09           O
ATOM   3042  N   PHE A 398      -0.957 -40.201  56.554  1.00129.91           N
ATOM   3043  CA  PHE A 398      -1.866 -41.319  56.811  1.00142.80           C
ATOM   3044  C   PHE A 398      -1.147 -42.325  57.670  1.00153.31           C
ATOM   3045  O   PHE A 398      -1.706 -42.854  58.613  1.00171.91           O
```

Fig. 7AX

```
ATOM   3046  CB  PHE A 398      -2.275 -42.609  55.511  1.00120.71           C
ATOM   3047  CG  PHE A 398      -3.740 -42.351  55.427  1.00133.95           C
ATOM   3048  CD1 PHE A 398      -4.683 -41.630  56.142  1.00144.67           C
ATOM   3049  CD2 PHE A 398      -4.172 -43.393  54.615  1.00136.26           C
ATOM   3050  CE1 PHE A 398      -6.028 -41.944  56.045  1.00157.68           C
ATOM   3051  CE2 PHE A 398      -5.510 -43.709  54.512  1.00149.21           C
ATOM   3052  CZ  PHE A 398      -6.441 -42.985  55.227  1.00159.94           C
ATOM   3053  N   LEU A 399       0.110 -42.877  57.339  1.00156.23           N
ATOM   3054  CA  LEU A 399       0.906 -43.541  58.074  1.00165.69           C
ATOM   3055  C   LEU A 399       1.209 -43.072  59.496  1.00181.13           C
ATOM   3056  O   LEU A 399       0.688 -43.631  60.459  1.00201.49           O
ATOM   3057  CB  LEU A 399       2.190 -43.842  57.316  1.00125.06           C
ATOM   3058  CG  LEU A 399       1.997 -44.253  55.852  1.00111.53           C
ATOM   3059  CD1 LEU A 399       3.112 -45.167  55.477  1.00104.75           C
ATOM   3060  CD2 LEU A 399       0.652 -44.903  55.644  1.00123.52           C
ATOM   3061  N   GLU A 400       2.041 -42.045  59.831  1.00180.92           N
ATOM   3062  CA  GLU A 400       2.407 -41.537  60.954  1.00192.32           C
ATOM   3063  C   GLU A 400       1.187 -41.195  61.809  1.00208.09           C
ATOM   3064  O   GLU A 400       1.232 -41.321  63.029  1.00224.87           O
ATOM   3065  CB  GLU A 400       3.335 -40.319  60.845  1.00261.38           C
ATOM   3066  CG  GLU A 400       4.793 -40.659  60.549  1.00251.94           C
ATOM   3067  CD  GLU A 400       5.667 -39.425  60.388  1.00237.94           C
ATOM   3068  OE1 GLU A 400       5.130 -38.297  60.452  1.00236.18           O
ATOM   3069  OE2 GLU A 400       6.892 -39.569  60.197  1.00229.79           O1-
ATOM   3070  N   LYS A 401       0.057 -40.783  61.169  1.00132.06           N
ATOM   3071  CA  LYS A 401      -1.083 -40.298  61.891  1.00146.39           C
ATOM   3072  C   LYS A 401      -2.211 -41.322  62.033  1.00165.27           C
ATOM   3073  O   LYS A 401      -3.094 -41.158  62.873  1.00183.09           O
ATOM   3074  CB  LYS A 401      -1.628 -38.997  61.279  1.00183.00           C
ATOM   3075  CG  LYS A 401      -2.310 -38.081  62.287  1.00195.52           C
ATOM   3076  CD  LYS A 401      -3.081 -36.952  61.625  1.00186.44           C
ATOM   3077  CE  LYS A 401      -3.795 -36.109  62.674  1.00201.75           C
ATOM   3078  NZ  LYS A 401      -4.830 -35.222  62.078  1.00197.31           N1+
ATOM   3079  N   LYS A 402      -2.192 -42.366  61.212  1.00176.82           N
ATOM   3080  CA  LYS A 402      -3.088 -43.501  61.419  1.00191.98           C
ATOM   3081  C   LYS A 402      -2.306 -44.564  62.183  1.00204.19           C
ATOM   3082  O   LYS A 402      -2.492 -45.762  61.974  1.00209.15           O
ATOM   3083  CB  LYS A 402      -3.592 -44.059  60.087  1.00133.14           C
ATOM   3084  CG  LYS A 402      -4.999 -44.623  60.118  1.00148.63           C
ATOM   3085  CD  LYS A 402      -6.012 -43.632  59.579  1.00153.39           C
ATOM   3086  CE  LYS A 402      -7.375 -44.276  59.453  1.00169.31           C
ATOM   3087  NZ  LYS A 402      -7.312 -44.855  60.754  1.00188.49           N1+
ATOM   3088  N   GLN A 403      -1.433 -44.095  63.068  1.00161.29           N
ATOM   3089  CA  GLN A 403      -0.550 -44.943  63.864  1.00174.04           C
ATOM   3090  C   GLN A 403       0.143 -45.992  63.024  1.00164.44           C
ATOM   3091  O   GLN A 403      -0.405 -47.052  62.754  1.00174.91           O
ATOM   3092  CB  GLN A 403      -1.268 -45.573  65.052  1.00146.24           C
ATOM   3093  CG  GLN A 403      -1.160 -44.780  66.356  1.00155.75           C
ATOM   3094  CD  GLN A 403      -1.831 -45.465  67.534  1.00185.61           C
ATOM   3095  NE2 GLN A 403      -2.640 -44.709  68.265  1.00196.10           N
ATOM   3096  OE1 GLN A 403      -1.632 -46.656  67.782  1.00200.18           O
ATOM   3097  N   ILE A 404       1.360 -45.677  62.610  1.00208.24           N
ATOM   3098  CA  ILE A 404       2.156 -46.599  61.812  1.00196.99           C
ATOM   3099  C   ILE A 404       3.633 -46.309  62.047  1.00190.83           C
ATOM   3100  O   ILE A 404       4.262 -45.544  61.309  1.00172.15           O
ATOM   3101  CB  ILE A 404       1.809 -46.486  60.309  1.00140.25           C
ATOM   3102  CG1 ILE A 404       0.471 -47.167  60.026  1.00149.71           C
ATOM   3103  CG2 ILE A 404       2.836 -47.123  59.454  1.00124.60           C
ATOM   3104  CD1 ILE A 404       0.142 -47.281  58.552  1.00132.39           C
ATOM   3105  N   LYS A 405       4.168 -46.913  63.105  1.00202.69           N
ATOM   3106  CA  LYS A 405       5.568 -46.819  63.412  1.00201.43           C
```

Fig. 7AY

```
ATOM  3107  C    LYS A 405       6.391  -47.022  62.131  1.00 178.81           C
ATOM  3108  O    LYS A 405       6.408  -48.121  61.567  1.00 177.44           O
ATOM  3109  CB   LYS A 405       5.994  -47.870  64.457  1.00 157.01           C
ATOM  3110  CG   LYS A 405       5.325  -47.736  65.829  1.00 177.80           C
ATOM  3111  CD   LYS A 405       5.829  -48.814  66.791  1.00 200.15           C
ATOM  3112  CE   LYS A 405       5.360  -48.574  68.216  1.00 220.11           C
ATOM  3113  NZ   LYS A 405       6.142  -49.385  69.188  1.00 238.45           N1+
ATOM  3114  N    LEU A 406       7.033  -45.954  61.664  1.00 175.87           N
ATOM  3115  CA   LEU A 406       7.903  -46.024  60.497  1.00 156.14           C
ATOM  3116  C    LEU A 406       9.207  -45.308  60.817  1.00 156.77           C
ATOM  3117  O    LEU A 406       9.218  -44.095  60.898  1.00 159.46           O
ATOM  3118  CB   LEU A 406       7.231  -45.378  59.283  1.00 133.51           C
ATOM  3119  CG   LEU A 406       7.369  -46.034  57.904  1.00 119.36           C
ATOM  3120  CD1  LEU A 406       7.608  -44.965  56.860  1.00  98.69           C
ATOM  3121  CD2  LEU A 406       6.481  -47.071  57.875  1.00 119.90           C
ATOM  3122  N    SER A 407      10.300  -46.061  60.897  1.00 183.40           N
ATOM  3123  CA   SER A 407      11.603  -45.494  61.227  1.00 184.78           C
ATOM  3124  C    SER A 407      12.075  -44.566  60.120  1.00 162.28           C
ATOM  3125  O    SER A 407      11.390  -44.407  59.111  1.00 146.95           O
ATOM  3126  CB   SER A 407      12.625  -46.604  61.447  1.00 180.15           C
ATOM  3127  OG   SER A 407      12.507  -47.592  60.441  1.00 170.14           O
ATOM  3128  N    LEU A 408      13.244  -43.961  60.300  1.00 210.57           N
ATOM  3129  CA   LEU A 408      13.738  -42.969  59.341  1.00 191.31           C
ATOM  3130  C    LEU A 408      14.421  -43.573  58.108  1.00 178.57           C
ATOM  3131  O    LEU A 408      14.272  -43.065  56.992  1.00 158.76           O
ATOM  3132  CB   LEU A 408      14.615  -41.932  60.036  1.00 131.96           C
ATOM  3133  CG   LEU A 408      13.856  -40.907  60.892  1.00 141.79           C
ATOM  3134  CD1  LEU A 408      14.382  -39.481  60.666  1.00 140.65           C
ATOM  3135  CD2  LEU A 408      12.359  -40.968  60.645  1.00 134.14           C
ATOM  3136  N    ARG A 409      15.170  -44.653  58.316  1.00 162.42           N
ATOM  3137  CA   ARG A 409      15.739  -45.418  57.213  1.00 151.38           C
ATOM  3138  C    ARG A 409      14.620  -45.762  56.245  1.00 140.97           C
ATOM  3139  O    ARG A 409      14.689  -45.448  55.061  1.00 125.42           O
ATOM  3140  CB   ARG A 409      16.416  -46.694  57.739  1.00 190.92           C
ATOM  3141  CG   ARG A 409      16.657  -47.777  56.700  1.00 182.06           C
ATOM  3142  CD   ARG A 409      17.701  -48.784  57.181  1.00 196.42           C
ATOM  3143  NE   ARG A 409      18.907  -49.749  56.353  1.00 189.20           N
ATOM  3144  CZ   ARG A 409      19.971  -49.528  56.531  1.00 200.82           C
ATOM  3145  NH1  ARG A 409      19.993  -50.412  57.520  1.00 220.67           N1+
ATOM  3146  NH2  ARG A 409      21.019  -49.429  55.719  1.00 193.60           N
ATOM  3147  N    ASN A 410      13.571  -46.378  56.770  1.00 211.95           N
ATOM  3148  CA   ASN A 410      12.457  -46.828  55.953  1.00 205.19           C
ATOM  3149  C    ASN A 410      11.705  -45.688  55.275  1.00 190.82           C
ATOM  3150  O    ASN A 410      11.392  -45.778  54.090  1.00 179.64           O
ATOM  3151  CB   ASN A 410      11.504  -47.660  56.789  1.00 161.88           C
ATOM  3152  CG   ASN A 410      12.226  -48.773  57.562  1.00 178.27           C
ATOM  3153  ND2  ASN A 410      11.618  -49.222  58.661  1.00 196.61           N
ATOM  3154  OD1  ASN A 410      13.319  -49.210  57.176  1.00 175.26           O
ATOM  3155  N    LYS A 411      11.414  -44.622  56.017  1.00 164.96           N
ATOM  3156  CA   LYS A 411      10.711  -43.485  55.425  1.00 152.32           C
ATOM  3157  C    LYS A 411      11.525  -42.879  54.291  1.00 135.12           C
ATOM  3158  O    LYS A 411      10.985  -42.520  53.249  1.00 124.45           O
ATOM  3159  CB   LYS A 411      10.386  -42.402  56.453  1.00 116.89           C
ATOM  3160  CG   LYS A 411       9.598  -41.218  55.844  1.00 106.47           C
ATOM  3161  CD   LYS A 411       9.733  -39.900  56.649  1.00 112.19           C
ATOM  3162  CE   LYS A 411       8.378  -39.313  57.057  1.00 115.18           C
ATOM  3163  NZ   LYS A 411       8.524  -38.161  58.006  1.00 121.31           N1+
ATOM  3164  N    ASN A 412      12.829  -42.768  54.493  1.00 147.27           N
ATOM  3165  CA   ASN A 412      13.678  -42.187  53.468  1.00 132.83           C
ATOM  3166  C    ASN A 412      13.847  -43.089  52.230  1.00 124.77           C
ATOM  3167  O    ASN A 412      13.776  -42.615  51.096  1.00 111.75           O
```

Fig. 7AZ

```
ATOM   3168  CB  ASN A 412      15.014 -41.731  54.067  1.00152.68           C
ATOM   3169  CG  ASN A 412      14.871 -40.457  54.907  1.00156.39           C
ATOM   3170  ND2 ASN A 412      15.980 -39.759  55.129  1.00159.31           N
ATOM   3171  OD1 ASN A 412      13.775 -40.105  55.338  1.00157.41           O
ATOM   3172  N   ILE A 413      14.045 -44.386  52.440  1.00145.90           N
ATOM   3173  CA  ILE A 413      14.098 -45.313  51.315  1.00140.15           C
ATOM   3174  C   ILE A 413      12.794 -45.222  50.532  1.00133.11           C
ATOM   3175  O   ILE A 413      12.796 -45.121  49.307  1.00122.41           O
ATOM   3176  CB  ILE A 413      14.278 -46.773  51.766  1.00116.65           C
ATOM   3177  CG1 ILE A 413      15.394 -46.898  52.794  1.00127.48           C
ATOM   3178  CG2 ILE A 413      14.574 -47.672  50.576  1.00110.99           C
ATOM   3179  CD1 ILE A 413      15.329 -48.201  53.564  1.00143.15           C
ATOM   3180  N   LEU A 414      11.677 -45.260  51.251  1.00144.72           N
ATOM   3181  CA  LEU A 414      10.363 -45.174  50.624  1.00142.09           C
ATOM   3182  C   LEU A 414      10.134 -43.977  49.824  1.00129.83           C
ATOM   3183  O   LEU A 414       9.697 -43.892  48.707  1.00123.70           O
ATOM   3184  CB  LEU A 414       9.238 -45.351  51.660  1.00105.28           C
ATOM   3185  CG  LEU A 414       8.848 -46.797  51.955  1.00118.55           C
ATOM   3186  CD1 LEU A 414       7.341 -46.986  51.866  1.00127.08           C
ATOM   3187  CD2 LEU A 414       9.554 -47.676  50.957  1.00112.81           C
ATOM   3188  N   LEU A 415      10.617 -42.755  50.383  1.00122.58           N
ATOM   3189  CA  LEU A 415      10.544 -41.520  49.629  1.00113.49           C
ATOM   3190  C   LEU A 415      11.379 -41.610  48.364  1.00101.72           C
ATOM   3191  O   LEU A 415      10.889 -41.313  47.265  1.00 95.26           O
ATOM   3192  CB  LEU A 415      10.981 -40.330  50.482  1.00102.56           C
ATOM   3193  CG  LEU A 415       9.804 -39.559  51.083  1.00107.98           C
ATOM   3194  CD1 LEU A 415      10.219 -39.679  52.265  1.00112.72           C
ATOM   3195  CD2 LEU A 415       9.080 -38.756  49.995  1.00 99.74           C
ATOM   3196  N   ILE A 416      12.637 -42.026  48.492  1.00139.06           N
ATOM   3197  CA  ILE A 416      13.564 -42.062  47.363  1.00131.25           C
ATOM   3198  C   ILE A 416      13.035 -42.949  46.251  1.00130.77           C
ATOM   3199  O   ILE A 416      13.139 -42.620  45.070  1.00125.04           O
ATOM   3200  CB  ILE A 416      14.362 -42.543  47.791  1.00116.97           C
ATOM   3201  CG1 ILE A 416      15.658 -41.455  48.607  1.00120.48           C
ATOM   3202  CG2 ILE A 416      15.800 -42.908  46.877  1.00112.16           C
ATOM   3203  CD1 ILE A 416      16.951 -41.883  49.232  1.00125.88           C
ATOM   3204  N   LEU A 417      12.446 -44.071  46.628  1.00117.92           N
ATOM   3205  CA  LEU A 417      11.881 -44.956  45.633  1.00118.70           C
ATOM   3206  C   LEU A 417      10.598 -44.391  45.018  1.00116.52           C
ATOM   3207  O   LEU A 417      10.523 -44.265  43.817  1.00111.95           O
ATOM   3208  CB  LEU A 417      11.716 -46.375  46.169  1.00103.13           C
ATOM   3209  CG  LEU A 417      13.072 -47.082  46.309  1.00165.22           C
ATOM   3210  CD1 LEU A 417      13.302 -47.544  47.734  1.00116.81           C
ATOM   3211  CD2 LEU A 417      13.193 -48.249  45.333  1.00165.12           C
ATOM   3212  N   ILE A 418       9.600 -44.024  45.814  1.00125.34           N
ATOM   3213  CA  ILE A 418       8.436 -43.328  45.250  1.00123.10           C
ATOM   3214  C   ILE A 418       8.900 -42.301  44.187  1.00112.56           C
ATOM   3215  O   ILE A 418       8.383 -42.249  43.064  1.00109.87           O
ATOM   3216  CB  ILE A 418       7.579 -42.644  46.359  1.00 90.14           C
ATOM   3217  CG1 ILE A 418       6.450 -43.569  46.862  1.00103.11           C
ATOM   3218  CG2 ILE A 418       6.999 -41.348  45.847  1.00 84.85           C
ATOM   3219  CD1 ILE A 418       5.195 -43.677  45.941  1.00107.86           C
ATOM   3220  N   ALA A 419       9.925 -41.532  44.537  1.00108.76           N
ATOM   3221  CA  ALA A 419      10.464 -40.476  43.679  1.00 99.83           C
ATOM   3222  C   ALA A 419      11.121 -40.942  42.361  1.00 96.86           C
ATOM   3223  O   ALA A 419      10.716 -40.516  41.250  1.00 93.67           O
ATOM   3224  CB  ALA A 419      11.437 -39.602  44.481  1.00 65.12           C
ATOM   3225  N   PHE A 420      12.154 -41.777  42.475  1.00129.18           N
ATOM   3226  CA  PHE A 420      12.817 -42.285  41.282  1.00127.90           C
ATOM   3227  C   PHE A 420      11.777 -42.935  40.389  1.00131.73           C
ATOM   3228  O   PHE A 420      11.798 -42.720  39.154  1.00131.29           O
```

Fig. 7BA

```
ATOM   3229  CB   PHE A 420      13.905 -43.305  41.617  1.00 150.96           C
ATOM   3230  CG   PHE A 420      14.411 -44.054  40.407  1.00 151.43           C
ATOM   3231  CD1  PHE A 420      15.412 -43.513  39.608  1.00 147.44           C
ATOM   3232  CD2  PHE A 420      13.867 -45.295  40.051  1.00 157.09           C
ATOM   3233  CE1  PHE A 420      15.871 -44.198  38.481  1.00 149.55           C
ATOM   3234  CE2  PHE A 420      14.323 -45.965  38.930  1.00 158.88           C
ATOM   3235  CZ   PHE A 420      15.325 -45.413  38.144  1.00 156.33           C
ATOM   3236  N    PHE A 421      10.914 -43.730  41.000  1.00 103.43           N
ATOM   3237  CA   PHE A 421       9.819 -44.366  40.309  1.00 108.08           C
ATOM   3238  C    PHE A 421       9.032 -43.334  39.509  1.00 104.74           C
ATOM   3239  O    PHE A 421       9.020 -43.407  38.285  1.00 105.11           O
ATOM   3240  CB   PHE A 421       8.909 -45.138  41.257  1.00 223.01           C
ATOM   3241  CG   PHE A 421       7.775 -45.819  40.558  1.00 228.86           C
ATOM   3242  CD1  PHE A 421       7.869 -47.151  40.188  1.00 233.62           C
ATOM   3243  CD2  PHE A 421       6.621 -45.111  40.238  1.00 230.01           C
ATOM   3244  CE1  PHE A 421       6.824 -47.772  39.531  1.00 240.21           C
ATOM   3245  CE2  PHE A 421       5.574 -45.723  39.580  1.00 236.52           C
ATOM   3246  CZ   PHE A 421       5.675 -47.058  39.225  1.00 241.74           C
ATOM   3247  N    SER A 422       8.416 -42.348  40.164  1.00 125.99           N
ATOM   3248  CA   SER A 422       7.597 -41.369  39.414  1.00 123.60           C
ATOM   3249  C    SER A 422       8.325 -40.450  38.385  1.00 117.77           C
ATOM   3250  O    SER A 422       7.706 -39.981  37.428  1.00 119.14           O
ATOM   3251  CB   SER A 422       6.719 -40.550  40.360  1.00 106.85           C
ATOM   3252  OG   SER A 422       7.514 -39.815  41.258  1.00 103.17           O
ATOM   3253  N    ILE A 423       9.623 -40.212  38.575  1.00  93.17           N
ATOM   3254  CA   ILE A 423      10.454 -39.410  37.651  1.00  88.72           C
ATOM   3255  C    ILE A 423      11.006 -40.147  36.379  1.00  92.27           C
ATOM   3256  O    ILE A 423      11.178 -39.584  35.232  1.00  92.10           O
ATOM   3257  CB   ILE A 423      11.619 -38.857  38.489  1.00 101.70           C
ATOM   3258  CG1  ILE A 423      11.108 -37.733  39.380  1.00  99.08           C
ATOM   3259  CG2  ILE A 423      12.780 -38.391  37.631  1.00  97.84           C
ATOM   3260  CD1  ILE A 423      12.082 -36.605  39.480  1.00  93.36           C
ATOM   3261  N    SER A 424      11.308 -41.421  36.596  1.00 100.12           N
ATOM   3262  CA   SER A 424      11.862 -42.253  35.542  1.00 104.79           C
ATOM   3263  C    SER A 424      11.103 -42.219  34.205  1.00 108.66           C
ATOM   3264  O    SER A 424      11.713 -42.372  33.172  1.00 109.80           O
ATOM   3265  CB   SER A 424      11.976 -43.686  36.030  1.00  89.94           C
ATOM   3266  OG   SER A 424      10.716 -44.119  36.472  1.00  93.80           O
ATOM   3267  N    PRO A 425       9.773 -42.044  34.219  1.00 106.96           N
ATOM   3268  CA   PRO A 425       9.039 -41.954  32.956  1.00 112.33           C
ATOM   3269  C    PRO A 425       9.436 -40.753  32.137  1.00 108.92           C
ATOM   3270  O    PRO A 425       9.581 -40.817  30.914  1.00 114.08           O
ATOM   3271  CB   PRO A 425       7.604 -41.728  33.419  1.00  97.17           C
ATOM   3272  CG   PRO A 425       7.552 -42.334  34.715  1.00  97.33           C
ATOM   3273  CD   PRO A 425       8.863 -42.089  35.366  1.00  91.10           C
ATOM   3274  N    ALA A 426       9.592 -39.636  32.824  1.00 118.31           N
ATOM   3275  CA   ALA A 426      10.089 -38.446  32.177  1.00 114.87           C
ATOM   3276  C    ALA A 426      11.529 -38.665  31.724  1.00 114.35           C
ATOM   3277  O    ALA A 426      11.893 -38.303  30.578  1.00 117.25           O
ATOM   3278  CB   ALA A 426       9.986 -37.298  33.092  1.00  54.65           C
ATOM   3279  N    LEU A 427      12.353 -39.278  32.584  1.00  87.72           N
ATOM   3280  CA   LEU A 427      13.694 -39.663  32.055  1.00  89.27           C
ATOM   3281  C    LEU A 427      13.665 -40.424  30.686  1.00  96.11           C
ATOM   3282  O    LEU A 427      14.330 -40.034  29.692  1.00 102.44           O
ATOM   3283  CB   LEU A 427      14.463 -40.505  33.062  1.00 112.10           C
ATOM   3284  CG   LEU A 427      14.874 -39.877  34.381  1.00 104.26           C
ATOM   3285  CD1  LEU A 427      15.366 -40.977  35.299  1.00 105.56           C
ATOM   3286  CD2  LEU A 427      15.929 -38.786  34.179  1.00  99.13           C
ATOM   3287  N    MET A 428      12.900 -41.520  30.673  1.00  96.26           N
ATOM   3288  CA   MET A 428      12.664 -42.390  29.525  1.00 107.25           C
ATOM   3289  C    MET A 428      12.264 -41.543  28.345  1.00 112.20           C
```

Fig. 7BB

```
ATOM  3290  O   MET A 428    12.849 -41.646  27.272  1.00119.86    O
ATOM  3291  CB  MET A 428    11.524 -43.369  29.830  1.00169.16    C
ATOM  3292  CG  MET A 428    11.933 -44.828  29.998  1.00174.17    C
ATOM  3293  SD  MET A 428    10.521 -45.959  30.207  1.00183.11    S
ATOM  3294  CE  MET A 428     9.972 -45.626  31.887  1.00177.23    C
ATOM  3295  N   HIS A 429    11.252 -40.704  28.546  1.00 94.96    N
ATOM  3296  CA  HIS A 429    10.804 -39.827  27.478  1.00 99.98    C
ATOM  3297  C   HIS A 429    11.938 -38.993  26.924  1.00 99.10    C
ATOM  3298  O   HIS A 429    12.040 -38.813  25.713  1.00107.45    O
ATOM  3299  CB  HIS A 429     9.698 -38.896  27.932  1.00105.98    C
ATOM  3300  CG  HIS A 429     9.337 -37.881  26.898  1.00110.88    C
ATOM  3301  CD2 HIS A 429     9.734 -36.599  26.731  1.00105.53    C
ATOM  3302  ND1 HIS A 429     8.497 -38.165  25.844  1.00125.32    N
ATOM  3303  CE1 HIS A 429     8.370 -37.090  25.085  1.00117.20    C
ATOM  3304  NE2 HIS A 429     9.116 -36.130  25.598  1.00108.93    N
ATOM  3305  N   ILE A 430    12.779 -38.467  27.814  1.00 93.53    N
ATOM  3306  CA  ILE A 430    13.923 -37.683  27.343  1.00 92.96    C
ATOM  3307  C   ILE A 430    14.882 -38.512  26.502  1.00101.57    C
ATOM  3308  O   ILE A 430    15.458 -38.002  26.534  1.00107.61    O
ATOM  3309  CB  ILE A 430    14.764 -37.101  26.473  1.00 95.24    C
ATOM  3310  CG1 ILE A 430    13.964 -36.179  29.359  1.00 87.30    C
ATOM  3311  CG2 ILE A 430    15.891 -36.264  27.911  1.00 96.04    C
ATOM  3312  CD1 ILE A 430    14.869 -35.555  30.373  1.00 78.11    C
ATOM  3313  N   TYR A 431    15.095 -39.769  26.900  1.00 89.19    N
ATOM  3314  CA  TYR A 431    15.984 -40.651  26.121  1.00 98.63    C
ATOM  3315  C   TYR A 431    15.406 -40.874  24.747  1.00112.01    C
ATOM  3316  O   TYR A 431    16.119 -40.970  23.748  1.00121.85    O
ATOM  3317  CB  TYR A 431    16.165 -42.095  26.811  1.00 90.27    C
ATOM  3318  CG  TYR A 431    16.796 -43.085  25.953  1.00101.87    C
ATOM  3319  CD1 TYR A 431    18.149 -43.387  26.049  1.00101.41    C
ATOM  3320  CD2 TYR A 431    16.026 -43.827  25.062  1.00114.44    C
ATOM  3321  CE1 TYR A 431    18.720 -44.394  25.264  1.00113.02    C
ATOM  3322  CE2 TYR A 431    16.585 -44.825  24.268  1.00126.33    C
ATOM  3323  CZ  TYR A 431    17.927 -45.104  24.374  1.00125.45    C
ATOM  3324  OH  TYR A 431    18.457 -46.098  23.585  1.00138.13    O
ATOM  3325  N   TYR A 432    14.096 -41.072  24.719  1.00 91.54    N
ATOM  3326  CA  TYR A 432    13.403 -41.431  23.509  1.00103.15    C
ATOM  3327  C   TYR A 432    13.135 -40.213  22.664  1.00101.73    C
ATOM  3328  O   TYR A 432    12.762 -40.335  21.514  1.00105.36    O
ATOM  3329  CB  TYR A 432    12.097 -42.161  23.837  1.00171.52    C
ATOM  3330  CG  TYR A 432    12.369 -43.598  24.035  1.00177.29    C
ATOM  3331  CD1 TYR A 432    11.396 -44.384  24.837  1.00174.34    C
ATOM  3332  CD2 TYR A 432    13.305 -44.342  23.415  1.00185.56    C
ATOM  3333  CE1 TYR A 432    11.556 -45.749  25.015  1.00179.02    C
ATOM  3334  CE2 TYR A 432    13.473 -45.703  23.589  1.00191.44    C
ATOM  3335  CZ  TYR A 432    12.597 -46.402  24.387  1.00187.32    C
ATOM  3336  OH  TYR A 432    12.766 -47.756  24.555  1.00192.53    O
ATOM  3337  N   TYR A 433    13.343 -39.031  23.229  1.00119.00    N
ATOM  3338  CA  TYR A 433    13.019 -37.781  22.529  1.00112.37    C
ATOM  3339  C   TYR A 433    14.227 -37.128  21.831  1.00113.26    C
ATOM  3340  O   TYR A 433    14.860 -36.298  22.377  1.00107.75    O
ATOM  3341  CB  TYR A 433    12.330 -36.802  23.491  1.00116.68    C
ATOM  3342  CG  TYR A 433    11.723 -35.579  22.839  1.00110.39    C
ATOM  3343  CD1 TYR A 433    10.372 -35.534  22.546  1.00111.81    C
ATOM  3344  CD2 TYR A 433    12.503 -34.472  22.534  1.00103.12    C
ATOM  3345  CE1 TYR A 433     9.819 -34.405  21.958  1.00106.37    C
ATOM  3346  CE2 TYR A 433    11.954 -33.351  21.946  1.00 97.26    C
ATOM  3347  CZ  TYR A 433    10.615 -33.322  21.661  1.00 98.98    C
ATOM  3348  OH  TYR A 433    10.082 -32.200  21.079  1.00 94.32    O
ATOM  3349  N   LYS A 434    14.513 -37.606  20.618  1.00109.61    N
ATOM  3350  CA  LYS A 434    15.711 -37.224  19.871  1.00113.68    C
```

Fig. 7BC

| | | | | | | | | |
|---|---|---|---|---|---|---|---|---|
| ATOM | 3351 | C | LYS | A | 434 | 15.417 -36.373 18.649 | 1.00 112.97 | C |
| ATOM | 3352 | O | LYS | A | 434 | 15.469 -36.878 17.534 | 1.00 120.29 | O |
| ATOM | 3353 | CB | LYS | A | 434 | 16.446 -38.469 19.377 | 1.00 108.63 | C |
| ATOM | 3354 | CG | LYS | A | 434 | 16.616 -39.555 20.397 | 1.00 112.32 | C |
| ATOM | 3355 | CD | LYS | A | 434 | 17.360 -40.717 19.791 | 1.00 121.07 | C |
| ATOM | 3356 | CE | LYS | A | 434 | 17.692 -41.780 20.819 | 1.00 124.01 | C |
| ATOM | 3357 | NZ | LYS | A | 434 | 18.911 -41.368 21.577 | 1.00 122.74 | N1+ |
| ATOM | 3358 | N | SER | A | 435 | 15.137 -35.086 18.834 | 1.00 118.24 | N |
| ATOM | 3359 | CA | SER | A | 435 | 14.859 -34.226 17.682 | 1.00 118.10 | C |
| ATOM | 3360 | C | SER | A | 435 | 16.063 -34.144 16.772 | 1.00 127.55 | C |
| ATOM | 3361 | O | SER | A | 435 | 17.192 -34.373 17.198 | 1.00 132.47 | O |
| ATOM | 3362 | CB | SER | A | 435 | 14.474 -32.804 18.109 | 1.00 100.73 | C |
| ATOM | 3363 | OG | SER | A | 435 | 14.128 -32.757 19.476 | 1.00 92.51 | O |
| ATOM | 3364 | N | SER | A | 436 | 15.817 -33.819 15.512 | 1.00 113.74 | N |
| ATOM | 3365 | CA | SER | A | 436 | 16.895 -33.387 14.658 | 1.00 122.88 | C |
| ATOM | 3366 | C | SER | A | 436 | 16.979 -31.861 14.836 | 1.00 115.55 | C |
| ATOM | 3367 | O | SER | A | 436 | 16.556 -31.339 15.841 | 1.00 102.65 | O |
| ATOM | 3368 | CB | SER | A | 436 | 16.652 -33.771 13.196 | 1.00 167.88 | C |
| ATOM | 3369 | OG | SER | A | 436 | 15.744 -32.893 12.569 | 1.00 162.67 | O |
| ATOM | 3370 | N | THR | A | 437 | 17.525 -31.198 13.857 | 1.00 106.34 | N |
| ATOM | 3371 | CA | THR | A | 437 | 17.649 -29.772 13.945 | 1.00 99.65 | C |
| ATOM | 3372 | C | THR | A | 437 | 16.526 -29.197 13.126 | 1.00 103.26 | C |
| ATOM | 3373 | O | THR | A | 437 | 15.941 -29.896 12.307 | 1.00 115.80 | O |
| ATOM | 3374 | CB | THR | A | 437 | 18.954 -29.368 13.304 | 1.00 106.36 | C |
| ATOM | 3375 | CG2 | THR | A | 437 | 19.126 -27.857 13.335 | 1.00 101.53 | C |
| ATOM | 3376 | OG1 | THR | A | 437 | 20.034 -30.019 13.981 | 1.00 104.29 | O |
| ATOM | 3377 | N | VAL | A | 438 | 16.209 -27.930 13.335 | 1.00 95.75 | N |
| ATOM | 3378 | CA | VAL | A | 438 | 15.336 -27.242 12.395 | 1.00 101.26 | C |
| ATOM | 3379 | C | VAL | A | 438 | 15.755 -27.670 10.995 | 1.00 120.74 | C |
| ATOM | 3380 | O | VAL | A | 438 | 14.942 -28.194 10.235 | 1.00 127.99 | O |
| ATOM | 3381 | CB | VAL | A | 438 | 15.442 -25.702 12.543 | 1.00 72.46 | C |
| ATOM | 3382 | CG1 | VAL | A | 438 | 14.581 -24.966 11.510 | 1.00 80.62 | C |
| ATOM | 3383 | CG2 | VAL | A | 438 | 15.068 -25.304 13.949 | 1.00 56.98 | C |
| ATOM | 3384 | N | PHE | A | 439 | 17.038 -27.471 10.686 | 1.00 83.77 | N |
| ATOM | 3385 | CA | PHE | A | 439 | 17.610 -27.793 9.386 | 1.00 103.87 | C |
| ATOM | 3386 | C | PHE | A | 439 | 18.820 -28.683 9.572 | 1.00 108.72 | C |
| ATOM | 3387 | O | PHE | A | 439 | 19.337 -28.820 10.673 | 1.00 96.51 | O |
| ATOM | 3388 | CB | PHE | A | 439 | 18.093 -26.537 8.678 | 1.00 89.77 | C |
| ATOM | 3389 | CG | PHE | A | 439 | 17.027 -25.782 7.982 | 1.00 94.21 | C |
| ATOM | 3390 | CD1 | PHE | A | 439 | 15.725 -26.174 8.068 | 1.00 84.39 | C |
| ATOM | 3391 | CD2 | PHE | A | 439 | 17.332 -24.672 7.231 | 1.00 108.13 | C |
| ATOM | 3392 | CE1 | PHE | A | 439 | 14.735 -25.467 7.422 | 1.00 88.39 | C |
| ATOM | 3393 | CE2 | PHE | A | 439 | 16.351 -23.967 6.581 | 1.00 112.92 | C |
| ATOM | 3394 | CZ | PHE | A | 439 | 15.050 -24.365 6.679 | 1.00 102.58 | C |
| ATOM | 3395 | N | THR | A | 440 | 19.289 -29.271 8.478 | 1.00 85.91 | N |
| ATOM | 3396 | CA | THR | A | 440 | 20.534 -30.011 8.487 | 1.00 98.28 | C |
| ATOM | 3397 | C | THR | A | 440 | 21.622 -29.101 7.964 | 1.00 110.01 | C |
| ATOM | 3398 | O | THR | A | 440 | 21.350 -28.173 7.206 | 1.00 111.18 | O |
| ATOM | 3399 | CB | THR | A | 440 | 20.460 -31.225 7.561 | 1.00 101.39 | C |
| ATOM | 3400 | CG2 | THR | A | 440 | 19.782 -32.394 8.262 | 1.00 89.49 | C |
| ATOM | 3401 | OG1 | THR | A | 440 | 19.729 -30.873 6.376 | 1.00 107.99 | O |
| ATOM | 3402 | N | SER | A | 441 | 22.857 -29.369 8.367 | 1.00 116.96 | N |
| ATOM | 3403 | CA | SER | A | 441 | 24.004 -28.702 7.773 | 1.00 115.60 | C |
| ATOM | 3404 | C | SER | A | 441 | 23.713 -28.364 6.326 | 1.00 113.60 | C |
| ATOM | 3405 | O | SER | A | 441 | 23.612 -27.206 5.961 | 1.00 107.54 | O |
| ATOM | 3406 | CB | SER | A | 441 | 25.227 -29.609 7.840 | 1.00 87.37 | C |
| ATOM | 3407 | OG | SER | A | 441 | 24.818 -30.939 8.089 | 1.00 93.46 | O |
| ATOM | 3408 | N | TYR | A | 442 | 23.559 -29.394 5.512 | 1.00 116.27 | N |
| ATOM | 3409 | CA | TYR | A | 442 | 23.371 -29.223 4.085 | 1.00 115.07 | C |
| ATOM | 3410 | C | TYR | A | 442 | 22.526 -27.988 3.760 | 1.00 107.16 | C |
| ATOM | 3411 | O | TYR | A | 442 | 22.967 -27.106 3.011 | 1.00 104.73 | O |

Fig. 7BD

```
ATOM   3412  CB   TYR A 442    22.755 -30.488   3.499  1.00120.75      C
ATOM   3413  CG   TYR A 442    23.484 -31.763   3.877  1.00130.41      C
ATOM   3414  CD1  TYR A 442    23.850 -32.013   5.185  1.00110.58      C
ATOM   3415  CD2  TYR A 442    23.792 -32.724   2.928  1.00112.55      C
ATOM   3416  CE1  TYR A 442    24.515 -33.179   5.542  1.00119.95      C
ATOM   3417  CE2  TYR A 442    24.447 -33.901   3.279  1.00121.79      C
ATOM   3418  CZ   TYR A 442    24.812 -34.124   4.593  1.00125.62      C
ATOM   3419  OH   TYR A 442    25.468 -35.283   4.969  1.00135.79      O
ATOM   3420  N    GLU A 443    21.331 -27.914   4.351  1.00123.91      N
ATOM   3421  CA   GLU A 443    20.361 -26.821   4.092  1.00117.18      C
ATOM   3422  C    GLU A 443    20.895 -25.449   4.564  1.00111.92      C
ATOM   3423  O    GLU A 443    20.893 -24.446   3.819  1.00107.74      O
ATOM   3424  CB   GLU A 443    19.024 -27.148   4.733  1.00111.88      C
ATOM   3425  CG   GLU A 443    18.603 -28.617   4.607  1.00119.25      C
ATOM   3426  CD   GLU A 443    17.096 -28.799   4.585  1.00119.81      C
ATOM   3427  OE1  GLU A 443    16.445 -28.403   5.558  1.00116.32      O
ATOM   3428  OE2  GLU A 443    16.550 -29.325   3.594  1.00121.14      O1-
ATOM   3429  N    ALA A 444    21.346 -25.415   5.809  1.00122.53      N
ATOM   3430  CA   ALA A 444    22.012 -24.240   6.335  1.00118.63      C
ATOM   3431  C    ALA A 444    22.960 -23.739   5.282  1.00119.01      C
ATOM   3432  O    ALA A 444    22.725 -22.727   4.644  1.00115.38      O
ATOM   3433  CB   ALA A 444    22.751 -24.575   7.584  1.00 65.20      C
ATOM   3434  N    SER A 445    24.075 -24.480   5.095  1.00127.66      N
ATOM   3435  CA   SER A 445    25.178 -24.082   4.222  1.00129.81      C
ATOM   3436  C    SER A 445    24.724 -23.720   2.816  1.00127.66      C
ATOM   3437  O    SER A 445    25.318 -22.855   2.179  1.00127.32      O
ATOM   3438  CB   SER A 445    26.274 -25.155   4.189  1.00152.70      C
ATOM   3439  OG   SER A 445    25.741 -26.423   3.861  1.00157.70      O
ATOM   3440  N    ILE A 446    23.680 -24.377   2.326  1.00123.83      N
ATOM   3441  CA   ILE A 446    23.096 -23.949   1.062  1.00122.77      C
ATOM   3442  C    ILE A 446    22.662 -22.487   1.218  1.00116.95      C
ATOM   3443  O    ILE A 446    22.983 -21.624   0.372  1.00117.06      O
ATOM   3444  CB   ILE A 446    21.921 -24.874   0.608  1.00 75.54      C
ATOM   3445  CG1  ILE A 446    22.467 -26.187   0.034  1.00 91.83      C
ATOM   3446  CG2  ILE A 446    21.044 -24.179  -0.433  1.00 83.25      C
ATOM   3447  CD1  ILE A 446    21.492 -27.322   0.055  1.00 84.15      C
ATOM   3448  N    LEU A 447    21.973 -22.199   2.324  1.00125.60      N
ATOM   3449  CA   LEU A 447    21.503 -20.826   2.571  1.00129.21      C
ATOM   3450  C    LEU A 447    22.617 -19.792   2.810  1.00119.44      C
ATOM   3451  O    LEU A 447    22.585 -18.686   2.258  1.00117.71      O
ATOM   3452  CB   LEU A 447    20.467 -20.813   3.694  1.00102.12      C
ATOM   3453  CG   LEU A 447    19.181 -21.523   3.250  1.00102.48      C
ATOM   3454  CD1  LEU A 447    18.419 -22.074   4.425  1.00101.03      C
ATOM   3455  CD2  LEU A 447    18.292 -20.623   2.403  1.00100.59      C
ATOM   3456  N    ASN A 448    23.598 -20.157   3.626  1.00110.23      N
ATOM   3457  CA   ASN A 448    24.802 -19.358   3.929  1.00110.55      C
ATOM   3458  C    ASN A 448    25.467 -19.006   2.561  1.00113.83      C
ATOM   3459  O    ASN A 448    25.738 -17.841   2.215  1.00111.10      O
ATOM   3460  CB   ASN A 448    25.794 -20.118   4.705  1.00127.34      C
ATOM   3461  CG   ASN A 448    26.855 -19.224   5.277  1.00126.05      C
ATOM   3462  ND2  ASN A 448    28.091 -19.711   5.282  1.00130.27      N
ATOM   3463  OD1  ASN A 448    26.574 -18.098   5.707  1.00119.26      O
ATOM   3464  N    ASP A 449    25.739 -20.028   1.699  1.00132.07      N
ATOM   3465  CA   ASP A 449    26.177 -19.826   0.331  1.00135.90      C
ATOM   3466  C    ASP A 449    25.250 -18.807  -0.350  1.00133.43      C
ATOM   3467  O    ASP A 449    25.739 -17.911  -1.043  1.00134.26      O
ATOM   3468  CB   ASP A 449    26.178 -21.156  -0.427  1.00193.50      C
ATOM   3469  CG   ASP A 449    27.037 -21.119  -1.677  1.00200.41      C
ATOM   3470  OD1  ASP A 449    27.290 -20.011  -2.192  1.00212.02      O
ATOM   3471  OD2  ASP A 449    27.456 -22.199  -2.146  1.00215.74      O1-
ATOM   3472  N    LEU A 450    23.941 -18.932  -0.144  1.00133.93      N
```

Fig. 7BE

```
ATOM   3473  CA  LEU A 450      22.983 -17.961  -0.717  1.00 130.48           C
ATOM   3474  C   LEU A 450      23.230 -16.518  -0.243  1.00 125.18           C
ATOM   3475  O   LEU A 450      22.928 -15.555  -0.957  1.00 122.72           O
ATOM   3476  CB  LEU A 450      21.520 -18.367  -0.445  1.00 100.33           C
ATOM   3477  CG  LEU A 450      20.416 -17.892  -1.416  1.00 101.11           C
ATOM   3478  CD1 LEU A 450      19.133 -17.503  -0.698  1.00  95.95           C
ATOM   3479  CD2 LEU A 450      20.872 -16.747  -2.310  1.00 105.21           C
ATOM   3480  N   LYS A 451      23.770 -16.373   0.965  1.00 136.76           N
ATOM   3481  CA  LYS A 451      24.095 -15.048   1.500  1.00 129.33           C
ATOM   3482  C   LYS A 451      25.076 -14.282   0.604  1.00 129.93           C
ATOM   3483  O   LYS A 451      24.821 -13.130   0.234  1.00 124.74           O
ATOM   3484  CB  LYS A 451      24.665 -15.181   2.910  1.00 112.43           C
ATOM   3485  CG  LYS A 451      24.473 -13.958   3.769  1.00 104.64           C
ATOM   3486  CD  LYS A 451      24.933 -14.209   5.211  1.00 103.39           C
ATOM   3487  CE  LYS A 451      25.455 -14.073   5.375  1.00 104.06           C
ATOM   3488  NZ  LYS A 451      25.946 -14.267   6.781  1.00 102.19           N1+
ATOM   3489  N   ASN A 452      26.186 -14.927   0.248  1.00 145.37           N
ATOM   3490  CA  ASN A 452      27.248 -14.311  -0.554  1.00 147.35           C
ATOM   3491  C   ASN A 452      26.915 -14.151  -2.028  1.00 150.15           C
ATOM   3492  O   ASN A 452      27.765 -13.740  -2.809  1.00 153.67           O
ATOM   3493  CB  ASN A 452      28.525 -15.138  -0.453  1.00 123.97           C
ATOM   3494  CG  ASN A 452      28.747 -15.660   0.930  1.00 122.11           C
ATOM   3495  ND2 ASN A 452      29.137 -16.951   1.020  1.00 127.59           N
ATOM   3496  OD1 ASN A 452      28.656 -14.969   1.917  1.00 115.90           O
ATOM   3497  N   LYS A 453      25.695 -14.499  -2.412  1.00 130.32           N
ATOM   3498  CA  LYS A 453      25.260 -14.343  -3.792  1.00 132.26           C
ATOM   3499  C   LYS A 453      24.212 -13.253  -3.877  1.00 124.11           C
ATOM   3500  O   LYS A 453      23.996 -12.656  -4.931  1.00 124.44           O
ATOM   3501  CB  LYS A 453      24.635 -15.635  -4.312  1.00 111.00           C
ATOM   3502  CG  LYS A 453      25.545 -16.820  -4.364  1.00 140.67           C
ATOM   3503  CD  LYS A 453      24.885 -17.905  -5.193  1.00 139.25           C
ATOM   3504  CE  LYS A 453      25.730 -19.143  -5.247  1.00 145.75           C
ATOM   3505  NZ  LYS A 453      25.340 -19.957  -6.414  1.00 149.71           N1+
ATOM   3506  N   ALA A 454      23.554 -13.007  -2.754  1.00 154.76           N
ATOM   3507  CA  ALA A 454      22.358 -12.192  -2.747  1.00 148.64           C
ATOM   3508  C   ALA A 454      22.537 -10.879  -1.995  1.00 140.56           C
ATOM   3509  O   ALA A 454      23.399 -10.767  -1.122  1.00 138.31           O
ATOM   3510  CB  ALA A 454      21.228 -12.984  -2.149  1.00  46.45           C
ATOM   3511  N   GLN A 455      21.722  -9.885  -2.339  1.00 146.39           N
ATOM   3512  CA  GLN A 455      21.778  -8.586  -1.668  1.00 139.31           C
ATOM   3513  C   GLN A 455      20.845  -8.529  -0.450  1.00 134.69           C
ATOM   3514  O   GLN A 455      19.763  -9.127  -0.443  1.00 136.48           O
ATOM   3515  CB  GLN A 455      21.492  -7.433  -2.647  1.00 143.24           C
ATOM   3516  CG  GLN A 455      22.462  -7.340  -3.829  1.00 147.36           C
ATOM   3517  CD  GLN A 455      23.924  -7.471  -3.419  1.00 165.39           C
ATOM   3518  NE2 GLN A 455      24.734  -8.051  -4.300  1.00 171.66           N
ATOM   3519  OE1 GLN A 455      24.319  -7.063  -2.323  1.00 160.44           O
ATOM   3520  N   ARG A 456      21.283  -7.601   0.574  1.00 121.82           N
ATOM   3521  CA  ARG A 456      20.609  -7.768   1.870  1.00 117.70           C
ATOM   3522  C   ARG A 456      19.146  -7.345   1.823  1.00 117.36           C
ATOM   3523  O   ARG A 456      19.391  -7.593  -2.771  1.00 115.59           O
ATOM   3524  CB  ARG A 456      21.382  -6.862   2.820  1.00 108.17           C
ATOM   3525  CG  ARG A 456      22.718  -7.424   3.209  1.00 108.54           C
ATOM   3526  CD  ARG A 456      22.532  -8.767   3.851  1.00 111.62           C
ATOM   3527  NE  ARG A 456      23.375  -9.787   3.242  1.00 118.52           N
ATOM   3528  CZ  ARG A 456      22.998 -10.865   2.233  1.00 124.83           C
ATOM   3529  NH1 ARG A 456      21.789 -10.440   1.711  1.00 124.91           N1+
ATOM   3530  NH2 ARG A 456      23.834 -11.473   1.747  1.00 131.67           N
ATOM   3531  N   GLU A 457      18.763  -6.705   0.722  1.00  83.40           N
ATOM   3532  CA  GLU A 457      17.413  -6.186   0.547  1.00  84.33           C
ATOM   3533  C   GLU A 457      16.567  -7.122  -0.377  1.00  90.22           C
```

Fig. 7BF

| | | | | | | | | | |
|---|---|---|---|---|---|---|---|---|---|
|ATOM|3534|O|GLU|A|457|16.396|-6.869|-0.544|1.00 92.63|O|
|ATOM|3535|CB|GLU|A|457|17.474|-4.727|0.029|1.00114.25|C|
|ATOM|3536|CG|GLU|A|457|16.198|-3.866|0.212|1.00119.35|C|
|ATOM|3537|CD|GLU|A|457|16.058|-3.188|1.595|1.00117.77|C|
|ATOM|3538|OE1|GLU|A|457|16.939|-3.360|2.474|1.00111.91|O|
|ATOM|3539|OE2|GLU|A|457|15.048|-2.479|1.801|1.00122.45|O1-|
|ATOM|3540|N|ASP|A|458|17.228|-8.210|-0.834|1.00 97.07|N|
|ATOM|3541|CA|ASP|A|458|16.623|-9.170|-1.768|1.00102.92|C|
|ATOM|3542|C|ASP|A|458|15.581|-10.050|-1.102|1.00104.26|C|
|ATOM|3543|O|ASP|A|458|15.831|-10.590|-0.035|1.00102.51|O|
|ATOM|3544|CB|ASP|A|458|17.699|-10.079|-2.358|1.00129.60|C|
|ATOM|3545|CG|ASP|A|458|18.359|-9.489|-3.585|1.00131.91|C|
|ATOM|3546|OD1|ASP|A|458|17.767|-8.558|-4.176|1.00132.98|O|
|ATOM|3547|OD2|ASP|A|458|19.439|-9.963|-3.973|1.00134.57|O1-|
|ATOM|3548|N|TYR|A|459|14.426|-10.228|-1.737|1.00113.70|N|
|ATOM|3549|CA|TYR|A|459|13.410|-11.134|-1.201|1.00114.33|C|
|ATOM|3550|C|TYR|A|459|13.569|-12.581|-1.625|1.00116.50|C|
|ATOM|3551|O|TYR|A|459|13.867|-12.882|-2.779|1.00116.79|O|
|ATOM|3552|CB|TYR|A|459|12.020|-10.658|-1.570|1.00144.77|C|
|ATOM|3553|CG|TYR|A|459|11.514|-9.705|-0.561|1.00141.23|C|
|ATOM|3554|CD1|TYR|A|459|11.942|-8.395|-0.556|1.00138.79|C|
|ATOM|3555|CD2|TYR|A|459|10.655|-10.119|0.426|1.00139.04|C|
|ATOM|3556|CE1|TYR|A|459|11.498|-7.505|0.396|1.00136.02|C|
|ATOM|3557|CE2|TYR|A|459|10.201|-9.243|1.383|1.00134.08|C|
|ATOM|3558|CZ|TYR|A|459|10.625|-7.933|1.367|1.00132.71|C|
|ATOM|3559|OH|TYR|A|459|10.176|-7.057|2.332|1.00126.18|O|
|ATOM|3560|N|VAL|A|460|13.354|-13.479|-0.678|1.00 91.18|N|
|ATOM|3561|CA|VAL|A|460|13.294|-14.903|-0.983|1.00 95.85|C|
|ATOM|3562|C|VAL|A|460|11.877|-15.478|-0.759|1.00 95.44|C|
|ATOM|3563|O|VAL|A|460|11.327|-15.408|0.336|1.00 92.15|O|
|ATOM|3564|CB|VAL|A|460|14.401|-15.689|-0.216|1.00 87.85|C|
|ATOM|3565|CG1|VAL|A|460|13.845|-16.593|0.856|1.00 87.88|C|
|ATOM|3566|CG2|VAL|A|460|15.159|-16.511|-1.171|1.00 61.91|C|
|ATOM|3567|N|VAL|A|461|11.257|-16.010|-1.803|1.00100.52|N|
|ATOM|3568|CA|VAL|A|461|9.978|-16.679|-1.606|1.00 97.78|C|
|ATOM|3569|C|VAL|A|461|10.242|-18.124|-1.196|1.00 98.08|C|
|ATOM|3570|O|VAL|A|461|10.970|-18.357|-1.871|1.00101.17|O|
|ATOM|3571|CB|VAL|A|461|9.066|-16.624|-2.851|1.00 69.93|C|
|ATOM|3572|CG1|VAL|A|461|7.867|-17.521|-2.658|1.00 67.17|C|
|ATOM|3573|CG2|VAL|A|461|8.616|-15.183|-3.140|1.00 71.04|C|
|ATOM|3574|N|ALA|A|462|9.679|-18.500|-0.053|1.00 93.86|N|
|ATOM|3575|CA|ALA|A|462|9.713|-19.865|0.449|1.00 94.82|C|
|ATOM|3576|C|ALA|A|462|8.453|-20.004|1.277|1.00 90.45|C|
|ATOM|3577|O|ALA|A|462|7.648|-19.079|1.322|1.00 85.60|O|
|ATOM|3578|CB|ALA|A|462|10.946|-20.101|1.290|1.00101.81|C|
|ATOM|3579|N|TRP|A|463|8.264|-21.153|1.906|1.00126.54|N|
|ATOM|3580|CA|TRP|A|463|7.129|-21.330|2.795|1.00121.67|C|
|ATOM|3581|C|TRP|A|463|7.473|-20.632|4.125|1.00117.18|C|
|ATOM|3582|O|TRP|A|463|8.646|-20.314|4.363|1.00119.50|O|
|ATOM|3583|CB|TRP|A|463|6.828|-22.826|2.962|1.00 97.46|C|
|ATOM|3584|CG|TRP|A|463|5.535|-23.115|3.657|1.00 92.12|C|
|ATOM|3585|CD1|TRP|A|463|5.343|-23.929|4.737|1.00 91.02|C|
|ATOM|3586|CD2|TRP|A|463|4.257|-22.579|3.326|1.00 88.32|C|
|ATOM|3587|CE2|TRP|A|463|3.338|-23.096|4.248|1.00 85.36|C|
|ATOM|3588|CE3|TRP|A|463|3.801|-21.706|2.336|1.00 87.81|C|
|ATOM|3589|NE1|TRP|A|463|4.027|-23.915|5.101|1.00 85.46|N|
|ATOM|3590|CZ2|TRP|A|463|1.983|-22.767|4.210|1.00 80.77|C|
|ATOM|3591|CZ3|TRP|A|463|2.456|-21.395|2.293|1.00 84.04|C|
|ATOM|3592|CH2|TRP|A|463|1.561|-21.912|3.229|1.00 81.39|C|
|ATOM|3593|N|TRP|A|464|6.473|-20.366|4.979|1.00 88.98|N|
|ATOM|3594|CA|TRP|A|464|6.698|-19.709|6.295|1.00 84.52|C|

Fig. 7BG

```
ATOM   3595  C    TRP A 464       7.453 -20.516   7.401  1.00 84.80           C
ATOM   3596  O    TRP A 464       8.136 -19.916   8.245  1.00 82.53           O
ATOM   3597  CB   TRP A 464       5.384 -19.148   6.851  1.00108.27           C
ATOM   3598  CG   TRP A 464       4.439 -20.160   7.383  1.00104.51           C
ATOM   3599  CD1  TRP A 464       3.387 -20.755   6.726  1.00104.85           C
ATOM   3600  CD2  TRP A 464       4.449 -20.751   8.683  1.00100.24           C
ATOM   3601  NE1  TRP A 464       3.393 -21.668   8.751  1.00 98.69           N
ATOM   3602  CE2  TRP A 464       5.256 -20.565   9.795  1.00 98.02           C
ATOM   3603  CE3  TRP A 464       2.754 -21.653   7.540  1.00101.40           N
ATOM   3604  CZ2  TRP A 464       3.127 -22.408   9.893  1.00 95.47           C
ATOM   3605  CZ3  TRP A 464       4.989 -21.321  10.922  1.00 94.45           C
ATOM   3606  CH2  TRP A 464       3.939 -22.215  10.959  1.00 93.46           C
ATOM   3607  N    ASP A 465       7.312 -21.849   7.392  1.00 92.05           N
ATOM   3608  CA   ASP A 465       8.069 -22.744   8.258  1.00 93.41           C
ATOM   3609  C    ASP A 465       9.539 -22.432   8.174  1.00 89.15           C
ATOM   3610  O    ASP A 465      10.283 -22.693   9.138  1.00 87.32           O
ATOM   3611  CB   ASP A 465       7.943 -24.100   7.792  1.00117.95           C
ATOM   3612  CG   ASP A 465       6.667 -24.819   8.211  1.00113.93           C
ATOM   3613  OD1  ASP A 465       6.716 -25.982   8.676  1.00115.05           O
ATOM   3614  OD2  ASP A 465       5.618 -24.165   8.050  1.00111.77           O1-
ATOM   3615  N    TYR A 466       9.964 -22.015   6.994  1.00 92.76           N
ATOM   3616  CA   TYR A 466      11.372 -21.908   6.688  1.00 97.79           C
ATOM   3617  C    TYR A 466      11.937 -20.511   6.911  1.00 94.36           C
ATOM   3618  O    TYR A 466      13.126 -20.362   7.254  1.00 95.54           O
ATOM   3619  CB   TYR A 466      11.556 -22.332   5.243  1.00 81.39           C
ATOM   3620  CG   TYR A 466      11.045 -23.722   5.091  1.00 84.22           C
ATOM   3621  CD1  TYR A 466      11.286 -24.725   5.937  1.00 84.84           C
ATOM   3622  CD2  TYR A 466      10.326 -24.032   3.857  1.00 86.34           C
ATOM   3623  CE1  TYR A 466      10.836 -25.993   5.725  1.00 87.42           C
ATOM   3624  CE2  TYR A 466       9.870 -25.300   3.639  1.00 88.56           C
ATOM   3625  CZ   TYR A 466      10.120 -26.283   4.583  1.00 89.33           C
ATOM   3626  OH   TYR A 466       9.650 -27.571   4.391  1.00 92.35           O
ATOM   3627  N    GLY A 467      11.076 -19.503   6.724  1.00111.17           N
ATOM   3628  CA   GLY A 467      11.445 -18.091   6.714  1.00109.46           C
ATOM   3629  C    GLY A 467      12.477 -17.598   7.713  1.00106.72           C
ATOM   3630  O    GLY A 467      13.433 -16.892   7.344  1.00109.73           O
ATOM   3631  N    TYR A 468      12.288 -17.942   8.984  1.00112.81           N
ATOM   3632  CA   TYR A 468      13.296 -17.635   9.995  1.00110.46           C
ATOM   3633  C    TYR A 468      14.674 -18.164   9.595  1.00117.01           C
ATOM   3634  O    TYR A 468      15.513 -17.351   9.253  1.00119.17           O
ATOM   3635  CB   TYR A 468      12.879 -18.127  11.370  1.00114.96           C
ATOM   3636  CG   TYR A 468      11.767 -17.319  11.963  1.00109.18           C
ATOM   3637  CD1  TYR A 468      10.730 -17.935  12.644  1.00103.56           C
ATOM   3638  CD2  TYR A 468      11.754 -15.943  11.852  1.00106.20           C
ATOM   3639  CE1  TYR A 468       9.713 -17.200  13.202  1.00 96.10           C
ATOM   3640  CE2  TYR A 468      10.735 -15.202  12.397  1.00 98.66           C
ATOM   3641  CZ   TYR A 468       9.717 -15.836  13.075  1.00 93.59           C
ATOM   3642  OH   TYR A 468       8.688 -15.114  13.633  1.00 87.09           O
ATOM   3643  N    PRO A 469      14.911 -19.509   9.623  1.00 71.08           N
ATOM   3644  CA   PRO A 469      16.181 -20.069   9.145  1.00 78.67           C
ATOM   3645  C    PRO A 469      16.664 -19.438   7.854  1.00 85.18           C
ATOM   3646  O    PRO A 469      17.791 -18.959   7.844  1.00 87.50           O
ATOM   3647  CB   PRO A 469      15.833 -21.538   8.907  1.00 95.87           C
ATOM   3648  CG   PRO A 469      14.912 -21.836   9.956  1.00 88.87           C
ATOM   3649  CD   PRO A 469      14.052 -20.593  10.138  1.00 82.59           C
ATOM   3650  N    ILE A 470      15.841 -19.435   6.803  1.00112.11           N
ATOM   3651  CA   ILE A 470      16.239 -18.797   5.565  1.00113.48           C
ATOM   3652  C    ILE A 470      16.916 -17.430   5.906  1.00109.28           C
ATOM   3653  O    ILE A 470      17.997 -17.097   5.386  1.00110.04           O
ATOM   3654  CB   ILE A 470      15.027 -18.433   4.657  1.00109.58           C
ATOM   3655  CG1  ILE A 470      14.333 -19.703   4.166  1.00111.95           C
```

Fig. 7BH

| | | | | | | | | |
|---|---|---|---|---|---|---|---|---|
| ATOM | 3656 | CG2 | ILE | A | 470 | 15.457 -17.561 3.477 | 1.00111.25 | C |
| ATOM | 3657 | CD1 | ILE | A | 470 | 15.171 -20.855 3.264 | 1.00133.99 | C |
| ATOM | 3658 | N | ARG | A | 471 | 16.277 -15.679 6.797 | 1.00110.83 | N |
| ATOM | 3659 | CA | ARG | A | 471 | 16.750 -15.344 7.143 | 1.00106.40 | C |
| ATOM | 3660 | C | ARG | A | 471 | 18.029 -15.283 8.011 | 1.00103.74 | C |
| ATOM | 3661 | O | ARG | A | 471 | 18.907 -14.464 7.782 | 1.00100.91 | O |
| ATOM | 3662 | CB | ARG | A | 471 | 15.612 -14.577 7.797 | 1.00104.40 | C |
| ATOM | 3663 | CG | ARG | A | 471 | 15.398 -13.244 7.171 | 1.00102.63 | C |
| ATOM | 3664 | CD | ARG | A | 471 | 14.027 -12.694 7.481 | 1.00100.94 | C |
| ATOM | 3665 | NE | ARG | A | 471 | 13.731 -12.718 8.906 | 1.00 94.88 | N |
| ATOM | 3666 | CZ | ARG | A | 471 | 12.555 -12.379 9.413 | 1.00 90.55 | C |
| ATOM | 3667 | NH1 | ARG | A | 471 | 11.588 -11.987 8.599 | 1.00 91.30 | N1+ |
| ATOM | 3668 | NH2 | ARG | A | 471 | 12.351 -12.438 10.722 | 1.00 85.64 | N |
| ATOM | 3669 | N | TYR | A | 472 | 18.135 -16.141 9.010 | 1.00108.86 | N |
| ATOM | 3670 | CA | TYR | A | 472 | 19.274 -16.103 9.894 | 1.00107.94 | C |
| ATOM | 3671 | C | TYR | A | 472 | 20.475 -16.550 9.126 | 1.00112.78 | C |
| ATOM | 3672 | O | TYR | A | 472 | 21.582 -16.077 9.351 | 1.00111.17 | O |
| ATOM | 3673 | CB | TYR | A | 472 | 19.088 -17.067 11.052 | 1.00107.57 | C |
| ATOM | 3674 | CG | TYR | A | 472 | 20.372 -17.328 11.800 | 1.00109.12 | C |
| ATOM | 3675 | CD1 | TYR | A | 472 | 20.763 -16.506 12.842 | 1.00103.06 | C |
| ATOM | 3676 | CD2 | TYR | A | 472 | 21.195 -18.381 11.451 | 1.00117.27 | C |
| ATOM | 3677 | CE1 | TYR | A | 472 | 21.937 -16.736 13.515 | 1.00104.86 | C |
| ATOM | 3678 | CE2 | TYR | A | 472 | 22.366 -18.611 12.123 | 1.00119.62 | C |
| ATOM | 3679 | CZ | TYR | A | 472 | 22.728 -17.796 13.151 | 1.00113.31 | C |
| ATOM | 3680 | OH | TYR | A | 472 | 23.893 -18.018 13.821 | 1.00115.96 | O |
| ATOM | 3681 | N | TYR | A | 473 | 20.266 -17.503 8.235 | 1.00 98.40 | N |
| ATOM | 3682 | CA | TYR | A | 473 | 21.371 -18.055 7.462 | 1.00103.25 | C |
| ATOM | 3683 | C | TYR | A | 473 | 21.764 -17.217 6.233 | 1.00103.11 | C |
| ATOM | 3684 | O | TYR | A | 473 | 22.923 -17.253 5.809 | 1.00105.53 | O |
| ATOM | 3685 | CB | TYR | A | 473 | 21.068 -19.545 7.076 | 1.00 87.79 | C |
| ATOM | 3686 | CG | TYR | A | 473 | 21.215 -20.468 8.232 | 1.00 90.97 | C |
| ATOM | 3687 | CD1 | TYR | A | 473 | 20.134 -21.168 8.737 | 1.00 91.62 | C |
| ATOM | 3688 | CD2 | TYR | A | 473 | 22.449 -20.662 8.818 | 1.00 93.71 | C |
| ATOM | 3689 | CE1 | TYR | A | 473 | 20.294 -22.042 9.787 | 1.00 92.97 | C |
| ATOM | 3690 | CE2 | TYR | A | 473 | 22.623 -21.527 9.860 | 1.00 97.49 | C |
| ATOM | 3691 | CZ | TYR | A | 473 | 21.551 -22.215 10.351 | 1.00 96.31 | C |
| ATOM | 3692 | OH | TYR | A | 473 | 21.771 -23.063 11.418 | 1.00 96.03 | O |
| ATOM | 3693 | N | SER | A | 474 | 20.812 -16.451 5.689 | 1.00 96.20 | N |
| ATOM | 3694 | CA | SER | A | 474 | 21.064 -15.675 4.473 | 1.00 96.30 | C |
| ATOM | 3695 | C | SER | A | 474 | 21.044 -14.157 4.607 | 1.00 88.34 | C |
| ATOM | 3696 | O | SER | A | 474 | 21.408 -13.464 3.703 | 1.00 87.71 | O |
| ATOM | 3697 | CB | SER | A | 474 | 20.071 -16.076 3.401 | 1.00 90.21 | C |
| ATOM | 3698 | OG | SER | A | 474 | 20.139 -17.468 3.200 | 1.00 93.26 | O |
| ATOM | 3699 | N | ASP | A | 475 | 20.518 -13.642 5.710 | 1.00123.77 | N |
| ATOM | 3700 | CA | ASP | A | 475 | 20.432 -12.192 5.922 | 1.00115.87 | C |
| ATOM | 3701 | C | ASP | A | 475 | 19.523 -11.533 4.874 | 1.00115.52 | C |
| ATOM | 3702 | O | ASP | A | 475 | 19.400 -10.304 4.808 | 1.00112.95 | O |
| ATOM | 3703 | CB | ASP | A | 475 | 21.828 -11.549 5.913 | 1.00146.68 | C |
| ATOM | 3704 | CG | ASP | A | 475 | 21.967 -10.395 6.924 | 1.00139.83 | C |
| ATOM | 3705 | OD1 | ASP | A | 475 | 20.960 -10.006 7.572 | 1.00137.43 | O |
| ATOM | 3706 | OD2 | ASP | A | 475 | 23.102 -9.878 7.056 | 1.00137.99 | O1- |
| ATOM | 3707 | N | VAL | A | 476 | 18.878 -12.365 4.065 | 1.00111.48 | N |
| ATOM | 3708 | CA | VAL | A | 476 | 17.902 -11.893 3.090 | 1.00112.65 | C |
| ATOM | 3709 | C | VAL | A | 476 | 16.853 -11.476 3.722 | 1.00110.68 | C |
| ATOM | 3710 | O | VAL | A | 476 | 16.359 -11.615 4.919 | 1.00108.89 | O |
| ATOM | 3711 | CB | VAL | A | 476 | 17.663 -12.977 2.031 | 1.00120.26 | C |
| ATOM | 3712 | CG1 | VAL | A | 476 | 18.980 -13.339 1.377 | 1.00123.31 | C |
| ATOM | 3713 | CG2 | VAL | A | 476 | 17.003 -14.223 2.655 | 1.00124.33 | C |
| ATOM | 3714 | N | LYS | A | 477 | 16.631 -10.950 2.910 | 1.00111.54 | N |
| ATOM | 3715 | CA | LYS | A | 477 | 14.266 -10.681 3.375 | 1.00111.60 | C |
| ATOM | 3716 | C | LYS | A | 477 | 13.346 -11.792 2.874 | 1.00117.40 | C |

Fig. 7BI

| | | | | | | | | | |
|---|---|---|---|---|---|---|---|---|---|
| ATOM | 3717 | O | LYS | A | 477 | 13.549 | -12.319 | 1.775 | 1.00 121.40 | O |
| ATOM | 3718 | CB | LYS | A | 477 | 13.745 | -9.356 | 2.812 | 1.00 99.69 | C |
| ATOM | 3719 | CG | LYS | A | 477 | 14.424 | -8.092 | 3.277 | 1.00 95.38 | C |
| ATOM | 3720 | CD | LYS | A | 477 | 13.706 | -6.879 | 2.693 | 1.00 97.08 | C |
| ATOM | 3721 | CE | LYS | A | 477 | 14.019 | -5.623 | 3.500 | 1.00 94.50 | C |
| ATOM | 3722 | NZ | LYS | A | 477 | 13.397 | -4.349 | 2.980 | 1.00 99.61 | N1+ |
| ATOM | 3723 | N | THR | A | 478 | 12.320 | -12.125 | 3.658 | 1.00 127.58 | N |
| ATOM | 3724 | CA | THR | A | 478 | 11.355 | -13.157 | 3.272 | 1.00 129.13 | C |
| ATOM | 3725 | C | THR | A | 478 | 9.930 | -12.621 | 3.243 | 1.00 122.89 | C |
| ATOM | 3726 | O | THR | A | 478 | 9.629 | -11.587 | 3.840 | 1.00 117.76 | O |
| ATOM | 3727 | CB | THR | A | 478 | 11.384 | -14.325 | 4.242 | 1.00 112.24 | C |
| ATOM | 3728 | CG2 | THR | A | 478 | 12.792 | -14.870 | 4.364 | 1.00 118.87 | C |
| ATOM | 3729 | OG1 | THR | A | 478 | 10.542 | -13.873 | 5.526 | 1.00 104.99 | O |
| ATOM | 3730 | N | LEU | A | 479 | 9.045 | -13.330 | 2.556 | 1.00 110.93 | N |
| ATOM | 3731 | CA | LEU | A | 479 | 7.678 | -12.856 | 2.420 | 1.00 106.43 | C |
| ATOM | 3732 | C | LEU | A | 479 | 6.889 | -13.170 | 3.678 | 1.00 100.06 | C |
| ATOM | 3733 | O | LEU | A | 479 | 6.081 | -12.356 | 4.138 | 1.00 95.39 | O |
| ATOM | 3734 | CB | LEU | A | 479 | 6.995 | -13.506 | 1.216 | 1.00 89.68 | C |
| ATOM | 3735 | CG | LEU | A | 479 | 6.939 | -12.796 | -0.138 | 1.00 85.88 | C |
| ATOM | 3736 | CD1 | LEU | A | 479 | 6.277 | -13.691 | -1.163 | 1.00 89.02 | C |
| ATOM | 3737 | CD2 | LEU | A | 479 | 6.293 | -11.476 | -0.048 | 1.00 81.59 | C |
| ATOM | 3738 | N | ILE | A | 480 | 7.113 | -14.365 | 4.224 | 1.00 100.23 | N |
| ATOM | 3739 | CA | ILE | A | 480 | 6.354 | -14.823 | 5.385 | 1.00 96.47 | C |
| ATOM | 3740 | C | ILE | A | 480 | 7.218 | -15.565 | 6.310 | 1.00 98.06 | C |
| ATOM | 3741 | O | ILE | A | 480 | 8.003 | -16.494 | 5.854 | 1.00 103.33 | O |
| ATOM | 3742 | CB | ILE | A | 480 | 5.057 | -15.620 | 4.986 | 1.00 79.36 | C |
| ATOM | 3743 | CG1 | ILE | A | 480 | 5.416 | -16.972 | 4.331 | 1.00 78.51 | C |
| ATOM | 3744 | CG2 | ILE | A | 480 | 4.137 | -14.754 | 4.115 | 1.00 81.57 | C |
| ATOM | 3745 | CD1 | ILE | A | 480 | 4.248 | -17.846 | 3.878 | 1.00 94.46 | C |
| ATOM | 3746 | N | ASP | A | 481 | 7.070 | -15.436 | 7.611 | 1.00 97.63 | N |
| ATOM | 3747 | CA | ASP | A | 481 | 7.760 | -16.230 | 8.624 | 1.00 98.10 | C |
| ATOM | 3748 | C | ASP | A | 481 | 6.793 | -16.778 | 9.686 | 1.00 91.32 | C |
| ATOM | 3749 | O | ASP | A | 481 | 5.600 | -16.451 | 9.692 | 1.00 87.66 | O |
| ATOM | 3750 | CB | ASP | A | 481 | 8.943 | -15.455 | 9.261 | 1.00 124.59 | C |
| ATOM | 3751 | CG | ASP | A | 481 | 8.523 | -14.140 | 9.862 | 1.00 118.16 | C |
| ATOM | 3752 | OD1 | ASP | A | 481 | 8.304 | -14.147 | 11.191 | 1.00 111.44 | O |
| ATOM | 3753 | OD2 | ASP | A | 481 | 8.455 | -13.085 | 9.295 | 1.00 120.78 | O1- |
| ATOM | 3754 | N | GLY | A | 482 | 7.319 | -17.619 | 10.574 | 1.00 102.26 | N |
| ATOM | 3755 | CA | GLY | A | 482 | 6.543 | -18.269 | 11.654 | 1.00 97.22 | C |
| ATOM | 3756 | C | GLY | A | 482 | 5.822 | -17.213 | 12.534 | 1.00 90.76 | C |
| ATOM | 3757 | O | GLY | A | 482 | 5.132 | -17.602 | 13.469 | 1.00 87.07 | O |
| ATOM | 3758 | N | GLY | A | 483 | 5.997 | -15.928 | 12.241 | 1.00 91.31 | N |
| ATOM | 3759 | CA | GLY | A | 483 | 5.317 | -14.869 | 12.958 | 1.00 86.06 | C |
| ATOM | 3760 | C | GLY | A | 483 | 4.329 | -14.196 | 12.025 | 1.00 86.75 | C |
| ATOM | 3761 | O | GLY | A | 483 | 3.170 | -13.960 | 12.392 | 1.00 83.34 | O |
| ATOM | 3762 | N | LYS | A | 484 | 4.781 | -13.902 | 10.809 | 1.00 97.85 | N |
| ATOM | 3763 | CA | LYS | A | 484 | 3.928 | -13.330 | 9.754 | 1.00 99.54 | C |
| ATOM | 3764 | C | LYS | A | 484 | 3.425 | -14.501 | 8.892 | 1.00 103.57 | C |
| ATOM | 3765 | O | LYS | A | 484 | 4.025 | -14.829 | 7.872 | 1.00 109.74 | O |
| ATOM | 3766 | CB | LYS | A | 484 | 4.733 | -12.362 | 8.897 | 1.00 100.39 | C |
| ATOM | 3767 | CG | LYS | A | 484 | 3.959 | -11.664 | 7.783 | 1.00 102.86 | C |
| ATOM | 3768 | CD | LYS | A | 484 | 4.892 | -10.895 | 6.856 | 1.00 108.16 | C |
| ATOM | 3769 | CE | LYS | A | 484 | 4.158 | -9.800 | 6.099 | 1.00 110.08 | C |
| ATOM | 3770 | NZ | LYS | A | 484 | 5.084 | -8.873 | 5.367 | 1.00 114.34 | N1+ |
| ATOM | 3771 | N | HIS | A | 485 | 2.340 | -15.136 | 9.312 | 1.00 102.78 | N |
| ATOM | 3772 | CA | HIS | A | 485 | 1.890 | -16.330 | 8.611 | 1.00 106.30 | C |
| ATOM | 3773 | C | HIS | A | 485 | 0.381 | -16.528 | 8.675 | 1.00 104.16 | C |
| ATOM | 3774 | O | HIS | A | 485 | -0.089 | -17.635 | 8.918 | 1.00 104.78 | O |
| ATOM | 3775 | CB | HIS | A | 485 | 2.635 | -17.593 | 9.088 | 1.00 99.81 | C |
| ATOM | 3776 | CG | HIS | A | 485 | 2.358 | -17.975 | 10.497 | 1.00 95.13 | C |
| ATOM | 3777 | CD2 | HIS | A | 485 | 3.007 | -17.697 | 11.657 | 1.00 95.01 | C |

Fig. 7BJ

```
ATOM  3778  ND1  HIS A 485    1.269  -16.754  10.879  1.00  90.63      N
ATOM  3779  CE1  HIS A 485    1.266  -18.925  12.175  1.00  88.10      C
ATOM  3780  NE2  HIS A 485    2.323  -18.292  12.683  1.00  90.58      N
ATOM  3781  N    LEU A 486   -0.374  -15.454   8.451  1.00 111.19      N
ATOM  3782  CA   LEU A 486   -1.823  -15.566   8.295  1.00 110.58      C
ATOM  3783  C    LEU A 486   -2.164  -16.116   6.910  1.00 115.35      C
ATOM  3784  O    LEU A 486   -1.327  -16.074   5.997  1.00 119.03      O
ATOM  3785  CB   LEU A 486   -2.515  -14.211   8.507  1.00 101.73      C
ATOM  3786  CG   LEU A 486   -2.603  -13.649   9.932  1.00  97.60      C
ATOM  3787  CD1  LEU A 486   -3.600  -12.496  10.013  1.00  96.90      C
ATOM  3788  CD2  LEU A 486   -2.984  -14.736  10.928  1.00  96.56      C
ATOM  3789  N    GLY A 487   -3.383  -16.638   6.754  1.00  87.43      N
ATOM  3790  CA   GLY A 487   -3.839  -17.111   5.457  1.00  91.88      C
ATOM  3791  C    GLY A 487   -3.541  -18.125   4.340  1.00  94.45      C
ATOM  3792  O    GLY A 487   -3.049  -19.533   3.265  1.00  98.85      O
ATOM  3793  N    LYS A 488   -3.846  -14.841   4.609  1.00  97.15      N
ATOM  3794  CA   LYS A 488   -3.571  -13.735   3.701  1.00  99.35      C
ATOM  3795  C    LYS A 488   -2.079  -13.626   3.342  1.00 101.27      C
ATOM  3796  O    LYS A 488   -1.738  -13.298   2.207  1.00 102.25      O
ATOM  3797  CB   LYS A 488   -4.132  -12.421   4.254  1.00 150.95      C
ATOM  3798  CG   LYS A 488   -3.356  -11.119   3.677  1.00 148.04      C
ATOM  3799  CD   LYS A 488   -2.670  -11.068   2.472  1.00 145.84      C
ATOM  3800  CE   LYS A 488   -3.556  -10.626   1.302  1.00 150.26      C
ATOM  3801  NZ   LYS A 488   -3.558   -9.144   1.129  1.00 148.69      N1+
ATOM  3802  N    ASP A 489   -1.186  -13.916   4.279  1.00  94.38      N
ATOM  3803  CA   ASP A 489    0.251  -13.790   3.990  1.00  95.73      C
ATOM  3804  C    ASP A 489    0.784  -15.056   3.341  1.00  99.01      C
ATOM  3805  O    ASP A 489    1.556  -14.993   2.380  1.00 102.57      O
ATOM  3806  CB   ASP A 489    1.933  -13.482   5.261  1.00 115.25      C
ATOM  3807  CG   ASP A 489    0.448  -12.320   6.042  1.00 110.36      C
ATOM  3808  OD1  ASP A 489    0.229  -11.240   5.442  1.00 111.88      O
ATOM  3809  OD2  ASP A 489    0.206  -12.499   7.259  1.00 105.39      O1-
ATOM  3810  N    ASN A 490    0.368  -16.201   3.872  1.00  84.05      N
ATOM  3811  CA   ASN A 490    0.691  -17.473   3.250  1.00  87.14      C
ATOM  3812  C    ASN A 490    0.290  -17.613   1.800  1.00  89.79      C
ATOM  3813  O    ASN A 490    0.738  -18.426   1.929  1.00  93.82      O
ATOM  3814  CB   ASN A 490    0.130  -18.622   4.068  1.00 112.58      C
ATOM  3815  CG   ASN A 490    0.520  -18.537   5.496  1.00 108.39      C
ATOM  3816  ND2  ASN A 490   -0.452  -18.423   6.364  1.00 108.31      N
ATOM  3817  OD1  ASN A 490    1.637  -18.577   5.824  1.00 105.77      O
ATOM  3818  N    PHE A 491   -0.823  -16.846   1.422  1.00  83.75      N
ATOM  3819  CA   PHE A 491   -1.384  -17.090   0.074  1.00  85.79      C
ATOM  3820  C    PHE A 491   -0.363  -16.911  -1.049  1.00  89.64      C
ATOM  3821  O    PHE A 491   -0.327  -17.773  -1.922  1.00  93.11      O
ATOM  3822  CB   PHE A 491   -2.504  -16.014  -0.201  1.00  90.47      C
ATOM  3823  CG   PHE A 491   -3.127  -16.291  -1.540  1.00  93.05      C
ATOM  3824  CD1  PHE A 491   -4.077  -17.193  -1.743  1.00  93.41      C
ATOM  3825  CD2  PHE A 491   -2.757  -15.404  -2.606  1.00  94.97      C
ATOM  3826  CE1  PHE A 491   -4.649  -17.380  -2.983  1.00  95.57      C
ATOM  3827  CE2  PHE A 491   -3.331  -15.583  -3.852  1.00  97.69      C
ATOM  3828  CZ   PHE A 491   -4.273  -16.575  -4.046  1.00  97.54      C
ATOM  3829  N    PHE A 492    0.452  -15.862  -1.024  1.00  88.15      N
ATOM  3830  CA   PHE A 492    1.477  -15.662  -2.047  1.00  93.06      C
ATOM  3831  C    PHE A 492    2.537  -16.781  -2.129  1.00  97.49      C
ATOM  3832  O    PHE A 492    2.648  -17.465  -3.157  1.00 102.64      O
ATOM  3833  CB   PHE A 492    2.143  -14.311  -1.854  1.00 123.56      C
ATOM  3834  CG   PHE A 492    1.171  -13.199  -1.685  1.00 113.27      C
ATOM  3835  CD1  PHE A 492    1.056  -12.537  -0.480  1.00 113.77      C
ATOM  3836  CD2  PHE A 492    0.352  -12.833  -2.719  1.00 120.95      C
ATOM  3837  CE1  PHE A 492    0.151  -11.509  -0.319  1.00 110.99      C
ATOM  3838  CE2  PHE A 492   -0.655  -11.809  -2.568  1.00 117.85      C
```

Fig. 7BK

```
ATOM   3839  CZ  PHE A 492      -0.659 -11.145  -1.365  1.00113.05           C
ATOM   3840  N   SER A 493       3.298 -18.970  -1.066  1.00 86.22           N
ATOM   3841  CA  SER A 493       4.256 -19.080  -1.081  1.00 96.75           C
ATOM   3842  C   SER A 493       3.618 -19.447  -1.429  1.00 91.73           C
ATOM   3843  O   SER A 493       4.261 -20.302  -2.040  1.00 97.28           O
ATOM   3844  CB  SER A 493       5.014 -18.139   0.276  1.00115.55           C
ATOM   3845  OG  SER A 493       5.912 -17.047   0.408  1.00139.09           O
ATOM   3846  N   SER A 494       2.355 -19.640  -1.054  1.00100.08           N
ATOM   3847  CA  SER A 494       1.615 -20.824  -1.472  1.00101.40           C
ATOM   3848  C   SER A 494       1.534 -20.849  -2.995  1.00106.52           C
ATOM   3849  O   SER A 494       1.906 -21.807  -3.630  1.00111.63           O
ATOM   3850  CB  SER A 494       0.191 -20.794  -0.906  1.00 94.44           C
ATOM   3851  OG  SER A 494      -0.558 -21.930  -1.306  1.00 95.27           O
ATOM   3852  N   PHE A 495       1.039 -19.753  -3.542  1.00 96.91           N
ATOM   3853  CA  PHE A 495       0.793 -19.633  -4.971  1.00101.33           C
ATOM   3854  C   PHE A 495       2.049 -19.851  -5.814  1.00108.04           C
ATOM   3855  O   PHE A 495       2.062 -20.699  -6.713  1.00110.76           O
ATOM   3856  CB  PHE A 495       0.227 -18.252  -5.254  1.00112.31           C
ATOM   3857  CG  PHE A 495      -0.262 -18.068  -6.652  1.00116.99           C
ATOM   3858  CD1 PHE A 495      -1.621 -17.985  -6.912  1.00132.98           C
ATOM   3859  CD2 PHE A 495       0.627 -17.963  -7.700  1.00121.76           C
ATOM   3860  CE1 PHE A 495      -2.078 -17.798  -8.186  1.00116.60           C
ATOM   3861  CE2 PHE A 495       0.177 -17.781  -8.974  1.00124.99           C
ATOM   3862  CZ  PHE A 495      -1.176 -17.697  -9.221  1.00123.17           C
ATOM   3863  N   VAL A 496       3.096 -19.078  -5.526  1.00 99.64           N
ATOM   3864  CA  VAL A 496       4.370 -19.186  -6.250  1.00104.08           C
ATOM   3865  C   VAL A 496       4.920 -20.602  -6.291  1.00105.22           C
ATOM   3866  O   VAL A 496       5.645 -20.971  -7.180  1.00107.79           O
ATOM   3867  CB  VAL A 496       5.439 -18.284  -5.628  1.00 88.70           C
ATOM   3868  CG1 VAL A 496       6.822 -18.758  -6.023  1.00107.13           C
ATOM   3869  CG2 VAL A 496       5.225 -16.857  -6.043  1.00104.21           C
ATOM   3870  N   LEU A 497       4.556 -21.388  -5.265  1.00 84.24           N
ATOM   3871  CA  LEU A 497       5.066 -22.730  -5.130  1.00 85.91           C
ATOM   3872  C   LEU A 497       4.142 -23.838  -5.577  1.00 86.49           C
ATOM   3873  O   LEU A 497       4.594 -24.969  -5.697  1.00 89.17           O
ATOM   3874  CB  LEU A 497       5.299 -22.994  -3.672  1.00 70.93           C
ATOM   3875  CG  LEU A 497       5.626 -22.861  -3.087  1.00 71.77           C
ATOM   3876  CD1 LEU A 497       6.348 -22.570  -1.624  1.00 70.15           C
ATOM   3877  CD2 LEU A 497       7.551 -23.787  -3.398  1.00 75.80           C
ATOM   3878  N   SER A 498       2.852 -23.567  -5.751  1.00 91.26           N
ATOM   3879  CA  SER A 498       1.944 -24.670  -6.092  1.00 91.67           C
ATOM   3880  C   SER A 498       1.148 -24.473  -7.378  1.00 93.65           C
ATOM   3881  O   SER A 498       0.596 -25.430  -7.933  1.00 95.86           O
ATOM   3882  CB  SER A 498       1.012 -25.093  -4.931  1.00 94.40           C
ATOM   3883  OG  SER A 498       0.173 -23.911  -4.625  1.00 91.46           O
ATOM   3884  N   LYS A 499       1.091 -23.240  -7.857  1.00121.61           N
ATOM   3885  CA  LYS A 499       0.423 -22.954  -9.114  1.00124.21           C
ATOM   3886  C   LYS A 499       1.397 -23.336 -10.229  1.00129.05           C
ATOM   3887  O   LYS A 499       2.513 -23.797  -9.965  1.00130.34           O
ATOM   3888  CB  LYS A 499      -0.065 -21.549  -9.193  1.00131.05           C
ATOM   3889  CG  LYS A 499      -1.046 -21.202  -8.060  1.00125.86           C
ATOM   3890  CD  LYS A 499      -2.134 -22.283  -7.957  1.00126.02           C
ATOM   3891  CE  LYS A 499      -3.261 -21.937  -6.963  1.00119.25           C
ATOM   3892  NZ  LYS A 499      -4.501 -22.712  -7.257  1.00119.76           N1+
ATOM   3893  N   GLU A 500       0.977 -23.128 -11.473  1.00118.18           N
ATOM   3894  CA  GLU A 500       1.833 -23.427 -12.620  1.00123.78           C
ATOM   3895  C   GLU A 500       3.080 -22.521 -12.704  1.00126.36           C
ATOM   3896  O   GLU A 500       3.085 -21.389 -12.233  1.00124.81           O
ATOM   3897  CB  GLU A 500       1.020 -23.390 -13.929  1.00147.06           C
ATOM   3898  CG  GLU A 500      -0.207 -24.316 -13.967  1.00144.75           C
ATOM   3899  CD  GLU A 500      -0.697 -24.899 -15.371  1.00159.20           C
```

Fig. 7BL

```
ATOM  3900  OE1 GLU A 500     -0.323 -23.944 -16.292  1.00164.81           O
ATOM  3901  OE2 GLU A 500     -1.446 -25.582 -15.565  1.00157.33           O1-
ATOM  3902  N   GLN A 501      4.138 -23.042 -13.309  1.00138.05           N
ATOM  3903  CA  GLN A 501      5.411 -22.341 -13.384  1.00135.63           C
ATOM  3904  C   GLN A 501      5.310 -20.860 -13.713  1.00129.23           C
ATOM  3905  O   GLN A 501      5.793 -20.025 -12.960  1.00123.15           O
ATOM  3906  CB  GLN A 501      6.296 -22.995 -14.424  1.00106.38           C
ATOM  3907  CG  GLN A 501      7.253 -23.997 -13.881  1.00113.55           C
ATOM  3908  CD  GLN A 501      8.370 -24.264 -14.863  1.00122.99           C
ATOM  3909  NE2 GLN A 501      8.765 -25.524 -14.995  1.00143.62           N
ATOM  3910  OE1 GLN A 501      8.858 -23.348 -15.518  1.00121.41           O
ATOM  3911  N   ILE A 502      4.712 -20.536 -14.852  1.00143.62           N
ATOM  3912  CA  ILE A 502      4.701 -19.135 -15.334  1.00139.54           C
ATOM  3913  C   ILE A 502      4.032 -18.206 -14.320  1.00132.85           C
ATOM  3914  O   ILE A 502      4.677 -17.258 -13.807  1.00128.79           O
ATOM  3915  CB  ILE A 502      4.042 -19.028 -16.760  1.00118.22           C
ATOM  3916  CG1 ILE A 502      4.686 -19.985 -17.785  1.00136.34           C
ATOM  3917  CG2 ILE A 502      4.121 -17.592 -17.273  1.00126.53           C
ATOM  3918  CD1 ILE A 502      4.695 -21.395 -17.836  1.00142.12           C
ATOM  3919  N   PRO A 503      2.742 -18.464 -14.006  1.00131.50           N
ATOM  3920  CA  PRO A 503      2.049 -17.585 -13.057  1.00127.12           C
ATOM  3921  C   PRO A 503      2.787 -17.612 -11.725  1.00122.15           C
ATOM  3922  O   PRO A 503      2.846 -16.448 -11.137  1.00119.68           O
ATOM  3923  CB  PRO A 503      0.660 -18.234 -12.910  1.00 92.54           C
ATOM  3924  CG  PRO A 503      0.825 -19.624 -13.380  1.00107.85           C
ATOM  3925  CD  PRO A 503      1.876 -19.571 -14.449  1.00109.67           C
ATOM  3926  N   ALA A 504      3.359 -18.621 -11.278  1.00116.43           N
ATOM  3927  CA  ALA A 504      4.193 -18.618 -10.087  1.00112.91           C
ATOM  3928  C   ALA A 504      5.239 -17.529 -10.225  1.00119.35           C
ATOM  3929  O   ALA A 504      5.361 -16.613  -9.386  1.00106.01           O
ATOM  3930  CB  ALA A 504      4.873 -19.983  -9.923  1.00 65.28           C
ATOM  3931  N   ALA A 505      5.995 -17.652 -11.307  1.00138.11           N
ATOM  3932  CA  ALA A 505      7.053 -16.722 -11.623  1.00138.10           C
ATOM  3933  C   ALA A 505      6.322 -15.301 -11.605  1.00134.95           C
ATOM  3934  O   ALA A 505      7.267 -14.377 -11.309  1.00133.32           O
ATOM  3935  CB  ALA A 505      7.638 -17.047 -12.952  1.00 65.96           C
ATOM  3936  N   ASN A 506      5.240 -15.117 -11.919  1.00138.16           N
ATOM  3937  CA  ASN A 506      4.647 -13.763 -11.801  1.00137.34           C
ATOM  3938  C   ASN A 506      4.293 -13.258 -10.377  1.00133.14           C
ATOM  3939  O   ASN A 506      4.640 -12.113  -9.982  1.00131.87           O
ATOM  3940  CB  ASN A 506      3.467 -13.600 -12.761  1.00124.62           C
ATOM  3941  CG  ASN A 506      3.911 -13.193 -14.155  1.00129.73           C
ATOM  3942  ND2 ASN A 506      3.001 -13.278 -15.121  1.00134.29           N
ATOM  3943  OD1 ASN A 506      5.060 -12.792 -14.354  1.00130.76           O
ATOM  3944  N   MET A 507      3.594 -14.099  -9.616  1.00132.66           N
ATOM  3945  CA  MET A 507      3.422 -13.847  -8.193  1.00128.78           C
ATOM  3946  C   MET A 507      4.782 -13.452  -7.679  1.00124.70           C
ATOM  3947  O   MET A 507      5.000 -12.295  -7.445  1.00122.74           O
ATOM  3948  CB  MET A 507      2.901 -15.061  -7.410  1.00107.35           C
ATOM  3949  CG  MET A 507      1.399 -15.111  -7.183  1.00105.09           C
ATOM  3950  SD  MET A 507      0.638 -13.518  -6.839  1.00108.13           S
ATOM  3951  CE  MET A 507      1.713 -13.910  -5.560  1.00103.53           C
ATOM  3952  N   ALA A 508      5.723 -14.382  -7.562  1.00141.27           N
ATOM  3953  CA  ALA A 508      7.005 -14.005  -6.961  1.00139.02           C
ATOM  3954  C   ALA A 508      7.277 -12.486  -7.086  1.00138.51           C
ATOM  3955  O   ALA A 508      7.239 -11.750  -6.079  1.00136.83           O
ATOM  3956  CB  ALA A 508      8.122 -14.819  -7.553  1.00111.47           C
ATOM  3957  N   ARG A 509      7.503 -12.021  -8.315  1.00137.14           N
ATOM  3958  CA  ARG A 509      7.648 -10.585  -8.607  1.00118.71           C
ATOM  3959  C   ARG A 509      6.598  -9.682  -7.929  1.00117.85           C
ATOM  3960  O   ARG A 509      6.928  -8.868  -7.040  1.00116.75           O
```

Fig. 7BM

| | | | | | | | | | |
|---|---|---|---|---|---|---|---|---|---|
| ATOM | 3961 | CB | ARG | A | 509 | 7.630 | -10.365 | -10.122 | 1.00 120.33 | C |
| ATOM | 3962 | CG | ARG | A | 509 | 7.972 | -8.923 | -10.573 | 1.00 123.83 | C |
| ATOM | 3963 | CD | ARG | A | 509 | 9.247 | -8.359 | -9.884 | 1.00 121.79 | C |
| ATOM | 3964 | NE | ARG | A | 509 | 10.501 | -9.086 | -10.150 | 1.00 122.55 | N |
| ATOM | 3965 | CZ | ARG | A | 509 | 11.624 | -8.946 | -9.437 | 1.00 122.43 | C |
| ATOM | 3966 | NH1 | ARG | A | 509 | 11.662 | -8.110 | -8.406 | 1.00 120.06 | N1+ |
| ATOM | 3967 | NH2 | ARG | A | 509 | 12.709 | -9.645 | -9.748 | 1.00 125.80 | N |
| ATOM | 3968 | N | LEU | A | 510 | 5.335 | -9.921 | -8.332 | 1.00 109.65 | N |
| ATOM | 3969 | CA | LEU | A | 510 | 4.304 | -8.939 | -7.761 | 1.00 111.25 | C |
| ATOM | 3970 | C | LEU | A | 510 | 4.074 | -9.010 | -6.229 | 1.00 107.50 | C |
| ATOM | 3971 | O | LEU | A | 510 | 3.807 | -8.002 | -5.599 | 1.00 109.05 | O |
| ATOM | 3972 | CB | LEU | A | 510 | 2.986 | -9.119 | -8.498 | 1.00 108.12 | C |
| ATOM | 3973 | CG | LEU | A | 510 | 2.933 | -8.446 | -9.860 | 1.00 114.74 | C |
| ATOM | 3974 | CD1 | LEU | A | 510 | 1.574 | -8.693 | -10.492 | 1.00 119.90 | C |
| ATOM | 3975 | CD2 | LEU | A | 510 | 3.223 | -6.981 | -9.739 | 1.00 118.77 | C |
| ATOM | 3976 | N | SER | A | 511 | 4.151 | -10.196 | -5.640 | 1.00 108.92 | N |
| ATOM | 3977 | CA | SER | A | 511 | 4.037 | -10.372 | -4.202 | 1.00 105.13 | C |
| ATOM | 3978 | C | SER | A | 511 | 5.211 | -9.742 | -3.469 | 1.00 103.30 | C |
| ATOM | 3979 | O | SER | A | 511 | 6.042 | -9.130 | -2.415 | 1.00 102.27 | O |
| ATOM | 3980 | CB | SER | A | 511 | 3.995 | -11.855 | -3.848 | 1.00 108.42 | C |
| ATOM | 3981 | OG | SER | A | 511 | 5.201 | -12.348 | -3.613 | 1.00 108.11 | O |
| ATOM | 3982 | N | VAL | A | 512 | 6.418 | -9.904 | -3.991 | 1.00 102.41 | N |
| ATOM | 3983 | CA | VAL | A | 512 | 7.311 | -9.258 | -3.291 | 1.00 101.55 | C |
| ATOM | 3984 | C | VAL | A | 512 | 7.410 | -7.744 | -3.419 | 1.00 105.46 | C |
| ATOM | 3985 | O | VAL | A | 512 | 7.473 | -7.010 | -2.418 | 1.00 105.73 | O |
| ATOM | 3986 | CB | VAL | A | 512 | 8.863 | -9.757 | -3.736 | 1.00 80.98 | C |
| ATOM | 3987 | CG1 | VAL | A | 512 | 9.302 | -8.717 | -3.434 | 1.00 82.23 | C |
| ATOM | 3988 | CG2 | VAL | A | 512 | 9.176 | -11.050 | -3.009 | 1.00 76.91 | C |
| ATOM | 3989 | N | GLU | A | 513 | 7.218 | -7.265 | -4.638 | 1.00 109.22 | N |
| ATOM | 3990 | CA | GLU | A | 513 | 7.111 | -5.827 | -4.813 | 1.00 115.09 | C |
| ATOM | 3991 | C | GLU | A | 513 | 6.006 | -5.200 | -3.960 | 1.00 117.41 | C |
| ATOM | 3992 | O | GLU | A | 513 | 6.239 | -4.208 | -3.245 | 1.00 119.63 | O |
| ATOM | 3993 | CB | GLU | A | 513 | 6.806 | -5.494 | -6.277 | 1.00 147.58 | C |
| ATOM | 3994 | CG | GLU | A | 513 | 8.103 | -5.646 | -7.099 | 1.00 147.63 | C |
| ATOM | 3995 | CD | GLU | A | 513 | 9.347 | -5.147 | -6.807 | 1.00 147.67 | C |
| ATOM | 3996 | OE1 | GLU | A | 513 | 9.216 | -4.086 | -5.957 | 1.00 149.87 | O |
| ATOM | 3997 | OE2 | GLU | A | 513 | 10.456 | -5.657 | -6.871 | 1.00 146.64 | O1- |
| ATOM | 3998 | N | TYR | A | 514 | 4.909 | -5.779 | -4.032 | 1.00 115.16 | N |
| ATOM | 3999 | CA | TYR | A | 514 | 3.853 | -5.274 | -3.291 | 1.00 119.05 | C |
| ATOM | 4000 | C | TYR | A | 514 | 3.760 | -5.479 | -1.781 | 1.00 114.73 | C |
| ATOM | 4001 | O | TYR | A | 514 | 3.148 | -4.738 | -1.000 | 1.00 114.65 | O |
| ATOM | 4002 | CB | TYR | A | 514 | 2.349 | -5.858 | -3.824 | 1.00 117.25 | C |
| ATOM | 4003 | CG | TYR | A | 514 | 1.760 | -5.002 | -4.893 | 1.00 125.00 | C |
| ATOM | 4004 | CD1 | TYR | A | 514 | 2.431 | -4.742 | -6.061 | 1.00 133.21 | C |
| ATOM | 4005 | CD2 | TYR | A | 514 | 0.484 | -4.443 | -4.739 | 1.00 125.59 | C |
| ATOM | 4006 | CE1 | TYR | A | 514 | 1.891 | -3.951 | -7.062 | 1.00 142.62 | C |
| ATOM | 4007 | CE2 | TYR | A | 514 | -0.074 | -3.649 | -5.738 | 1.00 134.74 | C |
| ATOM | 4008 | CZ | TYR | A | 514 | 0.640 | -3.401 | -6.893 | 1.00 143.35 | C |
| ATOM | 4009 | OH | TYR | A | 514 | 0.132 | -2.608 | -7.909 | 1.00 153.80 | O |
| ATOM | 4010 | N | THR | A | 515 | 4.337 | -6.475 | -1.363 | 1.00 104.06 | N |
| ATOM | 4011 | CA | THR | A | 515 | 4.832 | -6.830 | 0.062 | 1.00 101.22 | C |
| ATOM | 4012 | C | THR | A | 515 | 5.772 | -5.523 | 0.512 | 1.00 102.86 | C |
| ATOM | 4013 | O | THR | A | 515 | 5.865 | -5.039 | 1.633 | 1.00 103.25 | O |
| ATOM | 4014 | CB | THR | A | 515 | 5.416 | -8.023 | 0.436 | 1.00 103.45 | C |
| ATOM | 4015 | CG2 | THR | A | 515 | 6.896 | -7.924 | 0.747 | 1.00 109.16 | C |
| ATOM | 4016 | OG1 | THR | A | 515 | 4.753 | -8.526 | 1.592 | 1.00 101.96 | O |
| ATOM | 4017 | N | GLU | A | 516 | 6.685 | -5.112 | -0.365 | 1.00 95.77 | N |
| ATOM | 4018 | CA | GLU | A | 516 | 7.530 | -3.979 | -0.027 | 1.00 99.84 | C |
| ATOM | 4019 | C | GLU | A | 516 | 6.745 | -2.662 | -0.095 | 1.00 106.51 | C |
| ATOM | 4020 | O | GLU | A | 516 | 7.130 | -1.676 | 0.544 | 1.00 112.63 | O |
| ATOM | 4021 | CB | GLU | A | 516 | 8.763 | -3.922 | -0.919 | 1.00 116.43 | C |

Fig. 7BN

```
ATOM   4022  CG  GLU A 516       9.930  -3.149  -0.301  1.00 118.56           C
ATOM   4023  CD  GLU A 516      10.569  -3.930   0.808  1.00 113.08           C
ATOM   4024  OE1 GLU A 516      11.461  -3.382   1.493  1.00 113.52           O
ATOM   4025  OE2 GLU A 516      10.193  -5.105   0.987  1.00 109.02           O1-
ATOM   4026  N   LYS A 517       5.568  -2.628  -0.876  1.00 114.43           N
ATOM   4027  CA  LYS A 517       4.823  -1.429  -0.505  1.00 123.64           C
ATOM   4028  C   LYS A 517       3.882  -1.339   0.310  1.00 124.93           C
ATOM   4029  O   LYS A 517       3.535  -0.234   0.779  1.00 130.35           O
ATOM   4030  CB  LYS A 517       4.035  -1.366  -2.221  1.00 110.73           C
ATOM   4031  CG  LYS A 517       4.886  -1.356  -3.483  1.00 112.81           C
ATOM   4032  CD  LYS A 517       4.540  -0.179  -4.392  1.00 125.68           C
ATOM   4033  CE  LYS A 517       3.144  -0.297  -5.000  1.00 129.25           C
ATOM   4034  NZ  LYS A 517       2.703   0.930  -5.709  1.00 136.48           N1+
ATOM   4035  N   SER A 518       3.454  -2.494   0.915  1.00 154.41           N
ATOM   4036  CA  SER A 518       2.615  -2.518   2.012  1.00 152.45           C
ATOM   4037  C   SER A 518       3.276  -1.747   3.133  1.00 157.32           C
ATOM   4038  O   SER A 518       2.605  -1.293   4.057  1.00 158.78           O
ATOM   4039  CB  SER A 518       2.354  -3.951   2.475  1.00 144.47           C
ATOM   4040  OG  SER A 518       1.798  -3.979   3.781  1.00 144.56           O
ATOM   4041  N   PHE A 519       4.592  -1.580   3.021  1.00 113.91           N
ATOM   4042  CA  PHE A 519       5.412  -1.042   4.097  1.00 114.12           C
ATOM   4043  C   PHE A 519       5.349   0.469   4.148  1.00 125.83           C
ATOM   4044  O   PHE A 519       5.693   1.073   5.151  1.00 127.95           O
ATOM   4045  CB  PHE A 519       6.855  -1.513   3.937  1.00 161.76           C
ATOM   4046  CG  PHE A 519       7.086  -2.918   4.403  1.00 152.77           C
ATOM   4047  CD1 PHE A 519       8.110  -3.678   3.868  1.00 145.77           C
ATOM   4048  CD2 PHE A 519       6.285  -3.476   5.384  1.00 153.55           C
ATOM   4049  CE1 PHE A 519       8.332  -4.965   4.297  1.00 140.14           C
ATOM   4050  CE2 PHE A 519       6.500  -4.769   5.819  1.00 147.68           C
ATOM   4051  CZ  PHE A 519       7.525  -5.513   5.274  1.00 141.23           C
ATOM   4052  N   LYS A 520       4.903   1.077   3.056  1.00 147.12           N
ATOM   4053  CA  LYS A 520       4.660   2.511   3.034  1.00 161.34           C
ATOM   4054  C   LYS A 520       3.177   2.808   2.924  1.00 151.31           C
ATOM   4055  O   LYS A 520       2.627   3.516   3.763  1.00 149.99           O
ATOM   4056  CB  LYS A 520       5.426   3.176   1.889  1.00 168.70           C
ATOM   4057  CG  LYS A 520       6.922   2.969   1.973  1.00 173.69           C
ATOM   4058  CD  LYS A 520       7.722   4.086   1.309  1.00 199.45           C
ATOM   4059  CE  LYS A 520       9.208   3.956   1.655  1.00 186.14           C
ATOM   4060  NZ  LYS A 520      10.065   5.005   1.047  1.00 203.61           N1+
ATOM   4061  N   GLU A 521       2.527   2.248   1.900  1.00 165.27           N
ATOM   4062  CA  GLU A 521       1.113   2.584   1.667  1.00 156.60           C
ATOM   4063  C   GLU A 521       0.121   1.835   2.577  1.00 141.66           C
ATOM   4064  O   GLU A 521      -1.076   2.101   2.554  1.00 135.75           O
ATOM   4065  CB  GLU A 521       0.776   2.468   0.175  1.00 182.32           C
ATOM   4066  CG  GLU A 521       1.531   3.536  -0.647  1.00 201.21           C
ATOM   4067  CD  GLU A 521       3.249   3.459  -2.135  1.00 208.50           C
ATOM   4068  OE1 GLU A 521       0.303   2.750  -2.530  1.00 199.19           O
ATOM   4069  OE2 GLU A 521       1.978   4.110  -2.909  1.00 224.80           O1-
ATOM   4070  N   ASN A 522       0.646   0.930   3.400  1.00 171.10           N
ATOM   4071  CA  ASN A 522      -0.133   0.263   4.441  1.00 156.33           C
ATOM   4072  C   ASN A 522      -1.376  -0.469   3.975  1.00 143.84           C
ATOM   4073  O   ASN A 522      -2.465  -0.248   4.509  1.00 136.17           O
ATOM   4074  CB  ASN A 522      -0.512   1.251   5.534  1.00 155.64           C
ATOM   4075  CG  ASN A 522       0.325   1.325   6.613  1.00 161.45           C
ATOM   4076  ND2 ASN A 522       0.952   2.536   6.935  1.00 173.18           N
ATOM   4077  OD1 ASN A 522       0.953   0.303   7.149  1.00 156.75           O
ATOM   4078  N   TYR A 523      -1.205  -1.349   2.992  1.00 172.90           N
ATOM   4079  CA  TYR A 523      -2.310  -2.143   2.470  1.00 160.45           C
ATOM   4080  C   TYR A 523      -2.838  -3.052   3.572  1.00 141.59           C
ATOM   4081  O   TYR A 523      -2.072  -3.765   4.193  1.00 137.25           O
ATOM   4082  CB  TYR A 523      -1.865  -2.980   1.262  1.00  81.14           C
```

Fig. 7BO

```
ATOM   4083  CG  TYR A 523      -1.296  -2.168   0.093  1.00 99.45           C
ATOM   4084  CD1 TYR A 523      -0.026  -2.462  -0.407  1.00109.35           C
ATOM   4085  CD2 TYR A 523      -2.035  -1.177  -0.516  1.00110.28           C
ATOM   4086  CE1 TYR A 523       0.487  -1.750  -1.472  1.00129.61           C
ATOM   4087  CE2 TYR A 523      -1.524  -0.461  -1.576  1.00131.10           C
ATOM   4088  CZ  TYR A 523      -0.267  -0.751  -2.047  1.00140.53           C
ATOM   4089  OH  TYR A 523       0.233  -0.038  -3.107  1.00162.59           O
ATOM   4090  N   PRO A 524      -4.150  -2.992   3.832  1.00160.87           N
ATOM   4091  CA  PRO A 524      -4.750  -3.895   4.814  1.00143.73           C
ATOM   4092  C   PRO A 524      -4.887  -5.274   4.175  1.00132.24           C
ATOM   4093  O   PRO A 524      -4.915  -6.305   4.853  1.00119.81           O
ATOM   4094  CB  PRO A 524      -6.124  -3.271   5.048  1.00109.06           C
ATOM   4095  CG  PRO A 524      -6.459  -2.645   3.737  1.00119.25           C
ATOM   4096  CD  PRO A 524      -5.156  -2.157   3.155  1.00134.50           C
ATOM   4097  N   ASP A 525      -4.952  -5.273   2.847  1.00140.49           N
ATOM   4098  CA  ASP A 525      -5.085  -6.491   2.068  1.00132.51           C
ATOM   4099  C   ASP A 525      -4.256  -6.319   0.802  1.00146.32           C
ATOM   4100  O   ASP A 525      -4.666  -5.629  -0.127  1.00155.66           O
ATOM   4101  CB  ASP A 525      -6.559  -6.726   1.733  1.00186.15           C
ATOM   4102  CG  ASP A 525      -6.879  -8.183   1.502  1.00176.43           C
ATOM   4103  OD1 ASP A 525      -6.144  -8.819   0.724  1.00192.24           O
ATOM   4104  OD2 ASP A 525      -7.856  -8.693   2.098  1.00164.25           O1-
ATOM   4105  N   VAL A 526      -3.072  -6.924   0.296  1.00125.00           N
ATOM   4106  CA  VAL A 526      -2.108  -6.792  -0.296  1.00139.87           C
ATOM   4107  C   VAL A 526      -2.655  -7.271  -1.639  1.00143.30           C
ATOM   4108  O   VAL A 526      -2.626  -6.544  -2.647  1.00159.97           O
ATOM   4109  CB  VAL A 526      -0.841  -7.597   0.015  1.00 86.72           C
ATOM   4110  CG1 VAL A 526       0.076  -7.625  -1.177  1.00 96.37           C
ATOM   4111  CG2 VAL A 526      -0.135  -7.032   1.218  1.00 85.23           C
ATOM   4112  N   LEU A 527      -3.135  -8.510  -1.654  1.00104.88           N
ATOM   4113  CA  LEU A 527      -3.789  -9.062  -2.834  1.00109.99           C
ATOM   4114  C   LEU A 527      -4.833  -8.099  -3.427  1.00119.93           C
ATOM   4115  O   LEU A 527      -4.766  -7.760  -4.615  1.00137.11           O
ATOM   4116  CB  LEU A 527      -4.440 -10.395  -2.491  1.00 95.87           C
ATOM   4117  CG  LEU A 527      -4.794 -11.218  -3.719  1.00100.51           C
ATOM   4118  CD1 LEU A 527      -3.581 -11.985  -4.211  1.00 99.07           C
ATOM   4119  CD2 LEU A 527      -5.884 -12.162  -3.351  1.00 86.05           C
ATOM   4120  N   LYS A 528      -5.791  -7.670  -2.596  1.00 76.30           N
ATOM   4121  CA  LYS A 528      -6.767  -6.644  -2.979  1.00 85.58           C
ATOM   4122  C   LYS A 528      -6.072  -5.405  -3.568  1.00105.86           C
ATOM   4123  O   LYS A 528      -6.562  -4.806  -4.513  1.00120.59           O
ATOM   4124  CB  LYS A 528      -7.687  -6.265  -1.803  1.00203.92           C
ATOM   4125  CG  LYS A 528      -9.067  -5.754  -2.230  1.00194.37           C
ATOM   4126  CD  LYS A 528      -9.775  -4.986  -1.118  1.00185.36           C
ATOM   4127  CE  LYS A 528     -10.982  -4.193  -1.554  1.00161.62           C
ATOM   4128  NZ  LYS A 528     -11.516  -3.128  -0.718  1.00152.76           N1+
ATOM   4129  N   ALA A 529      -4.919  -5.034  -3.021  1.00 98.65           N
ATOM   4130  CA  ALA A 529      -4.128  -3.922  -3.557  1.00119.12           C
ATOM   4131  C   ALA A 529      -3.758  -4.177  -5.003  1.00136.06           C
ATOM   4132  O   ALA A 529      -4.038  -3.264  -5.890  1.00154.09           O
ATOM   4133  CB  ALA A 529      -2.870  -3.729  -2.738  1.00110.23           C
ATOM   4134  N   MET A 530      -3.112  -5.312  -5.232  1.00 95.34           N
ATOM   4135  CA  MET A 530      -2.732  -5.680  -6.586  1.00113.66           C
ATOM   4136  C   MET A 530      -3.941  -5.604  -7.492  1.00119.20           C
ATOM   4137  O   MET A 530      -3.893  -4.964  -8.537  1.00139.26           O
ATOM   4138  CB  MET A 530      -2.151  -7.080  -6.603  1.00148.49           C
ATOM   4139  CG  MET A 530      -1.064  -7.247  -5.589  1.00128.14           C
ATOM   4140  SD  MET A 530      -0.428  -8.916  -5.527  1.00112.19           S
ATOM   4141  CE  MET A 530       0.045  -9.114  -7.226  1.00117.57           C
ATOM   4142  N   VAL A 531      -5.030  -6.242  -7.072  1.00 97.90           N
ATOM   4143  CA  VAL A 531      -6.271  -6.259  -7.855  1.00104.32           C
```

Fig. 7BP

```
ATOM   4144  C   VAL A 531      -6.755  -4.858  -8.252  1.00122.46           C
ATOM   4145  O   VAL A 531      -6.889  -4.568  -9.439  1.00143.52           O
ATOM   4146  CB  VAL A 531      -7.411  -7.001  -7.117  1.00115.24           C
ATOM   4147  CG1 VAL A 531      -8.754  -6.764  -7.813  1.00111.76           C
ATOM   4148  CG2 VAL A 531      -7.101  -8.498  -7.001  1.00 88.46           C
ATOM   4149  N   LYS A 532      -7.021  -4.004  -7.261  1.00141.42           N
ATOM   4150  CA  LYS A 532      -7.487  -2.827  -7.513  1.00158.53           C
ATOM   4151  C   LYS A 532      -6.422  -1.857  -8.327  1.00183.06           C
ATOM   4152  O   LYS A 532      -6.731  -0.817  -8.912  1.00202.73           O
ATOM   4153  CB  LYS A 532      -7.735  -1.880  -6.201  1.00232.12           C
ATOM   4154  CG  LYS A 532      -9.149  -2.038  -5.656  1.00216.91           C
ATOM   4155  CD  LYS A 532      -9.346  -1.228  -4.375  1.00210.02           C
ATOM   4156  CE  LYS A 532     -10.719  -1.487  -3.754  1.00193.96           C
ATOM   4157  NZ  LYS A 532     -10.892  -0.826  -2.424  1.00166.10           N1+
ATOM   4158  N   ASP A 533      -5.192  -2.367  -8.369  1.00124.61           N
ATOM   4159  CA  ASP A 533      -4.127  -1.723  -9.124  1.00146.50           C
ATOM   4160  C   ASP A 533      -3.905  -2.357 -10.495  1.00165.43           C
ATOM   4161  O   ASP A 533      -3.093  -1.951 -11.225  1.00188.84           O
ATOM   4162  CB  ASP A 533      -2.824  -1.698  -8.324  1.00168.75           C
ATOM   4163  CG  ASP A 533      -2.927  -0.845  -7.077  1.00174.73           C
ATOM   4164  OD1 ASP A 533      -3.709   0.126  -7.078  1.00175.94           O
ATOM   4165  OD2 ASP A 533      -2.230  -1.185  -6.090  1.00163.87           O1-
ATOM   4166  N   TYR A 534      -4.723  -3.348 -10.842  1.00130.26           N
ATOM   4167  CA  TYR A 534      -4.746  -3.890 -12.204  1.00141.51           C
ATOM   4168  C   TYR A 534      -6.141  -3.910 -12.836  1.00146.74           C
ATOM   4169  O   TYR A 534      -6.407  -4.676 -13.759  1.00149.73           O
ATOM   4170  CB  TYR A 534      -4.191  -5.275 -12.266  1.00135.07           C
ATOM   4171  CG  TYR A 534      -2.596  -5.223 -12.230  1.00136.35           C
ATOM   4172  CD1 TYR A 534      -1.929  -5.126 -11.031  1.00127.85           C
ATOM   4173  CD2 TYR A 534      -1.843  -5.252 -13.389  1.00143.26           C
ATOM   4174  CE1 TYR A 534      -0.549  -5.072 -10.978  1.00126.72           C
ATOM   4175  CE2 TYR A 534      -0.455  -5.196 -13.341  1.00133.99           C
ATOM   4176  CZ  TYR A 534       0.183  -5.106 -12.125  1.00126.35           C
ATOM   4177  OH  TYR A 534       1.554  -5.043 -12.029  1.00118.62           O
ATOM   4178  N   ASN A 535      -7.023  -3.053 -12.339  1.00170.72           N
ATOM   4179  CA  ASN A 535      -8.349  -2.898 -12.919  1.00178.60           C
ATOM   4180  C   ASN A 535      -8.958  -4.227 -13.326  1.00166.49           C
ATOM   4181  O   ASN A 535      -9.440  -4.371 -14.450  1.00180.99           O
ATOM   4182  CB  ASN A 535      -8.284  -1.938 -14.107  1.00189.16           C
ATOM   4183  CG  ASN A 535      -7.889  -0.530 -13.691  1.00200.80           C
ATOM   4184  ND2 ASN A 535      -6.858   0.015 -14.329  1.00214.62           N
ATOM   4185  OD1 ASN A 535      -8.493   0.051 -12.792  1.00196.27           O
ATOM   4186  N   GLN A 536      -8.907  -5.195 -12.407  1.00185.03           N
ATOM   4187  CA  GLN A 536      -9.624  -6.470 -12.628  1.00168.96           C
ATOM   4188  C   GLN A 536     -10.828  -6.477 -11.563  1.00191.34           C
ATOM   4189  O   GLN A 536     -10.709  -6.046 -10.417  1.00134.88           O
ATOM   4190  CB  GLN A 536      -8.686  -7.653 -12.236  1.00143.08           C
ATOM   4191  CG  GLN A 536      -7.572  -7.870 -13.251  1.00153.25           C
ATOM   4192  CD  GLN A 536      -8.080  -9.447 -14.553  1.00158.00           C
ATOM   4193  NE2 GLN A 536      -7.163  -9.748 -15.460  1.00162.53           N
ATOM   4194  OE1 GLN A 536      -9.282  -9.623 -14.741  1.00159.14           O
ATOM   4195  N   THR A 537     -11.979  -6.962 -12.029  1.00181.32           N
ATOM   4196  CA  THR A 537     -13.229  -6.891 -11.256  1.00167.59           C
ATOM   4197  C   THR A 537     -13.308  -7.896 -10.096  1.00130.99           C
ATOM   4198  O   THR A 537     -13.999  -7.664  -9.106  1.00121.78           O
ATOM   4199  CB  THR A 537     -14.475  -7.091 -12.159  1.00151.17           C
ATOM   4200  CG2 THR A 537     -15.713  -6.463 -11.529  1.00136.62           C
ATOM   4201  OG1 THR A 537     -14.245  -6.515 -13.450  1.00173.97           O
ATOM   4202  N   SER A 538     -12.624  -9.026 -10.237  1.00186.41           N
ATOM   4203  CA  SER A 538     -12.535 -10.010  -9.158  1.00160.73           C
ATOM   4204  C   SER A 538     -11.095 -10.487  -8.954  1.00150.71           C
```

Fig. 7BQ

```
ATOM   4205  O    SER A 538     -10.143  -9.845  -9.389 1.00160.76           O
ATOM   4206  CB   SER A 538     -13.509 -11.192  -9.373 1.00209.89           C
ATOM   4207  OG   SER A 538     -13.491 -11.661 -10.716 1.00216.86           O
ATOM   4208  N    ALA A 539     -10.933 -11.611  -8.282 1.00134.00           N
ATOM   4209  CA   ALA A 539      -9.599 -12.061  -7.958 1.00124.54           C
ATOM   4210  C    ALA A 539      -9.205 -13.296  -8.767 1.00120.00           C
ATOM   4211  O    ALA A 539      -8.018 -13.580  -8.930 1.00119.33           O
ATOM   4212  CB   ALA A 539      -9.497 -12.315  -6.490 1.00 84.04           C
ATOM   4213  N    LYS A 540     -10.201 -14.022  -9.275 1.00141.27           N
ATOM   4214  CA   LYS A 540      -9.950 -15.141 -10.181 1.00139.09           C
ATOM   4215  C    LYS A 540      -9.613 -14.621 -11.577 1.00159.12           C
ATOM   4216  O    LYS A 540      -8.954 -15.306 -12.363 1.00160.16           O
ATOM   4217  CB   LYS A 540     -11.149 -16.086 -10.241 1.00271.41           C
ATOM   4218  CG   LYS A 540     -11.284 -16.974  -9.023 1.00251.04           C
ATOM   4219  CD   LYS A 540     -12.345 -18.119  -9.284 1.00242.77           C
ATOM   4220  CE   LYS A 540     -12.179 -19.161  -8.175 1.00223.91           C
ATOM   4221  NZ   LYS A 540     -12.946 -20.397  -8.513 1.00221.67           N1+
ATOM   4222  N    ASP A 541     -10.065 -13.405 -11.879 1.00123.48           N
ATOM   4223  CA   ASP A 541      -9.761 -12.785 -13.163 1.00145.38           C
ATOM   4224  C    ASP A 541      -8.343 -12.236 -13.107 1.00147.70           C
ATOM   4225  O    ASP A 541      -7.638 -12.231 -14.113 1.00159.94           O
ATOM   4226  CB   ASP A 541     -10.774 -11.683 -13.528 1.00189.44           C
ATOM   4227  CG   ASP A 541     -11.755 -12.111 -14.632 1.00199.89           C
ATOM   4228  OD1  ASP A 541     -11.484 -13.113 -15.335 1.00191.26           O
ATOM   4229  OD2  ASP A 541     -12.794 -11.432 -14.804 1.00210.06           O1-
ATOM   4230  N    PHE A 542      -7.923 -11.797 -11.925 1.00126.97           N
ATOM   4231  CA   PHE A 542      -6.539 -11.365 -11.717 1.00129.43           C
ATOM   4232  C    PHE A 542      -5.569 -12.546 -11.784 1.00113.70           C
ATOM   4233  O    PHE A 542      -4.540 -12.501 -12.462 1.00121.14           O
ATOM   4234  CB   PHE A 542      -6.389 -10.646 -10.368 1.00125.20           C
ATOM   4235  CG   PHE A 542      -4.961 -10.266 -10.030 1.00125.20           C
ATOM   4236  CD1  PHE A 542      -4.637  -8.961  -9.692 1.00133.28           C
ATOM   4237  CD2  PHE A 542      -3.947 -11.214 -10.040 1.00116.64           C
ATOM   4238  CE1  PHE A 542      -3.335  -8.612  -9.386 1.00132.79           C
ATOM   4239  CE2  PHE A 542      -2.646 -10.865  -9.737 1.00116.26           C
ATOM   4240  CZ   PHE A 542      -2.343  -9.565  -9.410 1.00124.26           C
ATOM   4241  N    LEU A 543      -5.903 -13.599 -11.059 1.00140.19           N
ATOM   4242  CA   LEU A 543      -5.038 -14.733 -10.936 1.00124.65           C
ATOM   4243  C    LEU A 543      -5.068 -15.630 -12.177 1.00131.78           C
ATOM   4244  O    LEU A 543      -3.979 -16.224 -12.497 1.00130.28           O
ATOM   4245  CB   LEU A 543      -5.385 -15.527  -9.693 1.00104.87           C
ATOM   4246  CG   LEU A 543      -5.324 -14.725  -8.408 1.00 98.80           C
ATOM   4247  CD1  LEU A 543      -6.050 -15.323  -7.289 1.00 83.41           C
ATOM   4248  CD2  LEU A 543      -3.755 -14.848  -8.029 1.00 95.04           C
ATOM   4249  N    GLU A 544      -6.134 -15.747 -12.876 1.00137.89           N
ATOM   4250  CA   GLU A 544      -6.135 -16.524 -14.111 1.00148.95           C
ATOM   4251  C    GLU A 544      -5.395 -15.716 -15.161 1.00170.95           C
ATOM   4252  O    GLU A 544      -5.361 -16.066 -16.337 1.00185.31           O
ATOM   4253  CB   GLU A 544      -7.556 -16.848 -14.568 1.00194.79           C
ATOM   4254  CG   GLU A 544      -8.070 -18.168 -14.071 1.00174.06           C
ATOM   4255  CD   GLU A 544      -9.337 -18.405 -14.394 1.00179.80           C
ATOM   4256  OE1  GLU A 544     -10.262 -17.399 -14.572 1.00194.93           O
ATOM   4257  OE2  GLU A 544      -9.964 -19.578 -14.472 1.00170.53           O1-
ATOM   4258  N    SER A 545      -4.764 -14.639 -14.699 1.00123.56           N
ATOM   4259  CA   SER A 545      -4.138 -13.641 -15.561 1.00141.81           C
ATOM   4260  C    SER A 545      -2.632 -13.488 -15.327 1.00130.56           C
ATOM   4261  O    SER A 545      -1.981 -12.857 -15.953 1.00141.98           O
ATOM   4262  CB   SER A 545      -4.819 -12.289 -15.357 1.00109.97           C
ATOM   4263  OG   SER A 545      -4.422 -11.373 -16.350 1.00129.32           O
ATOM   4264  N    LEU A 546      -2.088 -14.275 -14.405 1.00154.49           N
ATOM   4265  CB   LEU A 546      -0.647 -14.335 -14.195 1.00145.19           C
```

Fig. 7BR

```
ATOM   4266  C   LEU A 546      -0.120 -15.480 -15.032  1.00 139.58           C
ATOM   4267  O   LEU A 546       1.029 -15.879 -14.894  1.00 132.62           O
ATOM   4268  CB  LEU A 546      -0.311 -14.565 -12.722  1.00 101.75           C
ATOM   4269  CG  LEU A 546      -0.952 -13.637 -11.709  1.00 106.21           C
ATOM   4270  CD1 LEU A 546      -0.434 -13.912 -10.320  1.00  88.36           C
ATOM   4271  CD2 LEU A 546      -0.672 -12.214 -12.100  1.00 125.32           C
ATOM   4272  N   ASN A 547      -0.982 -16.011 -15.895  1.00 191.80           N
ATOM   4273  CA  ASN A 547      -0.622 -17.112 -16.773  1.00 190.57           C
ATOM   4274  C   ASN A 547       0.174 -16.639 -17.978  1.00 202.30           C
ATOM   4275  O   ASN A 547       1.264 -17.140 -18.249  1.00 197.62           O
ATOM   4276  CB  ASN A 547      -1.874 -17.850 -17.250  1.00 200.54           C
ATOM   4277  CG  ASN A 547      -2.038 -19.204 -16.594  1.00 180.93           C
ATOM   4278  ND2 ASN A 547      -2.833 -19.253 -15.531  1.00 180.57           N
ATOM   4279  OD1 ASN A 547      -1.462 -20.196 -17.039  1.00 172.34           O
ATOM   4280  N   ASP A 548      -0.372 -15.561 -18.692  1.00 148.42           N
ATOM   4281  CA  ASP A 548       0.179 -15.262 -19.988  1.00 163.30           C
ATOM   4282  C   ASP A 548       1.573 -14.616 -19.889  1.00 161.71           C
ATOM   4283  O   ASP A 548       1.694 -13.413 -19.674  1.00 156.70           O
ATOM   4284  CB  ASP A 548      -0.826 -14.389 -20.770  1.00 191.00           C
ATOM   4285  CG  ASP A 548      -2.097 -15.165 -21.190  1.00 196.26           C
ATOM   4286  OD1 ASP A 548      -1.987 -16.333 -21.650  1.00 194.97           O
ATOM   4287  OD2 ASP A 548      -3.216 -14.522 -21.061  1.00 199.87           O1-
ATOM   4288  N   LYS A 549       2.606 -15.450 -20.059  1.00 156.10           N
ATOM   4289  CA  LYS A 549       4.032 -15.087 -19.993  1.00 170.45           C
ATOM   4290  C   LYS A 549       4.406 -13.656 -20.414  1.00 171.01           C
ATOM   4291  O   LYS A 549       5.416 -13.113 -19.958  1.00 170.04           O
ATOM   4292  CB  LYS A 549       4.845 -16.087 -20.823  1.00 170.45           C
ATOM   4293  CG  LYS A 549       6.120 -16.588 -20.169  1.00 155.39           C
ATOM   4294  CD  LYS A 549       6.834 -17.577 -21.075  1.00 161.79           C
ATOM   4295  CE  LYS A 549       5.842 -18.568 -21.884  1.00 150.42           C
ATOM   4296  NZ  LYS A 549       6.412 -19.377 -22.816  1.00 159.90           N1+
ATOM   4297  N   ASN A 550       3.617 -13.069 -21.312  1.00 181.89           N
ATOM   4298  CA  ASN A 550       3.758 -11.656 -21.666  1.00 201.55           C
ATOM   4299  C   ASN A 550       2.860 -10.810 -20.768  1.00 204.92           C
ATOM   4300  O   ASN A 550       1.678 -10.603 -21.061  1.00 216.07           O
ATOM   4301  CB  ASN A 550       3.435 -11.410 -23.148  1.00 169.05           C
ATOM   4302  CG  ASN A 550       4.637 -11.642 -24.066  1.00 173.32           C
ATOM   4303  ND2 ASN A 550       4.375 -11.793 -25.367  1.00 173.29           N
ATOM   4304  OD1 ASN A 550       5.783 -11.671 -23.611  1.00 169.72           O
ATOM   4305  N   PHE A 551       3.437 -10.327 -19.670  1.00 167.36           N
ATOM   4306  CA  PHE A 551       2.668  -9.689 -18.609  1.00 168.49           C
ATOM   4307  C   PHE A 551       3.024  -8.212 -18.457  1.00 187.10           C
ATOM   4308  O   PHE A 551       4.200  -7.876 -18.286  1.00 165.23           O
ATOM   4309  CB  PHE A 551       2.916 -10.422 -17.287  1.00 167.59           C
ATOM   4310  CG  PHE A 551       1.988 -10.013 -16.179  1.00 156.90           C
ATOM   4311  CD1 PHE A 551       0.796 -10.681 -15.975  1.00 153.53           C
ATOM   4312  CD2 PHE A 551       2.309  -8.962 -15.338  1.00 161.51           C
ATOM   4313  CE1 PHE A 551      -0.059 -10.304 -14.862  1.00 154.77           C
ATOM   4314  CE2 PHE A 551       1.455  -8.578 -14.323  1.00 162.97           C
ATOM   4315  CZ  PHE A 551       0.271  -9.250 -14.137  1.00 159.55           C
ATOM   4316  N   LYS A 552       2.014  -7.337 -18.518  1.00 155.53           N
ATOM   4317  CA  LYS A 552       2.243  -5.901 -18.335  1.00 167.03           C
ATOM   4318  C   LYS A 552       2.899  -5.680 -16.984  1.00 174.76           C
ATOM   4319  O   LYS A 552       2.685  -6.446 -16.057  1.00 155.90           O
ATOM   4320  CB  LYS A 552       0.942  -5.085 -18.388  1.00 155.23           C
ATOM   4321  CG  LYS A 552      -0.302  -5.804 -18.903  1.00 159.34           C
ATOM   4322  CD  LYS A 552      -1.524  -4.885 -19.763  1.00 186.48           C
ATOM   4323  CE  LYS A 552      -2.773  -5.443 -19.436  1.00 202.77           C
ATOM   4324  NZ  LYS A 552      -3.906  -4.477 -19.366  1.00 234.33           N1+
ATOM   4325  N   PHE A 553       3.697  -4.634 -16.852  1.00 211.03           N
ATOM   4326  CA  PHE A 553       4.285  -4.369 -15.551  1.00 203.11           C
```

Fig. 7BS

```
ATOM  4327  C    PHE A 553     4.276  -2.881 -15.192  1.00229.72           C
ATOM  4328  O    PHE A 553     5.244  -2.194 -15.437  1.00244.00           O
ATOM  4329  CB   PHE A 553     5.673  -5.012 -15.429  1.00201.10           C
ATOM  4330  CG   PHE A 553     5.647  -6.416 -14.952  1.00184.03           C
ATOM  4331  CD1  PHE A 553     6.071  -7.504 -15.699  1.00161.41           C
ATOM  4332  CD2  PHE A 553     5.131  -6.642 -13.655  1.00150.65           C
ATOM  4333  CE1  PHE A 553     6.049  -8.790 -15.054  1.00129.71           C
ATOM  4334  CE2  PHE A 553     5.167  -7.922 -13.010  1.00126.86           C
ATOM  4335  CZ   PHE A 553     5.595  -8.994 -13.758  1.00116.80           C
ATOM  4336  N    ASP A 554     3.154  -2.491 -14.613  1.00176.91           N
ATOM  4337  CA   ASP A 554     2.950  -1.071 -14.182  1.00204.05           C
ATOM  4338  C    ASP A 554     3.697  -0.786 -12.878  1.00197.83           C
ATOM  4339  O    ASP A 554     3.869   0.371 -12.497  1.00221.27           O
ATOM  4340  CB   ASP A 554     1.455  -0.774 -13.997  1.00193.04           C
ATOM  4341  CG   ASP A 554     0.612  -1.181 -15.205  1.00200.63           C
ATOM  4342  OD1  ASP A 554    -0.623  -1.319 -15.056  1.00203.70           O
ATOM  4343  OD2  ASP A 554     1.179  -1.369 -16.303  1.00204.85           O1-
ATOM  4344  N    THR A 555     4.135  -1.846 -12.292  1.00132.97           N
ATOM  4345  CA   THR A 555     4.867  -1.734 -10.934  1.00184.54           C
ATOM  4346  C    THR A 555     6.351  -2.120 -11.079  1.00173.78           C
ATOM  4347  O    THR A 555     6.882  -3.160 -11.636  1.00155.71           O
ATOM  4348  CB   THR A 555     4.170  -2.555  -9.814  1.00177.83           C
ATOM  4349  CG2  THR A 555     2.854  -1.895  -9.418  1.00189.88           C
ATOM  4350  OG1  THR A 555     3.993  -3.886 -10.278  1.00154.67           O
ATOM  4351  N    ASN A 556     7.244  -1.275 -10.579  1.00177.05           N
ATOM  4352  CA   ASN A 556     8.664  -1.401 -10.911  1.00175.22           C
ATOM  4353  C    ASN A 556     9.431  -2.497 -10.164  1.00147.73           C
ATOM  4354  O    ASN A 556     9.905  -2.946  -9.090  1.00131.54           O
ATOM  4355  CB   ASN A 556     9.386  -0.052 -10.750  1.00180.55           C
ATOM  4356  CG   ASN A 556     9.027   0.937 -11.850  1.00209.48           C
ATOM  4357  ND2  ASN A 556     9.036   2.224 -11.515  1.00227.96           N
ATOM  4358  OD1  ASN A 556     8.755   0.549 -12.986  1.00206.28           O
ATOM  4359  N    LYS A 557    10.565  -2.898 -10.756  1.00181.25           N
ATOM  4360  CA   LYS A 557    11.493  -3.900 -10.209  1.00160.36           C
ATOM  4361  C    LYS A 557    12.534  -3.244  -9.309  1.00167.49           C
ATOM  4362  O    LYS A 557    13.347  -3.850  -9.783  1.00188.10           O
ATOM  4363  CB   LYS A 557    12.205  -4.652 -11.345  1.00216.56           C
ATOM  4364  CG   LYS A 557    11.302  -5.574 -12.166  1.00202.45           C
ATOM  4365  CD   LYS A 557    11.608  -5.533 -13.676  1.00212.25           C
ATOM  4366  CE   LYS A 557    12.867  -6.314 -14.052  1.00211.65           C
ATOM  4367  NZ   LYS A 557    13.064  -6.389 -15.532  1.00221.46           N1+
ATOM  4368  N    THR A 558    12.514  -3.591  -8.020  1.00139.28           N
ATOM  4369  CA   THR A 558    13.317  -2.898  -6.998  1.00146.11           C
ATOM  4370  C    THR A 558    14.477  -3.729  -6.402  1.00131.37           C
ATOM  4371  O    THR A 558    15.450  -3.178  -5.869  1.00142.88           O
ATOM  4372  CB   THR A 558    12.416  -2.384  -5.845  1.00137.87           C
ATOM  4373  CG2  THR A 558    11.269  -1.549  -6.394  1.00153.28           C
ATOM  4374  OG1  THR A 558    11.872  -3.498  -5.129  1.00112.70           O
ATOM  4375  N    ARG A 559    14.363  -5.049  -6.509  1.00155.54           N
ATOM  4376  CA   ARG A 559    15.319  -5.981  -5.920  1.00141.44           C
ATOM  4377  C    ARG A 559    15.119  -7.358  -6.567  1.00123.52           C
ATOM  4378  O    ARG A 559    14.045  -7.635  -7.103  1.00116.23           O
ATOM  4379  CB   ARG A 559    15.060  -6.063  -4.411  1.00140.27           C
ATOM  4380  CG   ARG A 559    13.986  -6.196  -4.025  1.00129.84           C
ATOM  4381  CD   ARG A 559    13.355  -6.152  -2.520  1.00123.80           C
ATOM  4382  NE   ARG A 559    13.837  -4.966  -1.824  1.00141.26           N
ATOM  4383  CZ   ARG A 559    13.207  -3.793  -1.814  1.00156.16           C
ATOM  4384  NH1  ARG A 559    12.070  -3.643  -2.476  1.00158.87           N1+
ATOM  4385  NH2  ARG A 559    13.720  -2.764  -1.151  1.00168.14           N
ATOM  4386  N    ASP A 560    16.134  -8.219  -6.529  1.00147.05           N
ATOM  4387  CA   ASP A 560    16.006  -9.592  -7.129  1.00132.38           C
```

Fig. 7BT

```
ATOM   4388  C   ASP A 560      15.265 -10.549  -6.217  1.00112.06           C
ATOM   4389  O   ASP A 560      15.437 -10.533  -5.000  1.00108.41           O
ATOM   4390  CB  ASP A 560      17.373 -10.093  -7.554  1.00148.07           C
ATOM   4391  CG  ASP A 560      17.740  -9.692  -8.977  1.00165.36           C
ATOM   4392  OD1 ASP A 560      16.820  -9.384  -9.770  1.00168.86           O
ATOM   4393  OD2 ASP A 560      18.945  -9.691  -9.309  1.00177.16           O1-
ATOM   4394  N   VAL A 561      14.432 -11.399  -6.807  1.00144.91           N
ATOM   4395  CA  VAL A 561      13.600 -12.325  -6.042  1.00126.15           C
ATOM   4396  C   VAL A 561      14.075 -13.754  -6.228  1.00116.94           C
ATOM   4397  O   VAL A 561      14.413 -14.141  -7.333  1.00121.60           O
ATOM   4398  CB  VAL A 561      12.142 -12.266  -6.528  1.00 99.93           C
ATOM   4399  CG1 VAL A 561      11.279 -13.223  -5.743  1.00 82.02           C
ATOM   4400  CG2 VAL A 561      11.804 -10.858  -6.431  1.00107.04           C
ATOM   4401  N   TYR A 562      14.087 -14.550  -5.166  1.00139.50           N
ATOM   4402  CA  TYR A 562      14.454 -15.959  -5.302  1.00129.85           C
ATOM   4403  C   TYR A 562      13.290 -16.860  -4.982  1.00116.39           C
ATOM   4404  O   TYR A 562      12.181 -16.466  -4.692  1.00112.36           O
ATOM   4405  CB  TYR A 562      15.647 -16.302  -4.410  1.00 98.70           C
ATOM   4406  CG  TYR A 562      16.910 -15.512  -4.686  1.00111.83           C
ATOM   4407  CD1 TYR A 562      16.868 -14.135  -4.868  1.00122.35           C
ATOM   4408  CD2 TYR A 562      18.155 -16.138  -4.737  1.00114.75           C
ATOM   4409  CE1 TYR A 562      18.029 -13.404  -5.113  1.00136.01           C
ATOM   4410  CE2 TYR A 562      19.317 -15.410  -4.981  1.00127.99           C
ATOM   4411  CZ  TYR A 562      19.241 -14.044  -5.167  1.00138.75           C
ATOM   4412  OH  TYR A 562      20.370 -13.303  -5.404  1.00154.10           O
ATOM   4413  N   ILE A 563      13.551 -18.198  -5.052  1.00115.19           N
ATOM   4414  CA  ILE A 563      12.603 -19.209  -4.613  1.00102.76           C
ATOM   4415  C   ILE A 563      13.374 -20.426  -4.150  1.00 96.97           C
ATOM   4416  O   ILE A 563      14.123 -21.030  -4.934  1.00100.90           O
ATOM   4417  CB  ILE A 563      11.679 -19.566  -5.728  1.00 72.84           C
ATOM   4418  CG1 ILE A 563      10.848 -18.512  -6.256  1.00 88.48           C
ATOM   4419  CG2 ILE A 563      10.730 -20.716  -5.215  1.00 71.20           C
ATOM   4420  CD1 ILE A 563       9.900 -18.944  -7.336  1.00 76.54           C
ATOM   4421  N   TYR A 564      13.186 -20.767  -2.878  1.00104.72           N
ATOM   4422  CA  TYR A 564      13.860 -21.882  -2.229  1.00101.86           C
ATOM   4423  C   TYR A 564      12.952 -23.098  -2.246  1.00 99.74           C
ATOM   4424  O   TYR A 564      11.813 -23.033  -1.767  1.00 94.74           O
ATOM   4425  CB  TYR A 564      14.181 -21.489  -0.792  1.00110.25           C
ATOM   4426  CG  TYR A 564      14.811 -22.561   0.078  1.00110.92           C
ATOM   4427  CD1 TYR A 564      16.146 -22.934  -0.071  1.00117.98           C
ATOM   4428  CD2 TYR A 564      14.086 -23.156   1.094  1.00106.27           C
ATOM   4429  CE1 TYR A 564      16.723 -23.859   0.755  1.00118.70           C
ATOM   4430  CE2 TYR A 564      14.653 -24.113   1.920  1.00109.00           C
ATOM   4431  CZ  TYR A 564      15.963 -24.481   1.748  1.00114.30           C
ATOM   4432  OH  TYR A 564      16.484 -25.438   2.584  1.00116.87           O
ATOM   4433  N   MET A 565      13.439 -24.198  -2.819  1.00107.85           N
ATOM   4434  CA  MET A 565      12.628 -25.409  -2.949  1.00107.22           C
ATOM   4435  C   MET A 565      13.403 -26.657  -2.566  1.00111.50           C
ATOM   4436  O   MET A 565      14.018 -27.289  -3.418  1.00117.88           O
ATOM   4437  CB  MET A 565      12.087 -25.534  -4.371  1.00 95.46           C
ATOM   4438  CG  MET A 565      11.151 -24.404  -4.738  1.00 93.44           C
ATOM   4439  SD  MET A 565      10.771 -24.333  -6.488  1.00102.70           S
ATOM   4440  CE  MET A 565      12.192 -25.201  -7.108  1.00111.47           C
ATOM   4441  N   PRO A 566      13.363 -27.010  -1.277  1.00 99.86           N
ATOM   4442  CA  PRO A 566      14.103 -28.041  -0.544  1.00104.24           C
ATOM   4443  C   PRO A 566      13.323 -29.324  -0.461  1.00104.16           C
ATOM   4444  O   PRO A 566      12.102 -29.267  -0.516  1.00 98.96           O
ATOM   4445  CB  PRO A 566      14.149 -27.460   0.841  1.00 77.95           C
ATOM   4446  CG  PRO A 566      12.804 -26.795   0.952  1.00 71.27           C
ATOM   4447  CD  PRO A 566      12.496 -26.234  -0.385  1.00 71.95           C
ATOM   4448  N   TYR A 567      13.990 -30.458  -0.304  1.00 98.25           N
```

Fig. 7BU

```
ATOM  4449  CA   TYR A 567     13.267 -31.709 -0.375  1.00 100.41      C
ATOM  4450  C    TYR A 567     12.312 -31.737  0.773  1.00  93.58      C
ATOM  4451  O    TYR A 567     11.182 -32.161  0.630  1.00  91.98      O
ATOM  4452  CB   TYR A 567     14.210 -32.893 -0.309  1.00  90.82      C
ATOM  4453  CG   TYR A 567     13.563 -34.249 -0.076  1.00  95.35      C
ATOM  4454  CD1  TYR A 567     13.330 -35.127 -1.118  1.00 101.35      C
ATOM  4455  CD2  TYR A 567     13.230 -34.670  1.194  1.00  93.61      C
ATOM  4456  CE1  TYR A 567     12.770 -36.369 -0.897  1.00 106.08      C
ATOM  4457  CE2  TYR A 567     12.669 -35.917  1.426  1.00  96.33      C
ATOM  4458  CZ   TYR A 567     12.446 -36.756  0.373  1.00 106.09      C
ATOM  4459  OH   TYR A 567     11.889 -37.986  0.612  1.00 110.03      O
ATOM  4460  N    ARG A 568     12.756 -31.245  1.911  1.00 125.75      N
ATOM  4461  CA   ARG A 568     11.945 -31.318  3.115  1.00 119.46      C
ATOM  4462  C    ARG A 568     10.492 -30.968  2.940  1.00 113.44      C
ATOM  4463  O    ARG A 568      9.599 -31.442  3.348  1.00 111.42      O
ATOM  4464  CB   ARG A 568     12.596 -30.527  4.236  1.00 126.34      C
ATOM  4465  CG   ARG A 568     11.742 -30.388  5.462  1.00 118.64      C
ATOM  4466  CD   ARG A 568     12.381 -29.360  6.314  1.00 114.15      C
ATOM  4467  NE   ARG A 568     13.805 -29.589  6.252  1.00 119.14      N
ATOM  4468  CZ   ARG A 568     14.479 -30.183  7.219  1.00 116.75      C
ATOM  4469  NH1  ARG A 568     13.835 -30.556  8.317  1.00 107.37      N1+
ATOM  4470  NH2  ARG A 568     15.786 -30.382  7.099  1.00 121.68      N
ATOM  4471  N    MET A 569     10.242 -29.853  2.121  1.00 107.77      N
ATOM  4472  CA   MET A 569      8.884 -29.346  1.973  1.00 102.19      C
ATOM  4473  C    MET A 569      7.937 -30.314  1.287  1.00 104.57      C
ATOM  4474  O    MET A 569      6.806 -29.945  0.999  1.00 102.14      O
ATOM  4475  CB   MET A 569      8.870 -28.034  1.190  1.00 112.08      C
ATOM  4476  CG   MET A 569      7.510 -27.346  1.191  1.00 108.13      C
ATOM  4477  SD   MET A 569      7.365 -25.929  0.092  1.00 109.37      S
ATOM  4478  CE   MET A 569      6.425 -26.602 -1.267  1.00 112.14      C
ATOM  4479  N    LEU A 570      8.373 -31.540  0.996  1.00  94.55      N
ATOM  4480  CA   LEU A 570      7.483 -32.458  0.272  1.00  98.60      C
ATOM  4481  C    LEU A 570      6.331 -32.931  1.133  1.00  96.29      C
ATOM  4482  O    LEU A 570      5.209 -32.897  0.678  1.00  96.25      O
ATOM  4483  CB   LEU A 570      8.225 -33.646 -0.371  1.00  96.95      C
ATOM  4484  CG   LEU A 570      8.419 -33.713 -1.804  1.00 113.60      C
ATOM  4485  CD1  LEU A 570      8.868 -35.076 -2.320  1.00 124.15      C
ATOM  4486  CD2  LEU A 570      7.149 -33.404 -2.686  1.00 112.34      C
ATOM  4487  N    ARG A 571      6.591 -33.346  2.372  1.00 123.35      N
ATOM  4488  CA   ARG A 571      5.525 -33.913  3.210  1.00 122.04      C
ATOM  4489  C    ARG A 571      4.352 -32.949  3.406  1.00 115.43      C
ATOM  4490  O    ARG A 571      3.217 -33.366  3.652  1.00 115.91      O
ATOM  4491  CB   ARG A 571      6.079 -34.406  4.552  1.00 186.11      C
ATOM  4492  CG   ARG A 571      5.630 -33.326  5.426  1.00 182.40      C
ATOM  4493  CD   ARG A 571      7.162 -33.862  6.725  1.00 196.35      C
ATOM  4494  NE   ARG A 571      7.598 -32.784  7.577  1.00 193.68      N
ATOM  4495  CZ   ARG A 571      8.339 -32.916  8.670  1.00 166.31      C
ATOM  4496  NH1  ARG A 571      8.739 -34.120  9.056  1.00 181.79      N1+
ATOM  4497  NH2  ARG A 571      8.684 -31.846  9.377  1.00 183.82      N
ATOM  4498  N    ILE A 572      4.661 -31.667  3.224  1.00  87.55      N
ATOM  4499  CA   ILE A 572      3.777 -30.514  3.421  1.00  81.95      C
ATOM  4500  C    ILE A 572      3.097 -29.977  2.132  1.00  82.68      C
ATOM  4501  O    ILE A 572      2.185 -29.162  2.197  1.00  79.49      O
ATOM  4502  CB   ILE A 572      4.617 -29.372  4.030  1.00  94.19      C
ATOM  4503  CG1  ILE A 572      5.269 -29.830  5.306  1.00  94.14      C
ATOM  4504  CG2  ILE A 572      3.819 -28.141  4.309  1.00  90.22      C
ATOM  4505  CD1  ILE A 572      6.027 -28.704  5.955  1.00  90.32      C
ATOM  4506  N    MET A 573      3.533 -30.421  0.963  1.00 121.94      N
ATOM  4507  CA   MET A 573      2.938 -29.946 -0.281  1.00 123.47      C
ATOM  4508  C    MET A 573      1.392 -29.860 -0.277  1.00 123.14      C
ATOM  4509  O    MET A 573      0.843 -29.869 -0.756  1.00 121.13      O
```

Fig. 7BV

```
ATOM   4510  CB  MET A 573       3.489 -30.740  -1.478  1.00140.07           C
ATOM   4511  CG  MET A 573       4.604 -30.044  -2.228  1.00140.62           C
ATOM   4512  SD  MET A 573       3.990 -28.632  -3.142  1.00149.79           S
ATOM   4513  CE  MET A 573       2.695 -29.442  -4.052  1.00156.42           C
ATOM   4514  N   PRO A 574       0.688 -30.867   0.282  1.00131.84           N
ATOM   4515  CA  PRO A 574      -0.770 -30.754   0.358  1.00132.52           C
ATOM   4516  C   PRO A 574      -1.190 -29.515   1.156  1.00125.62           C
ATOM   4517  O   PRO A 574      -1.890 -28.595   0.670  1.00124.13           O
ATOM   4518  CB  PRO A 574      -1.162 -32.002   1.150  1.00112.90           C
ATOM   4519  CG  PRO A 574      -0.037 -32.929   0.990  1.00126.03           C
ATOM   4520  CD  PRO A 574       1.154 -32.061   0.996  1.00122.94           C
ATOM   4521  N   VAL A 575      -0.744 -29.505   2.409  1.00103.06           N
ATOM   4522  CA  VAL A 575      -1.010 -28.429   3.359  1.00 97.34           C
ATOM   4523  C   VAL A 575      -0.626 -27.047   2.835  1.00 94.45           C
ATOM   4524  O   VAL A 575      -1.344 -26.076   3.047  1.00 92.53           O
ATOM   4525  CB  VAL A 575      -0.293 -28.693   4.666  1.00 66.36           C
ATOM   4526  CG1 VAL A 575      -0.817 -27.801   5.744  1.00 72.66           C
ATOM   4527  CG2 VAL A 575      -0.479 -30.141   5.079  1.00 70.68           C
ATOM   4528  N   VAL A 576       0.506 -26.951   2.157  1.00 82.47           N
ATOM   4529  CA  VAL A 576       0.913 -25.698   1.552  1.00 81.20           C
ATOM   4530  C   VAL A 576       0.003 -25.279   0.401  1.00 83.93           C
ATOM   4531  O   VAL A 576      -0.357 -24.120   0.256  1.00 82.62           O
ATOM   4532  CB  VAL A 576       2.346 -25.821   1.951  1.00 74.58           C
ATOM   4533  CG1 VAL A 576       2.653 -24.692   0.979  1.00 74.96           C
ATOM   4534  CG2 VAL A 576       3.289 -25.806   2.214  1.00 73.01           C
ATOM   4535  N   ALA A 577      -0.354 -26.244  -0.430  1.00112.44           N
ATOM   4536  CA  ALA A 577      -1.189 -25.947  -1.586  1.00116.71           C
ATOM   4537  C   ALA A 577      -2.578 -25.498  -1.194  1.00116.67           C
ATOM   4538  O   ALA A 577      -3.182 -24.681  -1.886  1.00118.20           O
ATOM   4539  CB  ALA A 577      -1.237 -27.135  -2.488  1.00164.91           C
ATOM   4540  N   GLN A 578      -3.097 -26.067  -0.103  1.00131.54           N
ATOM   4541  CA  GLN A 578      -4.468 -25.735   0.316  1.00133.09           C
ATOM   4542  C   GLN A 578      -4.726 -24.237   0.279  1.00131.43           C
ATOM   4543  O   GLN A 578      -5.779 -23.806  -0.165  1.00135.12           O
ATOM   4544  CB  GLN A 578      -4.758 -26.269   1.714  1.00149.23           C
ATOM   4545  CG  GLN A 578      -5.115 -27.728   1.773  1.00161.02           C
ATOM   4546  CD  GLN A 578      -5.237 -28.206   3.197  1.00158.55           C
ATOM   4547  NE2 GLN A 578      -5.517 -29.491   3.378  1.00163.07           N
ATOM   4548  OE1 GLN A 578      -5.075 -27.425   4.129  1.00153.24           O
ATOM   4549  N   PHE A 579      -3.751 -23.449   0.723  1.00109.73           N
ATOM   4550  CA  PHE A 579      -3.928 -22.007   0.899  1.00109.19           C
ATOM   4551  C   PHE A 579      -4.236 -21.244  -0.380  1.00113.68           C
ATOM   4552  O   PHE A 579      -5.057 -20.345  -0.366  1.00116.10           O
ATOM   4553  CB  PHE A 579      -2.707 -21.388   1.573  1.00 88.96           C
ATOM   4554  CG  PHE A 579      -2.612 -21.665   3.023  1.00 85.36           C
ATOM   4555  CD1 PHE A 579      -2.063 -22.860   3.465  1.00 83.63           C
ATOM   4556  CD2 PHE A 579      -3.074 -20.789   3.957  1.00 84.39           C
ATOM   4557  CE1 PHE A 579      -1.990 -23.144   4.793  1.00 81.15           C
ATOM   4558  CE2 PHE A 579      -2.997 -21.071   5.304  1.00 79.37           C
ATOM   4559  CZ  PHE A 579      -2.460 -22.249   5.719  1.00 80.03           C
ATOM   4560  N   ALA A 580      -3.528 -21.571  -1.466  1.00 86.54           N
ATOM   4561  CA  ALA A 580      -3.809 -20.961  -2.758  1.00 92.13           C
ATOM   4562  C   ALA A 580      -5.012 -21.667  -3.365  1.00 97.75           C
ATOM   4563  O   ALA A 580      -5.767 -21.102  -4.161  1.00105.63           O
ATOM   4564  CB  ALA A 580      -2.617 -21.073  -3.670  1.00 87.56           C
ATOM   4565  N   ASN A 581      -5.203 -22.920  -2.990  1.00151.21           N
ATOM   4566  CA  ASN A 581      -6.414 -23.616  -3.398  1.00158.29           C
ATOM   4567  C   ASN A 581      -7.668 -22.891  -2.925  1.00160.11           C
ATOM   4568  O   ASN A 581      -8.742 -23.052  -3.485  1.00167.26           O
ATOM   4569  CB  ASN A 581      -6.420 -25.046  -2.871  1.00123.14           C
ATOM   4570  CG  ASN A 581      -6.997 -26.014  -3.856  1.00131.65           C
```

Fig. 7BW

```
ATOM   4571  ND2 ASN A 581      -7.491 -27.139  -3.361  1.00 137.39           N
ATOM   4572  OD1 ASN A 581      -6.996 -25.761  -6.082  1.00 134.62           O
ATOM   4573  N   THR A 582      -7.822 -22.097  -1.878  1.00 129.76           N
ATOM   4574  CA  THR A 582      -8.650 -21.400  -1.290  1.00 123.14           C
ATOM   4575  C   THR A 582      -8.060 -20.049  -1.933  1.00 127.93           C
ATOM   4576  O   THR A 582      -8.157 -19.082  -1.607  1.00 124.93           O
ATOM   4577  CB  THR A 582      -8.426 -21.172   0.179  1.00 121.51           C
ATOM   4578  CG2 THR A 582      -9.293 -20.047   0.868  1.00 121.57           C
ATOM   4579  OG1 THR A 582      -8.762 -22.364   0.887  1.00 120.32           O
ATOM   4580  N   ASN A 583      -9.841 -19.979  -2.831  1.00 113.37           N
ATOM   4581  CA  ASN A 583     -10.043 -18.793  -3.670  1.00 121.60           C
ATOM   4582  C   ASN A 583     -10.352 -17.505  -2.901  1.00 124.43           C
ATOM   4583  O   ASN A 583     -11.439 -17.356  -2.329  1.00 126.78           O
ATOM   4584  CB  ASN A 583     -11.194 -19.066  -4.737  1.00 179.36           C
ATOM   4585  CG  ASN A 583     -11.952 -17.851  -5.041  1.00 184.07           C
ATOM   4586  ND2 ASN A 583     -11.366 -16.878  -5.728  1.00 184.07           N
ATOM   4587  OD1 ASN A 583     -13.124 -17.785  -4.656  1.00 183.14           O
ATOM   4588  N   PRO A 584      -9.391 -16.567  -2.893  1.00 151.78           N
ATOM   4589  CA  PRO A 584      -9.477 -15.339  -2.103  1.00 149.55           C
ATOM   4590  C   PRO A 584     -10.612 -14.624  -2.241  1.00 153.83           C
ATOM   4591  O   PRO A 584     -11.156 -13.816  -1.389  1.00 149.06           O
ATOM   4592  CB  PRO A 584      -8.351 -14.474  -2.679  1.00 154.56           C
ATOM   4593  CG  PRO A 584      -7.919 -15.154  -3.933  1.00 158.23           C
ATOM   4594  CD  PRO A 584      -8.170 -16.582  -3.708  1.00 150.50           C
ATOM   4595  N   ASP A 585     -11.554 -14.924  -3.297  1.00 137.05           N
ATOM   4596  CA  ASP A 585     -12.824 -14.252  -3.547  1.00 144.32           C
ATOM   4597  C   ASP A 585     -13.949 -14.790  -2.680  1.00 141.98           C
ATOM   4598  O   ASP A 585     -14.882 -14.062  -2.353  1.00 143.39           O
ATOM   4599  CB  ASP A 585     -13.225 -14.398  -5.018  1.00 144.04           C
ATOM   4600  CG  ASP A 585     -12.941 -13.156  -5.834  1.00 149.48           C
ATOM   4601  OD1 ASP A 585     -13.083 -12.038  -5.292  1.00 146.40           O
ATOM   4602  OD2 ASP A 585     -12.579 -13.303  -7.022  1.00 153.81           O1-
ATOM   4603  N   ASN A 586     -13.867 -16.067  -2.317  1.00 156.37           N
ATOM   4604  CA  ASN A 586     -15.017 -16.723  -1.714  1.00 162.86           C
ATOM   4605  C   ASN A 586     -14.789 -17.882  -0.748  1.00 156.09           C
ATOM   4606  O   ASN A 586     -15.677 -18.708  -0.581  1.00 158.58           O
ATOM   4607  CB  ASN A 586     -15.963 -17.180  -2.808  1.00 180.06           C
ATOM   4608  CG  ASN A 586     -17.370 -16.755  -2.536  1.00 191.46           C
ATOM   4609  ND2 ASN A 586     -18.293 -17.174  -3.394  1.00 198.65           N
ATOM   4610  OD1 ASN A 586     -17.632 -16.045  -1.561  1.00 193.73           O
ATOM   4611  N   GLY A 587     -13.625 -17.938  -0.107  1.00 135.35           N
ATOM   4612  CA  GLY A 587     -13.322 -18.998   0.856  1.00 129.15           C
ATOM   4613  C   GLY A 587     -13.290 -20.407   0.298  1.00 127.45           C
ATOM   4614  O   GLY A 587     -12.442 -21.232   0.631  1.00 124.79           O
ATOM   4615  N   GLU A 588     -13.942 -20.685  -0.777  1.00 170.62           N
ATOM   4616  CA  GLU A 588     -14.080 -22.038  -1.318  1.00 171.44           C
ATOM   4617  C   GLU A 588     -12.756 -22.630  -1.776  1.00 163.99           C
ATOM   4618  O   GLU A 588     -11.867 -21.909  -2.221  1.00 160.30           O
ATOM   4619  CB  GLU A 588     -15.104 -22.061  -2.458  1.00 176.22           C
ATOM   4620  CG  GLU A 588     -16.511 -21.598  -2.059  1.00 184.25           C
ATOM   4621  CD  GLU A 588     -17.194 -22.511  -1.028  1.00 190.03           C
ATOM   4622  OE1 GLU A 588     -16.550 -23.468  -0.552  1.00 188.40           O
ATOM   4623  OE2 GLU A 588     -18.381 -22.281  -0.699  1.00 196.34           O1-
ATOM   4624  N   GLN A 589     -12.619 -23.944  -1.642  1.00 129.49           N
ATOM   4625  CA  GLN A 589     -11.433 -24.612  -2.141  1.00 124.47           C
ATOM   4626  C   GLN A 589     -11.640 -24.680  -3.603  1.00 132.89           C
ATOM   4627  O   GLN A 589     -12.628 -25.494  -3.962  1.00 143.72           O
ATOM   4628  CB  GLN A 589     -11.166 -25.916  -1.406  1.00 184.99           C
ATOM   4629  CG  GLN A 589     -10.425 -25.714  -0.116  1.00 175.57           C
ATOM   4630  CD  GLN A 589      -9.617 -26.922   0.285  1.00 172.63           C
ATOM   4631  NE2 GLN A 589     -10.103 -27.649   1.284  1.00 173.36           N
```

Fig. 7BX

```
ATOM   4632  OE1 GLN A 589     -8.660 -27.198  -0.288  1.00170.48           O
ATOM   4633  N   GLU A 590    -10.725 -24.385  -4.425  1.00141.38           N
ATOM   4634  CA  GLU A 590    -10.779 -24.602  -5.863  1.00147.37           C
ATOM   4635  C   GLU A 590    -10.835 -26.104  -6.169  1.00151.32           C
ATOM   4636  O   GLU A 590    -11.921 -26.674  -6.241  1.00161.96           O
ATOM   4637  CB  GLU A 590     -9.583 -23.925  -6.566  1.00201.75           C
ATOM   4638  CG  GLU A 590     -9.645 -22.381  -6.628  1.00201.16           C
ATOM   4639  CD  GLU A 590     -8.397 -21.720  -7.001  1.00193.07           C
ATOM   4640  OE1 GLU A 590     -7.297 -22.434  -7.179  1.00187.17           O
ATOM   4641  OE2 GLU A 590     -8.267 -20.476  -7.111  1.00193.26           O1-
ATOM   4642  N   LYS A 591     -9.673 -26.745  -6.311  1.00165.14           N
ATOM   4643  CA  LYS A 591     -9.593 -28.125  -6.811  1.00159.30           C
ATOM   4644  C   LYS A 591     -9.748 -29.225  -5.759  1.00161.89           C
ATOM   4645  O   LYS A 591    -10.159 -28.971  -4.637  1.00168.59           O
ATOM   4646  CB  LYS A 591     -8.297 -28.327  -7.600  1.00169.00           C
ATOM   4647  CG  LYS A 591     -8.050 -27.248  -8.635  1.00166.92           C
ATOM   4648  CD  LYS A 591     -6.966 -27.644  -9.608  1.00159.38           C
ATOM   4649  CE  LYS A 591     -6.884 -26.653 -10.750  1.00159.27           C
ATOM   4650  NZ  LYS A 591     -6.418 -27.302 -12.002  1.00156.30           N1+
ATOM   4651  N   SER A 592     -9.419 -30.452  -6.140  1.00155.36           N
ATOM   4652  CA  SER A 592     -9.621 -31.607  -5.271  1.00158.00           C
ATOM   4653  C   SER A 592     -8.450 -31.637  -4.329  1.00147.43           C
ATOM   4654  O   SER A 592     -8.642 -32.089  -3.141  1.00147.44           O
ATOM   4655  CB  SER A 592     -9.860 -32.872  -6.101  1.00162.97           C
ATOM   4656  OG  SER A 592     -8.800 -33.122  -7.016  1.00139.85           O
ATOM   4657  N   LEU A 593     -7.240 -31.763  -4.879  1.00164.73           N
ATOM   4658  CA  LEU A 593     -6.001 -32.014  -4.138  1.00151.58           C
ATOM   4659  C   LEU A 593     -5.880 -33.425  -3.552  1.00151.38           C
ATOM   4660  O   LEU A 593     -6.288 -33.689  -2.417  1.00154.36           O
ATOM   4661  CB  LEU A 593     -5.767 -30.941  -3.069  1.00136.25           C
ATOM   4662  CG  LEU A 593     -5.117 -29.673  -3.620  1.00129.32           C
ATOM   4663  CD1 LEU A 593     -3.925 -29.301  -2.775  1.00118.27           C
ATOM   4664  CD2 LEU A 593     -4.703 -29.884  -5.078  1.00129.97           C
ATOM   4665  N   PHE A 594     -5.315 -34.323  -4.353  1.00144.79           N
ATOM   4666  CA  PHE A 594     -4.996 -35.671  -3.924  1.00143.85           C
ATOM   4667  C   PHE A 594     -3.496 -35.751  -3.983  1.00126.84           C
ATOM   4668  O   PHE A 594     -2.926 -35.576  -5.044  1.00124.04           O
ATOM   4669  CB  PHE A 594     -5.593 -36.691  -4.891  1.00169.24           C
ATOM   4670  CG  PHE A 594     -5.437 -38.121  -4.446  1.00157.89           C
ATOM   4671  CD1 PHE A 594     -6.317 -39.095  -4.886  1.00172.89           C
ATOM   4672  CD2 PHE A 594     -4.419 -38.493  -3.589  1.00145.21           C
ATOM   4673  CE1 PHE A 594     -6.183 -40.412  -4.475  1.00175.18           C
ATOM   4674  CE2 PHE A 594     -4.278 -39.808  -3.176  1.00147.28           C
ATOM   4675  CZ  PHE A 594     -5.160 -40.765  -3.618  1.00162.28           C
ATOM   4676  N   PHE A 595     -2.857 -36.006  -2.847  1.00159.56           N
ATOM   4677  CA  PHE A 595     -1.399 -36.059  -2.774  1.00145.80           C
ATOM   4678  C   PHE A 595     -0.953 -36.962  -1.636  1.00143.75           C
ATOM   4679  O   PHE A 595     -1.658 -37.085  -0.649  1.00148.22           O
ATOM   4680  CB  PHE A 595     -0.837 -34.663  -2.538  1.00149.56           C
ATOM   4681  CG  PHE A 595      0.633 -34.645  -2.268  1.00135.61           C
ATOM   4682  CD1 PHE A 595      1.499 -34.025  -3.142  1.00129.01           C
ATOM   4683  CD2 PHE A 595      1.147 -35.247  -1.142  1.00129.18           C
ATOM   4684  CE1 PHE A 595      2.843 -34.013  -2.998  1.00117.74           C
ATOM   4685  CE2 PHE A 595      2.483 -35.248  -0.900  1.00117.84           C
ATOM   4686  CZ  PHE A 595      3.337 -34.627  -1.778  1.00112.24           C
ATOM   4687  N   SER A 596      0.213 -37.594  -1.754  1.00148.06           N
ATOM   4688  CA  SER A 596      0.730 -38.361  -0.618  1.00144.60           C
ATOM   4689  C   SER A 596      2.119 -38.930  -0.815  1.00136.68           C
ATOM   4690  O   SER A 596      2.371 -39.606  -1.800  1.00138.80           O
ATOM   4691  CB  SER A 596     -0.205 -39.513  -0.292  1.00148.72           C
ATOM   4692  OG  SER A 596      0.511 -40.727  -0.317  1.00149.04           O
```

Fig. 7BY

```
ATOM   4693  N    GLN A 597       3.010 -38.687   0.143  1.00 145.42           N
ATOM   4694  CA   GLN A 597       4.360 -39.251   0.103  1.00 138.69           C
ATOM   4695  C    GLN A 597       4.560 -40.332   1.150  1.00 141.00           C
ATOM   4696  O    GLN A 597       4.321 -40.112   2.328  1.00 139.53           O
ATOM   4697  CB   GLN A 597       5.423 -38.170   0.302  1.00 195.95           C
ATOM   4698  CG   GLN A 597       6.827 -38.735   0.440  1.00 176.37           C
ATOM   4699  CD   GLN A 597       7.866 -37.676   0.725  1.00 165.77           C
ATOM   4700  NE2  GLN A 597       9.010 -38.098   1.240  1.00 160.30           N
ATOM   4701  OE1  GLN A 597       7.643 -36.493   0.492  1.00 164.47           O
ATOM   4702  N    ALA A 598       3.924 -41.497   0.721  1.00 144.43           N
ATOM   4703  CA   ALA A 598       5.174 -42.602   1.658  1.00 140.60           C
ATOM   4704  C    ALA A 598       6.256 -43.562   1.201  1.00 137.19           C
ATOM   4705  O    ALA A 598       6.820 -43.408   0.120  1.00 138.39           O
ATOM   4706  CB   ALA A 598       3.850 -43.329   1.860  1.00 162.09           C
ATOM   4707  N    ASN A 599       6.562 -44.552   2.033  1.00 184.69           N
ATOM   4708  CA   ASN A 599       7.613 -45.502   1.728  1.00 181.92           C
ATOM   4709  C    ASN A 599       7.110 -46.922   1.475  1.00 191.73           C
ATOM   4710  O    ASN A 599       5.943 -47.249   1.706  1.00 201.32           O
ATOM   4711  CB   ASN A 599       8.873 -45.610   2.840  1.00 181.33           C
ATOM   4712  CG   ASN A 599       9.580 -44.282   2.803  1.00 173.31           C
ATOM   4713  ND2  ASN A 599      10.354 -44.230   3.719  1.00 145.42           N
ATOM   4714  OD1  ASN A 599       9.401 -43.394   1.973  1.00 161.36           O
ATOM   4715  N    ALA A 600       8.016 -47.766   1.004  1.00 137.57           N
ATOM   4716  CA   ALA A 600       7.877 -49.133   0.665  1.00 136.50           C
ATOM   4717  C    ALA A 600       7.899 -50.062   1.846  1.00 136.24           C
ATOM   4718  O    ALA A 600       8.850 -49.888   2.597  1.00 135.95           O
ATOM   4719  CB   ALA A 600       8.523 -49.574  -0.503  1.00 139.82           C
ATOM   4720  N    ILE A 601       7.054 -51.075   2.002  1.00 194.09           N
ATOM   4721  CA   ILE A 601       7.250 -52.043   3.093  1.00 193.17           C
ATOM   4722  C    ILE A 601       7.341 -53.507   2.628  1.00 194.41           C
ATOM   4723  O    ILE A 601       8.037 -54.318   3.247  1.00 195.01           O
ATOM   4724  CB   ILE A 601       6.140 -51.923   4.118  1.00 146.35           C
ATOM   4725  CG1  ILE A 601       6.108 -50.513   4.668  1.00 124.13           C
ATOM   4726  CG2  ILE A 601       6.355 -52.910   5.237  1.00 132.67           C
ATOM   4727  CD1  ILE A 601       5.050 -50.306   5.710  1.00 140.90           C
ATOM   4728  N    ALA A 602       6.640 -53.836   1.547  1.00 283.43           N
ATOM   4729  CA   ALA A 602       6.540 -55.220   1.093  1.00 284.68           C
ATOM   4730  C    ALA A 602       6.403 -55.336  -0.427  1.00 268.43           C
ATOM   4731  O    ALA A 602       5.882 -54.437  -1.082  1.00 288.63           O
ATOM   4732  CB   ALA A 602       5.372 -55.905   1.781  1.00 143.30           C
ATOM   4733  N    GLN A 603       6.875 -56.458  -0.979  1.00 185.73           N
ATOM   4734  CA   GLN A 603       6.719 -56.730  -2.407  1.00 190.10           C
ATOM   4735  C    GLN A 603       6.704 -58.237  -2.671  1.00 193.01           C
ATOM   4736  O    GLN A 603       7.397 -58.994  -1.994  1.00 193.75           O
ATOM   4737  CB   GLN A 603       7.826 -56.053  -3.236  1.00 184.09           C
ATOM   4738  CG   GLN A 603       7.587 -56.061  -4.756  1.00 185.61           C
ATOM   4739  CD   GLN A 603       8.658 -55.399  -5.542  1.00 174.88           C
ATOM   4740  NE2  GLN A 603       8.881 -55.706  -6.790  1.00 173.51           N
ATOM   4741  OE1  GLN A 603       9.276 -54.362  -5.030  1.00 168.15           O
ATOM   4742  N    ASP A 604       5.906 -58.663  -3.650  1.00 384.25           N
ATOM   4743  CA   ASP A 604       5.820 -60.076  -4.029  1.00 386.59           C
ATOM   4744  C    ASP A 604       6.552 -60.349  -5.339  1.00 394.96           C
ATOM   4745  O    ASP A 604       6.064 -60.000  -6.413  1.00 396.22           O
ATOM   4746  CB   ASP A 604       4.360 -60.521  -4.154  1.00 221.56           C
ATOM   4747  CG   ASP A 604       3.669 -60.682  -2.826  1.00 216.72           C
ATOM   4748  OD1  ASP A 604       4.242 -61.336  -1.930  1.00 214.72           O
ATOM   4749  OD2  ASP A 604       2.550 -60.149  -2.673  1.00 216.32           O1-
TER    4750       ASP A 604
ATOM   4751  N    GLY A 608       3.241 -56.570  -7.745  1.00 165.09           N
ATOM   4752  CA   GLY A 608       4.087 -57.456  -7.351  1.00 162.87           C
ATOM   4753  C    GLY A 608       3.376 -58.444  -6.473  1.00 152.22           C
```

Fig. 7BZ

```
ATOM   4754  O    GLY A 608       3.493 -55.240  -6.688  1.00148.65           O
ATOM   4755  N    SER A 609       2.649 -56.945  -5.476  1.00270.65           N
ATOM   4756  CA   SER A 609       1.831 -56.116  -4.590  1.00259.93           C
ATOM   4757  C    SER A 609       2.689 -55.366  -3.558  1.00257.95           C
ATOM   4758  O    SER A 609       3.264 -55.983  -2.662  1.00257.44           O
ATOM   4759  CB   SER A 609       0.787 -56.992  -3.881  1.00173.55           C
ATOM   4760  OG   SER A 609      -0.497 -56.384  -3.860  1.00145.66           O
ATOM   4761  N    VAL A 610       2.771 -54.040  -3.684  1.00214.83           N
ATOM   4762  CA   VAL A 610       3.685 -53.239  -2.763  1.00212.97           C
ATOM   4763  C    VAL A 610       2.766 -52.451  -1.755  1.00203.48           C
ATOM   4764  O    VAL A 610       1.942 -51.631  -2.127  1.00200.67           O
ATOM   4765  CB   VAL A 610       4.450 -52.219  -3.508  1.00100.51           C
ATOM   4766  CG1  VAL A 610       5.249 -51.401  -2.504  1.00 98.66           C
ATOM   4767  CG2  VAL A 610       5.367 -52.913  -4.492  1.00105.56           C
ATOM   4768  N    MET A 611       3.018 -52.670  -0.473  1.00163.92           N
ATOM   4769  CA   MET A 611       2.251 -51.967   0.550  1.00155.09           C
ATOM   4770  C    MET A 611       2.857 -50.600   0.906  1.00154.07           C
ATOM   4771  O    MET A 611       4.072 -50.461   1.038  1.00156.55           O
ATOM   4772  CB   MET A 611       2.119 -52.830   1.808  1.00214.63           C
ATOM   4773  CG   MET A 611       1.189 -52.241   2.851  1.00206.81           C
ATOM   4774  SD   MET A 611      -0.538 -52.494   2.418  1.00182.22           S
ATOM   4775  CE   MET A 611      -0.698 -54.256   2.734  1.00182.21           C
ATOM   4776  N    LEU A 612       2.007 -49.589   1.064  1.00246.97           N
ATOM   4777  CA   LEU A 612       2.478 -48.271   1.469  1.00242.99           C
ATOM   4778  C    LEU A 612       1.845 -47.861   2.799  1.00237.42           C
ATOM   4779  O    LEU A 612       0.662 -48.091   3.029  1.00235.94           O
ATOM   4780  CB   LEU A 612       2.190 -47.224   0.385  1.00114.42           C
ATOM   4781  CG   LEU A 612       2.949 -47.366  -0.938  1.00113.86           C
ATOM   4782  CD1  LEU A 612       2.867 -46.076  -1.744  1.00100.74           C
ATOM   4783  CD2  LEU A 612       4.360 -47.794  -0.640  1.00117.00           C
ATOM   4784  N    ASP A 613       2.659 -47.285   3.679  1.00175.92           N
ATOM   4785  CA   ASP A 613       2.227 -46.802   4.997  1.00171.14           C
ATOM   4786  C    ASP A 613       0.757 -46.475   5.079  1.00169.03           C
ATOM   4787  O    ASP A 613      -0.002 -47.053   5.853  1.00169.10           O
ATOM   4788  CB   ASP A 613       2.992 -45.531   5.365  1.00184.44           C
ATOM   4789  CG   ASP A 613       4.477 -45.666   5.125  1.00168.76           C
ATOM   4790  OD1  ASP A 613       4.947 -46.823   5.136  1.00173.64           O
ATOM   4791  OD2  ASP A 613       5.166 -44.633   4.954  1.00168.36           O1-
ATOM   4792  N    ASN A 614       0.353 -45.511   4.275  1.00228.55           N
ATOM   4793  CA   ASN A 614      -1.024 -44.986   4.304  1.00227.78           C
ATOM   4794  C    ASN A 614      -2.136 -45.939   3.901  1.00228.84           C
ATOM   4795  O    ASN A 614      -3.259 -45.466   3.689  1.00228.41           O
ATOM   4796  CB   ASN A 614      -1.077 -43.683   3.481  1.00154.62           C
ATOM   4797  CG   ASN A 614      -0.179 -43.759   2.268  1.00157.63           C
ATOM   4798  ND2  ASN A 614      -0.116 -42.680   1.512  1.00152.71           N
ATOM   4799  OD1  ASN A 614       0.464 -44.809   2.016  1.00160.44           O
ATOM   4800  N    GLY A 615      -1.771 -47.190   3.647  1.00183.87           N
ATOM   4801  CA   GLY A 615      -2.727 -48.241   3.351  1.00183.26           C
ATOM   4802  C    GLY A 615      -3.014 -48.370   1.873  1.00187.85           C
ATOM   4803  O    GLY A 615      -3.983 -49.006   1.453  1.00189.71           O
ATOM   4804  N    VAL A 616      -2.152 -47.741   1.085  1.00127.19           N
ATOM   4805  CA   VAL A 616      -2.284 -47.683  -0.360  1.00131.58           C
ATOM   4806  C    VAL A 616      -1.388 -48.746  -0.307  1.00136.14           C
ATOM   4807  O    VAL A 616      -0.254 -48.855  -0.475  1.00135.54           O
ATOM   4808  CB   VAL A 616      -1.691 -46.378  -0.916  1.00 97.97           C
ATOM   4809  CG1  VAL A 616      -2.259 -46.066  -2.283  1.00 99.81           C
ATOM   4810  CG2  VAL A 616      -1.966 -45.260   0.025  1.00 94.37           C
ATOM   4811  N    GLU A 617      -1.869 -49.530  -1.860  1.00158.77           N
ATOM   4812  CA   GLU A 617      -0.958 -50.469  -2.488  1.00164.61           C
ATOM   4813  C    GLU A 617      -0.657 -50.133  -3.939  1.00167.44           C
ATOM   4814  O    GLU A 617      -1.391 -49.403  -4.599  1.00164.89           O
```

Fig. 7CA

```
ATOM   4815  CB  GLU A 617      -1.524 -51.873  -2.384  1.00 231.02           C
ATOM   4816  CG  GLU A 617      -1.926 -52.397  -1.016  1.00 291.15           C
ATOM   4817  CD  GLU A 617      -2.489 -53.700  -1.005  1.00 261.47           C
ATOM   4818  OE1 GLU A 617      -2.224 -54.476  -1.951  1.00 207.31           O
ATOM   4819  OE2 GLU A 617      -3.212 -54.019  -0.041  1.00 196.65           O1-
ATOM   4820  N   ILE A 618       0.439 -50.697  -4.422  1.00 169.37           N
ATOM   4821  CA  ILE A 618       0.795 -50.640  -5.827  1.00 170.41           C
ATOM   4822  C   ILE A 618       0.615 -52.046  -6.392  1.00 178.26           C
ATOM   4823  O   ILE A 618       1.313 -52.969  -5.951  1.00 183.81           O
ATOM   4824  CB  ILE A 618       2.264 -50.222  -5.990  1.00 161.06           C
ATOM   4825  CG1 ILE A 618       2.587 -49.055  -5.053  1.00 128.62           C
ATOM   4826  CG2 ILE A 618       2.577 -49.813  -7.429  1.00 133.12           C
ATOM   4827  CD1 ILE A 618       3.734 -48.189  -5.537  1.00 145.45           C
ATOM   4828  N   ILE A 619      -0.303 -52.218  -7.332  1.00 176.71           N
ATOM   4829  CA  ILE A 619      -0.528 -53.535  -7.914  1.00 184.12           C
ATOM   4830  C   ILE A 619      -0.459 -53.564  -9.447  1.00 168.01           C
ATOM   4831  O   ILE A 619      -0.205 -52.541 -10.094  1.00 187.20           O
ATOM   4832  CB  ILE A 619      -1.838 -54.184  -7.392  1.00 183.52           C
ATOM   4833  CG1 ILE A 619      -3.056 -53.442  -7.920  1.00 146.66           C
ATOM   4834  CG2 ILE A 619      -1.849 -54.221  -5.870  1.00 158.66           C
ATOM   4835  CD1 ILE A 619      -4.299 -54.310  -7.963  1.00 146.13           C
ATOM   4836  N   ASN A 620      -0.716 -54.749 -10.006  1.00 194.74           N
ATOM   4837  CA  ASN A 620      -0.353 -55.099 -11.393  1.00 202.02           C
ATOM   4838  C   ASN A 620       0.706 -54.215 -12.044  1.00 201.62           C
ATOM   4839  O   ASN A 620       0.374 -53.290 -12.769  1.00 199.78           O
ATOM   4840  CB  ASN A 620      -1.586 -55.322 -12.309  1.00 221.47           C
ATOM   4841  CG  ASN A 620      -2.643 -54.238 -12.194  1.00 214.77           C
ATOM   4842  ND2 ASN A 620      -3.885 -54.560 -12.528  1.00 188.66           N
ATOM   4843  OD1 ASN A 620      -2.348 -53.103 -11.796  1.00 208.42           O
ATOM   4844  N   ASP A 621       1.973 -54.537 -11.790  1.00 218.75           N
ATOM   4845  CA  ASP A 621       3.117 -53.859 -12.408  1.00 216.23           C
ATOM   4846  C   ASP A 621       2.377 -52.349 -12.457  1.00 207.85           C
ATOM   4847  O   ASP A 621       2.881 -51.778 -13.543  1.00 209.08           O
ATOM   4848  CB  ASP A 621       3.337 -54.359 -13.857  1.00 211.45           C
ATOM   4849  CG  ASP A 621       3.337 -55.865 -13.932  1.00 219.79           C
ATOM   4850  OD1 ASP A 621       3.738 -56.526 -12.953  1.00 223.06           O
ATOM   4851  OD2 ASP A 621       2.923 -56.389 -14.983  1.00 224.30           O1-
ATOM   4852  N   PHE A 622       2.990 -51.704 -11.293  1.00 155.04           N
ATOM   4853  CA  PHE A 622       2.984 -50.243 -11.205  1.00 148.20           C
ATOM   4854  C   PHE A 622       1.937 -49.586 -12.174  1.00 159.82           C
ATOM   4855  O   PHE A 622       2.274 -48.664 -12.921  1.00 156.78           O
ATOM   4856  CB  PHE A 622       4.364 -49.649 -11.382  1.00 221.75           C
ATOM   4857  CG  PHE A 622       4.905 -49.757 -12.791  1.00 225.97           C
ATOM   4858  CD1 PHE A 622       4.703 -48.732 -13.708  1.00 224.71           C
ATOM   4859  CD2 PHE A 622       5.621 -50.876 -13.198  1.00 233.16           C
ATOM   4860  CE1 PHE A 622       5.191 -48.824 -15.006  1.00 231.61           C
ATOM   4861  CE2 PHE A 622       6.116 -50.974 -14.496  1.00 238.44           C
ATOM   4862  CZ  PHE A 622       5.901 -49.945 -15.398  1.00 238.13           C
ATOM   4863  N   ARG A 623       0.689 -50.055 -12.150  1.00 118.77           N
ATOM   4864  CA  ARG A 623      -0.359 -49.452 -12.972  1.00 122.75           C
ATOM   4865  C   ARG A 623      -1.532 -48.927 -12.145  1.00 119.03           C
ATOM   4866  O   ARG A 623      -2.185 -47.956 -12.528  1.00 120.17           O
ATOM   4867  CB  ARG A 623      -0.877 -50.441 -14.023  1.00 155.06           C
ATOM   4868  CG  ARG A 623      -0.198 -50.343 -15.383  1.00 191.48           C
ATOM   4869  CD  ARG A 623      -0.866 -51.250 -16.413  1.00 202.57           C
ATOM   4870  NE  ARG A 623      -0.154 -51.230 -17.685  1.00 211.12           N
ATOM   4871  CZ  ARG A 623      -0.383 -52.075 -18.683  1.00 221.67           C
ATOM   4872  NH1 ARG A 623      -1.310 -53.014 -18.556  1.00 224.25           N1+
ATOM   4873  NH2 ARG A 623       0.317 -51.985 -19.805  1.00 230.63           N
ATOM   4874  N   ALA A 624      -1.806 -49.566 -11.017  1.00 167.10           N
ATOM   4875  CA  ALA A 624      -2.897 -49.220 -10.255  1.00 161.76           C
```

Fig. 7CB

```
ATOM  4876  C    ALA A 624    -2.765 -49.300  -6.754  1.00 138.77           C
ATOM  4877  O    ALA A 624    -2.060 -50.175  -6.269  1.00 139.27           O
ATOM  4878  CB   ALA A 624    -4.158 -50.119 -10.657  1.00 147.66           C
ATOM  4879  N    LEU A 625    -3.416 -48.397  -8.026  1.00 159.43           N
ATOM  4880  CA   LEU A 625    -3.256 -48.305  -6.580  1.00 156.54           C
ATOM  4881  C    LEU A 625    -4.483 -48.824  -5.830  1.00 157.52           C
ATOM  4882  O    LEU A 625    -5.604 -48.521  -6.220  1.00 156.36           O
ATOM  4883  CB   LEU A 625    -3.031 -46.847  -6.198  1.00 119.24           C
ATOM  4884  CG   LEU A 625    -2.270 -45.971  -7.192  1.00 116.58           C
ATOM  4885  CD1  LEU A 625    -1.918 -44.643  -6.544  1.00 109.09           C
ATOM  4886  CD2  LEU A 625    -1.019 -46.672  -7.677  1.00 118.80           C
ATOM  4887  N    LYS A 626    -4.279 -49.602  -4.764  1.00 171.72           N
ATOM  4888  CA   LYS A 626    -5.374 -50.004  -3.872  1.00 169.48           C
ATOM  4889  C    LYS A 626    -5.443 -49.037  -2.694  1.00 164.48           C
ATOM  4890  O    LYS A 626    -4.745 -49.312  -1.679  1.00 163.20           O
ATOM  4891  CB   LYS A 626    -5.208 -51.445  -3.377  1.00 163.97           C
ATOM  4892  CG   LYS A 626    -6.512 -52.112  -2.909  1.00 164.09           C
ATOM  4893  CD   LYS A 626    -6.335 -53.624  -2.818  1.00 166.07           C
ATOM  4894  CE   LYS A 626    -7.654 -54.382  -2.801  1.00 167.03           C
ATOM  4895  NZ   LYS A 626    -7.428 -55.846  -3.026  1.00 169.04           N1+
ATOM  4896  N    VAL A 627    -6.302 -48.024  -2.862  1.00 169.44           N
ATOM  4897  CA   VAL A 627    -6.453 -46.889  -1.948  1.00 165.38           C
ATOM  4898  C    VAL A 627    -7.716 -47.036  -1.087  1.00 161.87           C
ATOM  4899  O    VAL A 627    -8.716 -46.335  -1.295  1.00 156.07           O
ATOM  4900  CB   VAL A 627    -6.547 -45.553  -2.744  1.00 108.23           C
ATOM  4901  CG1  VAL A 627    -6.528 -44.348  -1.828  1.00 105.28           C
ATOM  4902  CG2  VAL A 627    -5.442 -45.434  -3.784  1.00 110.67           C
ATOM  4903  N    GLU A 628    -7.665 -47.960  -0.129  1.00 232.33           N
ATOM  4904  CA   GLU A 628    -8.804 -48.260   0.747  1.00 221.16           C
ATOM  4905  C    GLU A 628    -9.857 -49.182   0.108  1.00 223.09           C
ATOM  4906  O    GLU A 628   -11.059 -49.034   0.348  1.00 220.06           O
ATOM  4907  CB   GLU A 628    -9.454 -46.975   1.271  1.00 226.13           C
ATOM  4908  CG   GLU A 628   -10.361 -47.203   2.453  1.00 227.34           C
ATOM  4909  CD   GLU A 628   -10.836 -45.911   3.025  1.00 224.90           C
ATOM  4910  OE1  GLU A 628   -10.524 -44.825   2.561  1.00 231.08           O
ATOM  4911  OE2  GLU A 628   -11.786 -45.936   3.836  1.00 226.55           O1-
ATOM  4912  N    GLY A 629    -9.386 -50.148  -0.678  1.00 224.76           N
ATOM  4913  CA   GLY A 629   -10.234 -51.093  -1.358  1.00 227.85           C
ATOM  4914  C    GLY A 629   -10.439 -50.714  -2.813  1.00 228.83           C
ATOM  4915  O    GLY A 629   -10.730 -51.564  -3.655  1.00 234.14           O
ATOM  4916  N    ALA A 630   -10.254 -49.429  -3.100  1.00 226.01           N
ATOM  4917  CA   ALA A 630   -10.447 -48.874  -4.435  1.00 230.23           C
ATOM  4918  C    ALA A 630    -9.217 -49.054  -5.310  1.00 232.39           C
ATOM  4919  O    ALA A 630    -8.152 -48.535  -4.991  1.00 229.89           O
ATOM  4920  CB   ALA A 630   -10.775 -47.397  -4.331  1.00  94.97           C
ATOM  4921  N    SER A 631    -9.360 -49.776  -6.418  1.00 166.32           N
ATOM  4922  CA   SER A 631    -8.279 -49.863  -7.392  1.00 170.05           C
ATOM  4923  C    SER A 631    -8.342 -48.623  -8.275  1.00 167.36           C
ATOM  4924  O    SER A 631    -9.423 -48.154  -8.618  1.00 167.59           O
ATOM  4925  CB   SER A 631    -8.370 -51.142  -8.229  1.00 191.13           C
ATOM  4926  OG   SER A 631    -9.349 -51.034  -9.244  1.00 157.11           O
ATOM  4927  N    ILE A 632    -7.178 -48.077  -8.614  1.00 150.60           N
ATOM  4928  CA   ILE A 632    -7.116 -46.866  -9.425  1.00 151.03           C
ATOM  4929  C    ILE A 632    -6.050 -46.899 -10.501  1.00 156.40           C
ATOM  4930  O    ILE A 632    -4.920 -47.332 -10.267  1.00 155.89           O
ATOM  4931  CB   ILE A 632    -6.871 -45.630  -8.573  1.00 118.21           C
ATOM  4932  CG1  ILE A 632    -7.937 -45.518  -7.498  1.00 114.04           C
ATOM  4933  CG2  ILE A 632    -6.870 -44.375  -9.432  1.00 122.14           C
ATOM  4934  CD1  ILE A 632    -7.720 -44.338  -6.630  1.00  72.28           C
ATOM  4935  N    PRO A 633    -6.423 -46.421 -11.688  1.00 139.21           N
ATOM  4936  CA   PRO A 633    -5.575 -46.304 -12.871  1.00 147.80           C
```

Fig. 7CC

```
ATOM   4937  C   PRO A 633      -4.567 -45.177 -12.718  1.00145.31           C
ATOM   4938  O   PRO A 633      -4.993 -44.067 -12.352  1.00142.28           O
ATOM   4939  CB  PRO A 633      -6.576 -45.938 -13.968  1.00187.01           C
ATOM   4940  CG  PRO A 633      -7.691 -45.255 -13.239  1.00145.85           C
ATOM   4941  CD  PRO A 633      -7.807 -45.994 -11.957  1.00134.71           C
ATOM   4942  N   LEU A 634      -3.297 -45.459 -12.998  1.00 96.24           N
ATOM   4943  CA  LEU A 634      -2.270 -44.433 -12.950  1.00 91.20           C
ATOM   4944  C   LEU A 634      -2.165 -43.750 -14.269  1.00101.66           C
ATOM   4945  O   LEU A 634      -1.825 -44.379 -15.271  1.00109.10           O
ATOM   4946  CB  LEU A 634      -0.920 -45.030 -12.579  1.00152.45           C
ATOM   4947  CG  LEU A 634      -0.860 -45.534 -11.137  1.00168.38           C
ATOM   4948  CD1 LEU A 634       0.561 -45.795 -10.751  1.00104.80           C
ATOM   4949  CD2 LEU A 634      -1.445 -44.484 -10.214  1.00101.33           C
ATOM   4950  N   LYS A 635      -2.450 -42.456 -14.334  1.00127.43           N
ATOM   4951  CA  LYS A 635      -2.304 -41.714 -15.571  1.00129.74           C
ATOM   4952  C   LYS A 635      -0.910 -41.915 -16.085  1.00131.25           C
ATOM   4953  O   LYS A 635      -0.645 -41.708 -17.258  1.00134.57           O
ATOM   4954  CB  LYS A 635      -2.528 -40.221 -15.361  1.00149.32           C
ATOM   4955  CG  LYS A 635      -2.192 -39.407 -16.598  1.00152.01           C
ATOM   4956  CD  LYS A 635      -2.442 -37.932 -16.408  1.00120.85           C
ATOM   4957  CE  LYS A 635      -2.777 -37.259 -17.730  1.00124.35           C
ATOM   4958  NZ  LYS A 635      -4.254 -37.203 -17.975  1.00126.57           N1+
ATOM   4959  N   ALA A 636      -0.012 -43.303 -15.193  1.00136.60           N
ATOM   4960  CA  ALA A 636       1.364 -42.563 -15.566  1.00137.84           C
ATOM   4961  C   ALA A 636       2.117 -42.944 -14.332  1.00134.72           C
ATOM   4962  O   ALA A 636       1.549 -42.967 -13.251  1.00131.62           O
ATOM   4963  CB  ALA A 636       1.998 -41.344 -16.190  1.00127.24           C
ATOM   4964  N   PHE A 637       3.397 -43.232 -14.519  1.00123.29           N
ATOM   4965  CA  PHE A 637       4.323 -43.504 -13.438  1.00120.31           C
ATOM   4966  C   PHE A 637       5.613 -42.850 -13.836  1.00120.93           C
ATOM   4967  O   PHE A 637       6.184 -43.199 -14.860  1.00124.46           O
ATOM   4968  CB  PHE A 637       4.566 -44.936 -13.279  1.00168.46           C
ATOM   4969  CG  PHE A 637       5.767 -45.332 -12.434  1.00137.26           C
ATOM   4970  CD1 PHE A 637       5.619 -45.916 -11.195  1.00163.80           C
ATOM   4971  CD2 PHE A 637       7.049 -45.074 -12.887  1.00139.00           C
ATOM   4972  CE1 PHE A 637       6.721 -46.231 -10.433  1.00132.92           C
ATOM   4973  CE2 PHE A 637       8.151 -45.383 -12.123  1.00137.71           C
ATOM   4974  CZ  PHE A 637       7.985 -45.960 -10.899  1.00134.65           C
ATOM   4975  N   VAL A 638       6.072 -41.903 -13.034  1.00129.92           N
ATOM   4976  CA  VAL A 638       7.342 -41.242 -13.286  1.00130.49           C
ATOM   4977  C   VAL A 638       8.421 -41.619 -12.379  1.00129.63           C
ATOM   4978  O   VAL A 638       8.193 -42.060 -11.199  1.00125.62           O
ATOM   4979  CB  VAL A 638       7.215 -39.728 -13.112  1.00102.94           C
ATOM   4980  CG1 VAL A 638       8.571 -39.055 -13.160  1.00104.57           C
ATOM   4981  CG2 VAL A 638       6.293 -39.167 -14.174  1.00104.69           C
ATOM   4982  N   ASP A 639       9.593 -42.050 -12.950  1.00132.95           N
ATOM   4983  CA  ASP A 639      10.676 -42.743 -12.278  1.00132.14           C
ATOM   4984  C   ASP A 639      11.859 -41.795 -12.282  1.00132.32           C
ATOM   4985  O   ASP A 639      12.569 -41.718 -13.275  1.00135.30           O
ATOM   4986  CB  ASP A 639      10.999 -44.011 -13.076  1.00166.50           C
ATOM   4987  CG  ASP A 639      11.989 -44.916 -12.384  1.00166.29           C
ATOM   4988  OD1 ASP A 639      13.119 -44.479 -12.104  1.00139.40           O
ATOM   4989  OD2 ASP A 639      11.643 -46.083 -12.133  1.00139.45           O1-
ATOM   4990  N   ILE A 640      12.063 -41.051 -11.200  1.00144.57           N
ATOM   4991  CA  ILE A 640      13.122 -40.039 -11.191  1.00145.37           C
ATOM   4992  C   ILE A 640      14.428 -40.544 -10.585  1.00144.68           C
ATOM   4993  O   ILE A 640      14.465 -40.379  -9.435  1.00141.93           O
ATOM   4994  CB  ILE A 640      12.682 -38.743 -10.500  1.00123.47           C
ATOM   4995  CG1 ILE A 640      11.372 -38.260 -11.110  1.00124.12           C
ATOM   4996  CG2 ILE A 640      13.775 -37.666 -10.611  1.00125.82           C
ATOM   4997  CD1 ILE A 640      10.918 -36.966 -10.363  1.00124.34           C
```

Fig. 7CD

```
ATOM   4998  N    GLU A 641      15.496 -40.471 -11.371  1.00142.75           N
ATOM   4999  CA   GLU A 641      16.762 -41.068 -10.985  1.00142.58           C
ATOM   5000  C    GLU A 641      17.845 -40.026 -10.720  1.00143.61           C
ATOM   5001  O    GLU A 641      18.848 -40.329 -10.082  1.00143.28           O
ATOM   5002  CB   GLU A 641      17.216 -42.082 -12.039  1.00235.36           C
ATOM   5003  CG   GLU A 641      18.225 -43.065 -11.536  1.00235.24           C
ATOM   5004  CD   GLU A 641      18.307 -44.315 -12.414  1.00213.45           C
ATOM   5005  OE1  GLU A 641      17.246 -44.788 -12.861  1.00215.33           O
ATOM   5006  OE2  GLU A 641      19.433 -44.809 -12.632  1.00215.19           O1-
ATOM   5007  N    SER A 642      17.647 -38.800 -11.191  1.00154.68           N
ATOM   5008  CA   SER A 642      18.609 -37.734 -10.897  1.00156.28           C
ATOM   5009  C    SER A 642      17.946 -36.361 -10.791  1.00157.45           C
ATOM   5010  O    SER A 642      17.750 -35.690 -11.801  1.00160.21           O
ATOM   5011  CB   SER A 642      19.725 -37.707 -11.943  1.00371.97           C
ATOM   5012  OG   SER A 642      20.534 -38.865 -11.843  1.00371.32           O
ATOM   5013  N    ILE A 643      17.606 -35.967  -9.663  1.00125.44           N
ATOM   5014  CA   ILE A 643      16.943 -34.676  -9.297  1.00127.37           C
ATOM   5015  C    ILE A 643      17.833 -33.519  -9.722  1.00131.93           C
ATOM   5016  O    ILE A 643      17.372 -32.479 -10.200  1.00134.64           O
ATOM   5017  CB   ILE A 643      16.630 -34.498  -7.795  1.00112.20           C
ATOM   5018  CG1  ILE A 643      15.719 -35.612  -7.288  1.00107.67           C
ATOM   5019  CG2  ILE A 643      16.001 -33.152  -7.562  1.00118.68           C
ATOM   5020  CD1  ILE A 643      15.298 -35.433  -5.863  1.00105.12           C
ATOM   5021  N    THR A 644      19.125 -33.724  -9.530  1.00128.86           N
ATOM   5022  CA   THR A 644      20.109 -32.710  -9.812  1.00132.66           C
ATOM   5023  C    THR A 644      20.151 -32.454 -11.308  1.00135.14           C
ATOM   5024  O    THR A 644      20.192 -31.298 -11.728  1.00137.03           O
ATOM   5025  CB   THR A 644      21.483 -33.161  -9.311  1.00165.24           C
ATOM   5026  CG2  THR A 644      22.027 -32.168  -8.296  1.00141.81           C
ATOM   5027  OG1  THR A 644      21.359 -34.453  -8.696  1.00134.53           O
ATOM   5028  N    ASN A 645      20.106 -33.523 -12.101  1.00137.58           N
ATOM   5029  CA   ASN A 645      20.340 -33.496 -13.557  1.00140.35           C
ATOM   5030  C    ASN A 645      19.088 -33.463 -14.431  1.00140.61           C
ATOM   5031  O    ASN A 645      19.095 -32.931 -15.543  1.00143.80           O
ATOM   5032  CB   ASN A 645      21.267 -34.632 -13.993  1.00183.84           C
ATOM   5033  CG   ASN A 645      22.479 -34.792 -13.087  1.00183.61           C
ATOM   5034  ND2  ASN A 645      22.385 -35.688 -12.114  1.00154.95           N
ATOM   5035  OD1  ASN A 645      23.504 -34.125 -13.260  1.00160.91           O
ATOM   5036  N    GLY A 646      18.011 -34.044 -13.922  1.00136.03           N
ATOM   5037  CA   GLY A 646      16.717 -33.871 -14.575  1.00136.26           C
ATOM   5038  C    GLY A 646      16.346 -35.276 -15.236  1.00134.93           C
ATOM   5039  O    GLY A 646      15.484 -35.324 -16.091  1.00136.69           O
ATOM   5040  N    LYS A 647      17.032 -36.341 -14.833  1.00147.23           N
ATOM   5041  CA   LYS A 647      16.957 -37.631 -15.510  1.00147.46           C
ATOM   5042  C    LYS A 647      15.866 -38.508 -14.921  1.00144.35           C
ATOM   5043  O    LYS A 647      16.016 -39.049 -13.819  1.00141.49           O
ATOM   5044  CB   LYS A 647      18.398 -38.342 -15.425  1.00199.83           C
ATOM   5045  CG   LYS A 647      18.439 -39.605 -16.261  1.00202.07           C
ATOM   5046  CD   LYS A 647      19.799 -40.233 -15.989  1.00203.68           C
ATOM   5047  CE   LYS A 647      20.096 -41.393 -16.918  1.00190.78           C
ATOM   5048  NZ   LYS A 647      21.540 -41.791 -16.855  1.00183.33           N1+
ATOM   5049  N    PHE A 648      14.770 -38.632 -15.676  1.00118.40           N
ATOM   5050  CA   PHE A 648      13.633 -39.498 -15.343  1.00116.32           C
ATOM   5051  C    PHE A 648      13.023 -40.160 -16.574  1.00119.25           C
ATOM   5052  O    PHE A 648      13.263 -39.830 -17.728  1.00122.57           O
ATOM   5053  CB   PHE A 648      12.545 -38.718 -14.580  1.00129.73           C
ATOM   5054  CG   PHE A 648      12.967 -37.480 -15.261  1.00137.69           C
ATOM   5055  CD1  PHE A 648      11.170 -37.567 -16.347  1.00132.92           C
ATOM   5056  CD2  PHE A 648      12.514 -36.231 -14.905  1.00132.84           C
ATOM   5057  CE1  PHE A 648      10.734 -36.433 -17.053  1.00135.03           C
ATOM   5058  CE2  PHE A 648      12.087 -35.098 -15.557  1.00135.42           C
```

Fig. 7CE

```
ATOM   5059  CZ   PHE A 648      11.194 -35.199 -16.507  1.00136.32           C
ATOM   5060  N    TYR A 649      12.226 -41.331 -16.308  1.00144.11           N
ATOM   5061  CA   TYR A 649      11.569 -41.962 -17.367  1.00147.48           C
ATOM   5062  C    TYR A 649      10.062 -41.897 -17.174  1.00145.64           C
ATOM   5063  O    TYR A 649       9.509 -42.593 -16.331  1.00143.07           O
ATOM   5064  CB   TYR A 649      12.041 -43.411 -17.371  1.00396.41           C
ATOM   5065  CG   TYR A 649      13.532 -43.573 -17.153  1.00197.04           C
ATOM   5066  CD1  TYR A 649      14.018 -44.272 -16.057  1.00169.17           C
ATOM   5067  CD2  TYR A 649      14.456 -43.026 -18.038  1.00173.45           C
ATOM   5068  CE1  TYR A 649      15.384 -44.430 -15.852  1.00168.87           C
ATOM   5069  CE2  TYR A 649      15.826 -43.179 -17.837  1.00174.17           C
ATOM   5070  CZ   TYR A 649      16.276 -43.882 -16.743  1.00171.89           C
ATOM   5071  OH   TYR A 649      17.620 -44.039 -16.531  1.00172.68           O
ATOM   5072  N    TYR A 650       9.404 -41.057 -17.964  1.00162.52           N
ATOM   5073  CA   TYR A 650       7.957 -40.892 -17.898  1.00161.22           C
ATOM   5074  C    TYR A 650       7.223 -42.073 -18.553  1.00163.59           C
ATOM   5075  O    TYR A 650       7.062 -42.106 -19.769  1.00167.29           O
ATOM   5076  CB   TYR A 650       7.368 -39.556 -18.546  1.00152.65           C
ATOM   5077  CG   TYR A 650       6.089 -39.227 -19.556  1.00124.93           C
ATOM   5078  CD1  TYR A 650       5.411 -38.893 -17.391  1.00148.47           C
ATOM   5079  CD2  TYR A 650       5.375 -39.234 -19.741  1.00127.62           C
ATOM   5080  CE1  TYR A 650       4.054 -38.597 -17.408  1.00121.05           C
ATOM   5081  CE2  TYR A 650       4.015 -38.940 -19.770  1.00126.85           C
ATOM   5082  CZ   TYR A 650       3.357 -38.621 -18.604  1.00123.54           C
ATOM   5083  OH   TYR A 650       2.006 -38.332 -18.665  1.00123.15           O
ATOM   5084  N    ASN A 651       6.800 -43.046 -17.741  1.00130.34           N
ATOM   5085  CA   ASN A 651       5.992 -44.182 -18.213  1.00133.05           C
ATOM   5086  C    ASN A 651       4.512 -43.844 -18.410  1.00132.39           C
ATOM   5087  O    ASN A 651       3.841 -43.458 -17.464  1.00128.46           O
ATOM   5088  CB   ASN A 651       6.074 -45.368 -17.227  1.00193.47           C
ATOM   5089  CG   ASN A 651       7.362 -46.116 -17.337  1.00169.61           C
ATOM   5090  ND2  ASN A 651       7.295 -47.422 -17.101  1.00171.89           N
ATOM   5091  OD1  ASN A 651       8.410 -45.547 -17.635  1.00170.16           O
ATOM   5092  N    GLU A 652       3.983 -44.014 -19.613  1.00129.28           N
ATOM   5093  CA   GLU A 652       2.601 -43.625 -19.853  1.00128.89           C
ATOM   5094  C    GLU A 652       1.629 -44.778 -19.615  1.00123.74           C
ATOM   5095  O    GLU A 652       1.799 -45.842 -20.189  1.00134.33           O
ATOM   5096  CB   GLU A 652       2.457 -43.094 -21.276  1.00246.75           C
ATOM   5097  CG   GLU A 652       1.228 -42.242 -21.486  1.00245.87           C
ATOM   5098  CD   GLU A 652       1.181 -41.649 -22.872  1.00250.05           C
ATOM   5099  OE1  GLU A 652       2.146 -41.865 -23.638  1.00227.18           O
ATOM   5100  OE2  GLU A 652       0.181 -40.971 -23.194  1.00223.70           O1-
ATOM   5101  N    ILE A 653       0.625 -44.570 -18.762  1.00211.16           N
ATOM   5102  CA   ILE A 653      -0.465 -45.537 -18.574  1.00211.63           C
ATOM   5103  C    ILE A 653      -1.799 -44.812 -18.621  1.00209.25           C
ATOM   5104  O    ILE A 653      -1.854 -43.613 -18.376  1.00204.65           O
ATOM   5105  CB   ILE A 653      -0.439 -46.223 -17.197  1.00124.02           C
ATOM   5106  CG1  ILE A 653       0.950 -46.731 -16.836  1.00125.08           C
ATOM   5107  CG2  ILE A 653      -1.443 -47.358 -17.157  1.00125.59           C
ATOM   5108  CD1  ILE A 653       1.862 -45.689 -16.314  1.00122.04           C
ATOM   5109  N    ASP A 654      -2.878 -45.542 -18.891  1.00136.15           N
ATOM   5110  CA   ASP A 654      -4.227 -44.952 -18.940  1.00136.19           C
ATOM   5111  C    ASP A 654      -4.214 -43.448 -19.216  1.00133.68           C
ATOM   5112  O    ASP A 654      -4.310 -42.633 -18.306  1.00129.24           O
ATOM   5113  CB   ASP A 654      -5.020 -45.257 -17.664  1.00151.52           C
ATOM   5114  CG   ASP A 654      -6.345 -45.948 -17.952  1.00153.64           C
ATOM   5115  OD1  ASP A 654      -6.397 -45.609 -18.961  1.00156.10           O
ATOM   5116  OD2  ASP A 654      -6.729 -46.842 -17.173  1.00153.15           O1-
ATOM   5117  N    SER A 655      -4.090 -43.100 -20.491  1.00148.87           N
ATOM   5118  CA   SER A 655      -3.983 -41.716 -20.914  1.00147.56           C
ATOM   5119  C    SER A 655      -5.149 -40.932 -20.377  1.00144.78           C
```

Fig. 7CF

```
ATOM  5120  O   SER A 655      -5.094 -39.710 -20.293  1.00 143.57           O
ATOM  5121  CB  SER A 655      -3.972 -41.632 -22.443  1.00 172.89           C
ATOM  5122  OG  SER A 655      -5.196 -42.115 -22.993  1.00 152.42           O
ATOM  5123  N   LYS A 656      -6.293 -41.649 -20.008  1.00 145.94           N
ATOM  5124  CA  LYS A 656      -7.432 -41.038 -19.658  1.00 143.58           C
ATOM  5125  C   LYS A 656      -7.674 -41.084 -18.038  1.00 139.66           C
ATOM  5126  O   LYS A 656      -8.812 -41.205 -17.598  1.00 137.71           O
ATOM  5127  CB  LYS A 656      -8.632 -41.563 -20.337  1.00 131.32           C
ATOM  5128  CG  LYS A 656      -8.774 -43.073 -20.381  1.00 133.74           C
ATOM  5129  CD  LYS A 656      -9.749 -43.463 -21.504  1.00 117.44           C
ATOM  5130  CE  LYS A 656     -10.435 -44.823 -21.276  1.00 120.86           C
ATOM  5131  NZ  LYS A 656      -9.992 -46.028 -22.000  1.00 127.56           N1+
ATOM  5132  N   ALA A 657      -6.608 -40.975 -17.246  1.00 151.62           N
ATOM  5133  CA  ALA A 657      -6.721 -40.975 -15.782  1.00 146.95           C
ATOM  5134  C   ALA A 657      -6.320 -39.676 -15.160  1.00 144.88           C
ATOM  5135  O   ALA A 657      -5.880 -38.743 -15.902  1.00 146.98           O
ATOM  5136  CB  ALA A 657      -5.953 -42.126 -15.192  1.00  77.86           C
ATOM  5137  N   GLN A 658      -6.143 -39.621 -13.856  1.00 142.81           N
ATOM  5138  CA  GLN A 658      -5.709 -38.387 -13.215  1.00 141.25           C
ATOM  5139  C   GLN A 658      -4.591 -38.507 -12.163  1.00 136.26           C
ATOM  5140  O   GLN A 658      -4.069 -37.431 -11.703  1.00 138.85           O
ATOM  5141  CB  GLN A 658      -6.909 -37.535 -12.625  1.00 277.94           C
ATOM  5142  CG  GLN A 658      -6.617 -36.168 -12.323  1.00 276.80           C
ATOM  5143  CD  GLN A 658      -7.687 -35.502 -11.476  1.00 279.33           C
ATOM  5144  NE2 GLN A 658      -7.392 -34.314 -10.970  1.00 279.91           N
ATOM  5145  OE1 GLN A 658      -8.770 -36.050 -11.277  1.00 279.43           O
ATOM  5146  N   ILE A 659      -4.202 -39.720 -11.791  1.00 126.24           N
ATOM  5147  CA  ILE A 659      -3.272 -39.882 -10.667  1.00 123.12           C
ATOM  5148  C   ILE A 659      -1.858 -40.294 -11.045  1.00 123.23           C
ATOM  5149  O   ILE A 659      -1.625 -41.359 -11.600  1.00 124.18           O
ATOM  5150  CB  ILE A 659      -3.858 -40.854  -9.633  1.00 142.77           C
ATOM  5151  CG1 ILE A 659      -5.079 -40.214  -8.977  1.00 125.89           C
ATOM  5152  CG2 ILE A 659      -2.824 -41.215  -8.589  1.00 124.35           C
ATOM  5153  CD1 ILE A 659      -6.040 -41.200  -8.367  1.00 149.84           C
ATOM  5154  N   TYR A 660      -0.853 -39.459 -10.735  1.00 120.62           N
ATOM  5155  CA  TYR A 660       0.526 -39.788 -11.099  1.00 120.52           C
ATOM  5156  C   TYR A 660       1.263 -40.480  -9.961  1.00 117.42           C
ATOM  5157  O   TYR A 660       1.284 -40.025  -8.829  1.00 115.29           O
ATOM  5158  CB  TYR A 660       1.313 -38.525 -11.433  1.00 122.54           C
ATOM  5159  CG  TYR A 660       0.922 -37.805 -12.692  1.00 125.19           C
ATOM  5160  CD1 TYR A 660      -0.197 -37.005 -12.728  1.00 125.86           C
ATOM  5161  CD2 TYR A 660       1.702 -37.884 -13.827  1.00 127.14           C
ATOM  5162  CE1 TYR A 660      -0.548 -36.326 -13.870  1.00 128.83           C
ATOM  5163  CE2 TYR A 660       1.358 -37.209 -14.973  1.00 129.98           C
ATOM  5164  CZ  TYR A 660       0.230 -36.434 -14.992  1.00 130.75           C
ATOM  5165  OH  TYR A 660      -0.128 -35.754 -16.133  1.00 133.62           O
ATOM  5166  N   LEU A 661       1.993 -41.549 -10.250  1.00 129.05           N
ATOM  5167  CA  LEU A 661       2.852 -42.159  -9.230  1.00 126.40           C
ATOM  5168  C   LEU A 661       4.308 -41.790  -9.510  1.00 127.06           C
ATOM  5169  O   LEU A 661       4.766 -41.928 -10.631  1.00 129.70           O
ATOM  5170  CB  LEU A 661       2.641 -43.672  -9.148  1.00 111.94           C
ATOM  5171  CG  LEU A 661       3.638 -44.622  -8.462  1.00  98.27           C
ATOM  5172  CD1 LEU A 661       4.411 -43.963  -7.352  1.00 107.06           C
ATOM  5173  CD2 LEU A 661       2.948 -45.859  -7.919  1.00  98.35           C
ATOM  5174  N   LEU A 662       5.022 -41.302  -8.496  1.00 133.88           N
ATOM  5175  CA  LEU A 662       6.439 -40.988  -8.658  1.00 133.36           C
ATOM  5176  C   LEU A 662       7.272 -41.933  -7.729  1.00 131.07           C
ATOM  5177  O   LEU A 662       6.815 -42.236  -6.661  1.00 128.40           O
ATOM  5178  CB  LEU A 662       6.742 -39.541  -8.303  1.00 102.03           C
ATOM  5179  CG  LEU A 662       5.905 -38.406  -8.868  1.00 103.64           C
ATOM  5180  CD1 LEU A 662       6.330 -37.063  -8.259  1.00  94.78           C
```

Fig. 7CG

```
ATOM   5181  CD2 LEU A 662       5.999 -38.389 -10.369  1.00 96.04           C
ATOM   5182  N   PHE A 663       8.514 -42.065  -8.141  1.00136.15           N
ATOM   5183  CA  PHE A 663       9.510 -42.697  -7.292  1.00134.58           C
ATOM   5184  C   PHE A 663      10.793 -41.908  -7.353  1.00136.72           C
ATOM   5185  O   PHE A 663      11.333 -41.661  -8.424  1.00138.39           O
ATOM   5186  CB  PHE A 663       9.777 -44.137  -7.713  1.00155.61           C
ATOM   5187  CG  PHE A 663      10.684 -44.880  -6.775  1.00154.41           C
ATOM   5188  CD1 PHE A 663      10.229 -45.292  -5.544  1.00151.53           C
ATOM   5189  CD2 PHE A 663      11.984 -45.168  -7.122  1.00156.42           C
ATOM   5190  CE1 PHE A 663      11.039 -45.978  -4.692  1.00150.85           C
ATOM   5191  CE2 PHE A 663      12.806 -45.854  -6.256  1.00155.80           C
ATOM   5192  CZ  PHE A 663      12.328 -46.256  -5.034  1.00152.97           C
ATOM   5193  N   LEU A 664      11.259 -41.505  -6.181  1.00126.12           N
ATOM   5194  CA  LEU A 664      12.521 -40.849  -5.983  1.00127.35           C
ATOM   5195  C   LEU A 664      13.469 -41.910  -5.325  1.00126.74           C
ATOM   5196  O   LEU A 664      13.373 -42.364  -4.379  1.00124.43           O
ATOM   5197  CB  LEU A 664      12.372 -39.849  -4.861  1.00117.36           C
ATOM   5198  CG  LEU A 664      11.352 -38.760  -5.121  1.00118.13           C
ATOM   5199  CD1 LEU A 664      10.684 -38.375  -3.831  1.00118.04           C
ATOM   5200  CD2 LEU A 664      12.050 -37.581  -5.749  1.00121.58           C
ATOM   5201  N   ARG A 665      14.423 -42.312  -6.398  1.00130.75           N
ATOM   5202  CA  ARG A 665      15.289 -43.468  -6.124  1.00130.85           C
ATOM   5203  C   ARG A 665      16.420 -43.045  -5.213  1.00129.99           C
ATOM   5204  O   ARG A 665      16.992 -43.859  -4.492  1.00128.99           O
ATOM   5205  CB  ARG A 665      15.836 -44.115  -7.412  1.00223.43           C
ATOM   5206  CG  ARG A 665      16.411 -45.526  -7.194  1.00224.53           C
ATOM   5207  CD  ARG A 665      17.268 -46.019  -8.358  1.00229.18           C
ATOM   5208  NE  ARG A 665      18.145 -47.144  -7.957  1.00221.52           N
ATOM   5209  CZ  ARG A 665      19.144 -47.651  -8.685  1.00225.90           C
ATOM   5210  NH1 ARG A 665      19.439 -47.145  -9.875  1.00228.62           N1+
ATOM   5211  NH2 ARG A 665      19.858 -48.670  -8.220  1.00227.75           N
ATOM   5212  N   GLU A 666      16.716 -41.753  -5.240  1.00130.86           N
ATOM   5213  CA  GLU A 666      17.752 -41.197  -4.401  1.00130.66           C
ATOM   5214  C   GLU A 666      17.287 -41.112  -2.949  1.00127.97           C
ATOM   5215  O   GLU A 666      18.102 -41.038  -2.043  1.00127.65           O
ATOM   5216  CB  GLU A 666      18.143 -39.816  -4.908  1.00151.70           C
ATOM   5217  CG  GLU A 666      18.056 -39.667  -6.406  1.00154.71           C
ATOM   5218  CD  GLU A 666      18.625 -38.348  -6.894  1.00148.21           C
ATOM   5219  OE1 GLU A 666      19.691 -37.923  -6.395  1.00148.32           O
ATOM   5220  OE2 GLU A 666      18.003 -37.731  -7.778  1.00150.78           O1-
ATOM   5221  N   TYR A 667      15.977 -41.116  -2.727  1.00108.58           N
ATOM   5222  CA  TYR A 667      15.424 -41.103  -1.372  1.00105.93           C
ATOM   5223  C   TYR A 667      14.588 -42.344  -1.082  1.00103.20           C
ATOM   5224  O   TYR A 667      13.880 -42.391  -0.086  1.00101.36           O
ATOM   5225  CB  TYR A 667      14.537 -39.879  -1.161  1.00 97.96           C
ATOM   5226  CG  TYR A 667      15.287 -38.556  -1.126  1.00101.19           C
ATOM   5227  CD1 TYR A 667      15.366 -37.769  -2.260  1.00104.34           C
ATOM   5228  CD2 TYR A 667      15.807 -38.085   0.052  1.00102.20           C
ATOM   5229  CE1 TYR A 667      16.022 -36.551  -2.219  1.00108.08           C
ATOM   5230  CE2 TYR A 667      16.468 -36.877   0.107  1.00106.38           C
ATOM   5231  CZ  TYR A 667      16.575 -36.109  -1.026  1.00109.30           C
ATOM   5232  OH  TYR A 667      17.230 -34.899  -0.954  1.00114.06           O
ATOM   5233  N   LYS A 668      14.672 -43.339  -1.962  1.00127.00           N
ATOM   5234  CA  LYS A 668      13.815 -44.523  -1.904  1.00125.38           C
ATOM   5235  C   LYS A 668      12.423 -44.165  -1.441  1.00123.33           C
ATOM   5236  O   LYS A 668      11.871 -44.836  -0.581  1.00121.76           O
ATOM   5237  CB  LYS A 668      14.417 -45.605  -1.004  1.00202.12           C
ATOM   5238  CG  LYS A 668      15.455 -46.470  -1.702  1.00196.80           C
ATOM   5239  CD  LYS A 668      16.313 -47.219  -0.699  1.00197.02           C
ATOM   5240  CE  LYS A 668      17.405 -48.020  -1.386  1.00209.16           C
ATOM   5241  NZ  LYS A 668      18.410 -48.504  -0.403  1.00200.66           N1+
```

Fig. 7CH

```
ATOM   5242  N   SER A 669      11.852 -43.110  -2.020  1.00134.85           N
ATOM   5243  CA  SER A 669      10.554 -42.628  -1.549  1.00133.43           C
ATOM   5244  C   SER A 669       9.504 -42.489  -2.647  1.00134.44           C
ATOM   5245  O   SER A 669       9.793 -42.012  -3.731  1.00136.57           O
ATOM   5246  CB  SER A 669      10.712 -41.303  -0.797  1.00122.06           C
ATOM   5247  OG  SER A 669       9.554 -41.002  -0.026  1.00111.33           O
ATOM   5248  N   PHE A 670       8.277 -42.897  -2.335  1.00127.10           N
ATOM   5249  CA  PHE A 670       7.175 -42.853  -3.281  1.00129.06           C
ATOM   5250  C   PHE A 670       6.335 -41.616  -3.079  1.00129.46           C
ATOM   5251  O   PHE A 670       6.132 -41.168  -1.945  1.00127.73           O
ATOM   5252  CB  PHE A 670       6.276 -44.067  -3.093  1.00138.56           C
ATOM   5253  CG  PHE A 670       6.773 -45.299  -3.767  1.00139.27           C
ATOM   5254  CD1 PHE A 670       6.688 -46.527  -3.139  1.00139.09           C
ATOM   5255  CD2 PHE A 670       7.308 -45.241  -5.039  1.00141.59           C
ATOM   5256  CE1 PHE A 670       7.147 -47.667  -3.763  1.00139.80           C
ATOM   5257  CE2 PHE A 670       7.763 -46.380  -5.666  1.00143.29           C
ATOM   5258  CZ  PHE A 670       7.691 -47.599  -5.027  1.00142.75           C
ATOM   5259  N   VAL A 671       5.821 -41.108  -4.186  1.00118.30           N
ATOM   5260  CA  VAL A 671       4.921 -39.958  -4.182  1.00119.87           C
ATOM   5261  C   VAL A 671       3.670 -40.274  -5.006  1.00120.16           C
ATOM   5262  O   VAL A 671       3.709 -41.100  -5.915  1.00120.49           O
ATOM   5263  CB  VAL A 671       5.614 -38.730  -4.766  1.00 89.23           C
ATOM   5264  CG1 VAL A 671       4.664 -37.562  -4.836  1.00 91.37           C
ATOM   5265  CG2 VAL A 671       6.807 -38.386  -3.944  1.00 89.15           C
ATOM   5266  N   ILE A 672       2.569 -39.604  -4.693  1.00106.34           N
ATOM   5267  CA  ILE A 672       1.296 -39.825  -5.361  1.00106.69           C
ATOM   5268  C   ILE A 672       0.615 -38.475  -5.592  1.00109.16           C
ATOM   5269  O   ILE A 672       0.157 -37.854  -4.647  1.00109.15           O
ATOM   5270  CB  ILE A 672       0.402 -40.697  -4.483  1.00 98.90           C
ATOM   5271  CG1 ILE A 672       0.891 -42.144  -4.498  1.00 91.16           C
ATOM   5272  CG2 ILE A 672      -1.011 -40.622  -4.939  1.00 93.76           C
ATOM   5273  CD1 ILE A 672       0.116 -43.068  -3.572  1.00 95.28           C
ATOM   5274  N   LEU A 673       0.556 -38.017  -6.837  1.00126.38           N
ATOM   5275  CA  LEU A 673       0.017 -36.692  -7.144  1.00129.65           C
ATOM   5276  C   LEU A 673      -1.244 -36.703  -7.990  1.00130.36           C
ATOM   5277  O   LEU A 673      -1.649 -37.728  -8.542  1.00128.55           O
ATOM   5278  CB  LEU A 673       1.040 -35.894  -7.937  1.00139.73           C
ATOM   5279  CG  LEU A 673       2.349 -35.806  -7.243  1.00 81.21           C
ATOM   5280  CD1 LEU A 673       3.361 -35.066  -8.233  1.00236.43           C
ATOM   5281  CD2 LEU A 673       2.099 -34.620  -6.142  1.00235.87           C
ATOM   5282  N   ASP A 674      -1.837 -35.526  -8.127  1.00115.66           N
ATOM   5283  CA  ASP A 674      -2.838 -35.292  -9.156  1.00117.50           C
ATOM   5284  C   ASP A 674      -2.275 -34.398 -10.164  1.00121.40           C
ATOM   5285  O   ASP A 674      -1.367 -33.531  -9.840  1.00123.56           O
ATOM   5286  CB  ASP A 674      -4.158 -34.805  -8.546  1.00151.48           C
ATOM   5287  CG  ASP A 674      -4.023 -33.458  -7.865  1.00155.51           C
ATOM   5288  OD1 ASP A 674      -3.473 -32.524  -8.486  1.00159.60           O
ATOM   5289  OD2 ASP A 674      -4.490 -33.324  -6.709  1.00156.23           O1-
ATOM   5290  N   GLU A 675      -2.869 -34.285 -11.380  1.00124.33           N
ATOM   5291  CA  GLU A 675      -2.251 -33.476 -12.461  1.00127.76           C
ATOM   5292  C   GLU A 675      -1.698 -32.124 -12.030  1.00131.04           C
ATOM   5293  O   GLU A 675      -0.594 -31.744 -12.424  1.00133.03           O
ATOM   5294  CB  GLU A 675      -3.291 -33.258 -13.553  1.00142.59           C
ATOM   5295  CG  GLU A 675      -3.603 -34.491 -14.353  1.00141.41           C
ATOM   5296  CD  GLU A 675      -3.649 -34.213 -15.836  1.00145.11           C
ATOM   5297  OE1 GLU A 675      -2.668 -33.633 -16.367  1.00140.19           O
ATOM   5298  OE2 GLU A 675      -4.673 -34.579 -16.466  1.00138.97           O1-
ATOM   5299  N   SER A 676      -2.466 -31.396 -11.225  1.00146.26           N
ATOM   5300  CA  SER A 676      -2.132 -30.097 -10.902  1.00158.88           C
ATOM   5301  C   SER A 676      -1.003 -29.971  -9.882  1.00150.51           C
ATOM   5302  O   SER A 676      -0.329 -28.938  -9.821  1.00152.79           O
```

Fig. 7CI

```
ATOM   5303  CB  SER A 676      -3.373 -29.228 -10.442  1.00118.98           C
ATOM   5304  OG  SER A 676      -3.778 -29.584  -9.131  1.00111.66           O
ATOM   5305  N   LEU A 677      -0.806 -30.909  -9.078  1.00111.41           N
ATOM   5306  CA  LEU A 677       0.349 -30.955  -8.188  1.00110.36           C
ATOM   5307  C   LEU A 677       1.573 -31.460  -8.969  1.00108.46           C
ATOM   5308  O   LEU A 677       2.696 -30.968  -8.792  1.00110.22           O
ATOM   5309  CB  LEU A 677       0.070 -31.816  -6.952  1.00 89.31           C
ATOM   5310  CG  LEU A 677      -0.916 -31.306  -5.894  1.00 91.70           C
ATOM   5311  CD1 LEU A 677      -0.842 -32.236  -4.702  1.00 79.75           C
ATOM   5312  CD2 LEU A 677      -0.656 -29.845  -5.487  1.00 91.50           C
ATOM   5313  N   TYR A 678       1.347 -32.431  -9.851  1.00105.28           N
ATOM   5314  CA  TYR A 678       2.361 -32.786 -10.827  1.00104.57           C
ATOM   5315  C   TYR A 678       2.856 -31.548 -11.582  1.00109.03           C
ATOM   5316  O   TYR A 678       4.022 -31.483 -11.947  1.00109.50           O
ATOM   5317  CB  TYR A 678       1.867 -33.850 -11.817  1.00126.14           C
ATOM   5318  CG  TYR A 678       2.986 -34.385 -12.670  1.00126.97           C
ATOM   5319  CD1 TYR A 678       3.659 -35.557 -12.329  1.00122.87           C
ATOM   5320  CD2 TYR A 678       3.437 -33.668 -13.786  1.00129.04           C
ATOM   5321  CE1 TYR A 678       4.712 -36.032 -13.093  1.00123.24           C
ATOM   5322  CE2 TYR A 678       4.493 -34.155 -14.552  1.00129.41           C
ATOM   5323  CZ  TYR A 678       5.126 -35.324 -14.203  1.00126.63           C
ATOM   5324  OH  TYR A 678       6.173 -35.780 -14.968  1.00126.26           O
ATOM   5325  N   ASN A 679       1.987 -30.566 -11.811  1.00100.36           N
ATOM   5326  CA  ASN A 679       2.388 -29.395 -12.598  1.00103.18           C
ATOM   5327  C   ASN A 679       2.755 -28.141 -11.789  1.00104.30           C
ATOM   5328  O   ASN A 679       3.188 -27.124 -12.339  1.00107.07           O
ATOM   5329  CB  ASN A 679       1.366 -29.095 -13.705  1.00132.53           C
ATOM   5330  CG  ASN A 679       1.445 -30.092 -14.864  1.00132.40           C
ATOM   5331  ND2 ASN A 679       0.335 -30.754 -15.136  1.00131.08           N
ATOM   5332  OD1 ASN A 679       2.492 -30.269 -15.497  1.00132.99           O
ATOM   5333  N   SER A 680       2.609 -28.239 -10.476  1.00113.86           N
ATOM   5334  CA  SER A 680       2.984 -27.168  -9.567  1.00115.24           C
ATOM   5335  C   SER A 680       4.469 -26.856  -9.677  1.00115.39           C
ATOM   5336  O   SER A 680       5.300 -27.760  -8.679  1.00112.56           O
ATOM   5337  CB  SER A 680       2.681 -27.611  -8.143  1.00161.77           C
ATOM   5338  OG  SER A 680       3.416 -28.785  -7.840  1.00157.67           O
ATOM   5339  N   ALA A 681       4.805 -25.574  -9.729  1.00126.38           N
ATOM   5340  CA  ALA A 681       6.189 -25.148  -9.916  1.00127.27           C
ATOM   5341  C   ALA A 681       7.206 -25.895  -9.058  1.00123.95           C
ATOM   5342  O   ALA A 681       8.372 -25.992  -9.410  1.00123.81           O
ATOM   5343  CB  ALA A 681       6.313 -23.654  -9.708  1.00 84.44           C
ATOM   5344  N   TYR A 682       6.772 -26.424  -7.930  1.00133.95           N
ATOM   5345  CA  TYR A 682       7.693 -27.122  -7.056  1.00131.09           C
ATOM   5346  C   TYR A 682       7.999 -28.500  -7.613  1.00127.53           C
ATOM   5347  O   TYR A 682       9.148 -28.798  -7.896  1.00127.43           O
ATOM   5348  CB  TYR A 682       7.133 -27.195  -6.641  1.00122.19           C
ATOM   5349  CG  TYR A 682       7.917 -28.094  -4.688  1.00118.60           C
ATOM   5350  CD1 TYR A 682       9.000 -27.549  -3.997  1.00115.86           C
ATOM   5351  CD2 TYR A 682       7.552 -29.366  -4.457  1.00114.40           C
ATOM   5352  CE1 TYR A 682       9.705 -28.333  -3.114  1.00111.49           C
ATOM   5353  CE2 TYR A 682       8.247 -30.155  -3.575  1.00111.64           C
ATOM   5354  CZ  TYR A 682       9.322 -29.634  -2.908  1.00109.29           C
ATOM   5355  OH  TYR A 682      10.013 -30.423  -2.030  1.00104.77           O
ATOM   5356  N   ILE A 683       6.981 -29.334  -7.795  1.00120.22           N
ATOM   5357  CA  ILE A 683       7.224 -30.680  -8.317  1.00117.68           C
ATOM   5358  C   ILE A 683       7.895 -30.696  -9.675  1.00119.41           C
ATOM   5359  O   ILE A 683       8.718 -31.437 -10.025  1.00118.63           O
ATOM   5360  CB  ILE A 683       5.941 -31.541  -8.440  1.00 83.84           C
ATOM   5361  CG1 ILE A 683       5.277 -31.728  -7.089  1.00 82.12           C
ATOM   5362  CG2 ILE A 683       6.295 -32.842  -8.972  1.00 79.18           C
ATOM   5363  CD1 ILE A 683       5.761 -32.960  -6.377  1.00 80.92           C
```

Fig. 7CJ

```
ATOM   5364  N   GLN A 684       7.540 -29.566 -10.432  1.00 95.48           N
ATOM   5365  CA  GLN A 684       8.089 -29.385 -11.783  1.00 97.39           C
ATOM   5366  C   GLN A 684       9.556 -28.999 -11.699  1.00 98.26           C
ATOM   5367  O   GLN A 684      10.389 -29.658 -12.302  1.00 97.69           O
ATOM   5368  CB  GLN A 684       7.297 -28.335 -12.543  1.00131.41           C
ATOM   5369  CG  GLN A 684       6.057 -28.874 -13.211  1.00130.97           C
ATOM   5370  CD  GLN A 684       6.369 -30.047 -14.111  1.00129.68           C
ATOM   5371  NE2 GLN A 684       5.974 -31.241 -13.694  1.00126.61           N
ATOM   5372  OE1 GLN A 684       6.974 -29.882 -15.166  1.00131.77           O
ATOM   5373  N   MET A 685       9.865 -27.944 -10.948  1.00114.98           N
ATOM   5374  CA  MET A 685      11.202 -27.367 -10.913  1.00115.94           C
ATOM   5375  C   MET A 685      12.170 -28.032  -9.950  1.00114.51           C
ATOM   5376  O   MET A 685      13.368 -27.811 -10.026  1.00115.25           O
ATOM   5377  CB  MET A 685      11.115 -25.894 -10.574  1.00106.98           C
ATOM   5378  CG  MET A 685      10.477 -25.081 -11.692  1.00111.53           C
ATOM   5379  SD  MET A 685      10.270 -23.415 -11.040  1.00114.40           S
ATOM   5380  CE  MET A 685      11.951 -22.900 -10.764  1.00110.17           C
ATOM   5381  N   PHE A 686      11.668 -28.834  -9.030  1.00129.08           N
ATOM   5382  CA  PHE A 686      12.558 -29.493  -8.089  1.00126.79           C
ATOM   5383  C   PHE A 686      12.749 -30.959  -8.461  1.00128.23           C
ATOM   5384  O   PHE A 686      13.830 -31.372  -8.874  1.00124.98           O
ATOM   5385  CB  PHE A 686      12.028 -29.350  -6.639  1.00127.26           C
ATOM   5386  CG  PHE A 686      12.898 -30.049  -5.635  1.00124.69           C
ATOM   5387  CD1 PHE A 686      14.122 -29.606  -5.335  1.00123.29           C
ATOM   5388  CD2 PHE A 686      12.370 -31.149  -4.971  1.00121.04           C
ATOM   5389  CE1 PHE A 686      14.875 -30.259  -4.404  1.00121.00           C
ATOM   5390  CE2 PHE A 686      13.120 -31.792  -4.037  1.00118.84           C
ATOM   5391  CZ  PHE A 686      14.370 -31.347  -3.753  1.00119.42           C
ATOM   5392  N   LEU A 687      11.684 -31.736  -8.327  1.00144.98           N
ATOM   5393  CA  LEU A 687      11.727 -33.163  -8.609  1.00142.14           C
ATOM   5394  C   LEU A 687      12.121 -33.522 -10.054  1.00143.09           C
ATOM   5395  O   LEU A 687      12.782 -34.536 -10.294  1.00141.15           O
ATOM   5396  CB  LEU A 687      10.372 -33.786  -8.273  1.00117.39           C
ATOM   5397  CG  LEU A 687      10.084 -34.057  -6.808  1.00114.53           C
ATOM   5398  CD1 LEU A 687       8.934 -35.030  -6.681  1.00110.84           C
ATOM   5399  CD2 LEU A 687      11.322 -34.619  -6.179  1.00112.59           C
ATOM   5400  N   LEU A 688      11.763 -32.700 -11.013  1.00103.01           N
ATOM   5401  CA  LEU A 688      11.904 -32.994 -12.428  1.00104.36           C
ATOM   5402  C   LEU A 688      12.951 -32.067 -13.051  1.00108.42           C
ATOM   5403  O   LEU A 688      13.342 -32.223 -14.199  1.00110.26           O
ATOM   5404  CB  LEU A 688      10.574 -32.871 -13.175  1.00 95.69           C
ATOM   5405  CG  LEU A 688       9.403 -33.771 -12.754  1.00 92.26           C
ATOM   5406  CD1 LEU A 688       8.162 -33.504 -13.621  1.00 93.64           C
ATOM   5407  CD2 LEU A 688       9.752 -35.256 -12.783  1.00 89.40           C
ATOM   5408  N   ASN A 689      13.393 -31.093 -12.272  1.00169.75           N
ATOM   5409  CA  ASN A 689      14.397 -30.132 -12.708  1.00172.52           C
ATOM   5410  C   ASN A 689      14.130 -29.455 -14.049  1.00175.24           C
ATOM   5411  O   ASN A 689      15.062 -29.156 -14.780  1.00177.25           O
ATOM   5412  CB  ASN A 689      15.773 -30.770 -12.731  1.00137.96           C
ATOM   5413  CG  ASN A 689      15.872 -29.355 -12.964  1.00140.46           C
ATOM   5414  ND2 ASN A 689      18.044 -30.228 -13.353  1.00141.05           N
ATOM   5415  OD1 ASN A 689      16.664 -28.553 -12.804  1.00142.38           O
ATOM   5416  N   GLN A 690      12.867 -29.192 -14.365  1.00122.83           N
ATOM   5417  CA  GLN A 690      12.526 -28.467 -15.587  1.00125.68           C
ATOM   5418  C   GLN A 690      11.929 -27.086 -15.344  1.00127.79           C
ATOM   5419  O   GLN A 690      10.905 -26.951 -14.694  1.00126.84           O
ATOM   5420  CB  GLN A 690      11.564 -29.289 -16.417  1.00189.36           C
ATOM   5421  CG  GLN A 690      12.133 -30.603 -16.813  1.00189.65           C
ATOM   5422  CD  GLN A 690      11.059 -31.543 -17.216  1.00190.85           C
ATOM   5423  NE2 GLN A 690      11.389 -32.486 -18.087  1.00190.92           N
ATOM   5424  OE1 GLN A 690       9.920 -31.418 -16.763  1.00189.60           O
```

Fig. 7CK

```
ATOM   5425  N    TYR A 691      12.552 -26.062 -15.907  1.00146.63           N
ATOM   5426  CA   TYR A 691      12.131 -24.709 -15.620  1.00149.64           C
ATOM   5427  C    TYR A 691      12.343 -23.729 -16.774  1.00153.86           C
ATOM   5428  O    TYR A 691      13.408 -23.692 -17.385  1.00153.86           O
ATOM   5429  CB   TYR A 691      12.864 -24.232 -14.383  1.00164.43           C
ATOM   5430  CG   TYR A 691      14.332 -24.024 -14.608  1.00142.09           C
ATOM   5431  CD1  TYR A 691      15.209 -25.096 -14.665  1.00141.37           C
ATOM   5432  CD2  TYR A 691      14.845 -22.745 -14.757  1.00140.98           C
ATOM   5433  CE1  TYR A 691      16.571 -24.895 -14.874  1.00139.69           C
ATOM   5434  CE2  TYR A 691      16.194 -22.528 -14.962  1.00139.22           C
ATOM   5435  CZ   TYR A 691      17.057 -23.602 -15.024  1.00138.43           C
ATOM   5436  OH   TYR A 691      18.401 -23.359 -15.232  1.00137.19           O
ATOM   5437  N    ASP A 692      11.311 -22.943 -17.059  1.00145.09           N
ATOM   5438  CA   ASP A 692      11.336 -21.964 -18.144  1.00148.97           C
ATOM   5439  C    ASP A 692      12.502 -20.985 -17.990  1.00146.90           C
ATOM   5440  O    ASP A 692      12.478 -20.162 -17.137  1.00145.19           O
ATOM   5441  CB   ASP A 692       9.998 -21.217 -18.205  1.00164.79           C
ATOM   5442  CG   ASP A 692       9.812 -20.447 -19.496  1.00169.19           C
ATOM   5443  OD1  ASP A 692       8.734 -20.559 -20.113  1.00169.04           O
ATOM   5444  OD2  ASP A 692      10.742 -19.720 -19.894  1.00170.64           O1-
ATOM   5445  N    GLN A 693      13.508 -21.343 -18.847  1.00135.45           N
ATOM   5446  CA   GLN A 693      14.794 -20.459 -18.699  1.00133.36           C
ATOM   5447  C    GLN A 693      14.794 -19.952 -18.982  1.00135.83           C
ATOM   5448  O    GLN A 693      15.779 -19.262 -18.698  1.00133.94           O
ATOM   5449  CB   GLN A 693      15.857 -21.163 -19.544  1.00148.28           C
ATOM   5450  CG   GLN A 693      15.715 -22.672 -19.531  1.00148.65           C
ATOM   5451  CD   GLN A 693      16.996 -23.371 -19.140  1.00147.93           C
ATOM   5452  NE2  GLN A 693      16.909 -24.881 -18.907  1.00149.43           N
ATOM   5453  OE1  GLN A 693      18.053 -22.744 -19.045  1.00147.61           O
ATOM   5454  N    ASP A 694      13.694 -18.445 -19.536  1.00157.78           N
ATOM   5455  CA   ASP A 694      13.537 -17.011 -19.772  1.00161.26           C
ATOM   5456  C    ASP A 694      12.800 -16.353 -18.605  1.00160.91           C
ATOM   5457  O    ASP A 694      12.463 -15.173 -18.665  1.00165.02           O
ATOM   5458  CB   ASP A 694      12.784 -16.751 -21.085  1.00204.27           C
ATOM   5459  CG   ASP A 694      13.541 -17.245 -22.308  1.00205.22           C
ATOM   5460  OD1  ASP A 694      14.735 -16.904 -22.451  1.00203.96           O
ATOM   5461  OD2  ASP A 694      12.934 -17.977 -23.120  1.00210.48           O1-
ATOM   5462  N    LEU A 695      12.545 -17.131 -17.552  1.00148.03           N
ATOM   5463  CA   LEU A 695      11.863 -16.652 -16.347  1.00147.26           C
ATOM   5464  C    LEU A 695      12.757 -16.794 -15.124  1.00141.60           C
ATOM   5465  O    LEU A 695      12.872 -15.885 -14.303  1.00141.43           O
ATOM   5466  CB   LEU A 695      10.574 -17.445 -16.108  1.00100.16           C
ATOM   5467  CG   LEU A 695       9.366 -17.070 -16.959  1.00106.09           C
ATOM   5468  CD1  LEU A 695       8.061 -17.528 -16.336  1.00106.81           C
ATOM   5469  CD2  LEU A 695       9.372 -15.578 -17.121  1.00109.81           C
ATOM   5470  N    PHE A 696      13.392 -17.955 -15.019  1.00132.51           N
ATOM   5471  CA   PHE A 696      14.202 -18.294 -13.866  1.00127.26           C
ATOM   5472  C    PHE A 696      15.696 -18.422 -14.205  1.00128.97           C
ATOM   5473  O    PHE A 696      16.136 -19.179 -15.324  1.00127.43           O
ATOM   5474  CB   PHE A 696      13.701 -19.614 -13.267  1.00102.80           C
ATOM   5475  CG   PHE A 696      12.242 -19.604 -12.859  1.00104.59           C
ATOM   5476  CD1  PHE A 696      11.433 -20.691 -13.130  1.00106.40           C
ATOM   5477  CD2  PHE A 696      11.693 -18.532 -12.182  1.00105.47           C
ATOM   5478  CE1  PHE A 696      10.113 -20.703 -12.763  1.00109.69           C
ATOM   5479  CE2  PHE A 696      10.356 -19.546 -11.803  1.00107.79           C
ATOM   5480  CZ   PHE A 696       9.569 -19.635 -12.102  1.00103.32           C
ATOM   5481  N    GLU A 697      16.473 -18.789 -13.198  1.00137.89           N
ATOM   5482  CA   GLU A 697      17.856 -19.188 -13.347  1.00135.20           C
ATOM   5483  C    GLU A 697      18.039 -20.069 -12.136  1.00130.83           C
ATOM   5484  O    GLU A 697      17.828 -19.739 -11.032  1.00129.24           O
ATOM   5485  CB   GLU A 697      18.791 -17.966 -13.327  1.00193.74           C
```

Fig. 7CL

```
ATOM   5486  CG   GLU A 697      19.785 -17.872 -12.158  1.00190.87           C
ATOM   5487  CD   GLU A 697      21.050 -18.694 -12.366  1.00192.11           C
ATOM   5488  OE1  GLU A 697      21.024 -19.629 -13.205  1.00193.95           O
ATOM   5489  OE2  GLU A 697      22.068 -18.415 -11.689  1.00189.46           O1-
ATOM   5490  N    GLN A 698      18.578 -21.281 -12.334  1.00143.23           N
ATOM   5491  CA   GLN A 698      18.733 -22.188 -11.212  1.00139.83           C
ATOM   5492  C    GLN A 698      19.983 -21.822 -10.452  1.00136.48           C
ATOM   5493  O    GLN A 698      21.054 -22.354 -10.718  1.00135.45           O
ATOM   5494  CB   GLN A 698      18.819 -23.626 -11.682  1.00116.99           C
ATOM   5495  CG   GLN A 698      19.268 -24.579 -10.619  1.00114.29           C
ATOM   5496  CD   GLN A 698      19.377 -25.995 -11.133  1.00121.80           C
ATOM   5497  NE2  GLN A 698      20.605 -26.457 -11.347  1.00121.91           N
ATOM   5498  OE1  GLN A 698      18.370 -26.667 -11.346  1.00124.53           O
ATOM   5499  N    VAL A 699      19.842 -20.893  -9.514  1.00140.67           N
ATOM   5500  CA   VAL A 699      20.983 -20.439  -8.708  1.00137.65           C
ATOM   5501  C    VAL A 699      21.600 -21.595  -7.964  1.00134.91           C
ATOM   5502  O    VAL A 699      22.807 -21.764  -8.000  1.00134.01           O
ATOM   5503  CB   VAL A 699      20.541 -19.398  -7.691  1.00104.62           C
ATOM   5504  CG1  VAL A 699      21.656 -19.175  -6.718  1.00101.44           C
ATOM   5505  CG2  VAL A 699      20.166 -18.114  -8.353  1.00108.25           C
ATOM   5506  N    THR A 700      20.810 -22.404  -7.276  1.00130.38           N
ATOM   5507  CA   THR A 700      21.457 -23.509  -6.561  1.00128.68           C
ATOM   5508  C    THR A 700      20.776 -24.836  -6.889  1.00131.17           C
ATOM   5509  O    THR A 700      19.561 -24.876  -7.085  1.00132.73           O
ATOM   5510  CB   THR A 700      21.511 -23.276  -5.021  1.00148.75           C
ATOM   5511  CG2  THR A 700      22.692 -23.994  -4.400  1.00146.47           C
ATOM   5512  OG1  THR A 700      21.644 -21.873  -4.749  1.00152.43           O
ATOM   5513  N    ASN A 701      21.558 -25.913  -6.947  1.00131.16           N
ATOM   5514  CA   ASN A 701      21.035 -27.236  -7.283  1.00134.57           C
ATOM   5515  C    ASN A 701      21.634 -28.333  -6.407  1.00134.17           C
ATOM   5516  O    ASN A 701      22.819 -28.627  -6.496  1.00134.54           O
ATOM   5517  CB   ASN A 701      21.308 -27.538  -8.761  1.00159.13           C
ATOM   5518  CG   ASN A 701      20.648 -28.823  -9.240  1.00163.79           C
ATOM   5519  ND2  ASN A 701      20.605 -29.096 -10.556  1.00168.21           N
ATOM   5520  OD1  ASN A 701      20.196 -29.641  -8.442  1.00163.74           O
ATOM   5521  N    ASP A 702      20.816 -28.941  -5.561  1.00113.11           N
ATOM   5522  CA   ASP A 702      21.276 -30.032  -4.710  1.00113.78           C
ATOM   5523  C    ASP A 702      20.121 -31.008  -4.552  1.00116.32           C
ATOM   5524  O    ASP A 702      18.962 -30.603  -4.552  1.00117.02           O
ATOM   5525  CB   ASP A 702      21.746 -29.487  -3.342  1.00164.66           C
ATOM   5526  CG   ASP A 702      22.486 -30.527  -2.483  1.00169.07           C
ATOM   5527  OD1  ASP A 702      22.147 -31.727  -2.537  1.00173.89           O
ATOM   5528  OD2  ASP A 702      23.408 -30.133  -1.729  1.00165.60           O1-
ATOM   5529  N    THR A 703      20.432 -32.290  -4.433  1.00128.82           N
ATOM   5530  CA   THR A 703      19.425 -33.294  -4.117  1.00129.00           C
ATOM   5531  C    THR A 703      18.577 -32.896  -2.904  1.00126.23           C
ATOM   5532  O    THR A 703      17.472 -33.407  -2.701  1.00125.70           O
ATOM   5533  CB   THR A 703      20.110 -34.624  -3.826  1.00121.07           C
ATOM   5534  CG2  THR A 703      19.152 -35.606  -3.169  1.00118.95           C
ATOM   5535  OG1  THR A 703      20.595 -35.169  -5.054  1.00123.71           O
ATOM   5536  N    ARG A 704      19.111 -31.969  -2.112  1.00128.07           N
ATOM   5537  CA   ARG A 704      18.514 -31.563  -0.856  1.00125.28           C
ATOM   5538  C    ARG A 704      17.828 -30.342  -1.034  1.00122.93           C
ATOM   5539  O    ARG A 704      16.695 -30.128  -0.256  1.00121.39           O
ATOM   5540  CB   ARG A 704      19.615 -31.254   0.149  1.00154.65           C
ATOM   5541  CG   ARG A 704      20.574 -32.396   0.361  1.00157.97           C
ATOM   5542  CD   ARG A 704      20.836 -32.593   1.830  1.00157.37           C
ATOM   5543  NE   ARG A 704      21.125 -33.969   2.165  1.00159.72           N
ATOM   5544  CZ   ARG A 704      20.530 -34.643   3.132  1.00155.83           C
ATOM   5545  NH1  ARG A 704      19.575 -34.052   3.857  1.00147.73           N1+
ATOM   5546  NH2  ARG A 704      20.832 -35.909   3.365  1.00156.66           N
```

Fig. 7CM

```
ATOM   5547  N    ALA A 705      17.907 -29.548  -2.063  1.00113.35           N
ATOM   5548  CA   ALA A 705      17.169 -28.308  -2.278  1.00111.79           C
ATOM   5549  C    ALA A 705      17.658 -27.557  -3.493  1.00113.62           C
ATOM   5550  O    ALA A 705      16.796 -27.697  -3.891  1.00112.54           O
ATOM   5551  CB   ALA A 705      17.295 -27.426  -1.064  1.00110.53           C
ATOM   5552  N    LYS A 706      16.789 -26.742  -4.074  1.00 89.63           N
ATOM   5553  CA   LYS A 706      17.180 -25.894  -5.193  1.00 90.66           C
ATOM   5554  C    LYS A 706      16.658 -24.458  -4.889  1.00 88.91           C
ATOM   5555  O    LYS A 706      16.099 -24.165  -3.981  1.00 87.51           O
ATOM   5556  CB   LYS A 706      16.444 -26.302  -6.470  1.00 78.89           C
ATOM   5557  CG   LYS A 706      16.612 -27.773  -6.827  1.00 81.76           C
ATOM   5558  CD   LYS A 706      16.343 -28.073  -8.263  1.00 86.85           C
ATOM   5559  CE   LYS A 706      16.696 -29.500  -8.543  1.00 89.63           C
ATOM   5560  NZ   LYS A 706      16.373 -29.886  -9.917  1.00 92.42           N1+
ATOM   5561  N    ILE A 707      17.415 -23.546  -5.657  1.00 90.71           N
ATOM   5562  CA   ILE A 707      17.054 -22.150  -5.486  1.00 90.43           C
ATOM   5563  C    ILE A 707      17.033 -21.536  -6.857  1.00 93.59           C
ATOM   5564  O    ILE A 707      18.013 -21.667  -7.595  1.00 93.81           O
ATOM   5565  CB   ILE A 707      18.086 -21.375  -4.625  1.00 99.37           C
ATOM   5566  CG1  ILE A 707      16.254 -21.999  -3.244  1.00 95.76           C
ATOM   5567  CG2  ILE A 707      17.712 -19.898  -4.497  1.00100.52           C
ATOM   5568  CD1  ILE A 707      19.167 -21.197  -2.352  1.00 99.86           C
ATOM   5569  N    TYR A 708      15.931 -20.882  -7.205  1.00105.65           N
ATOM   5570  CA   TYR A 708      15.865 -20.214  -8.498  1.00105.29           C
ATOM   5571  C    TYR A 708      15.763 -18.727  -8.269  1.00110.93           C
ATOM   5572  O    TYR A 708      15.553 -18.295  -7.140  1.00109.47           O
ATOM   5573  CB   TYR A 708      14.674 -20.713  -9.313  1.00 95.75           C
ATOM   5574  CG   TYR A 708      14.775 -22.172  -9.705  1.00 95.15           C
ATOM   5575  CD1  TYR A 708      14.695 -23.166  -8.756  1.00 92.65           C
ATOM   5576  CD2  TYR A 708      15.055 -22.558 -11.000  1.00 97.22           C
ATOM   5577  CE1  TYR A 708      14.710 -24.495  -9.080  1.00 93.02           C
ATOM   5578  CE2  TYR A 708      15.159 -23.889 -11.328  1.00 97.58           C
ATOM   5579  CZ   TYR A 708      14.981 -24.851 -10.363  1.00 95.84           C
ATOM   5580  OH   TYR A 708      15.084 -26.183 -10.675  1.00105.45           O
ATOM   5581  N    ARG A 709      15.924 -17.941  -9.326  1.00105.46           N
ATOM   5582  CA   ARG A 709      15.849 -16.492  -9.226  1.00112.72           C
ATOM   5583  C    ARG A 709      15.067 -15.898 -10.412  1.00118.53           C
ATOM   5584  O    ARG A 709      15.100 -16.434 -11.513  1.00119.72           O
ATOM   5585  CB   ARG A 709      17.254 -15.881  -9.119  1.00121.23           C
ATOM   5586  CG   ARG A 709      17.353 -14.434  -9.510  1.00126.00           C
ATOM   5587  CD   ARG A 709      18.767 -14.086  -9.955  1.00126.21           C
ATOM   5588  NE   ARG A 709      18.764 -12.983 -10.912  1.00137.13           N
ATOM   5589  CZ   ARG A 709      19.377 -12.998 -12.094  1.00137.42           C
ATOM   5590  NH1  ARG A 709      20.068 -14.067 -12.472  1.00133.08           N1+
ATOM   5591  NH2  ARG A 709      19.299 -11.941 -12.897  1.00142.64           N
ATOM   5592  N    LEU A 710      14.324 -14.825 -10.190  1.00147.24           N
ATOM   5593  CA   LEU A 710      13.546 -14.262 -11.282  1.00153.54           C
ATOM   5594  C    LEU A 710      14.485 -13.422 -12.130  1.00156.48           C
ATOM   5595  O    LEU A 710      15.427 -12.845 -11.592  1.00155.40           O
ATOM   5596  CB   LEU A 710      12.397 -13.398 -10.757  1.00106.46           C
ATOM   5597  CG   LEU A 710      11.263 -14.028  -9.959  1.00105.58           C
ATOM   5598  CD1  LEU A 710      10.240 -12.964  -9.559  1.00131.57           C
ATOM   5599  CD2  LEU A 710      10.605 -15.153 -10.725  1.00105.63           C
ATOM   5600  N    LYS A 711      14.241 -13.356 -13.441  1.00117.67           N
ATOM   5601  CA   LYS A 711      15.037 -12.497 -14.331  1.00121.40           C
ATOM   5602  C    LYS A 711      14.321 -11.202 -14.759  1.00129.26           C
ATOM   5603  O    LYS A 711      13.794 -11.103 -15.865  1.00133.81           O
ATOM   5604  CB   LYS A 711      15.528 -13.289 -15.543  1.00144.85           C
ATOM   5605  CG   LYS A 711      16.386 -14.506 -15.184  1.00140.44           C
ATOM   5606  CD   LYS A 711      16.914 -15.231 -16.428  1.00141.02           C
ATOM   5607  CE   LYS A 711      17.942 -14.386 -17.186  1.00144.33           C
```

Fig. 7CN

```
ATOM    5608  N2   LYS A 711      18.459 -15.054 -18.416  1.00145.28           N1+
TER     5609       LYS A 711
HETATM  5610  MG   MG  A 725       7.238 -20.902  20.363  1.00 78.14           MG
HETATM  5611  MG   MG  A 726      18.551  -8.728   7.448  1.00 65.51           MG
HETATM  5612  O    HOH A 901       8.245 -15.698  17.364  1.00 38.74           O
ATOM    5613  N    GLY B  10       6.225 -32.247  17.123  0.00137.40           N
ATOM    5614  CA   GLY B  10       4.949 -31.771  17.625  0.00136.00           C
ATOM    5615  C    GLY B  10       5.004 -30.350  18.175  1.00139.91           C
ATOM    5616  O    GLY B  10       4.295 -29.457  17.713  1.00139.47           O
ATOM    5617  N    ASP B  11       5.843 -30.143  19.180  1.00 95.22           N
ATOM    5618  CA   ASP B  11       5.984 -28.830  19.814  1.00 99.36           C
ATOM    5619  C    ASP B  11       6.595 -27.878  19.029  1.00101.34           C
ATOM    5620  O    ASP B  11       7.072 -26.739  19.652  1.00102.01           O
ATOM    5621  CB   ASP B  11       6.863 -28.969  21.035  1.00100.55           C
ATOM    5622  CG   ASP B  11       6.093 -29.278  22.244  1.00100.15           C
ATOM    5623  OD1  ASP B  11       5.562 -28.326  22.849  1.00103.83           O
ATOM    5624  OD2  ASP B  11       6.004 -30.474  22.581  1.00 95.33           O1-
ATOM    5625  N    GLN B  12       6.619 -27.720  17.703  1.00 89.48           N
ATOM    5626  CA   GLN B  12       7.335 -26.673  16.991  1.00 91.72           C
ATOM    5627  C    GLN B  12       6.461 -25.860  16.041  1.00101.19           C
ATOM    5628  O    GLN B  12       5.528 -26.387  15.456  1.00 96.32           O
ATOM    5629  CB   GLN B  12       8.370 -27.237  16.305  1.00161.37           C
ATOM    5630  CG   GLN B  12       9.614 -27.655  17.294  1.00147.52           C
ATOM    5631  CD   GLN B  12      10.747 -28.386  16.647  1.00138.34           C
ATOM    5632  NE2  GLN B  12      11.196 -27.879  15.504  1.00149.24           N
ATOM    5633  OE1  GLN B  12      11.227 -29.399  17.165  1.00139.01           O
ATOM    5634  N    ASN B  13       6.758 -24.564  15.915  1.00 84.63           N
ATOM    5635  CA   ASN B  13       5.990 -23.672  15.071  1.00 86.29           C
ATOM    5636  C    ASN B  13       6.239 -24.000  13.612  1.00 86.87           C
ATOM    5637  O    ASN B  13       6.857 -23.331  12.878  1.00 87.48           O
ATOM    5638  CB   ASN B  13       6.357 -22.226  15.354  1.00 86.64           C
ATOM    5639  CG   ASN B  13       5.266 -21.272  14.969  1.00 89.79           C
ATOM    5640  ND2  ASN B  13       4.763 -20.521  15.936  1.00 93.82           N
ATOM    5641  OD1  ASN B  13       4.864 -21.203  13.813  1.00 90.59           O
ATOM    5642  N    ALA B  14       5.762 -25.168  13.206  1.00101.34           N
ATOM    5643  CA   ALA B  14       5.931 -25.663  11.851  1.00 99.99           C
ATOM    5644  C    ALA B  14       4.564 -26.041  11.319  1.00 97.38           C
ATOM    5645  O    ALA B  14       3.577 -26.074  12.066  1.00 97.56           O
ATOM    5646  CB   ALA B  14       6.893 -26.842  11.813  1.00267.77           C
ATOM    5647  N    THR B  15       4.520 -26.356  10.035  1.00130.89           N
ATOM    5648  CA   THR B  15       3.304 -26.829   9.408  1.00129.51           C
ATOM    5649  C    THR B  15       3.222 -28.348   9.458  1.00121.11           C
ATOM    5650  O    THR B  15       4.237 -29.024   9.513  1.00116.50           O
ATOM    5651  CB   THR B  15       3.215 -26.349   7.962  1.00 95.48           C
ATOM    5652  CG2  THR B  15       2.079 -27.058   7.248  1.00 97.08           C
ATOM    5653  OG1  THR B  15       2.998 -24.929   7.954  1.00101.80           O
TER     5654       THR B  15
HETATM  5655  N    PPN B  16       1.996 -28.853   9.534  1.00119.43           N
HETATM  5656  CA   PPN B  16       1.646 -30.214   9.225  1.00112.66           C
HETATM  5657  C    PPN B  16       0.212 -30.058   8.834  1.00117.55           C
HETATM  5658  O    PPN B  16      -0.329 -28.966   9.142  1.00118.14           O
HETATM  5659  CB   PPN B  16       1.690 -31.092  10.418  1.00115.33           C
HETATM  5660  CG   PPN B  16       0.440 -30.774  11.156  1.00114.71           C
HETATM  5661  CD1  PPN B  16      -0.703 -31.540  11.007  1.00114.68           C
HETATM  5662  CD2  PPN B  16       0.424 -29.671  11.983  1.00119.20           C
HETATM  5663  CE1  PPN B  16      -1.860 -31.200  11.690  1.00119.79           C
HETATM  5664  CE2  PPN B  16      -0.726 -29.330  12.671  1.00123.87           C
HETATM  5665  CZ   PPN B  16      -1.873 -30.092  12.526  1.00124.26           C
HETATM  5666  N1   PPN B  16      -3.040 -29.712  13.271  1.00130.64           N
HETATM  5667  O1   PPN B  16      -3.089 -28.598  13.773  1.00135.59           O
HETATM  5668  O2   PPN B  16      -4.036 -30.532  13.438  1.00131.91           O
```

Fig. 7CO

```
ATOM   5669  N   GLY B  17      -0.437 -31.032   8.185  1.00114.32           N
ATOM   5670  CA  GLY B  17       0.188 -32.283   7.792  0.00113.36           C
ATOM   5671  C   GLY B  17      -0.761 -33.174   6.997  0.00120.47           C
ATOM   5672  O   GLY B  17      -0.916 -32.995   5.792  0.00122.60           O
CONECT 5649 5655
CONECT 5655 5649 5656
CONECT 5656 5655 5657 5659
CONECT 5657 5656
CONECT 5657 5658
CONECT 5657 5658
CONECT 5657 5659
CONECT 5658 5657
CONECT 5658 5657
CONECT 5659 5656 5660
CONECT 5660 5659
CONECT 5660 5661
CONECT 5660 5661
CONECT 5660 5661
CONECT 5660 5661
CONECT 5660 5662
CONECT 5660 5662
CONECT 5660 5662
CONECT 5660 5662
CONECT 5661 5660
CONECT 5661 5660
CONECT 5661 5660
CONECT 5661 5660
CONECT 5661 5663
CONECT 5661 5663
CONECT 5661 5663
CONECT 5661 5663
CONECT 5662 5660
CONECT 5662 5660
CONECT 5662 5660
CONECT 5662 5660
CONECT 5662 5664
CONECT 5662 5664
CONECT 5662 5664
CONECT 5662 5664
CONECT 5663 5661
CONECT 5663 5661
CONECT 5663 5661
CONECT 5663 5661
CONECT 5663 5665
CONECT 5663 5665
CONECT 5663 5665
CONECT 5663 5665
CONECT 5664 5662
CONECT 5664 5662
CONECT 5664 5662
CONECT 5664 5662
CONECT 5664 5665
CONECT 5664 5665
CONECT 5664 5665
CONECT 5664 5665
CONECT 5665 5663
CONECT 5665 5663
CONECT 5665 5663
CONECT 5665 5664
CONECT 5665 5664
```

Fig. 7CP

```
CONECT 5665 5664
CONECT 5665 5664
CONECT 5665 5666
CONECT 5666 5665
CONECT 5666 5667
CONECT 5666 5667
CONECT 5666 5667
CONECT 5666 5667
CONECT 5666 5668
CONECT 5666 5668
CONECT 5666 5668
CONECT 5666 5668
CONECT 5667 5666
CONECT 5667 5666
CONECT 5667 5666
CONECT 5667 5666
CONECT 5668 5666
CONECT 5668 5666
CONECT 5668 5666
CONECT 5668 5666
CONECT 5669 5657
END
```

RATIONAL DESIGN OF COMPONENTS OF THE OLIGO-SACCHARYLTRANSFERASE-CATALYSED ASPARAGINE-LINKED GLYCOSYLATION

This is a National Phase Application filed under 35 U.S.C. 371 as a national stage of PCT/EP2012/001902, filed May 3, 2012, and claiming the benefit from European Application No. 11003648, filed May 4, 2011, the content of each of which is hereby incorporated by reference in its entirety.

FIELD OF THE INVENTION

The present invention is directed to methods for identifying or designing (a) a potential oligosaccharide donor, (b) a potential oligosaccharyltransferase (OST), (c) a potential consensus sequence motif polypeptide, and/or (d) a potential glycosylation inhibitor for use in the oligosaccharyltransferase (OST)-catalysed asparagine-linked ("N-linked") glycosylation, comprising the steps of generating a three-dimensional model of the catalytic domain and/or the polypeptide binding site of the oligosaccharyltransferase (OST) of Campylobacter lari (SEQ ID NO:1), and designing or selecting a potential component selected from (a) to (d) which optimizes the stereochemical complementarity of said three-dimensional model(s) and the potential component.

The Sequence Listing submitted in text format (.txt) filed on Oct. 31, 2013, named "50241PCTsequencelisting.txt", (created on Oct 31, 2013, 9 KB), is incorporated herein by reference.

RELEVANT BACKGROUND OF THE INVENTION

It is estimated that more than half of all eukaryotic proteins are glycoproteins, which implies that specific amino acid side chains are chemically modified with carbohydrates. The most abundant form of these modifications is asparagine-linked ("N-linked") glycosylation, which affects a multitude of cellular functions that range from protein folding, quality control, sorting and secretion to organism development and host-pathogen interactions. Asparagines facing the lumen of the endoplasmic reticulum (ER) are specifically glycosylated when located in the consensus "sequon" Asn-X-Ser/Thr, where X may be any amino acid except proline. The reaction takes place at the membrane surrounding the ER and is catalysed by the enzyme oligosaccharyltransferase (OST), a hetero-oligomeric protein complex embedded in the ER membrane of higher eukaryotes (see FIG. 1b). A hallmark of N-linked glycosylation is its broad specificity with respect to the polypeptide substrate, which is a direct consequence of the short recognition sequon. This characteristic distinguishes OST from glycosyltransferases that modify serine or threonine residues (O-linked glycosylation) and exhibit a higher specificity for their protein substrates.

The key step in OST-catalysed glycosylation is the formation of an N-glycosidic linkage between the amide nitrogen of an acceptor asparagine and the C1 carbon of the first saccharide moiety of a lipid-linked oligosaccharide (LLO) donor (see FIG. 1a). This results in the en bloc transfer of the oligosaccharide onto the acceptor asparagine. Details of the underlying reaction mechanism are poorly understood. This is due to the absence of structural insight into OST at high resolution, but also to the complex chemical nature of the LLO substrate, its low abundance in biological samples, and its insolubility in water. In contrast, crystal structures of various soluble O-glycosyltransferases have been published and their reaction mechanisms were investigated in great detail. For OST, the currently accepted model suggests that glycosylation sequons are recognized when located in unfolded protein segments, which can occur during protein translocation into the ER or after translocation is completed. The central catalytically active component within OST is the STT3 subunit, whereas the other subunits are thought to assist and refine the process by facilitating OST complex assembly or by interacting with a subset of acceptor proteins or the LLO substrate, leading to an increased number of accessible and modified glycosylation sites.

N-linked glycosylation is not restricted to eukaryotes. Homologous processes are found in archaea and in defined taxa of proteobacteria. However, prokaryotes and eukaryotic kinetoplastids contain a single-subunit OST enzyme that is homologous to the STT3 subunit of higher eukaryotes. The best-studied prokaryotic N-glycosylation process is mediated by the protein glycosylation locus pgl from the bacterium Campylobacter jejuni (Szymanski et al. (1999) Molecular Microbiology 32, 1022-1030). The locus contains an integral membrane protein termed PglB that shares significant sequence similarity with eukaryotic STT3, suggesting a common membrane topology and reaction mechanism (see FIG. 1b). This gene cluster is sufficient for catalyzing protein glycosylation when transferred into Escherichia coli cells. OST-catalysed prokaryotic protein glycosylation of sequon-containing protein substrates is an economic, effective and convenient way of glycosylating recombinantly produced proteins (Wacker et al. (2002), Science 298, 1790-1793). N-linked protein glycosylation can be engineered with diverse O antigen lipopolysaccharide structures of non-C. jejuni origin in E. coli (Feldman et al. (2005) PNAS 102(8), 3016-3021), thus allowing for the prokaryotic transfer of eukaryotic N-glycans to recombinant protein substrates. Glover et al. (2005, Chemistry & Biology 12, 1311-1315) demonstrated for the first time the in vitro protein glycosylation using E. coli cell membranes comprising overexpressed PglB and an undecaprenyl pyrophosphate bound oligosaccharide. In 2006 Kowarik et al. (2006, EMBO J. 25(9), 1957-1966) further defined the bacterial N-glycosylation site consensus sequence by showing that the substrate specificity of bacterial OST is extended to a negatively charged amino acid in the −2 position of the acceptor asparagine, resulting in the consensus sequon Asp/Glu-$X_1$-Asn-$X_2$-Ser/Thr (wherein $X_1$ and $X_2$ are both not proline; SEQ ID NO: 3). By using a peptide substrate library, Chen et al. (2007, Biochemistry 46, 5579 -5585) confirmed the necessity for a negative charge in the −2 position of the acceptor asparagine and identified the sequence DQNAT (SEQ ID NO: 4) as the optimal substrate for C. jejuni PglB.

From the above it follows that the prokaryotic oligosaccharyltransferase (OST) has a broad, because small sequon-based specificity for protein substrates and can be used to transfer eukaryotic, prokaryotic as well as synthetic N-glycans. Essentially the prokaryotic OST-based N-glycosylation system requires three components, (a) an oligosaccharide donor, preferably a lipid- or undecaprenyl pyrophosphate-linked oligosaccharide donor, (b) a prokaryotic oligosaccharyltransferase (OST), (c) a potential consensus sequence motif polypeptide substrate and last but not least a suitable physiological microenvironment, e.g. cell membranes in vitro or in vivo.

The problem underlying the present information is that one cannot predict or design components essential for the very versatile prokaryotic OST-based N-glycosylation system beyond the information given for already known OST-components. In addition, there is no clue what structural requirements a potential OST glycosylation inhibitor must have. Such inhibitors would be expected to have pronounced biological effects and could be of great medical, diagnostic and scientific value. The other problem is that up to now it had not been possible to provide a three-dimensional model of the catalytic domain and the polypeptide binding site of an OST that could have provided the scientific community with insight regarding the possible variation of the components involved in OST-mediated glycosylation.

The above problems have been solved by the provision of the three-dimensional X-ray structure of a bacterial OST, the PglB protein from *Campylobacter lari* (SEQ ID NO:1; sharing 56% sequence identity with PglB of the *C. Jejuni*) in complex with the acceptor hexapeptide DQNATF (SEQ ID NO: 5). *C. lari* PglB (SEQ ID NO:1) is active when co-expressed with the *C. jejuni* pgl cluster in *E. coli* cells, as evidenced by glycosylation of an acceptor protein containing a consensus sequon (see FIG. 2). For its structural analysis, *C. lari* PglB (SEQ ID NO:1) was co-crystallized with the hexapeptide DQNATF (SEQ ID NO: 5) that contains the sequon glycosylated in the in vivo assay, which had been identified as the optimal acceptor sequence for *C. jejuni* PglB (see Chen et al. above). The structure of *C. lari* PglB (712 amino acid residues, SEQ ID NO: 1) was determined using a combination of experimental phasing and molecular replacement, making use of the previously determined structure of the periplasmic domain of *C. jejuni* PglB. Co-crystals of PglB (SEQ ID NO:1) were small, fragile, and diffracted X-rays anisotropically, with the best native data extending to 3.4 Å resolution. The structure was refined to R/R$_{free}$ values of 23.8 and 27.1%, respectively (Table 2). Further details of the structure of *C. lari* PglB (SEQ ID NO:1) are provided in the experimental section below.

This new three-dimensional structure provides insight into the molecular basis for sequon recognition and reveals a catalytic site that is formed by the transmembrane domain of the protein and features conserved, acidic side chain residues and a bound divalent cation. These results suggest for the first time a mechanism for amide nitrogen activation and glycosylation and provide a reasoned approach for identifying and designing new oligosaccharide donors, new oligosaccharyltransferase variants (OST), new consensus sequence motif polypeptides, as well as OST glycosylation inhibitors, all of which have utility in recombinant glycoprotein production, diagnostics, medicine and as scientific tools.

In view of the above, a first aspect of the invention relates to a method for identifying a potential component for the oligosaccharyltransferase (OST)-catalysed asparagine-linked ("N-linked") glycosylation selected from the group consisting of
(a) a potential oligosaccharide donor, preferably a lipid-linked oligosaccharide (LLO) or an undecaprenyl pyrophosphate bound oligosaccharide donor,
(b) a potential oligosaccharyltransferase (OST),
(c) a potential consensus sequence motif polypeptide, and
(d) a potential glycosylation inhibitor, comprising the steps of
(i) using the atomic coordinates of Table 1, preferably +2, more preferably +1.5, most preferably +1.0 Å root mean square deviation (rmsd) from the backbone atoms, for generating a three-dimensional model of the catalytic domain of the oligosaccharyl-transferase (OST) of *Campylobacter lari* (SEQ ID NO:1), comprising at least one, two, three, four, five, six, seven, most preferably all amino acids D56, R147, D154, D156, E319, R375, Y468, and H485 of SEQ ID NO:1, and/or, preferably and
(ii) using the atomic coordinates of Table 1, preferably +2, more preferably +1.5, most preferably +1.0 Å root mean square deviation (rmsd) from the backbone atoms, for generating a three-dimensional model of the polypeptide binding site of the oligosaccharyltransferase (OST) of *Campylobacter lari* (SEQ ID NO:1), comprising at least one, two, three, four, five, most preferably all of amino acids M318, R331, W463, W464, D465, and I572 of SEQ ID NO:1,
(iii) preferably performing whole body translations and/or rotations on the coordinates of the amino acids of the three-dimensional models of (i) and/or (ii),
(iv) using said three-dimensional model(s) of (i), (ii) and/or (iii) for designing or selecting at least one of potential components (a) to (d),
(v) providing at least one of said potential components (a) to (d), and
(vi) contacting at least one of said potential components (a) to (d) with the further functional components necessary for an oligosaccharyltransferase (OST)-catalysed asparagine-linked ("N-linked") glycosylation,
(vii) identifying a functional component selected from the group consisting of
(A) a functional oligosaccharide donor, preferably a functional lipid-linked oligosaccharide (LLO) donor or an undecaprenyl pyrophosphate bound oligosaccharide donor,
(B) a functional oligosaccharyltransferase (OST),
(C) a functional consensus sequence motif polypeptide, and
(D) a functional glycosylation inhibitor.

In a preferred embodiment, in step (ii) the three-dimensional model of the polypeptide binding site of the oligosaccharyltransferase (OST) of *Campylobacter lari* (SEQ ID NO:1) comprises at least two, preferably at least three, more preferably at least four, most preferably all of amino acids M318, A331, W463, W464, D465 and I572 of SEQ ID NO: 1.

The atomic coordinates of Table 1 for use in the methods of the present invention are shown in FIG. 7. The X-ray coordinates of the OST of *C. lari* (SEQ ID NO:1), in particular of the catalytic site and/or the polypeptide binding site complexed with the optimized polypeptide substrate DQNAT (SEQ ID NO: 4) provide the skilled person with the three-dimensional information necessary for identifying a potential component for OST catalysis and catalytic inhibition. The spatial restrictions in combination with the chemical functional nature of the individual atoms of the amino acids involved in catalytic action and polypeptide binding, e.g. electron densities, position of van der Waals forces, ionic interactions, hydrophobic interactions, etc., inform the person skilled in computer-assisted molecular modelling of the structural and spatial prerequisites of (a) a potential oligosaccharide donor, preferably a lipid-linked oligosaccharide (LLO) or an undecaprenyl pyrophosphate bound oligosaccharide donor; (b) a potential oligosaccharyltransferase (OST), (c) a potential consensus sequence motif polypeptide, and/or (d) a potential glycosylation inhibitor.

As described before bacterial OSTs have a broad specificity for oligosaccharide donor molecules. With the coordinate information and the method of the invention, the repertoire of useful oligosaccharide donors can be rationally designed and extended without having to revert to trial and error synthetic strategies. Also, the OST itself can be rationally varied without rendering the catalytic site and the polypeptide binding pocket non-functional. This OST variation is useful, for example for modifying the catalytic potential, polypeptide substrate specificity and/or oligosaccharide donor specificity of OSTs. Moreover, the consensus motif of the polypeptide oligosaccharide acceptor can be rationally varied and designed, thus leading to the broadening of the OST utility such as e.g. glycosylation of eukaryotic sites. Last but not least, the inventive three-dimensional X-ray model provides an excellent basis for designing potential glycosylation inhibitors, which can be expected to be physiologically active by interrupting, modifying or slowing OST activity. These inhibitors have a great potential for providing scientific, diagnostic and therapeutic tools.

The term "root mean square deviation" or "rms deviation" or "rmsd" means the square root of the arithmetic mean of the square of the deviations from the mean. In the context of atomic objects the numbers are given in angstroms (Å). It is a way of expressing the deviation or variation from a trend or object.

The method of the invention comprises the step of using the atomic coordinates of Table 1, preferably +2, more preferably +1.5, most preferably +1.0 Å root mean square deviation (rmsd) from the backbone atoms, for generating a three-dimensional model of the catalytic domain of the oligosaccharyltransferase (OST) of *Campylobacter lari* (SEQ ID NO:1), comprising at least one, two or three, preferably at least four, more preferably at least five or six, most preferably seven or all of amino acids D56, R147, D154, D156, E319, R375, Y468, and H485 of SEQ ID NO:1, and/or, preferably and using the atomic coordinates of Table 1, preferably +2, more preferably +1.5, most preferably +1.0 Å root mean square deviation (rmsd) from the backbone atoms, for generating a three-dimensional model of the polypeptide binding site of the oligosac-charyltransferase (OST) of *Campylobacter lari* (SEQ ID NO:1), comprising at least one or two, preferably at least three, more preferably at least four or five, most preferably all of amino acids M318, R331 (or A331), W463, W464, D465, and I572 of SEQ ID NO:1.

At the polypeptide binding site W463, W464 and D465 of SEQ ID NO:1 form strong hydrogen bonds to the β-hydroxyl group of T in the bound acceptor sequon. These residues strongly contribute to acceptor sequon binding and are the reason why an S or T is located at the +2 position of the acceptor asparagine (N—X—S/T). R331 of SEQ ID NO:1 forms a salt bridge to the negatively charged D of the acceptor polypeptide and therefore contributes to acceptor sequon binding. R331 of SEQ ID NO:1 is responsible for the requirement of a negatively charged amino acid in the −2 position of the acceptor asparagine and is responsible for the extension of the consensus sequon for bacterial N-linked protein glycosylation (D/E-$X_1$—N—$X_2$—S/T; SEQ ID NO: 3) (FIG. 4*a*). R331 of SEQ ID NO:1 is only conserved in bacterial OSTs and can serve as a target for changing the substrate specificity of PglB towards the recognition of eukaryotic glycosylation sites. In fact, when R331 of SEQ ID NO:1 is mutated to A, the resulting glycosylation site AQNAT (SEQ ID NO: 8) in an acceptor protein, e.g. modified scFv fragment 3D5 originally containing the sequon DQNAT (SEQ ID NO: 4), can be glycosylated, whereas this site does not serve as a substrate for the wild type enzyme (FIG. 4*b*).

At the catalytic site, D56, D154 and E319 of SEQ ID NO:1 seem responsible for the coordination of the bound divalent metal ion, which is essential for catalysis. More importantly, D56 and E319 of SEQ ID NO:1 form hydrogen bonds to the amido group of the asparagine side chain of the bound acceptor sequon. This interaction causes a rotation of the C—N bond in the amido group, which is important for the nucleophilic activation of the nitrogen. D156 and R147 of SEQ ID NO:1 stabilize the hydrogen bonding network and R375 of SEQ ID NO:1 complexes the negative charge of one of the phosphates of a bound lipid-linked oligosaccharide (LLO).

For example, in the polypeptide binding site W463, W464 and D456 of SEQ ID NO:1 could be replaced by two H and an E (WWD→HHE). To keep the requirement of the negative charge in the −2 position of the acceptor asparagine, R331 of SEQ ID NO:1 could be replaced by K. To create the requirement of a positive charge in this position, R331 of SEQ ID NO:1 could be replaced by D or E. To overcome the requirement of the negative charge in the −2 position of the acceptor asparagine, R331 of SEQ ID NO:1 can be replaced by A (FIG. 4). At the catalytic site D154 and D156 of SEQ ID NO:1 can be replaced by E each. E319 of SEQ ID NO:1 could be replaced by D and D56 of SEQ ID NO:1 could be replaced by E, respectively (see below). To modify PglB activity, for example, D56, D154 and E319 of SEQ ID NO:1 could be replaced by alanines or the corresponding amino function (N or Q). H485 of SEQ ID NO:1 could be replaced by W as W appears in eukaryotic OSTs at this position.

The structure coordinates of PglB from *C. lari* (SEQ ID NO:1) as listed in Table1 in FIG. 7 are accessible for download to the skilled person from the pdb database. (The research collaboratory for structural bioinformatics (RCSB) Protein Database (PDB)). With the help of a computer and freely accessible structure programs such as PyMOL or commercially available structure programs the skilled person can easily generate three-dimensional models useful for the claimed method.

Those of skill in the art will understand that a set of structure coordinates for a protein, protein/substrate or protein/inhibitor complex or a portion thereof is a relative set of points that defines a shape in three dimensions. Thus, it is possible that an entirely different set of coordinates could define a similar or identical shape. For this reason it is preferred to perform whole body translations and/or rotations on the coordinates of the amino acids of the three-dimensional models (i) and/or (ii) obtained from the atomic coordinates of Table 1. These variations in coordinates may be generated by mathematical manipulations of the structure coordinates, for example manipulation by crystallographic permutations of the structure coordinates, fractionalization or matrix operations to sets of structure coordinates or any combination of the above.

Next, the above generated three-dimensional models are used for designing or selecting at least one of the potential components of the OST glycosylation or a potential inhibitor. Various computational analyses are necessary to determine whether a molecule such as a specific oligosaccharide donor, a modified OST, an oligosaccharide acceptor consensus sequence motif polypeptide or a glycosylation inhibitor is sufficiently designed to rationally predict its functionality in the OST-catalysed reaction. Spatial, functional and chemical considerations such as the nature, position of atoms, rotational degree of freedom, electron density, steric hindrance, van der Waals, ionic and hydrophobic interactions, etc. will have to be made. Such analysis may be carried out conveniently on computers by standard software applications such as CCP4 (COLLABORATIVE COMPUTATIONAL PROJECT, NUMBER 4. 1994. "The CCP4 Suite: Programs for Protein Crystallography". Acta Cryst. D50, 760-763.)

Current computational molecular similarity applications permit comparisons between different structures, different conformations of the same structure and different parts of the same structure. The comparison procedure is typically divided into four steps: (1) loading the structural information, (2) defining atom equivalence on these structures, (3) performing a fitting (superimposition) operation and (4) analysis of the results. Each structure is identified by a name. One structure is then identified as the potential OST component or OST inhibitor (i.e. the target or fixed structure), all remaining structures are working structures (i.e. moving structures). When a rigid fitting method is used the working structure is translated and rotated to obtain an optimum fit (spatial and functional complementarity) with the target structure, e.g. an OST inhibitor is the fixed structure and the OST amino acids are translated and rotated to obtain the optimum fit. The fitting operation uses an algorithm that computes the optimum translation and rotation to be applied to the moving structure, such that the rmsd of the fit over the specified pairs of equivalent atom is an absolute minimum. After superimposition of the two structures an rmsd value can be calculated for specific sets of equivalent atoms.

The potential functional component or inhibitor of the OST reaction selected or designed according to the inventive method as described above will provide the skilled person with a reasonable expectation of success when verifying its functionality in a routine OST activity assay. For said purpose the potential component must be provided by purchase, modification of purchased materials, chemical and/or recombinant synthesis, etc. This potential component will then have to be contacted with the further functional components necessary for an OST-catalysed asparagine-linked ("N-linked") glycosylation, of course under conditions that allow for OST activity. Preferred OST activity assays are described in (1) 2005 Chemistry & Biology 12, 1311-1315, (2) 2006 Science 314, 1148-1150, (3) 2007 Biochemistry 46, 5579-5585, (4) 2007 Glycobiology 11, 1175-1182 and (5) 2011 Glycobiology 5, 575-583. Whether or not the potential components or inhibitor is OST active is preferably verified in comparison to positive or negative standards. For example, functionality of the OST assay is established with a known oligosaccharide acceptor polypeptide, e.g. the hexapeptide DQNATF (SEQ ID NO: 5), and then the potential functional consensus sequence motif polypeptide is substituted for the hexapeptide and glycosylation of the substitute polypeptide is determined. This simple OST assay system can be adapted for identifying any functional OST components, preferably one selected from the group consisting of (A) a functional oligosaccharide donor, preferably a functional lipid-linked oligosaccharide (LLO) or an undecaprenyl pyrophosphate bound oligosaccharide donor, (B) a functional oligosaccharyltransferase (OST), (C) a functional consensus sequence motif polypeptide, and (D) a functional glycosylation inhibitor.

In a second aspect, the present invention relates to a method for designing a potential component for the oligosaccharyltransferase (OST)-catalysed asparagine-linked ("N-linked") glycosylation selected from the group consisting of (a) a potential oligosaccharide donor, preferably a lipid-linked oligosaccharide (LLO) or an undecaprenyl pyrophosphate bound oligosaccharide donor, (b) a potential oligosaccharyltransferase (OST), (c) a potential consensus sequence motif polypeptide, and (d) a potential glycosylation inhibitor, comprising the steps of (i) using the atomic coordinates of Table 1, preferably +2, more preferably +1.5, most preferably +1.0 Å root mean square deviation (rmsd) from the backbone atoms, for generating a three-dimensional model of the catalytic domain of the oligosaccharyl-transferase (OST) of Campylobacter lari (SEQ ID NO:1), comprising at least one, two or three, preferably at least four or five, more preferably at least six or seven, most preferably all amino acids D56, R147, D154, D156, E319, R375, Y468, and H485 of SEQ ID NO:1, and/or, preferably and (ii) using the atomic coordinates of Table 1, preferably +2, more preferably +1.5, most preferably +1.0 Å root mean square deviation (rmsd) from the backbone atoms, for generating a three-dimensional model of the polypeptide binding site of the oligo-saccharyltransferase (OST) of *Campylobacter lari* (SEQ ID NO:1), comprising at least one or two, preferably at least three, more preferably at least four or five, most preferably all of amino acids M318, R331, W463, W464, D465, and I572 of SEQ ID NO:1, (iii) preferably performing whole body translations and/or rotations on the coordinates of the amino acids of the three-dimensional models of (i) and/or (ii), (iii.1) using said three-dimensional model of (i), (ii) and/or (iii) for assessing the stereochemical complementarity between said three-dimensional model(s) (i), (ii) and/or (iii) and a known or potential component for the oligosaccharyltransferase (OST)-catalysed asparagine-linked ("N-linked") glycosylation selected from an oligosaccharide donor, preferably a lipid-linked oligosaccharide (LLO) donor or an undecaprenyl pyrophosphate bound oligosaccharide donor, a consensus sequence motif polypeptide, and a potential glycosylation inhibitor, or (iii.2)varying at least one amino acid in said three-dimensional model of (i), (ii) and/or (iii) and using said varied three-dimensional model of (i), (ii) and/or (iii) for assessing the stereochemical complementarity between said three-dimensional models (i), (ii) and/or (iii) and a known or potential component for the oligosaccharyltransferase (OST)-catalysed asparagine-linked ("N-linked") glycosylation selected from an oligosaccharide (LLO) donor, preferably a lipid-linked oligosaccharide (LLO) donor or an undecaprenyl pyrophosphate bound oligosaccharide donor, a consensus sequence motif polypeptide, and a potential glycosylation inhibitor, (iv) optimizing said sterochemical complementarity in an iterative approach by observing changes in the three-dimensional model of (iii.1), (iii.2) or the component for the oligosaccharyltransferase (OST)-catalysed asparagine-linked ("N-linked") glycosylation, (v) designing a potential component selected from (a) to (d) which optimizes said stereo-chemical complementarity of said three-dimensional model(s) and potential component, (vi.1)optionally providing the optimized potential component, and (vi.2)contacting at least one of said potential components (a) to (d) with the further functional components necessary for an oligosaccharyltransferase (OST)-catalysed asparagine-linked ("N-linked") glycosylation, (vi.3)identifying a functional component selected from the group consisting of (A) a functional oligosaccharide donor, preferably a functional lipid-linked oligosaccharide (LLO) or an undecaprenyl pyrophosphate bound oligosaccharide donor, (B) a functional oligosaccharyltransferase (OST), (C) a functional consensus sequence motif polypeptide, and (D) a functional glycosylation inhibitor.

In a preferred embodiment, in step (ii) the three-dimensional model of the polypeptide binding site of the oligosaccharyltransferase (OST) of *Campylobacter lari* (SEQ ID NO:1) comprises at least two, preferably at least three, more preferably at least four, most preferably all of amino acids M318, A331, W463, W464, D465 and I572 of SEQ ID NO:1.

This method is basically very similar to the method of the first aspect except that in the method directly above the potential OST component is designed by optimizing its stereochemical complementarity to the three-dimensional models with or without whole body translations and rotations in an iterative approach by observing changes in the three-dimensional models or the component for the oligosaccharyltransferase (OST)-catalysed asparagine-linked ("N-linked") glycosylation, when varying at least one amino acid in at least one of said three-dimensional models.

Once the designed potential OST component is selected based on its optimized stereo-chemical complementarity to said three-dimensional model(s) it can optionally be verified in an OST assay, preferably by providing the optimized potential component (by chemical and/or recombinant synthesis, purchase, modification of known compounds, etc.), contacting said optimized potential component with the further functional components necessary for an oligosaccharyltransferase (OST)-catalysed asparagine-linked ("N-linked") glycosylation. In a last optional step the functional component of the OST reaction or an inhibitor thereof is identified by its impact on the OST reaction. Typically, positive and negative reference components are used to verify OST assay activity.

In a preferred embodiment of the methods of the present invention for identifying or designing potential OST components, the specific three-dimensional catalytic site model of step (i) further comprises one or more, preferably at least 5, more preferably at least 10, most preferably all of the amino acids selected from the group having residues located within Van der Waals distance to the bound peptide of SEQ ID NO: 2, preferably selected from those within a distance of 5 Å to said peptide, more preferably selected from the group consisting of T53, T54, N55, D56, N146, R147, Y152, E315, T316, I317, M318, E319, V320, N321, R331, L374, R375, Y433, S435, V438, W463, W464, D465, G482, H485, I572, V575 of SEQ ID NO:1.

In a further aspect the present invention relates to a machine-readable medium comprising, e.g. storing
(i) the atomic coordinates of Table 1, preferably +2, more preferably +1.5, most preferably +1.0 Å root mean square deviation (rmsd) from the backbone atoms, preferably comprising at least one, two or three, preferably at least four or five, more preferably at least six or 7, most preferably all of amino acids D56, R147, D154, D156, E319, R375, Y468, and H485 of SEQ ID NO:1, and/or, preferably and
(ii) the atomic coordinates of Table 1, preferably +2, more preferably +1.5, most preferably +1.0 Å root mean square deviation (rmsd) from the backbone atoms, for generating a three-dimensional model of the polypeptide binding site of the oligosaccharyltransferase (OST) of Campylobacter lari (SEQ ID NO:1), comprising at least one or two, preferably at least three, more preferably at least four or five, most preferably all of amino acids M318, R331 (or A331) , W463, W464, D465, and I572 of SEQ ID NO:1,
(iii) preferably the atomic coordinates of (i) or (ii) modified by performing whole body translations and/or rotations on said coordinates.

The above medium is particularly useful for a variety of purposes such as computer-assisted drug design, drug discovery and the X-ray crystallographic analysis of OSTs from other bacteria.

In the following the present invention will be further illustrated with reference to specific embodiments and experiments which are not intended to be interpreted as limiting the scope of the invention as presented by the appended claims.

SEQ ID NO: 1 lists the 712 amino acids of the oligosaccharyltransferase (OST) of C. lari PglB.

MELQQNFTDNNSIKYTCILILIAFAFSVLCRLYWVAWASEFYEFFFNDQL

MITTNDGYAFAEGARFDMIAGFHQPNDLSYFGSSLSTLTYWLYSILPFSF

ESIILYMSTFFASLIVVPIILIAREYKLTTYGFIAALLGSIANSYYNRTM

SGYYDTDMLVLVLPMLILLTFIRLTINKDIFTLLLSPIFIMIYLWWYPSS

YSLNFAMIGLFGLYTLVFHRKEKIFYLAIALMIIALSMLAWQYKLALIVL

LFAIFAFKEEKINFYMIWALIFISISILHLSGGLDPVLYQLKFYVFKASD

VQNLKDAAFMYFNVNETIMEVNTIDPEVFMQRISSSVLVFILSFIGFILL

CKDHKSMLLALPMLALGFMALRAGLRFTIYAVPVMALGFGYFLYAFFNFL

EKKQIKLSLRNKNILLILIAFFSISPALMHIYYYKSSTVFTSYEASILND

LKNKAQREDYVVAWWDYGYPIRYYSDVKTLIDGGKHLGKDNFFSSFVLSK

EQIPAANMARLSVEYTEKSFKENYPDVLKAMVKDYNQTSAKDFLESLNDK

NFKFDTNKTRDVYIYMPYRMLRIMPVVAQFANTNPDNGEQEKSLFFSQAN

AIAQDKTTGSVMLDNGVEIINDFRALKVEGASIPLKAFVDIESITNGKFY

YNEIDSKAQIYLLFLREYKSFVILDESLYNSAYIQMFLLNQYDQDLFEQV

TNDTRAKIYRLKR

SEQ ID NO: 2 lists the amino acids of the hexapeptide DQNATF{pNO₂} (where F{pNO₂} is paranitro-phenylalanine) representing the optimised oligosaccharide acceptor substrate for the OST (SEQ ID NO:1). This hexapaptide was crystallized together with the OST of C. lari PglB (SEQ ID NO:1) to give the atomic structure coordinates of Table 1 below, the statistics of which are provided in Table 2.

Table 1 is shown in FIG. 7. It lists the atomic structure coordinates of the crystallized oligosaccharyltransferase (OST, chain A) of Campylobacter lari (SEQ ID NO:1) complexed with peptide sequence DQNATF{pNO₂} (SEQ ID NO: 2) (chain B), the optimal substrate for OST glycosylation and a bound divalent metal ion (chain C), useful for generating a three-dimensional model of the catalytic domain of the oligosaccharyltransferase (OST) of Campylobacter lari (SEQ ID NO:1). The table contains following information:

| COLUMNS | CONTENTS |
|---|---|
| 1-6 | Atom |
| 7-11 | Atom serial number |
| 13-16 | Atom name |
| 17 | Alternate location indicator |
| 18-20 | Residue name |
| 22 | Chain identifier |
| 23-26 | Residue sequence number |
| 27 | Code for insertion of residues |
| 31-38 | Orthogonal coordinates for X in Angstroms |
| 39-46 | Orthogonal coordinates for Y in Angstroms |
| 47-54 | Orthogonal coordinates for Z in Angstroms |
| 55-60 | Occupancy |

-continued

| COLUMNS | CONTENTS |
|---|---|
| 61-66 | Temperature factor (Default = 0.0) |
| 73-76 | Segment identifier, left-justified |
| 77-78 | Element symbol, right-justified |
| 79-80 | Charge on the atom |

Table 2 lists the X-ray data collection and refinement statistics for Table 1 in FIG. 7.

A. Data Collection Statistics

| Data set | Native | EMP1 | EMP2 | EMP3 |
|---|---|---|---|---|
| Beamline/detector | MD2 at SLS S06SA/PX1 (Mar225) | HighRes at SLS S06SA/PX1 (Pilatus) | MD2 at SLS S06SA/PX1 (Mar225) | MD2 at SLS S06SA/PX1 (Mar225) |
| Software | XDS/HKL | XDS | HKL | HKL |
| Wavelength (Å) | 1.0 | 1.0 | 1.0 | 1.0 |
| Space group | $P2_12_12_1$ | $P2_12_12_1$ | $P2_12_12_1$ | $P2_12_12_1$ |
| Unit cell: a (Å) | 85.06 | 85.5 | 86.1 | 87.8 |
| b (Å) | 116.1 | 116.4 | 117.0 | 119.4 |
| c (Å) | 175.04 | 175.2 | 174.8 | 169.9 |
| Resolution | 30-3.4 | 30-4.45 | 30-3.8 | 30-4.2 |
| Crystal positions collected | 12 | 3 | | 4 |
| Completenes (%) | 99.3% (97.6%) | 99.6% (100%) | 92.3 (68.3) | 96.9 (84.2) |
| Redundancy | 9.6 (8.7) | 11.1 | 9.2 (7.3) | 9.2 (7.2) |
| <I/□(I)> | 13.2 (1.3) | 10.8 (2.25) | 11.1 (0.8) | 13.2 (2.6) |
| $R_{mgd}$-F (XDS) (%) | 13.9 (132.8) | 15.2 (86.3) | | |
| Rmrgd (HKL) (%) | | | $13.3^a$ | 16 (50.7) |

$^a$No Rmrgd factors indicated by HKL due to severe anisotropy

B. Refinement Statistics (Native Data)

| Resolution (Å) | 30-3.4 |
|---|---|
| No. of reflections working set (test set) | 21834 (2000) |
| $R_{work}/R_{free}$ (%) | 23.8/27.1 |
| rmsd from ideality | |
| bond lengths (Å) | 0.011 |
| bond angles (°) | 1.475 |
| Average B factor (Å$^2$) | |
| PglB | 129 |
| Peptide | 117 |
| Ramachandran analysis (Molprobity) | |
| Ramachandran favored | 82.6% |
| Ramachandran outliers | 1.5% |

BRIEF DESCRIPTION OF THE DRAWINGS

FIG. 2 shows the activity of C. lari oligosaccharyltransferase PglB (SEQ ID NO:1). E. coli cells were transformed with a combination of three separate plasmids: (i) The glycosylation machinery of C. jejuni that generates LLO, but contains inactivated PglB; (ii) An acceptor protein (modified scFv fragment 3D5) containing the sequon DQNAT (SEQ ID NO: 4) and (iii) Functional C. lari PglB (SEQ ID NO:1). Note that the co-crystal structure presented here contains C. lari PglB (SEQ ID NO:1) bound to an acceptor peptide containing the sequence used in the assay. Glycosylation of the acceptor protein was analyzed from periplasmic extracts, whereas expression of PglB was analyzed from whole cell extracts. Proteins were analyzed by immunoblot using anti-c-Myc antibody detecting scFv substrate (top), glycan-specific antiserum hR6 (middle), or anti-HA antiserum detecting PglB (bottom). PglB constructs are indicated above the lanes: Vector control (ev), wild type (wt), or mutations in single letter code. Glycosylation of 3D5 results in a mobility shift from the unmodified form (g0) to the glycosylated form (g1). Functional PglB is partially auto-glycosylated at N535 and N556 of SEQ ID NO:1, resulting in two additional bands (g1 and g2). All experiments were performed at least in triplicate, and representative samples are shown.

FIG. 7: Table 1, which contains the atomic coordinates for the three-dimensional structure of residues 2-711 of SEQ ID NO:1 (SEQ ID NO:9) complexed with its peptide substrate (SEQ ID NO:2).

EXAMPLES

Figure 1:
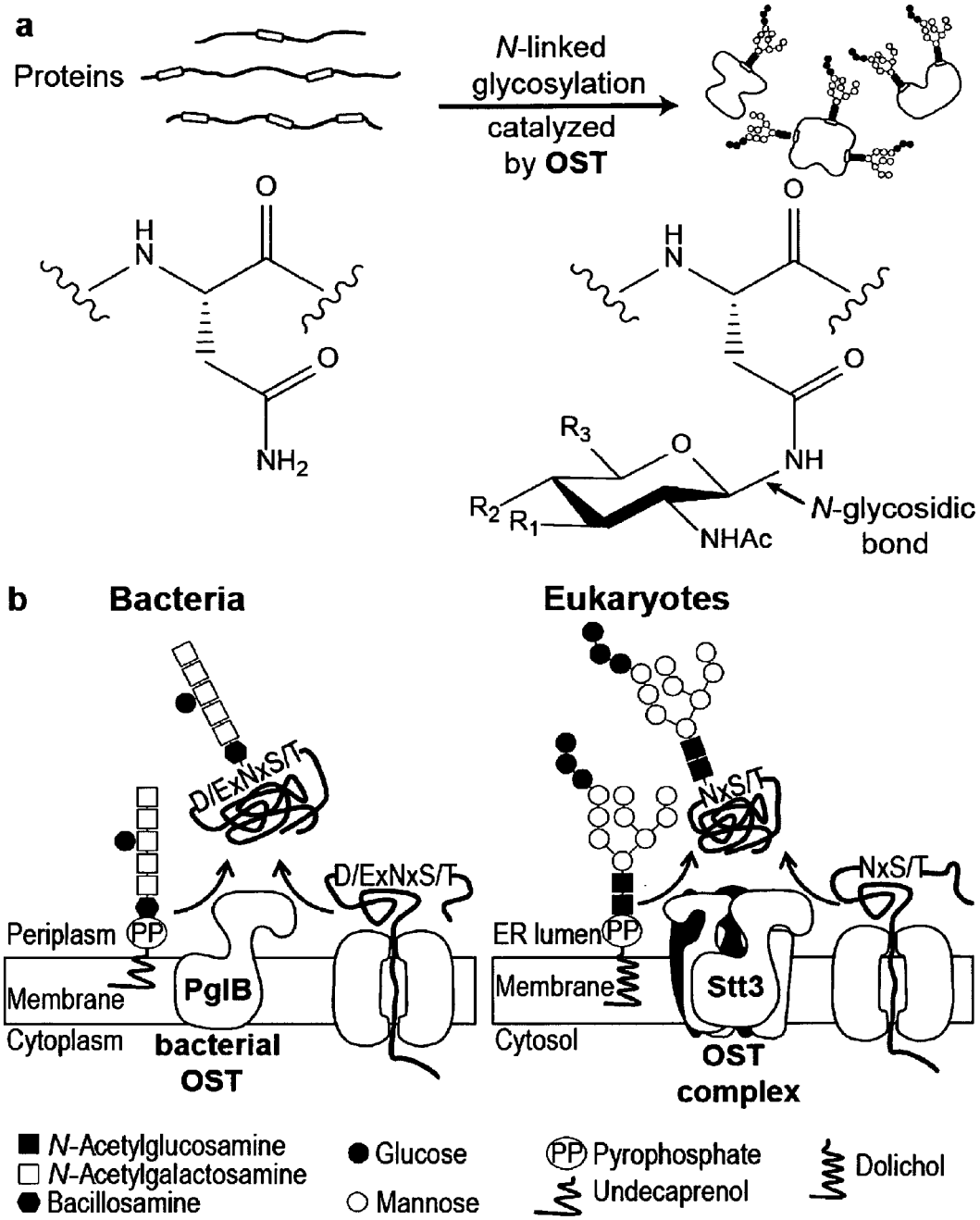
FIG. 1 shows schematically the process of N-linked protein glycosylation. a. Proteins containing acceptor sequons (NxT/S in eukaryotes, D/Ex$_1$Nx$_2$T/S (SEQ ID NO: 3) in bacteria) are glycosylated at the asparagine residue by the action of OST. The chemical reaction includes an activation of the amide nitrogen and the formation of a glycosidic bond. b. Similarities and distinct characteristics of N-linked glycosylation in bacteria (left panel) and eukaryotes (right panel). The central enzyme of OST is STT3 (PglB in bacteria), which is conserved in sequence and structure in all domains of life. The lipid moieties and the oligosaccharide are similar but non-identical in bacteria and eukaryotes, as indicated. Both contain an isoprenoid-pyrophosphate moiety that is hydrolysed after the glycosylation step.

Methods
In Vivo Complementation

To analyze the activity of PglB from C. lari (SEQ ID NO:1) in vivo the gene encoding pgIB was amplified from the pgl gene cluster of Campylobacter lari isolate (sample kindly provided by H. Hächler, Luzern, Switzerland) genomic DNA by polymerase chain reaction (PCR) and was cloned into a pMLBAD plasmid (Lefebre & Valvano, Appl. Environ. Microb. 68, 5956-5964 (2002) with a C-terminal HA-tag fused to PglB, resulting in the plasmid pMIK71. For complementation studies pMIK71 or pMLBAD empty vector were transformed into E. Coli SCM6 cells carrying the plasmids pCL21 (2011 Bioconjug Chem. 3, 488-496) or pCL64 and pACYCpgl$_{mut}$ (Wacker et al., Science 298, 1790-1793 (2002). pCL21 encodes for the expression of the single-chain Fv fragment of 3D5 carrying a DQNAT (SEQ ID NO: 4) glycosylation site in the linker region and a C-terminal Myc-tag fused to 3D5. In pCL64 the DQNAT site of pCL21 was replaced by an AQNAT (SEQ ID NO: 8) glycosylation site. pACYCpgl$_{mut}$ encodes for the biosynthesis of the C. jejuni lipid-linked oligosaccharide (LLO) with an inactivated C. Jejuni pgIB gene (W458A and D459A). A 5 mL pre-culture was inoculated from a single clone and grown over night at 37° C. in LB medium. The main culture was inoculated to an optical density ($A_{600}$) of 0.05 in 15 mL LB medium and grown at 37° C. to $A_{600}$ of 0.5. The culture was induced by addition of arabinose to 0.1% (w/v) and grown for 4 h at 24° C. For extraction of periplasmic proteins an equivalent of 1mL culture volume with an $A_{600}$ of 3.0 was harvested by centrifugation, resuspended in 150 µL extraction buffer, consisting of 30 mM Tris-HC1, pH 8.5; 20% (w/v) sucrose; 1 mM EDTA and 1 mg/mL lysozyme (Sigma) and incubated for 1 h at 4° C. A final centrifugation step yielded periplasmic proteins in the supernatant. Glycosylation of 3D5 and expression of PglB were analyzed by SDS-PAGE (performed according to Lämmli). Immunodetection was performed with anti-c-Myc monoclonal antibody (Calbiochem) and anti-glycan serum hR6 (Amber S. and Aebi M., personal communication) to observe glycosylated 3D5. Immunodetection of C. lari PglB was performed with anti-HA antiserum (Santa Cruz).

Mutagenesis Study

Mutant PglB was generated by QuickChange method. Plasmid pCL64 was generated by ligation of phosphorylated, double stranded DNA of oligonucleotides CTAGCG-GTGGTGGTGGTTCTGGTGGTGGTGCCCA-GAACGCCA fSEQ ID NO:10) and CCGGTGGCGTTCTGGGCACCACCACCAGAACCAC-CACCACCG k SEQ ID NO:11) and into the plasmid pCL21 digested with Nhel and Agel. The resulting plasmids of all constructs were validated by DNA sequencing. The mutant PglB variants were cloned into pMLBAD as above and used in complementation assays.

PglB Purification

The gene encoding pgIB was cloned into a modified pBAD (Invitrogen) expression plasmid with a C-terminal decahistidine affinity tag fused to PglB, resulting in the plasmid pSF2. Due to the applied cloning strategy PglB carried the mutation K2E and the plasmid was confirmed by DNA sequencing (Microsynth). PglB from C. lari (SEQ ID NO:1) was overexpressed from pSF2 in Escherichia coli BL21-Gold (DE3) (Stratagene) cells in a 30 L fermentor (Infors). Cells were grown at 37° C. in Terrific Broth medium supplemented with 1% glycerol (w/v) to an optical density ($A_{600}$) of 10.0 before the culture was induced by the addition of 0.1% arabinose (w/v) for 2h. All following steps were performed at 4° C. unless specified differently. Cells were harvested by centrifugation, resuspended in 25 mM Tris-HC1, pH 8.0; 250 mM NaCl and disrupted in a M-110L microfluidizer (Microfluidics) at 15.000 psi external pressure. Membranes were pelleted by ultracentrifugation at 100.000 g for 0.5 h. PglB was solubilized in 25 mM Tris-HC1, pH 8.0; 250 mM NaCl; 10% glycerol (v/v) and 1% N-dodecyl-β-D-maltopyranoside (w/v) (DDM, Anatrace) for 1 h. All subsequent buffers contained DDM as detergent. The supernatant was supplemented with 25 mM imidazole and loaded onto a NiNTA superflow affinity column (Qiagen), washed with 60 mM imidazole before PglB was eluted with 200 mM imidazole. The protein was desalted into 10 mM MES-NaOH, pH6.5; 100 mM NaCl; 0.5 mM EDTA; 3% glycerol (v/v); 3% polyethylene glycol 400 (v/v) and concentrated to 7-10 mg/mL in an Amicon Ultra-15 concentrator (Millipore) with a molecular weight cut off of 100 kDa.

Native Crystals

The peptide Ac-DQNATF{4NO$_2$}-NH$_2$ (SEQ ID NO: 6) was added to concentrated PglB to a final concentration of 0.75 mM, incubated for 0.5 h, and crystallized by vapor diffusion in sitting drops at 20° C. against a reservoir of 100 mM glycine, pH 9.4; 50 mM magnesium acetate; 6% Dimethyl sulfoxide (DMSO) (v/v) and 23-34% (v/v) polyethylene glycol 400. The protein to reservoir volume ratio in the sitting drop was 2:1. Crystals typically appeared after three to four weeks and matured to full size within six weeks. Crystals were directly flash-frozen by immersion in liquid nitrogen prior to data collection.

Heavy Metal Derivatives

Native crystals were soaked for 30-60 min in 1 mM ethyl mercury phosphate (EMP) prior to back-soaking and flash-freezing by immersion in liquid nitrogen.

Data Collection

Crystals belonged to the space group $P2_12_12_1$, with one PglB-peptide complex in the asymmetric unit. Native data were collected at the micro-diffractometer beamline X06SA at the Swiss Light Source (SLS, Villigen) because not all sections of the crystals diffracted equally well. EMP2 and EMP3 derivative data sets (see Table 2 above) were collected at the same station, whereas EMP1 was collected at the high resolution station of the same beam line. Data were processed and merged with XDS (Kabsch, W. Xds. *Acta Crystallogr* D66, 125-132, (2010) or HKL2000 (HKL Research, Inc.).

Structure Determination

The structure was determined using a combination of molecular replacement using the periplasmic domain of *C. jejuni* PglB (pdb code 3AAG) as a search model and Phaser (Mccoy et al., Phaser crystallographic software. *J. Appl. Crystallogr*. 40, 658-674, 2007) on the one hand and multiple isomorphous replacement with anomalous scattering (MIRAS) using SHARP (Global Phasing Limited) on the other. The process of phase calculation and model building (using O; Jones et al., *Acta Crystallogr*. A47, 110-119, 1991) and refinement (using Phenix; Adams et al., *Acta Crystallogr* D66, 213-221, 2010) was iterated, starting with the periplasmic domain and extending into the best-ordered regions of the TM domain (TM1-4 and TM10-13) followed by TM5-9. The locations of three cysteines in the TM domain (indicated by Hg anomalous peaks) served as starting points for tracing until very good density allowed placement of bulky residues, confirming the sequence register. The final structure excludes two disordered loops of PglB (residues 283-306 and residues 605-607 of SEQ ID NO:1) as well as the C-terminal polyhistidine tag. Data collection and refinement statistics are given in Table 2 above.

Results and Conclusions

Structure of *C. lari* PglB (SEQ ID NO:1)

In agreement with earlier predictions (Kelleher & Gilmore, Glycobiology 16, 47-62, 2006) the X-ray structure revealed that PglB consists of two domains (FIG. 3a), a transmembrane (TM) domain comprising residues 1-432 and a periplasmic domain comprising residues 433-712. In addition to the covalent linkage, the two domains interact extensively through non-covalent interactions, primarily provided by the first external loop (EL1) of the TM domain that forms two helices positioned parallel to the membrane plane (EL1-h1 and EL1-h2,). The periplasmic domain reveals a mixed α/β structure that harbors the most conserved sequence motif of the protein family (see below). The structures of two related periplasmic domains, one from *C. jejuni* PglB and another from *Pyrococcus furiosus* AgIB, have been reported previously (Maita et al., *J. Biol. Chem*. 285, 4941-4950, 2010; Iguraet al., *Embo J*27, 234-243, 2008). However, these isolated domains were catalytically inactive and unable to bind acceptor peptides. The present structure of full-length PglB provides a molecular basis for this observation by revealing that the TM domain is indispensible both for peptide binding and catalysis.

Figure 3:
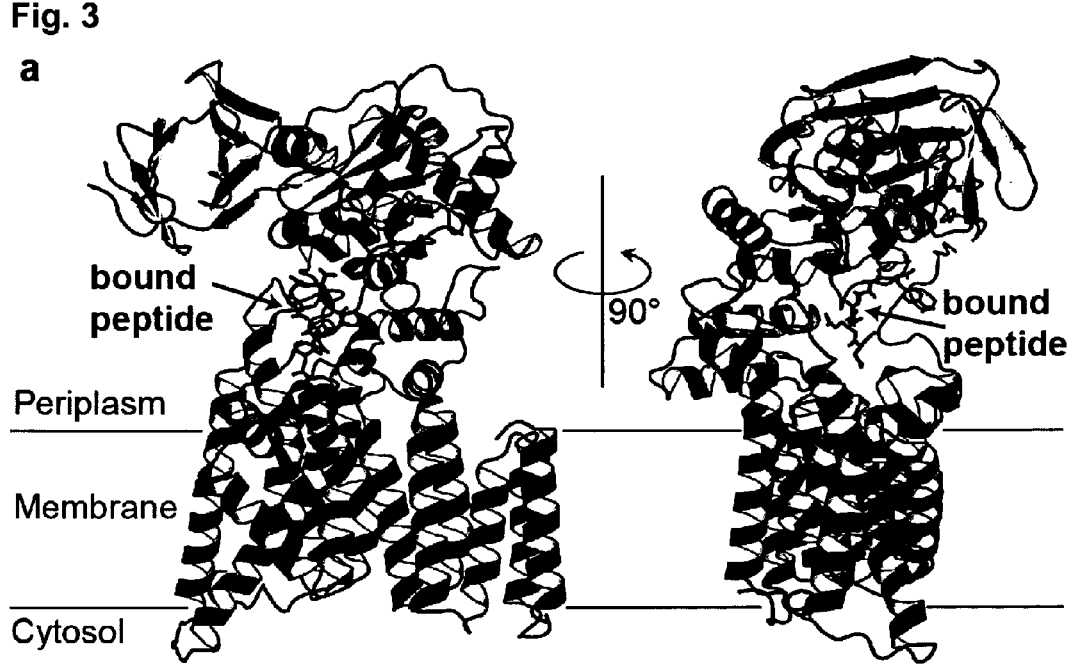
FIG. 3 is a picture showing the structure and substrate binding cavities of C. lari PglB (SEQ ID NO:1). a. Ribbon diagram of PglB in two orientations, with TM and periplasmic domains. The presumed position of the membrane is indicated by lines and the location of the bound substrate peptide is shown. b. Line representation of PglB with bound acceptor peptide. Two cavities are present on opposite sides of the protein (as marked), providing access for the substrates. The cavities are connected by a porthole that accommodates the side chain of the acceptor asparagine (not visible in this presentation mode).
Figure 3:
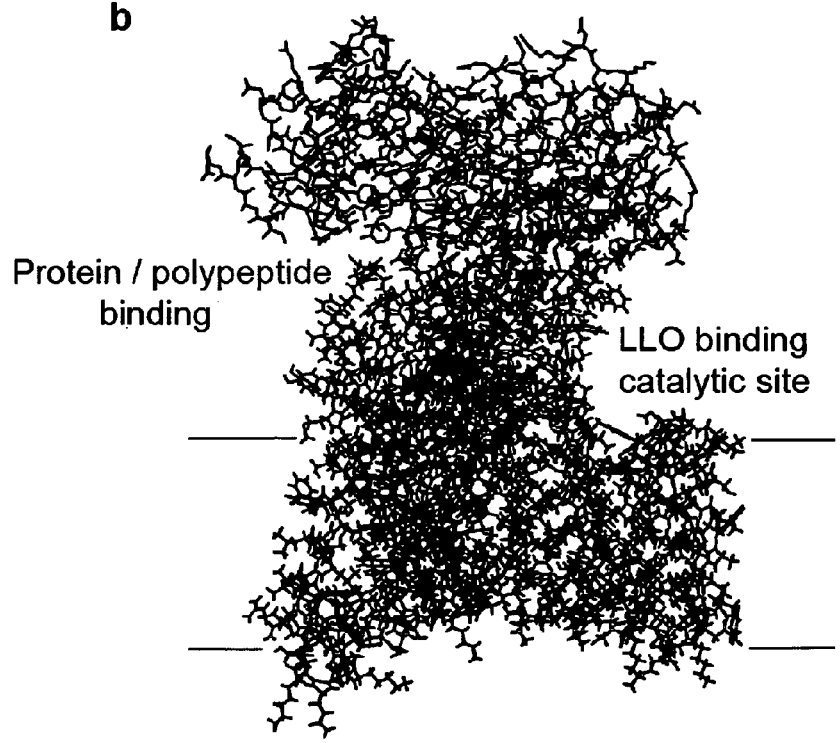

In contrast to the periplasmic domain, the TM domain features a novel fold, with 13 TM segments connected by relatively short cytoplasmic and external (extracytoplasmic) loops, with the notable exception of the long external loops EL1 and EL5. Based on sequence alignments and TM segment predictions, the observed topology appears to be conserved in the STT3 protein family. TM1-4 and TM10-13 form the sequon-binding and catalytic sites and provide the bulk of the interface with the periplasmic domain, whereas TM5-9 are short, parallel TM helices normal to the membrane plane. They may interact with the oligosaccharide or bactoprenol moieties or provide a spacer for the remote attachment of EL5 (see below). Whereas EL1 is well-ordered and firmly interacts with the periplasmic domain, EL5 is only partially ordered, with 25 residues poorly or completely disordered in the electron density maps. The ordered section of EL5 interacts both with the periplasmic domain and with the bound acceptor peptide, suggesting a crucial role in the recruitment and binding of the sequon. It is conceivable that in the absence of peptide, EL5 is completely flexible and disordered, accounting for the finding that no crystals of PglB grew in the absence of acceptor peptide. In the peptide-bound state, PglB forms two large cavities above the membrane surface, both accessible from the periplasmic space, but located at opposite sides of the protein (FIG. 3). The left-side cavity provides access for acceptor proteins as suggested by the presence of bound peptide in the structure, whereas the right-side cavity harbors the catalytic residues (see below) and probably serves as the binding pocket for the LLO substrate. The two cavities are connected by a small porthole, through which the acceptor asparagine of the bound peptide reaches from the peptide-binding site into the presumed catalytic site.

Acceptor Sequon Binding and Recognition

Figure 4:
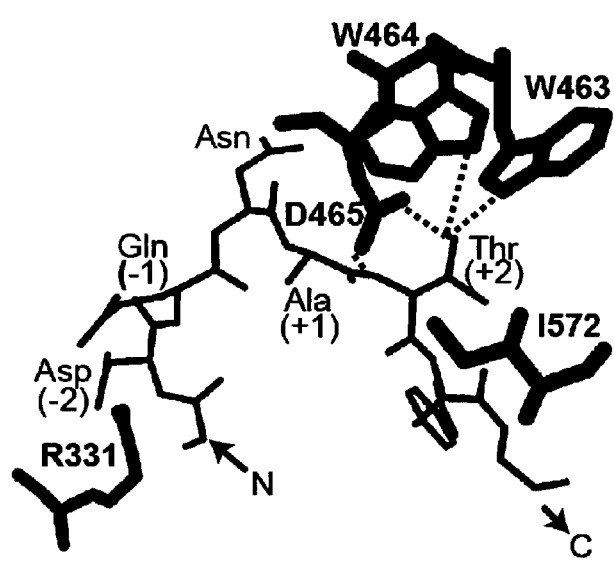
FIG. 4 shows glycosylation sequon recognition by PglB. a. A picture showing the peptide binding site and sequon recognition in PglB. The acceptor peptide is shown in line format and individual amino acids are labeled in three letter code. PglB residues contributing to specific sequon binding are in ball and stick format and are labeled in single letter code including amino acid numbers. Hydrogen bonds between the WWD motif and the +2 Thr of the acceptor peptide are indicated by dashed lines. b. Activity of C. lari oligosaccharyltransferase PglB (SEQ ID NO:1) and PglB mutant R331A against different glycosylation sequons: E. coli cells were transformed with a combination of three separate plasmids: (i) The glycosylation machinery of C. jejuni that generates LLO, but contains inactivated PglB; (ii) An acceptor protein (modified scFv fragment 3D5) containing either the sequon DQNAT (SEQ ID NO: 4) or the sequon AQNAT (SEQ ID NO: 8) and (iii) Functional C. lari PglB (SEQ ID NO:1) or PglB mutant R331A. Glycosylation of the acceptor protein was analyzed from periplasmic extracts, whereas expression of PglB was analyzed from whole cell extracts. Proteins were analyzed by immunoblot using anti-c-Myc antibody detecting scFv substrate (top), glycan-specific antiserum hR6 (middle), or anti-HA antiserum detecting PglB (bottom). PglB constructs are indicated above the lanes and acceptor sequons are indicated above the lines. Glycosylation of 3D5 results in a mobility shift from the unmodified form (g0) to the glycosylated form (g1). Functional PglB is partially auto-glycosylated at N535 and N556 of SEQ ID NO:1, resulting in two additional bands (g1and g2).
Figure 4:

The structure of PglB (SEQ ID NO:1) was determined in complex with the hexapeptide DQNATF (SEQ ID NO: 5), and clear density for the peptide was observed in a location that placed the acceptor asparagine some 15 Å above the membrane surface (FIG. 3a). The peptide-binding and catalytic sites are the best-ordered regions of the structure, and the electron density allowed an unambiguous assignment of the acceptor peptide register. Almost 80% of the contact surface (as calculated by areaimol; Bailey, S., *Acta Crystallogr* D50, 760-763, 1994) of the peptide is buried at the interface of the TM and periplasmic domains suggesting a very tight binding along with a firmly imposed conformation. The hexapeptide forms a loop that almost completes a 180° turn; accordingly, polypeptide substrates have to present their glycosylation sequons in sufficiently large, flexible and surface-exposed loops, because the peptide-binding cavity of PglB does not appear to fit fully folded protein domains. A significant part of the interaction of the TM domain with the peptide is provided by the external loop EL5, which also features a methionine residue that resembles a saddle for the peptide. The observed conformation of the peptide would be incompatible with a proline residue at the +1 position, in agreement with the observation that +1 prolines are not allowed in glycosylation sequons. A hallmark of N-linked glycosylation is the requirement of a serine or threonine at the +2 position of the acceptor sequon. The PglB structure provides a molecular explanation by revealing that the β-hydroxyl group of the +2 Thr of the bound peptide forms three hydrogen bonds, one with each of the side chains of the "WWD motif", which is strictly conserved in STT3 proteins (FIG. 4). The WWD motif is located in the periplasmic domain, and the interaction of the two tryptophan and the aspartate side chains saturate the hydrogen-bonding capacity of the β-hydroxyl group, a functional group that is only present in serines and threonines. The arrangement physically separates the +2 Thr from the acceptor asparagine, and it is assumed that the WWD motif defines the polypeptide substrate specificity, but is not directly involved in the catalytic activity of the enzyme. Notably, the structure can also explain preferences and deviations at the +2 position of glycosylation sequons. The γ-methyl group of the +2 Thr is in Van der Waals contact with the conserved isoleucine I572 of PglB (SEQ ID NO:1) (3.6 Å distance to the γ-methyl group of I572, FIG. 4). This stabilizing interaction is absent if a serine is in the +2 position. This may explain that acceptor sequons containing a +2 Thr are glycosylated 40 times more efficiently than if they contain a +2 serine (Bause, E., *Biochem. Soc.* T12, 514-517, 1984). The structure suggests that the non-natural, S-configured threonine would cause a steric clash with I572 of SEQ ID NO:1. S-configured threonine is indeed not allowed at the +2 position, with a 15'000-fold reduction in glycosylation efficiency compared to R-configured threonine (Breuer et al., *Febs Lett.* 501, 106-110, 2001). I572 of SEQ ID NO:1 is conserved in bacteria and has been suggested to be part of a MxxI motif (SEQ ID NO: 7; Maita et al., *J. Biol. Chem.* 285, 4941-4950, 2010). However, the corresponding residue in the archaeal AgIB protein was found to be a lysine (Iguraet al., *Embo J* 27, 234-243, 2008) and sequence alignments with eukaryotic STT3 homologues reveal no clear conservation of I572 of SEQ ID NO:1, suggesting that residues other than isoleucine can provide contacts to the +2 Thr in homologous proteins. The PglB structure can also explain allowed deviations from the consensus sequons: The acceptor sequence N—X—C, present in ~2.2% of experimentally determined glycosylation sites of the mouse glycoproteome (Zielinska et al., *Cell* 141, 897-907, 2010), is probably allowed because the β-sulfhydryl group of cysteine can form similar hydrogen bonds as a β-hydroxyl group. Glycines, alanines and valines have also been reported at the +2 position of glycosylated sequons, albeit only at low abundance (Zielinska et al., *Cell* 141, 897-907, 2010; ; Schwarz et al., *Glycobiology* 21, 45-54, 2011; Valliere-Douglass et al.*J. Biol. Chem.* 284, 32493-32506, 2009). These residues can in principle be accommodated in the binding pocket of PglB because they are equal in size or smaller than threonine. However, glycosylation of sequons such as N-G-X with X being larger than threonine, or of T/S—X—N ("reverse sequons") (Valliere-Douglass et al.*J. Biol. Chem.* 284, 32493-32506, 2009) cannot be explained by the structure of PglB. Compared to eukaryotic enzymes bacterial OST have an additional requirement for the acceptor sequon: Glycosylation is only efficient if a negatively charged residue (Asp or Glu) is present at the −2 position, resulting in a consensus sequon D/E-$x_1$-N-$x_2$-S/T (SEQ ID NO: 3; Kowarik et al., *Embo. J.* 25, 1957-1966, 2006). In PglB the arginine residue R331 provides a salt bridge to the −2 Asp of the acceptor peptide (FIG. 4a), thereby strengthening the PglB-peptide interaction. R331 is conserved in bacteria, but not in eukaryotes, where no requirement for a negative charge at the −2 position is observed. The extended sequon recognition may reflect the need for tighter peptide binding in bacteria, where the local concentration of the acceptor polypeptide is likely lower than in eukaryotes. In fact, mutation of R331 of SEQ ID NO:1 to Ala results in a reduced glycosylation efficiency of the 3D5 acceptor protein containing a DQNAT glycosylation site (FIG. 4b). However, the R331A mutant enables glycosylation of 3D5 containing an AQNAT (SEQ ID NO: 8) site, which is not glycosylated by wild type PglB (FIG. 4b). Therefore, the R331A mutant can be used to selectively occupy glycosylation sites that are not used by wild type PglB. Consequently, a combination of wild type enzyme and the R331A mutant allows the site specific attachment of different glycans within the same glycoprotein.

Catalytic Site

Figure 5:
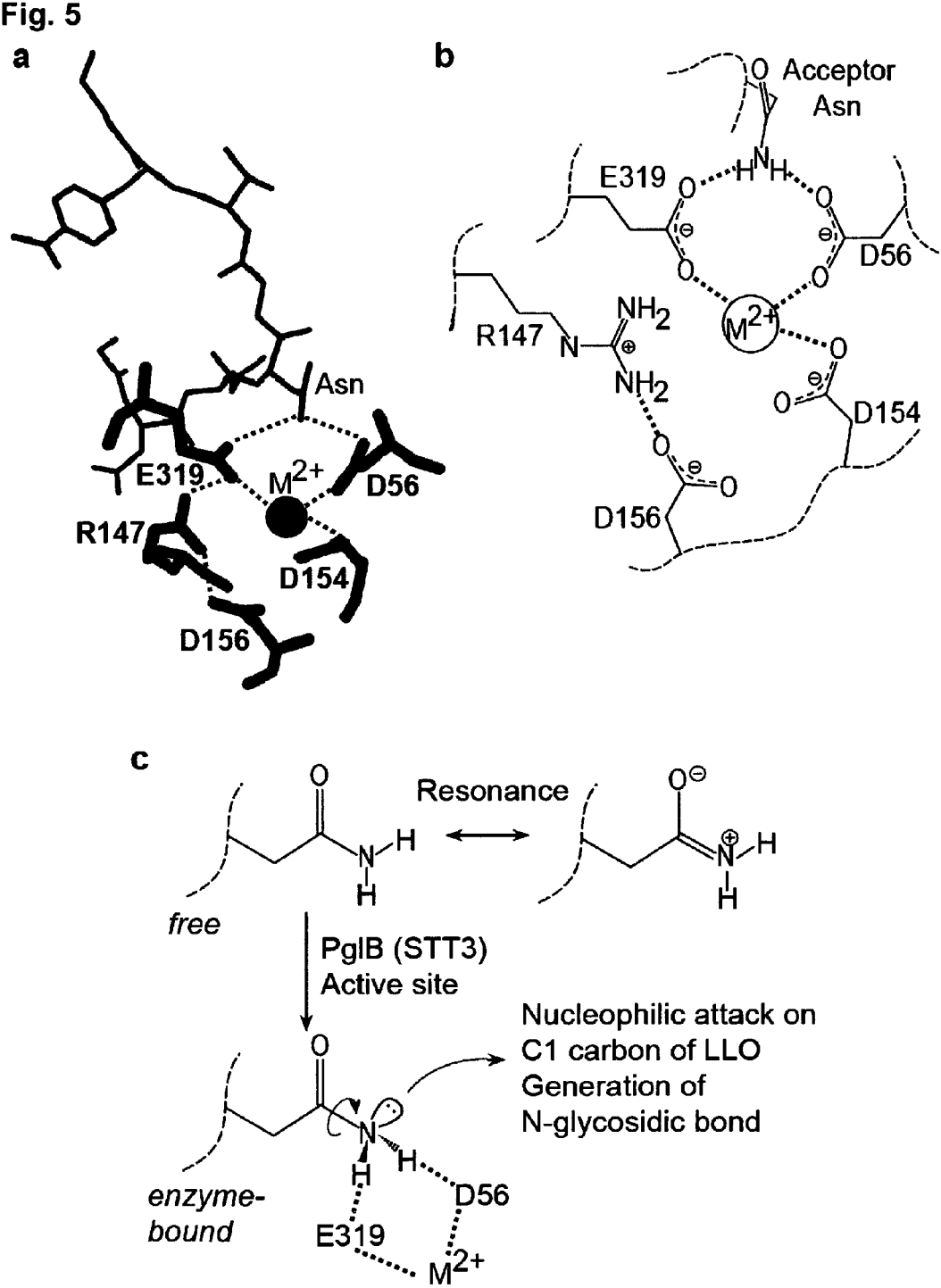
FIG. 5 shows the catalytic site and activation of amide nitrogen. a. Selected side chains of PglB are in ball and stick format and are labeled in single letter code including amino acid numbers. The acceptor peptide is shown in line format and the activated asparagine is labeled. The catalytic divalent cation is shown as a sphere. Dashed lines indicate hydrogen bonds or ligand-metal interactions as suggested by distance measurements. b. Chemical structure of the catalytic site, indicating interactions as in a. Thin dashed lines indicate protein and peptide backbones. c. Presumed mechanism of activation of the amido group nitrogen. Free asparagine side chain features delocalization/conjugation of the electron pair of the nitrogen, as indicated by resonance formulae. When bound to PglB, the amido group of the acceptor asparagine may form hydrogen bonds with the carboxyl groups of the catalytically essential D56 and E319 of SEQ ID NO:1, requiring rotation around the C—N bond (arrow). This would result in breaking of the conjugation and an increased nucleophilicity of the nitrogen.

The catalytic pocket is located in the right-side cavity of PglB (FIG. 3b) and is marked by a bound cation, located ~8 Å above the membrane boundary. Due to the high concentration of magnesium salt in the crystallization solution, it was modelled as $Mg^{2+}$. Like all OSTs PglB is only functional with a bound divalent cation (Imperiali & Rickert, *P. Natl. Acad. Sci. USA* 92, 97-101, 1995; Sharma et al., *Eur. J. Biochem.* 116, 101-108, 1981). The physiological cation has been suggested to be $Mn^{2+}$, but PglB is also active in $Mg^{2+}$(unpublished), a property that has previously been observed for other metal-dependent glycosyltransferases (Liu & Mushegian, *Protein Sci.* 12, 1418-1431, 2003). The catalytic pocket of PglB features three acidic side chains (D56, D154, E319) that are provided by the TM domain and that coordinate the $M^{2+}$(FIG. 5a). At the current resolution, water molecules that might be additional ligands of $M^{2+}$cannot be modelled. The residues located in the catalytic pocket are conserved in STT3 proteins. The aspartates D154 and D156belong to a previously reported D-X-D motif and mutation of either aspartate to alanine in the mannosyltransferase GPI-MT-1, a member of the same glycosyltransferase family as PglB (GT-C) (Lairson et al., *Annu. Rev. Biochem.* 77, 521-555, 2008); Liu & Mushegian, *Protein Sci.* 12, 1418-1431, 2003), abolished the activity of this enzyme (Maeda et al., *Embo J* 20, 250-261, 2001). In contrast, D56 and E319 have not been previously identified as catalytic relevant, but their carboxyl groups are interacting both with the metal ion and the amido group of the acceptor asparagine. To confirm the catalytic involvement of the three acidic, $M^{2+}$-binding residues, they were mutated individually to alanines and the activity of the resulting PglB mutants was tested in a complementation assay (FIG. 2). Even though OST is not limiting in our assay, the mutation D154A in SEQ ID NO:1 reduced the observed glycosylation yield by >50%, the mutants D56A and E319A in SEQ ID NO:1 reduced it by >90%, and the double mutant D56A/E319A in SEQ ID NO:1 was completely inactive.

There is a controversial discussion on how the amido group of the acceptor asparagine might be activated to perform a nucleophilic attack on the C1 carbon of the LLO substrate, the key step in N-linked glycosylation. Amides are poor nucleophiles because the free electron pair of the nitrogen is conjugated to the double bond of the carbonyl group (FIG. 5c). As a consequence, the N—C bond has double bond character, and the nucleophilicity of the nitrogen is low. To explain the reactivity of the amido group, specific conformations of the acceptor peptide such as a "β-turn" or an "Asx-turn" have been proposed, invoking direct involvement of the β-hydroxyl group of the +2 Ser/Thr for increased nucleophilicity of the amide group (Bause & Legler, Biochem. J. 195, 639-644, 1981; Imperiali et al., J. Am. Chem. Soc. 114, 7942-7944, 1992). Given the firm binding of the +2 Thr to the WWD motif in our PglB structure, such a mechanism can be ruled out. Instead, the structure of PglB presents a distinct possibility for explaining amide nitrogen activation: The two catalytically essential, acidic residues D56 and E319 of SEQ ID NO:1 are optimally positioned to form hydrogen bonds with the amide protons of the acceptor asparagine. Forming such hydrogen bonds would require a rotation of the N—C bond of the amide group, thereby abolishing the delocalization of the free electrons of the nitrogen atom and breaking the conjugation with the carbonyl group (FIG. 5c). Not only would this increase the electronegative nature of the amide nitrogen (by polarizing the N—H bonds and increasing the electron density on the nitrogen), but it would also generate an $sp^3$ hybridized nitrogen with a reactive lone pair optimally positioned for the nucleophilic attack on the C1 carbon of the activated oligosaccharide substrate (LLO). The energy barrier for rotating the N—C bond in most amides is estimated to be 16-20 kcal/mol, and the 270° amide conformation shown in FIG. 5c has been calculated to have an energy of ~18.6 kcal/mol relative to the planar conformation (Wiberg & Breneman, J Am Chem Soc. 114, 7942-7944, 1992). Hence it would take 1-2 low barrier hydrogen bonds (Cleland & Kreevoy, Science 264, 1887-1890, 1994)(each worth ~10 kcal/mol) to provide sufficient energy to permanently break the conjugation of the carboxamido group of the acceptor asparagine. The carboxylates of D56 or of SEQ ID NO:1 might provide such interactions in the transition state of the glycosylation reaction, although it will require a higher resolution structure to reliably measure lengths of hydrogen bonds. Mutating D56 in SEQ ID NO:1 to asparagine (D56N) has an even more pronounced inhibitory effect than the truncation to alanine, and the E319Q mutant is completely inactive (FIG. 2). This demonstrates that the negative charges provided by the carboxyl groups of D56 and E319 of SEQ ID NO:1 are essential for catalysis and the acidic side chains cannot be replaced by the corresponding iso-electronic amides. Steric effects might explain the increased inhibition of D56N relative to D56A and of E319Q compared with E319A.

Glycosylation Mechanism

Figure 6A:
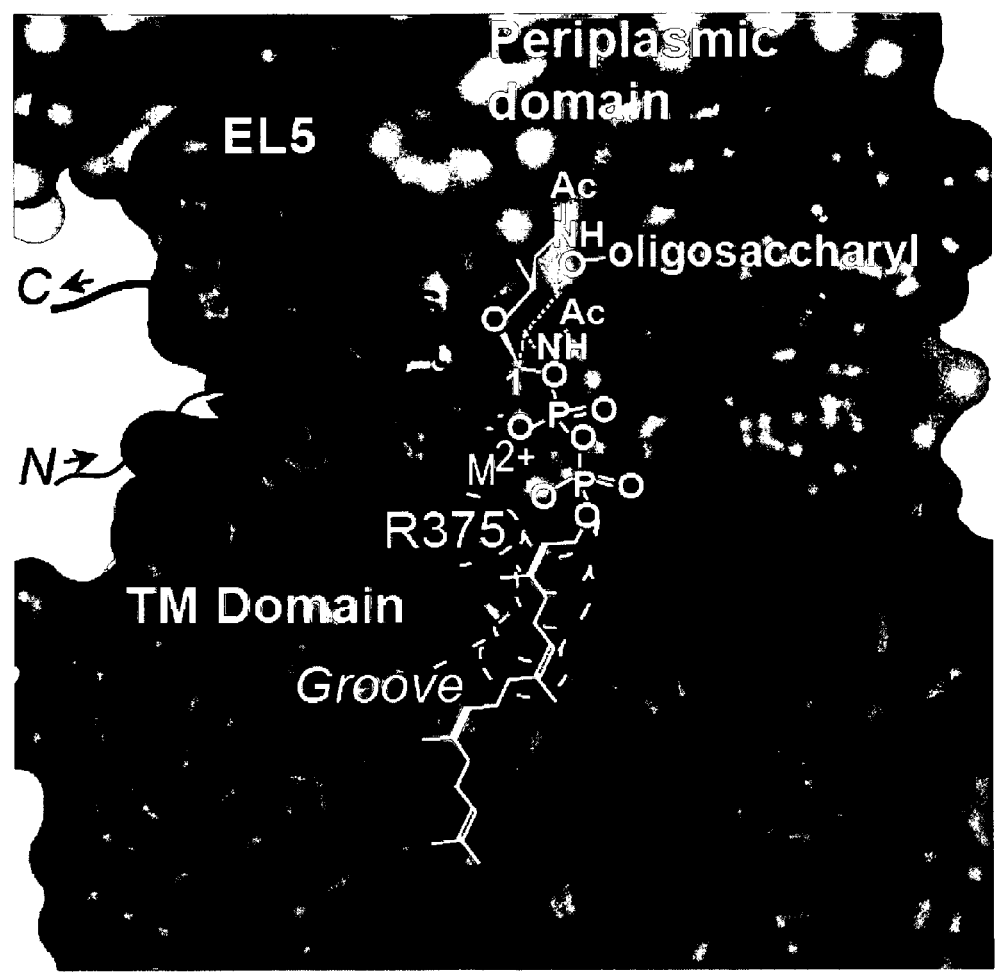
FIG. 6: Proposed glycosylation mechanism. a. Surfaces of TM and periplasmic domains of PglB are shown. Bound acceptor peptide is in ball and stick format, and black lines indicate the N- and C-termini. The chemical structure of bacterial LLO is shown schematically in white to highlight the presumed interactions of the pyrophosphate group with the divalent cation (M2+) and with the conserved R375 of SEQ ID NO:1, while allowing for a collinear arrangement of the attacking and leaving groups of the nucleophilic substitution. An arrow indicates the attack of the activated amide nitrogen. A predominantly hydrophobic groove is indicated on the surface of PglB, where the isoprenoid moieties are expected to enter the lipid bilayer. b. Proposed three step mechanism of PglB-catalyzed glycosylation. The molecular events leading from one step to the next are indicated next to the arrows. The observed crystal structure reflects the top state, with the acceptor peptide bound to the protein and the C-terminal half of the external loop EL5 ordered. The bottom left state reflects the ground state, with no substrates bound and with the external loop EL5 disordered, indicated by dashed lines. In the bottom right state, LLO from C. jejuni (black line for isoprenoid moieties, P for phosphate, ellipsoids for saccharide moieties) is bound and the acceptor asparagine is glycosylated.

Given that PglB is active even when solubilized in detergent (used for purification and crystallization) the provided structure has likely captured a functionally competent state. The glycosylation reaction occurs with inversion of configuration at the substituted C1 carbon of the first sugar moiety. The LLO substrate was modelled into the PglB structure such that the di-N-acetyl-bacillosamine moiety is properly aligned for a nucleophilic attack by the activated amide nitrogen, while the leaving pyrophosphate group is in contact with the divalent metal ion and the conserved R375 (FIG. 6a). This arrangement places the additional saccharide moieties in the right hand cavity of PglB, where they can interact with surface residues from both the TM and the periplasmic domains. The arrangement also places the C2 substituent of the first saccharide moiety, a N-acetyl group present in LLOs of bacteria and eukaryotes, in the vicinity of a conserved tyrosine residue (Y468), where density consistent with a bound water molecule is observed. When modelled as shown in FIG. 6a, the lipid tail of the LLO is located in a mostly hydrophobic groove on the surface of PglB, pointing its isoprenoid moieties into the lipid bilayer. The function of the bound divalent cation in PglB thus appears to be two-fold: On the one hand, it orients the acidic side chains that interact with the acceptor asparagine, and, on the other hand, it stabilizes the leaving group of the substitution (lipid-pyrophosphate), thus accelerating the reaction. This would be distinct from metal-dependent, configuration-inverting glycosyltransferases of the GT-A family, where the metal ion only serves the stabilization of the leaving group (see Lairson above).

Figure 6B:
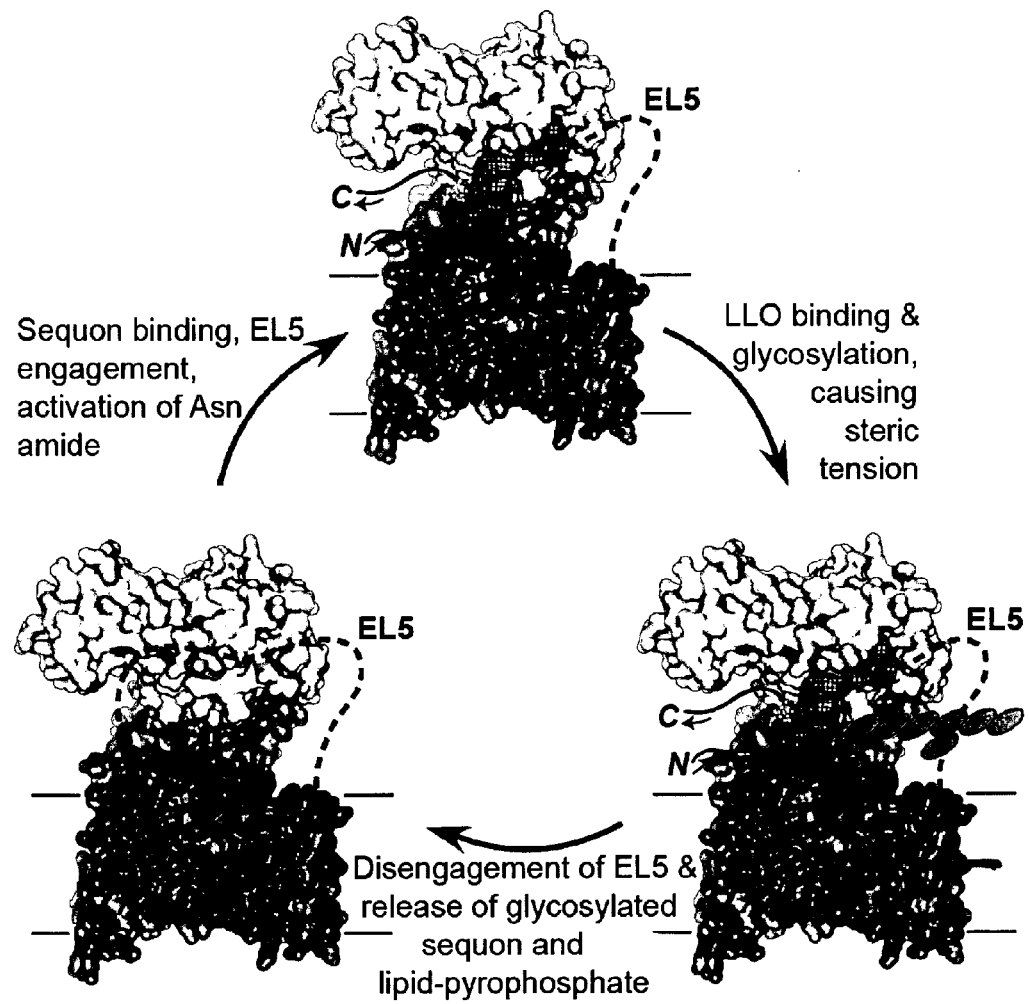

With the acceptor peptide present in the structure and the LLO molecule tentatively modelled, a basic, three-state catalytic cycle for PglB-catalysed glycosylation can be proposed (FIG. 6b). A critical element of the proposed mechanism is the engagement and disengagement of the external loop EL5, which is suspected to be flexible and disordered in the absence of bound acceptor peptide (ground state). Upon binding of peptide, this loop becomes partially ordered and pins the peptide against the periplasmic domain, thereby restricting its motion. Because the essential E319 of SEQ ID NO:1 is part of EL5, this simultaneously results in the formation of the catalytic site, where the acceptor Asn is correctly oriented and activated. This state can only be reached if a consensus sequon from a flexible, exposed protein loop is inserted in the binding pocket. In the following step, LLO binding is expected, whereupon the activated amide nitrogen performs a nucleophilic attack on the first saccharide moiety, resulting in glycosylation. Once the glycosidic bond is formed, the newly attached sugars are tightly pressed against PglB (specifically against Ile317 and His485 of SEQ ID NO:1), causing steric tension that can be released by disengagement of EL5. This opens the acceptor Asn porthole and allows the glycopeptide to dissociate from the enzyme. Subsequent cleavage of the lipid-linked pyrophosphate anhydride and the folding of the glycosylated protein domain likely provide the main contributions to the driving force of the reaction. It is noted that PglB might also bind LLO before binding peptide, and there is no experimental evidence suggesting a strict sequence of events.

The invention claimed is:

1. A method for identifying an oligosaccharyltransferase (OST), said method comprising the steps of:
(i) employing the atomic coordinates of Table 1 on a computer to generate a three-dimensional model of the catalytic domain of the oligosaccharyltransferase (OST) of *Campylobacter lari* (SEQ ID NO:1), comprising at least three, at least four, at least six, or all of amino acids D56, R147, D154, D156, E319, R375, Y468, and H485 of SEQ ID NO:1, and/or
(ii) employing the atomic coordinates of Table 1 on a computer to generate a three-dimensional model of the polypeptide binding site of the oligosaccharyltransferase (OST) of *Campylobacter lari* (SEQ ID NO:1), comprising at least four or all of amino acids M318, R331, W463, W464, D465, and I572 of SEQ ID NO:1,
(iii) using said three-dimensional model(s) of (i) or (ii) for selecting a potential OST, said use comprising
(a) providing said potential OST, and
(b) contacting, as part of an in vitro or in vivo assay for determining oligosaccharyltransferase function, said potential OST with further functional components necessary for OST-catalysed asparagine-linked ("N-Linked") glycosylation, and
(c) determining whether said potential OST is a functional OST.

2. The method of claim 1, wherein in step (ii) the three-dimensional model of the polypeptide binding site of the oligosaccharyltransferase (OST) of *Campylobacter lari* comprises at least four or all of amino acids M318, R331, W463, W464, D465 and I572 of SEQ ID NO:1.

3. The method according to claim 1, wherein the specific three-dimensional catalytic site model of step (i) further comprises one or more or all of the amino acids selected from the group having residues located within Van der Waals distance to the bound peptide of SEQ ID NO: 2, selected from the group consisting of Thr53, Thr54, Asn55, Asp56, Asn146, Arg147, Tyr152, Glu315, Thr316, Ile317, Met318, Glu319, Val320, Asn321, Arg331, Leu374, Arg375, Tyr433, Ser435, Val438, Trp463, Trp464, Asp465, Gly482, His485, Lle572, Val575 of SEQ ID NO:1.

4. The method according to claim 1, wherein the specific three-dimensional catalytic site model of step (i) further comprises one or more or all of the amino acids selected from the group having residues located within Vander Waals distance to the bound peptide of SEQ ID NO: 2, selected from the group consisting of Thr53, Thr54, Asn55, Asp56, Asn146, Arg147, Tyr152, Glu315, Thr316, Lle317, Met318, Glu319, Val320, Asn321, Ala331, Leu374, Arg375, Tyr433, Ser435, Val438, Trp463, Trp464, Asp465, Gly482, His485, Lle572, Val575 of SEQ ID NO:1.

5. The method according to claim 1, wherein the atomic coordinates of Table 1 of step (i) or step (ii) comprise ±2, ±1.5, or ±1.0 Å root mean square deviation (rmsd) from a backbone atom.

6. A method for identifying an oligosaccharyltransferase (OST), said method comprising the steps of:

(i) employing the atomic coordinates of Table 1 on a computer to generate a three-dimensional model of the catalytic domain of the oligosaccharyltransferase (OST) of *Campylobacter lari* (SEQ ID NO:1), comprising at least three, at least four, at least six, or all of amino acids D56, R147, D154, D156, E319, R375, Y468, and H485 of SEQ ID NO:1, and/or (ii) employing the atomic coordinates of Table 1 on a computer to generate a three-dimensional model of the polypeptide binding site of the oligosaccharyltransferase (OST) of *Campylobacter lari* (SEQ ID NO:1), comprising at least two or at least three of M318, R331, W464, D465, and I572 of SEQ ID NO:1 that are not contiguous in the primary structure of SEQ ID NO:1, or at least two or at least three of M318, R331, W463, W464, and I572 of SEQ ID NO:1 that are not contiguous in the primary structure of SEQ ID NO:1, (iii) using said three-dimensional model(s) of (i) or (ii) for selecting a potential OST, said use comprising (a) providing said potential OST, and (b) contacting, as part of an in vitro or in vivo assay for determining oligosaccharyltransferase function, said potential OST with further functional components necessary for OST-catalysed asparagine-linked ("N-Linked") glycosylation, and (c) determining whether said potential OST is a functional OST.

* * * * *

SEQUENCE LISTING

<160> NUMBER OF SEQ ID NOS: 11

<210> SEQ ID NO 1
<211> LENGTH: 712
<212> TYPE: PRT
<213> ORGANISM: Campylobacter lari

<400> SEQUENCE: 1

```
Met Glu Leu Gln Gln Asn Phe Thr Asp Asn Ser Ile Lys Tyr Thr
1               5                   10                  15

Cys Ile Leu Ile Leu Ile Ala Phe Ala Phe Ser Val Leu Cys Arg Leu
                20                  25                  30

Tyr Trp Val Ala Trp Ala Ser Glu Phe Tyr Glu Phe Phe Asn Asp
            35                  40                  45

Gln Leu Met Ile Thr Thr Asn Asp Gly Tyr Ala Phe Ala Glu Gly Ala
    50                  55                  60

Arg Asp Met Ile Ala Gly Phe His Gln Pro Asn Asp Leu Ser Tyr Phe
65                  70                  75                  80

Gly Ser Ser Leu Ser Thr Leu Thr Tyr Trp Leu Tyr Ser Ile Leu Pro
                85                  90                  95

Phe Ser Phe Glu Ser Ile Ile Leu Tyr Met Ser Thr Phe Phe Ala Ser
                100                 105                 110

Leu Ile Val Val Pro Ile Ile Leu Ile Ala Arg Glu Tyr Lys Leu Thr
            115                 120                 125

Thr Tyr Gly Phe Ile Ala Ala Leu Leu Gly Ser Ile Ala Asn Ser Tyr
    130                 135                 140

Tyr Asn Arg Thr Met Ser Gly Tyr Tyr Asp Thr Asp Met Leu Val Leu
145                 150                 155                 160

Val Leu Pro Met Leu Ile Leu Leu Thr Phe Ile Arg Leu Thr Ile Asn
            165                 170                 175

Lys Asp Ile Phe Thr Leu Leu Leu Ser Pro Ile Phe Ile Met Ile Tyr
            180                 185                 190

Leu Trp Trp Tyr Pro Ser Ser Tyr Ser Leu Asn Phe Ala Met Ile Gly
            195                 200                 205

Leu Phe Gly Leu Tyr Thr Leu Val Phe His Arg Lys Glu Lys Ile Phe
    210                 215                 220

Tyr Leu Ala Ile Ala Leu Met Ile Ile Ala Leu Ser Met Leu Ala Trp
225                 230                 235                 240

Gln Tyr Lys Leu Ala Leu Ile Val Leu Leu Phe Ala Ile Phe Ala Phe
            245                 250                 255

Lys Glu Glu Lys Ile Asn Phe Tyr Met Ile Trp Ala Leu Ile Phe Ile
            260                 265                 270

Ser Ile Ser Ile Leu His Leu Ser Gly Gly Leu Asp Pro Val Leu Tyr
            275                 280                 285

Gln Leu Lys Phe Tyr Val Phe Lys Ala Ser Asp Val Gln Asn Leu Lys
    290                 295                 300

Asp Ala Ala Phe Met Tyr Phe Asn Val Asn Glu Thr Ile Met Glu Val
305                 310                 315                 320

Asn Thr Ile Asp Pro Glu Val Phe Met Gln Arg Ile Ser Ser Ser Val
            325                 330                 335

Leu Val Phe Ile Leu Ser Phe Ile Gly Phe Ile Leu Leu Cys Lys Asp
            340                 345                 350

His Lys Ser Met Leu Leu Ala Leu Pro Met Leu Ala Leu Gly Phe Met
            355                 360                 365

Ala Leu Arg Ala Gly Leu Arg Phe Thr Ile Tyr Ala Val Pro Val Met
    370                 375                 380

Ala Leu Gly Phe Gly Tyr Phe Leu Tyr Ala Phe Phe Asn Phe Leu Glu
385                 390                 395                 400

Lys Lys Gln Ile Lys Leu Ser Leu Arg Asn Lys Asn Ile Leu Leu Ile
            405                 410                 415
```

-continued

```
Leu Ile Ala Phe Phe Ser Ile Ser Pro Ala Leu Met His Ile Tyr Tyr
                420                 425                 430

Tyr Lys Ser Ser Thr Val Phe Thr Ser Tyr Glu Ala Ser Ile Leu Asn
            435                 440                 445

Asp Leu Lys Asn Lys Ala Gln Arg Glu Asp Tyr Val Val Ala Trp Trp
    450                 455                 460

Asp Tyr Gly Tyr Pro Ile Arg Tyr Tyr Ser Asp Val Lys Thr Leu Ile
465                 470                 475                 480

Asp Gly Gly Lys His Leu Gly Lys Asp Asn Phe Phe Ser Ser Phe Val
                485                 490                 495

Leu Ser Lys Glu Gln Ile Pro Ala Ala Asn Met Ala Arg Leu Ser Val
            500                 505                 510

Glu Tyr Thr Glu Lys Ser Phe Lys Glu Asn Tyr Pro Asp Val Leu Lys
        515                 520                 525

Ala Met Val Lys Asp Tyr Asn Gln Thr Ser Ala Lys Asp Phe Leu Glu
    530                 535                 540

Ser Leu Asn Asp Lys Asn Phe Lys Phe Asp Thr Asn Lys Thr Arg Asp
545                 550                 555                 560

Val Tyr Ile Tyr Met Pro Tyr Arg Met Leu Arg Ile Met Pro Val Val
                565                 570                 575

Ala Gln Phe Ala Asn Thr Asn Pro Asp Asn Gly Glu Gln Glu Lys Ser
            580                 585                 590

Leu Phe Phe Ser Gln Ala Asn Ala Ile Ala Gln Asp Lys Thr Thr Gly
        595                 600                 605

Ser Val Met Leu Asp Asn Gly Val Glu Ile Ile Asn Asp Phe Arg Ala
    610                 615                 620

Leu Lys Val Glu Gly Ala Ser Ile Pro Leu Lys Ala Phe Val Asp Ile
625                 630                 635                 640

Glu Ser Ile Thr Asn Gly Lys Phe Tyr Tyr Asn Glu Ile Asp Ser Lys
                645                 650                 655

Ala Gln Ile Tyr Leu Leu Phe Leu Arg Glu Tyr Lys Ser Phe Val Ile
            660                 665                 670

Leu Asp Glu Ser Leu Tyr Asn Ser Ala Tyr Ile Gln Met Phe Leu Leu
        675                 680                 685

Asn Gln Tyr Asp Gln Asp Leu Phe Glu Gln Val Thr Asn Asp Thr Arg
    690                 695                 700

Ala Lys Ile Tyr Arg Leu Lys Arg
705                 710

<210> SEQ ID NO 2
<211> LENGTH: 6
<212> TYPE: PRT
<213> ORGANISM: Artificial Sequence
<220> FEATURE:
<223> OTHER INFORMATION: Artificial hexapeptide substrate for OST
<220> FEATURE:
<221> NAME/KEY: MISC_FEATURE
<222> LOCATION: (6)..(6)
<223> OTHER INFORMATION: substituted with nitro group in para position

<400> SEQUENCE: 2

Asp Gln Asn Ala Thr Phe
1               5

<210> SEQ ID NO 3
<211> LENGTH: 5
<212> TYPE: PRT
<213> ORGANISM: Artificial Sequence
```

```
<220> FEATURE:
<223> OTHER INFORMATION: Consensus sequon for bacterial OST
<220> FEATURE:
<221> NAME/KEY: VARIANT
<222> LOCATION: (1)..(1)
<223> OTHER INFORMATION: Glu
<220> FEATURE:
<221> NAME/KEY: VARIANT
<222> LOCATION: (2)..(2)
<223> OTHER INFORMATION: Ala or Cys or Asp or Glu or Phe or Gly or His
      or Ile or Lys or Leu or Met or Asn or Arg or Ser or Thr or Val or
      Trp or Tyr
<220> FEATURE:
<221> NAME/KEY: VARIANT
<222> LOCATION: (4)..(4)
<223> OTHER INFORMATION: Cys or Asp or Glu or Phe or Gly or His or Ile
      or Lys or Leu or Met or Asn or Gln or Arg or Ser or Thr or Val or
      Trp or Tyr
<220> FEATURE:
<221> NAME/KEY: VARIANT
<222> LOCATION: (5)..(5)
<223> OTHER INFORMATION: Ser

<400> SEQUENCE: 3

Asp Gln Asn Ala Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Optimal substrate sequence for C. jejuni PglB
      OTS

<400> SEQUENCE: 4

Asp Gln Asn Ala Thr
1               5

<210> SEQ ID NO 5
<211> LENGTH: 6
<212> TYPE: PRT
<213> ORGANISM: Artificial Sequence
<220> FEATURE:
<223> OTHER INFORMATION: Hexapeptide substrate used in crystallization

<400> SEQUENCE: 5

Asp Gln Asn Ala Thr Phe
1               5

<210> SEQ ID NO 6
<211> LENGTH: 6
<212> TYPE: PRT
<213> ORGANISM: Artificial Sequence
<220> FEATURE:
<223> OTHER INFORMATION: Peptide used in crystallization
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: substituted with nitro group in para position

<400> SEQUENCE: 6

Asp Gln Asn Ala Thr Phe
1               5

<210> SEQ ID NO 7
<211> LENGTH: 4
```

```
<212> TYPE: PRT
<213> ORGANISM: Artificial Sequence
<220> FEATURE:
<223> OTHER INFORMATION: Bacterial sequence motif
<220> FEATURE:
<221> NAME/KEY: VARIANT
<222> LOCATION: (2)..(2)
<223> OTHER INFORMATION: Cys or Asp or Glu or Phe or Gly or His or Ile
      or Lys or Leu or Met or Asn or Pro or Gln or Arg or Ser or Thr or
      Val or Trp or Tyr
<220> FEATURE:
<221> NAME/KEY: VARIANT
<222> LOCATION: (3)..(3)
<223> OTHER INFORMATION: Cys or Asp or Glu or Phe or Gly or His or Ile
      or Lys or Leu or Met or Asn or Pro or Gln or Arg or Ser or Thr or
      Val or Trp or Tyr

<400> SEQUENCE: 7

Met Ala Ala Ile
1

<210> SEQ ID NO 8
<211> LENGTH: 5
<212> TYPE: PRT
<213> ORGANISM: Artificial Sequence
<220> FEATURE:
<223> OTHER INFORMATION: Pentapeptide substrate for OTS

<400> SEQUENCE: 8

Ala Gln Asn Ala Thr
1               5

<210> SEQ ID NO 9
<211> LENGTH: 710
<212> TYPE: PRT
<213> ORGANISM: Artificial Sequence
<220> FEATURE:
<223> OTHER INFORMATION: amino acids 2-711 of SEQ ID NO. 1

<400> SEQUENCE: 9

Glu Leu Gln Gln Asn Phe Thr Asp Asn Asn Ser Ile Lys Tyr Thr Cys
1               5                   10                  15

Ile Leu Ile Leu Ile Ala Phe Ala Phe Ser Val Leu Cys Arg Leu Tyr
            20                  25                  30

Trp Val Ala Trp Ala Ser Glu Phe Tyr Glu Phe Phe Asn Asp Gln
        35                  40                  45

Leu Met Ile Thr Thr Asn Asp Gly Tyr Ala Phe Ala Glu Gly Ala Arg
    50                  55                  60

Asp Met Ile Ala Gly Phe His Gln Pro Asn Asp Leu Ser Tyr Phe Gly
65                  70                  75                  80

Ser Ser Leu Ser Thr Leu Thr Tyr Trp Leu Tyr Ser Ile Leu Pro Phe
                85                  90                  95

Ser Phe Glu Ser Ile Ile Leu Tyr Met Ser Thr Phe Phe Ala Ser Leu
            100                 105                 110

Ile Val Val Pro Ile Ile Leu Ile Ala Arg Glu Tyr Lys Leu Thr Thr
            115                 120                 125

Tyr Gly Phe Ile Ala Ala Leu Leu Gly Ser Ile Ala Asn Ser Tyr Tyr
        130                 135                 140

Asn Arg Thr Met Ser Gly Tyr Tyr Asp Thr Asp Met Leu Val Leu Val
145                 150                 155                 160

Leu Pro Met Leu Ile Leu Leu Thr Phe Ile Arg Leu Thr Ile Asn Lys
                165                 170                 175

Asp Ile Phe Thr Leu Leu Leu Ser Pro Ile Phe Ile Met Ile Tyr Leu
```

-continued

```
                180                 185                 190
Trp Trp Tyr Pro Ser Ser Tyr Ser Leu Asn Phe Ala Met Ile Gly Leu
            195                 200                 205
Phe Gly Leu Tyr Thr Leu Val Phe His Arg Lys Glu Lys Ile Phe Tyr
            210                 215                 220
Leu Ala Ile Ala Leu Met Ile Ile Ala Leu Ser Met Leu Ala Trp Gln
225                 230                 235                 240
Tyr Lys Leu Ala Leu Ile Val Leu Leu Phe Ala Ile Phe Ala Phe Lys
                245                 250                 255
Glu Glu Lys Ile Asn Phe Tyr Met Ile Trp Ala Leu Ile Phe Ile Ser
            260                 265                 270
Ile Ser Ile Leu His Leu Ser Gly Gly Leu Asp Pro Val Leu Tyr Gln
            275                 280                 285
Leu Lys Phe Tyr Val Phe Lys Ala Ser Asp Val Gln Asn Leu Lys Asp
            290                 295                 300
Ala Ala Phe Met Tyr Phe Asn Val Asn Glu Thr Ile Met Glu Val Asn
305                 310                 315                 320
Thr Ile Asp Pro Glu Val Phe Met Gln Arg Ile Ser Ser Val Leu
                325                 330                 335
Val Phe Ile Leu Ser Phe Ile Gly Phe Ile Leu Leu Cys Lys Asp His
            340                 345                 350
Lys Ser Met Leu Leu Ala Leu Pro Met Leu Ala Leu Gly Phe Met Ala
            355                 360                 365
Leu Arg Ala Gly Leu Arg Phe Thr Ile Tyr Ala Val Pro Val Met Ala
            370                 375                 380
Leu Gly Phe Gly Tyr Phe Leu Tyr Ala Phe Phe Asn Phe Leu Glu Lys
385                 390                 395                 400
Lys Gln Ile Lys Leu Ser Leu Arg Asn Lys Asn Ile Leu Leu Ile Leu
                405                 410                 415
Ile Ala Phe Phe Ser Ile Ser Pro Ala Leu Met His Ile Tyr Tyr Tyr
                420                 425                 430
Lys Ser Ser Thr Val Phe Thr Ser Tyr Glu Ala Ser Ile Leu Asn Asp
            435                 440                 445
Leu Lys Asn Lys Ala Gln Arg Glu Asp Tyr Val Val Ala Trp Trp Asp
            450                 455                 460
Tyr Gly Tyr Pro Ile Arg Tyr Tyr Ser Asp Val Lys Thr Leu Ile Asp
465                 470                 475                 480
Gly Gly Lys His Leu Gly Lys Asp Asn Phe Phe Ser Ser Phe Val Leu
                485                 490                 495
Ser Lys Glu Gln Ile Pro Ala Ala Asn Met Ala Arg Leu Ser Val Glu
            500                 505                 510
Tyr Thr Glu Lys Ser Phe Lys Glu Asn Tyr Pro Asp Val Leu Lys Ala
            515                 520                 525
Met Val Lys Asp Tyr Asn Gln Thr Ser Ala Lys Asp Phe Leu Glu Ser
            530                 535                 540
Leu Asn Asp Lys Asn Phe Lys Phe Asp Thr Asn Lys Thr Arg Asp Val
545                 550                 555                 560
Tyr Ile Tyr Met Pro Tyr Arg Met Leu Arg Ile Met Pro Val Val Ala
                565                 570                 575
Gln Phe Ala Asn Thr Asn Pro Asp Asn Gly Glu Gln Glu Lys Ser Leu
            580                 585                 590
Phe Phe Ser Gln Ala Asn Ala Ile Ala Gln Asp Lys Thr Thr Gly Ser
            595                 600                 605
```

```
Val Met Leu Asp Asn Gly Val Glu Ile Ile Asn Asp Phe Arg Ala Leu
    610             615             620

Lys Val Glu Gly Ala Ser Ile Pro Leu Lys Ala Phe Val Asp Ile Glu
625             630             635             640

Ser Ile Thr Asn Gly Lys Phe Tyr Tyr Asn Glu Ile Asp Ser Lys Ala
                645             650             655

Gln Ile Tyr Leu Leu Phe Leu Arg Glu Tyr Lys Ser Phe Val Ile Leu
            660             665             670

Asp Glu Ser Leu Tyr Asn Ser Ala Tyr Ile Gln Met Phe Leu Leu Asn
        675             680             685

Gln Tyr Asp Gln Asp Leu Phe Glu Gln Val Thr Asn Asp Thr Arg Ala
    690             695             700

Lys Ile Tyr Arg Leu Lys
705             710

<210> SEQ ID NO 10
<211> LENGTH: 42
<212> TYPE: DNA
<213> ORGANISM: Artificial Sequence
<220> FEATURE:
<223> OTHER INFORMATION: oligonucleotide primer

<400> SEQUENCE: 10
ctagcggtgg tggtggttct ggtggtggtg cccagaacgc ca                          42

<210> SEQ ID NO 11
<211> LENGTH: 42
<212> TYPE: DNA
<213> ORGANISM: Artificial Sequence
<220> FEATURE:
<223> OTHER INFORMATION: oligonucleotide primer

<400> SEQUENCE: 11
ccggtggcgt tctgggcacc accaccagaa ccaccaccac cg                          42
```